(12) United States Patent
Wu et al.

(10) Patent No.: US 9,695,168 B2
(45) Date of Patent: Jul. 4, 2017

(54) SUBSTITUTED IMIDAZO[1,5-α]PYRIDINES AND IMIDAZO[1,5-α]PYRAZINES AS LSD1 INHIBITORS

(71) Applicant: Incyte Corporation, Wilmington, DE (US)

(72) Inventors: Liangxing Wu, Wilmington, DE (US); Leah C. Konkol, Wilmington, DE (US); Neil Lajkiewicz, Garnet Valley, PA (US); Liang Lu, Hockessin, DE (US); Meizhong Xu, Hockessin, DE (US); Wenqing Yao, Chadds Ford, PA (US); Zhiyong Yu, Wilmington, DE (US); Colin Zhang, Ambler, PA (US); Chunhong He, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 48 days.

(21) Appl. No.: 14/795,536

(22) Filed: Jul. 9, 2015

(65) Prior Publication Data

US 2016/0009712 A1    Jan. 14, 2016

Related U.S. Application Data

(63) Continuation of application No. 62/022,933, filed on Jul. 10, 2014.

(51) Int. Cl.
| | |
|---|---|
| *A61K 31/4745* | (2006.01) |
| *A61K 31/4985* | (2006.01) |
| *C07D 471/04* | (2006.01) |
| *C07D 487/04* | (2006.01) |
| *C07D 519/00* | (2006.01) |

(52) U.S. Cl.
CPC ......... *C07D 471/04* (2013.01); *C07D 487/04* (2013.01); *C07D 519/00* (2013.01)

(58) Field of Classification Search
CPC ............ A61K 31/4745; A61K 31/4985; C07D 471/04; C07D 487/04
USPC .................. 514/249, 303; 544/350; 546/119
See application file for complete search history.

(56) References Cited

U.S. PATENT DOCUMENTS

| | | | |
|---|---|---|---|
| 5,658,857 A | 8/1997 | Andree et al. | |
| 8,115,000 B2 | 2/2012 | Rajagopalan et al. | |
| 8,349,210 B2 | 1/2013 | Xu et al. | |
| 8,546,394 B2 | 10/2013 | Li | |
| 8,853,408 B2 | 10/2014 | Johnson | |
| 2002/0151549 A1 | 10/2002 | Hayakawa et al. | |
| 2004/0023972 A1 | 2/2004 | Sundermann et al. | |
| 2004/0058938 A1 | 3/2004 | Cullmann et al. | |
| 2004/0082635 A1 | 4/2004 | Hashimoto et al. | |
| 2004/0082781 A1 | 4/2004 | Hibi et al. | |
| 2004/0220189 A1 | 11/2004 | Sun et al. | |
| 2005/0009832 A1 | 1/2005 | Sun et al. | |
| 2005/0113283 A1 | 5/2005 | Solow-Cordero et al. | |
| 2006/0178399 A1 | 8/2006 | Nishizawa et al. | |
| 2006/0194842 A1 | 8/2006 | Uchida et al. | |
| 2007/0004772 A1 | 1/2007 | Sun et al. | |
| 2007/0191395 A1 | 8/2007 | Kawakami | |
| 2008/0249154 A1 | 10/2008 | Ohmoto et al. | |
| 2009/0203690 A1 | 8/2009 | Akritopoulou-Zanze et al. | |
| 2009/0318436 A1 | 12/2009 | Albrecht et al. | |
| 2010/0113441 A1 | 5/2010 | Siegel et al. | |
| 2011/0105457 A1 | 5/2011 | Taniyama et al. | |
| 2011/0112067 A1 | 5/2011 | Hartmann et al. | |
| 2012/0004262 A1 | 1/2012 | Guibourt et al. | |
| 2012/0108500 A1 | 5/2012 | Sakane et al. | |
| 2012/0220582 A1 | 8/2012 | Mitchell et al. | |
| 2012/0283266 A1 | 11/2012 | Ortega Munoz et al. | |
| 2012/0322877 A1 | 12/2012 | Casero et al. | |
| 2013/0035377 A1 | 2/2013 | Minucci et al. | |
| 2013/0040946 A1 | 2/2013 | Siegel et al. | |
| 2013/0090386 A1 | 4/2013 | Ortega Munoz et al. | |
| 2013/0095067 A1 | 4/2013 | Baker et al. | |
| 2013/0109751 A1 | 5/2013 | Salvatore | |
| 2013/0197013 A1 | 8/2013 | Fyfe et al. | |

(Continued)

FOREIGN PATENT DOCUMENTS

| | | |
|---|---|---|
| CA | 2831143 | 10/2012 |
| CA | 2844525 | 2/2013 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Guiles et al. "preparation of triazolopyrimidine derivatives as P2T receptor antagonists," CA130:168386 (1999).
Improper Markush Fed. Reg. 76(27) p. 7612-75, slide 1, 64-67 (2011).
"LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.

(Continued)

*Primary Examiner* — Douglas M Willis
(74) *Attorney, Agent, or Firm* — Fish & Richardson P.C.

(57) ABSTRACT

The present invention is directed to imidazo[1,5-a]pyridine and imidazo[1,5-a]pyrazine derivatives of Formula I, or a pharmaceutically acceptable salt thereof, which are LSD1 inhibitors useful in the treatment of diseases such as cancer.

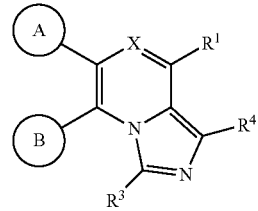

63 Claims, No Drawings

(56) References Cited

U.S. PATENT DOCUMENTS

| | | |
|---|---|---|
| 2013/0203754 A1 | 8/2013 | Yang et al. |
| 2013/0217878 A1 | 8/2013 | Lizuka et al. |
| 2013/0231342 A1 | 9/2013 | Munoz et al. |
| 2013/0303545 A1 | 11/2013 | Maes et al. |
| 2014/0011857 A1 | 1/2014 | Casero et al. |
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0232436 A1 | 8/2015 | Baker et al. |
| 2016/0009711 A1 | 1/2016 | Wu et al. |
| 2016/0009720 A1 | 1/2016 | Wu et al. |
| 2016/0009721 A1 | 1/2016 | Wu et al. |
| 2016/0289238 A1 | 10/2016 | He et al. |

FOREIGN PATENT DOCUMENTS

| | | |
|---|---|---|
| CA | 2887598 | 4/2014 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| DE | 102006041292 | 3/2008 |
| EP | 0404190 | 12/1990 |
| EP | 0430385 | 6/1991 |
| EP | 2524918 | 11/2012 |
| EP | 2740474 | 6/2014 |
| EP | 2743256 | 6/2014 |
| FR | 2662163 | 11/1991 |
| FR | 2920090 | 2/2009 |
| FR | 2920091 | 2/2009 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |
| JP | 2010070503 | 4/2010 |
| WO | WO 8804298 | 6/1988 |
| WO | WO 9325553 | 12/1993 |
| WO | WO 9418198 | 8/1994 |
| WO | WO 95/12594 | 5/1995 |
| WO | WO 9924434 | 5/1999 |
| WO | WO 0127119 | 4/2001 |
| WO | WO 0183481 | 8/2001 |
| WO | WO 02/00196 | 1/2002 |
| WO | WO 0206286 | 1/2002 |
| WO | WO 0234748 | 5/2002 |
| WO | WO 0238562 | 5/2002 |
| WO | WO 02051831 | 7/2002 |
| WO | WO 02072549 | 9/2002 |
| WO | WO 03006471 | 1/2003 |
| WO | WO 03044021 | 5/2003 |
| WO | WO 03062392 | 7/2003 |
| WO | WO 2004/017950 | 3/2004 |
| WO | WO 2004/021989 | 3/2004 |
| WO | WO 2004/058762 | 7/2004 |
| WO | WO 2004/072081 | 8/2004 |
| WO | WO 2004/074290 | 9/2004 |
| WO | WO 2004/089380 | 10/2004 |
| WO | WO 2004/089416 | 10/2004 |
| WO | WO 2004/096131 | 11/2004 |
| WO | WO 2004/108692 | 12/2004 |
| WO | WO 2005/007658 | 1/2005 |
| WO | WO 2005/025558 | 3/2005 |
| WO | WO 2005/035532 | 4/2005 |
| WO | WO 2005/042537 | 5/2005 |
| WO | WO 2005/044793 | 5/2005 |
| WO | WO 2005/097052 | 10/2005 |
| WO | WO 2006/015263 | 2/2006 |
| WO | WO 2006/018727 | 2/2006 |
| WO | WO 2006/038116 | 4/2006 |
| WO | WO 2006/057946 | 6/2006 |
| WO | WO 2006/058752 | 6/2006 |
| WO | WO 2006/073938 | 7/2006 |
| WO | WO 2006/074041 | 7/2006 |
| WO | WO 2006/113704 | 10/2006 |
| WO | WO 2006/131003 | 12/2006 |
| WO | WO 2006/135667 | 12/2006 |
| WO | WO 2006/135795 | 12/2006 |
| WO | WO 2006/138657 | 12/2006 |
| WO | WO 2006/138695 | 12/2006 |
| WO | WO 2006/138734 | 12/2006 |
| WO | WO 2007/022529 | 2/2007 |
| WO | WO 2007/028051 | 3/2007 |
| WO | WO 2007/058942 | 5/2007 |
| WO | WO 2007/074491 | 7/2007 |
| WO | WO 2007/095588 | 8/2007 |
| WO | WO 2007/113226 | 10/2007 |
| WO | WO 2007/145921 | 12/2007 |
| WO | WO 2007/149478 | 12/2007 |
| WO | WO 2008/005262 | 1/2008 |
| WO | WO 2008/005423 | 1/2008 |
| WO | WO 2008/005908 | 1/2008 |
| WO | WO 2008/008539 | 1/2008 |
| WO | WO 2008/011560 | 1/2008 |
| WO | WO 2008/027812 | 3/2008 |
| WO | WO 2008/037607 | 4/2008 |
| WO | WO 2008/045393 | 4/2008 |
| WO | WO 2008/056176 | 5/2008 |
| WO | WO 2008/064157 | 5/2008 |
| WO | WO 2008/065198 | 6/2008 |
| WO | WO 2008/113559 | 9/2008 |
| WO | WO 2008/125111 | 10/2008 |
| WO | WO 2008/130951 | 10/2008 |
| WO | WO 2008/141239 | 11/2008 |
| WO | WO 2008/154241 | 12/2008 |
| WO | WO 2008/156614 | 12/2008 |
| WO | WO 2008/157752 | 12/2008 |
| WO | WO 2009/010530 | 1/2009 |
| WO | WO 2009/017701 | 2/2009 |
| WO | WO 2009/017954 | 2/2009 |
| WO | WO 2009/023179 | 2/2009 |
| WO | WO 2009/045753 | 4/2009 |
| WO | WO 2009/047514 | 4/2009 |
| WO | WO 2009/047563 | 4/2009 |
| WO | WO 2009/085230 | 7/2009 |
| WO | WO 2009/085980 | 7/2009 |
| WO | WO 2009/091374 | 7/2009 |
| WO | WO 2009/114180 | 9/2009 |
| WO | WO 2009/114512 | 9/2009 |
| WO | WO 2009/128520 | 10/2009 |
| WO | WO 2010/010184 | 1/2010 |
| WO | WO 2010/010187 | 1/2010 |
| WO | WO 2010/010188 | 1/2010 |
| WO | WO 2010/010189 | 1/2010 |
| WO | WO 2010/019899 | 2/2010 |
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/091067 | 8/2010 |
| WO | WO 2010/104306 | 9/2010 |
| WO | WO 2010/108059 | 9/2010 |
| WO | WO 2010/113942 | 10/2010 |

(56) References Cited

FOREIGN PATENT DOCUMENTS

| | | |
|---|---|---|
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/160548 | 12/2011 |
| WO | WO 2012/003392 | 1/2012 |
| WO | WO 2012/007345 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |
| WO | WO 2013/022047 | 2/2013 |
| WO | WO 2013/025805 | 2/2013 |
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/058071 | 4/2014 |
| WO | WO 2014/078479 | 5/2014 |
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/164867 | 10/2014 |
| WO | WO 2014/194280 | 12/2014 |
| WO | WO 2014/205213 | 12/2014 |
| WO | WO 2015/031564 | 3/2015 |
| WO | WO 2015/089192 | 6/2015 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |

OTHER PUBLICATIONS

Adamo et al., "LSD1 and pluripotency: a new player in the network," Cell Cycle, Oct. 2011, 10(19): 3215-6.

Adamo et al., "LSD1 regulates the balance between self-renewal and differentiation in human embryonic stem cells," Nat. Cell Biol, Jun. 2011, 13(6): 652-9.

Anand and Marmorstein, "Structure and mechanism of lysine-specific demethylase enzymes," J Biol Chem, Dec. 2007, 282(49): 35425-9.

Baron et al., "Molecular Mimicry and Ligand Recognition in Binding and Catalysis by the Histone Demethylase LSD1-CoREST Complex," Structure, Feb. 2011, 19: 212-220.

Bauer et al., "Reawakening fetal hemoglobin: prospects for new therapies for the β-globin disorders," Blood, Oct. 2012, 120(15): 3945-53.

Beck and Blanpain, "Unravelling cancer stem cell potential," Nat Rev Cancer, Oct. 2013, 13(10): 727-38.

Benelkebir et al., "Enantioselective synthesis of tranylcypromine analogues as lysine demethylase (LSD1) inhibitors," Bioorganic & Medicinal Chemistry, 2011, 19: 3709-3716.

Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.

Berge and Robiette, "Development of a Regioselective N-Methylation of (Benz)imidazoles Providing the More Sterically Hindered Isomer," The Journal of Organic Chemistry, 2013, A-D.

Berge et al., "Pharmaceutical salts," J Pharm Sci, 1977, 66(1): 1-19.

Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.

Binda et al., "Molecular Insights into Human Monoamine Oxidase B Inhibition by the Glitazone Antidiabetes Drugs," ACS Med. Chem. Letter, 2012, 3: 39-42.

Blom et al., "Optimizing Preparative LC/MS Configurations and Methods for Parallel Synthesis Purification," J. Comb. Chem., 2003, 5(5): 670-683.

Blom et al., "Preparative LC-MS Purification: Improved Compound-Specific Method Optimization," J. Comb. Chem., 2004, 6(6): 874-883.

Blom, "Two-Pump at-Column-Dilution Configuration for Preparative Liquid Chomratography-Mass Spectrometry," J. Comb. Chem, 2002, 4(4): 295-301.

Cain, "AML takes LSD1," SciBX, Apr. 2012, 1-3.

Cao et al., "One-Pot Regiospecific Synthesis of Imidazo[1,2-a]pyridines: A Novel, Metal-Free, Three-Component Reaction for the Formation of C—N, C—O, and C—S Bonds," Org. Lett., 2013, A-D.

Chen and Flies, "Molecular mechanisms of T cell co-stimulation and co-inhibition," Nat Rev Immunol, Apr. 2013, 13(4): 227-42.

Chen et al., "Crystal structure of human histone lysine-specific demethylase 1 (LSD1)," Proc Natl Acad Sci USA, Sep. 2006, 103(38): 13956-61.

Chen et al., "Lysine-specific histone demethylase 1 (LSD1): A potential molecular target for tumor therapy," Crit Rev Eukaryot Gene Expre, 2012, 22(1): 53-9.

Cho et al., "Demethylation of RB regulator MYPT1 by histone demethylase LSD1 promotes cell cycle progression in cancer cells," Cancer Res., Feb. 2011, 71(3): 655-60.

(56) References Cited

OTHER PUBLICATIONS

Clevers, "The cancer stem cell: premises, promises and challenges," Nat Med., Mar. 2011, 17(3): 313-9.

Crea et al., "The emerging role of histone lysine demethylases in prostate cancer," Mol Cancer, Aug. 2012, 11:52.

Cui et al., "The LSD1 inhibitor RN-1 induces fetal hemoglobin synthesis and reduces disease pathology in sickle cell mice," Blood, 2015, 1-31.

Culhane and Cole, "LSD1 and the chemistry of histone demethylation," Current Opinion in Chemical Biology, 2007, 11: 561-568.

Culhane et al., "A Mechanism-Based Inactivator for Histone Demethylase LSD1," J. Am. Chem. Soc., 2006, 128: 4536-4537.

Culhane et al., "Comparative Analysis of Small Molecules and Histone Substrate Analogues as LSD1 Lysine Demethylase Inhibitors," J. Am. Chem. Soc., 2010, 132: 3164-3176.

Dancy et al., "Azalysine Analogues as Probes for Protein Lysine Deacetylation and Demethylation," J. Am. Chem. Soc., 2012, 5138-5148.

Dawson and Kouzarides, "Cancer epigenetics: from mechanism to therapy," Cell, Jul. 2012, 150(1): 12-27.

Dhanak, "Cracking the Code: The Promise of Epigenetics," ACS Med. Chem. Letter, 2012, 3: 521-523.

Dhudshia and Thadani, "Diastereoselective allylation and crotylation of N-unsubstituted imines derived from ketones," Chem. Commun., 33 pages.

Dhudshia et al., "Diastereoselective allylation and crotylation of N-unsubstituted imines derived from ketones," Chem Commun, 2005, 5551-5553.

Ding et al., "LSD1-mediated epigenetic modification contributes to proliferation and metastasis of colon cancer," Br J Cancer, Aug. 2013, 109(4): 994-1003.

Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.

Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.

Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.

Forneris et al., "LSD1: oxidative chemistry for multifaceted functions in chormatin regulation," Cell Press, Mar. 2008, 181-189.

Forneris, F., et al., Structural basis of LSD1-CoREST selectivity in histone H3 recognition. J Biol Chem, 2007. 282(28): p. 20070-4.

Ganesan, "Targeting Epigenetic Demethylation," University of East Anglia (School of Pharmacy), PowerPoint presentation, Presented from the World Epigenetics Summit, London, Jul. 24, 2012, 26 pages.

Ge et al., "Pd-Catalyzed α-Arylation of α,α-Difluoroketones with Aryl Bromides and Chlorides. A Route to Difluoromethylarenes," J. Am. Chem. Soc., 2014, A-D.

Gonzalez et al., "Selective and Potent Morpholinone Inhibitors of the MDM2-p53 Protein-Protein Interaction," J. Med. Chem., 2013, A-Q.

Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.

Greaves and Gribben, "The role of B7 family molecules in hematologic malignancy," Blood, Jan. 2013, 121(5): 734-44.

Gui et al., "C—H Methylation of Heteroarenes Inspired by Radical SAM Methyl Transferase," J. Am. Chem. Soc., 2014, A-D.

Hakimi et al., "A core-BRAF35 complex containing histone deacetylase mediates repression of neuronal-specific genes," Proc Natl Acad Sci USA, May 2002, 99(11): 7420-5.

Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.

Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.

Han et al., "Synergistic re-activation of epigenetically silenced genes by combinatorial inhibition of DNMTs and LSD1 in cancer cells," pLoS One, Sep. 2013, 8(9): e75136.

Harris et al., "The histone demethylase KDM1A sustains the oncogenic potential of MLL-AF9 leukemia stem cells," Cancer Cell, Apr. 2012, 21(4): 473-87.

Hayami et al., "Overexpression of LSD1 contributes to human carcinogenesis through chromatin regulation in various cancers," Int J Cancer, Feb. 2011, 128(3): 574-86.

Hazeldine et al., "Low Molecular Weight Amidoximes that Act as Potent Inhibitors of Lysine-Specific Demethylase 1," J. Med. Chem., 2012, 55: 7378-7391.

Hesp et al., "Expedient Synthesis of α-Heteroaryl Piperidines Using a Pd-Catalyzed Suzuki Cross-Coupling—Reduction Sequence," Org. Lett., 2013, A-C.

Hicken et al., "Discovery of a Novel Class of Imidazo[1,2-a]Pyridines with Potent PDGFR Activity and Oral Bioavailability," ACS Med. Chem. Lett., 2013, A-F.

Hitchin et al., "Development and evaluation of selective, reversible LSD1 inhibitors derived from fragments," Med. Chem. Commun., 2013, 4: 1513-1522.

Hoffmann et al., "The role of histone demethylases in cancer therapy," Molecular Oncology, 2012, 6: 683-703.

Hou and Yu, "Structural insights into histone lysine demethylation," Current Opinion in Structural Biology, 2010, 20: 739-748.

Hruschka et al., "Fluorinated phenylcyclopropylamines. Part 5: Effects of electron-withdrawing or—donating aryl substituents on the inhibition of monoamine oxidases A and B by 2-aryl-2-fluoro-cyclopropylamines," Bioorganic & Medicinal Chemistry, 2008, 16: 7148-7166.

Huang et al., "Rhodium(III)-Catalyzed Direct Selective C(5)-H Oxidative Annulations of 2-Substituted Imidazoles and Alkynes by Double C—H Activation," Organic Letters, Feb. 2013, 15(8): 1878-1881.

Huang et al., "p53 is regulated by the lysine demethylase LSD1," Nature, Sep. 2007, 449(7158): 105-8.

International Search Report and Written Opinion in International Application No. PCT/US2015/015635, dated May 8, 2015, 10 pages.

International Search Report and Written Opinion in International Application No. PCT/US2015/015663, dated May 6, 2015, 10 pages.

International Search Report and Written Opinion in International Application No. PCT/US2015/015706, dated May 6, 2015, 16 pages.

International Search Report and Written Opinion in International Application No. PCT/US2015/015600, dated May 18, 2015, 9 pages.

International Search Report and Written Opinion in International Application No. PCT/US2015/039734, dated Sep. 18, 2015, 14 pages.

International Search Report and Written Opinion in International Application No. PCT/US2015/039724, dated Sep. 15, 2015, 14 pages.

International Search Report and Written Opinion in International Application No. PCT/US2015/039718, dated Sep. 15, 2015, 13 pages.

Jalluri, Drug Analysis Table, LSD1 KDM1a Cortellis Update, retrieved on May 6, 2013, 3 pages.

(56) References Cited

OTHER PUBLICATIONS

Kahl et al., "Androgen Receptor Coactivators Lysine-Specific Histone Demethylase 1 and Four and a Half LIM Domain Protein 2 Predict Risk of Prostate Cancer Recurrence," Cancer Res., 2006, 66(23): 11341-7.
Kakizawa et al., "Histone H3 peptide based LSD1-selective inhibitors," Bioorganic & Medicinal Chemistry Letters, 2015, 25: 1925-1928.
Karytinos et al., "A novel mammalian flavin-dependent histone demethylase," J Biol Chem, Jan. 2009, 284(26): 17775-82.
Kelly and Lipshutz, "Chemoselective Reductions of Nitroaromatics in Water at Room Temperature," Org. Lett., 2013, A-D.
Kettle et al., "Diverse Heterocyclic Scaffolds as Allosteric Inhibitors of AKT," Journal of Medicinal Chemistry, Mar. 2012, 55(3): 1261-1273.
Khan et al., "An Overview of Phenylcyclopropylamine Derivatives: Biochemical and Biological Significance and Recent Developments," Medicinal Research Reviews, 2012, 874-910.
Khoury et al., "Efficient Assembly of Iminodicarboxamides by a "Truly" Four-Component Reaction," Angew. Chem. Int. Ed., 2012, 51: 10280-10283.
Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.
Kjer-Nielsen et al., "MR1 presents microbial vitamin B metabolites to MAIT cells," Nature, Nov. 2012, 491: 717-725.
Kong et al., "Immunohistochemical expression of RBP2 and LSD1 in papillary thyroid carcinoma," Rom J Morphol Embryol, 2013, 54(3): 499-503.
Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.
Kontaki and Talianidis, "Lysine methylation regulates E2F1-induced cell death," Mol Cell, Jul. 2010, 39(1): 152-60.
Kooistra and Helin, "Molecular mechanisms and potential functions of histone demethylases," Nat Rev Mol Cell Biol, Apr. 2012, 13(5): 297-311.
Kutz et al., "3,5-Diamino-1,2,4-triazoles as a novel scaffold for potent, reversible LSD1 (KDM1A) inhibitors," Med. Chem. Commun., 2014, 5: 1863-1870.
Lan et al., "Recognition of unmethylated histone H3 lysine 4 links BHC80 to LSD1-mediated gene repression," Nature, 2007, 718-723.
Larsen and Hartwig, "Iridium-Catalyzed C—H Borylation of Heteroarenes: Scope, Regioselectivity, Application to Late-Stage Functionalization, and Mechanism," J. Am. Chem. Soc., 2013, A-M.
Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.
Liang et al., "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS One, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Lynch et al., "LSD1 Inhibition: A therapeutic strategy in cancer?," Expert Opinion on Therapeutic Targets, 2012, 16(12): 1239-1249.
Merck KGaA, "Product comparison—EMD4Biosciences," Comparison of LSD1 inhibitors, EMD Millipore USA, retrieved on May 6, 2013, 3 pages.
Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistry, 2010, 49: 6494-6503.
Moon et al., "Copper-Catalyzed Chan-Lam Coupling between Sulfonyl Azides and Boronic Acids at Room Temperature," Org. Lett., 2013, A-D.
Moormann et al., "Potential Antisecretory Antidiarrheals. 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Neelamegam et al., "Brain-penetrant LSD1 inhibitors can block memory consolidation," Supplementary Data, 24 pages.
Neelamegam et al., "Brain-Penetrant LSD1 Inhibitors Can Block Memory Consolidation," ACS Chem. Neurosci., 2012, 3:120-128.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery Mechanism," Supporting Information.
Patani et al., "Bioisosterism: A Rational Approach in Drug Design," Chemical Reviews, 1996, 96: 3147-3176.
Pitt "Heteroaromatic Rings of the Future" J. Med. Chem. 2009, 52, 2952-2963.
Potts et al., "The mass spectra of somes-triazolo[4,3-a]pyrazines," Organic Mass Spectrometry, Jun. 1971, 5(6): 663-674.
Portela and Esteller, "Epigenetic modifications and human disease," Nat Biotechnol, Oct. 2010, 28(10): 1057-68.
Pozharskii et. al. Heterocycles in Life and Society Wiley, 1997, pp. 1-6.
*Remington's Pharmaceutical Sciences*, 17$^{th}$ Ed., (Mack Publishing Company, Easton, 1985), p. 1418.
Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rotilli and Mai, "Targeting Histone Demethylases: A New Avenue for the Fight against Cancer," Genes and Cancer, 2011, 2(6): 663-679.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.
Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Samann et al., "Full Functionalization of the Imidazole Scaffold by Selective Metalation and Sulfoxide/Magnesium Exchange," Angew. Chem. Int. Ed., 2013, 52: 1-6.

(56) References Cited

OTHER PUBLICATIONS

Sankaran and Orkin, "The switch from fetal to adult hemoglobin," Cold Spring Harb Perspect Med., Jan. 2013, 3(1): a011643.

Sareddy et al., "KDM1 is a novel therapeutic target for the treatment of gliomas," Oncotarget, Jan. 2013, 4(1): 18-28.

Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.

Schmitt et al., "Nonpeptidic Propargylamines as Inhibitors of Lysine Specific Demethylase 1 (LSD1) with Cellular Activity," J. Med. Chem., 2013, A-I.

Schulte et al., "Lysine-Specific Demethylase 1 is Strongly Expressed in Poorly Differentiated Neuroblastoma: Implications for Therapy," Cancer Res, 2009, 69(5): 2065-71.

Senecal et al., "A General, Practical Palladium-Catalyzed Cyanation of (Hetero) Aryl Chlorides and Bromides," Angew. Chem. Int. Ed., 2013, 52: 1-6.

Serce et al., "Elecated expression of LSD1 (Lysine-specific demethylase 1) during tumour progression from re-invasive to invasive ductal carcinoma of the breast," BMC Clin Pathol, Aug. 2012, 12:13.

Sharma et al., "(Bis)urea and (Bis)thiourea Inhibitors of Lysine-Specific Demethylase 1 as Epigenetic Modulators," J. Med. Chem., 2010, 53: 5197-5212.

Search Report, May 30, 2014, 6 pages.
Search Report, May 30, 2014, 109 pages.
Search Report, Jun. 3, 2014, 7 pages.

Shen and Laird, "Interplay between the cancer genome and epigenome," Cell, Mar. 2013, 153(1): 38-55.

Shi et al., "Histone demethylation mediated by the nuclear amine oxidase homolog LSD1," Cell, Dec. 2004, 119(7): 941-53.

Shi et al., "Lysine-specific demethylase 1 is a therapeutic target for fetal hemoglobin induction," Nat Med, Mar. 2013, 19(3): 291-4.

Shi et al., "Regulation of LSD1 Histone Demethylase Activity by Its Associated Factors," Molecular Cell, Sep. 2005, 19: 857-864.

Singh et al., "Inhibition of LSD1 sensitizes gliobastoma cells to histone deacetylase inhibitors," Neuro Oncol, Aug. 2011, 13(8): 894-903.

Son et al., "Structure of human monoamine oxidase A at 2.2-A resolution: The control of opening the entry for substrates/inhibitors," PNAS, Apr. 2008, 105(15): 5739-5744.

Stavropoulos et al., "Crystal structure and mechanism of human lysine-specific demethylase-1," Nat Struct Mol Biol, Jul. 2006, 13(7): 626-32.

Suikki et al., "Genetic alterations and changes in expression of histone demethylases in prostate cancer," Prostate, Jun. 2010, 70(8): 889-96.

Sun et al., "Histone demethylase LSD1 regulates neural stem cell proliferation," Mol Cell Biol, Apr. 2010, 30(8): 1997-2005.

Suzuki and Miyata, "Lysine Demethylases Inhibitors," J. Med. Chem., 2011, 54: 8236-8250.

Szewczuk et al., "Mechanistic Analysis of a Suicide Inactivator of Histone Demethylase LSD1," Biochemistry, 2007, 46: 6892-6902.

Szostak et al., "Highly Chemoselective Reduction of Amides (Primary, Secondary, Tertiary) to Alcohols using $Sml_2/Amine/H_2O$ under Mild Conditions," J. Am. Chem. Soc., 2013, A-D.

Theisen et al., "Reversible inhibition of lysine specific demethylase 1 is a novel anti-tumor strategy for poorly differentiated endometrial carcinoma," BMC Cancer, 2014, 14:752 1-12.

Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.

Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.

Ueda et al., "Identification of Cell-Active Lysine Specific Demethylase 1-Selective Inhibitors," J. Am. Chem. Soc., 2009, 131: 17536-17537.

Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.

Wakefield, Basil "Fluorinated Pharamceuticals" Innovations in Pharamceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).

Waldmann and Schneider, "Targeting histone modifications—epigenetics in cancer," Curr Opin Cell Biol, Apr. 2013, 25(2): 184-9.

Wang et al., "Novel Histone Demethylase LSD1 Inhibitors Selectively Target Cancer Cells with Pluripotent Stem Cell Properties," Cancer Res, Dec. 2011, 7238-7249.

Wang et al., "The lysine demethylase LSD1 (KDM1) is required for maintenance of global DNA methylation," Nat Genet, Jan. 2009, 41(1): 125-9.

Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.

Wengryniuk et al., "Regioselective Bromination of Fused Heterocyclic N-Oxides," American Chemical Society, 2013, 15(4): 792-795.

Willmann et al., "Impairment of prostate cancer cell growth by a selective and reversible lysine-specific demethylase 1 inhibitor," Int. J. Cancer, 2012, 131: 2704-2709.

Xu et al., "Corepressor-dependent silencing of fetal hemoglobin expression by BCL11A," Proc Natl Acad Sci USA, Apr. 2013, 110(16): 6518-23.

Yang et al., "Reversible methylation of promoter-bound STAT3 by histone-modifying enzymes," Proc Natl Acad Sci USA, Dec. 2010, 107(50): 21499-504.

Yang et al., "Structural Basis for the Inhibition of the LSD1 Histone Demethylase by the Antidepressant trans-2-Phenylcyclopropylamine," Biochemistry, 2007, 46: 8058-8065.

Yang et al., "Structural basis of histone demethylation by LSD1 revealed by suicide inactivation," Nature Structural & Molecular Biology, Jun. 2007, 14(6): 535-539.

Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.

You et al., "CoREST is an integral component of the CoREST-human histone deacetylase complex," Proc Natl Acad Sci USA, Feb. 2001, 98(4): 1454-8.

Yu et al., "Energetic factos determining the binding of type I inhibitors to c-Met kinase: experimental studies and quantum mechanical calculations," Acta Pharmacologica Sinica, Nov. 2013, 34(11): 1475-1783.

Yu et al., "High expression of lysine-specific demethylase 1 correlates with poor prognosis of patients with esophageal squamous cell carcinoma," Biochem Biophys Res Commun, Jul. 2013, 437(2): 192-8.

Zhang et al., "Pluripotent stem cell protein Sox2 confers sensitivity to LSD1 inhibition in cancer cells," Cell Rep, Oct. 2013, 5(2): 445-57.

Zheng et al., "A Systematic Review of Histone Lysine-Specific Demethylase 1 and Its Inhibitors," 2015, 1-40.

Carey, FA. Organic Chemistry 6th Ed. McGraw Hill. 2006, chapter 1, p. 9.

Hackam et al., JAMA, 296(14), 2006, 1731-1732.

International Preliminary Report on Patentability in International Application No. PCT/US2015/015600, dated Aug. 25, 2016, 7 pages.

International Preliminary Report on Patentability in International Application No. PCT/US2015/015635, dated Aug. 16, 2016, 8 pages.

International Preliminary Report on Patentability in International Application No. PCT/US2015/015663, dated Aug. 16, 2016, 7 pages.

International Preliminary Report on Patentability in International Application No. PCT/US2015/015706, dated Aug. 16, 2016, 10 pages.

(56) References Cited

OTHER PUBLICATIONS

International Preliminary Report on Patentability in International Application No. PCT/US2015/039734, dated Jan. 10, 2017, 10 pages.
International Preliminary Report on Patentability in International Application No. PCT/US2015/039706, dated Jan. 10, 2017, 10 pages.
International Preliminary Report on Patentability in International Application No. PCT/US2015/039724, dated Jan. 10, 2017, 10 pages.
International Preliminary Report on Patentability in International Application No. PCT/US2015/039718, dated Jan. 10, 2017, 9 pages.
International Search Report and Written Opinion in International Application No. PCT/US2016/025550, dated Aug. 30, 2016, 12 pages.
International Search Report and Written Opinion in International Application No. PCT/US2016/046497, dated Oct. 21, 2016, 13 pages.
International Search Report and Written Opinion in International Application No. PCT/US2015/039706, dated Sep. 16, 2015, 12 pages.
Jordan, V.C. Nature Reviews: Drug Discovery, 2, 2003, 205.
Kocienski, PJ. Et al. Protecting Groups. Thieme. 2005, p. 52.
Kuroyanagi et al., "Novel anti fungal agents: Triazolopyridines as inhibitors of beta-1,6-glucan synthesis," Bioorgan IC & Medicinal Chemistry, Aug. 2010, 18(16):5845-5854.
Kuroyanagi et al., "1,3-Benzoxazole-4-carbonitrile as a novel antifungal scaffold of beta-1,6-glucan synthesis inhibitors," Bioorganic & Medicinal Chemistry, Nov. 2010, 18(21):7593-7606.
Zhu et al., "Preparation of imidazolidin-2-imines and their analogs as aspartyl protease inhibitors for treating various diseases," CA149: 307842 (2008).

* cited by examiner

SUBSTITUTED IMIDAZO[1,5-α]PYRIDINES AND IMIDAZO[1,5-α]PYRAZINES AS LSD1 INHIBITORS

FIELD OF THE INVENTION

The present invention is directed to imidazo[1,5-a]pyridine and imidazo[1,5-a]pyrazine derivatives which are LSD1 inhibitors useful in the treatment of diseases such as cancer.

BACKGROUND OF THE INVENTION

Epigenetic modifications can impact genetic variation but, when dysregulated, can also contribute to the development of various diseases (Portela, A. and M. Esteller, *Epigenetic modifications and human disease*. Nat Biotechnol, 2010. 28(10): p. 1057-68; Lund, A. H. and M. van Lohuizen, *Epigenetics and cancer*. Genes Dev, 2004. 18(19): p. 2315-35). Recently, in depth cancer genomics studies have discovered many epigenetic regulatory genes are often mutated or their own expression is abnormal in a variety of cancers (Dawson, M. A. and T. Kouzarides, *Cancer epigenetics: from mechanism to therapy*. Cell, 2012. 150(1): p. 12-27; Waldmann, T. and R. Schneider, *Targeting histone modifications—epigenetics in cancer*. Curr Opin Cell Biol, 2013. 25(2): p. 184-9; Shen, H. and P. W. Laird, *Interplay between the cancer genome and epigenome*. Cell, 2013. 153(1): p. 38-55). This implies epigenetic regulators function as cancer drivers or are permissive for tumorigenesis or disease progression. Therefore, deregulated epigenetic regulators are attractive therapeutic targets.

One particular enzyme which is associated with human diseases is lysine specific demethylase-1 (LSD1), the first discovered histone demethylase (Shi, Y., et al., *Histone demethylation mediated by the nuclear amine oxidase homolog LSD1*. Cell, 2004. 119(7): p. 941-53). It consists of three major domains: the N-terminal SWIRM which functions in nucleosome targeting, the tower domain which is involved in protein-protein interaction, such as transcriptional co-repressor, co-repressor of RE1-silencing transcription factor (CoREST), and lastly the C terminal catalytic domain whose sequence and structure share homology with the flavin adenine dinucleotide (FAD)-dependent monoamine oxidases (i.e., MAO-A and MAO-B) (Forneris, F., et al., *Structural basis of LSD1-CoREST selectivity in histone H3 recognition*. J Biol Chem, 2007. 282(28): p. 20070-4; Anand, R. and R. Marmorstein, *Structure and mechanism of lysine-specific demethylase enzymes*. J Biol Chem, 2007. 282(49): p. 35425-9; Stavropoulos, P., G. Blobel, and A. Hoelz, *Crystal structure and mechanism of human lysine-specific demethylase-1*. Nat Struct Mol Biol, 2006. 13(7): p. 626-32; Chen, Y., et al., *Crystal structure of human histone lysine-specific demethylase 1* (LSD1). Proc Natl Acad Sci USA, 2006. 103(38): p. 13956-61). LSD1 also shares a fair degree of homology with another lysine specific demethylase (LSD2) (Karytinos, A., et al., *A novel mammalian flavin-dependent histone demethylase*. J Biol Chem, 2009. 284(26): p. 17775-82). Although the biochemical mechanism of action is conserved in two isoforms, the substrate specificities are thought to be distinct with relatively small overlap. The enzymatic reactions of LSD1 and LSD2 are dependent on the redox process of FAD and the requirement of a protonated nitrogen in the methylated lysine is thought to limit the activity of LSD1/2 to mono- and di-methylated lysines at the position of 4 or 9 of histone 3 (H3K4 or H3K9). These mechanisms make LSD1/2 distinct from other histone demethylase families (i.e. Jumonji domain containing family) that can demethylate mono-, di-, and tri-methylated lysines through alpha-ketoglutarate dependent reactions (Kooistra, S. M. and K. Helie, *Molecular mechanisms and potential functions of histone demethylases*. Nat Rev Mol Cell Biol, 2012. 13(5): p. 297-311; Mosammaparast, N. and Y. Shi, *Reversal of histone methylation: biochemical and molecular mechanisms of histone demethylases*. Annu Rev Biochem, 2010. 79: p. 155-79).

Methylated histone marks on H3K4 and H3K9 are generally coupled with transcriptional activation and repression, respectively. As part of corepressor complexes (e.g., CoREST), LSD1 has been reported to demethylate H3K4 and repress transcription, whereas LSD1, in nuclear hormone receptor complex (e.g., androgen receptor), may demethylate H3K9 to activate gene expression (Metzger, E., et al., *LSD1 demethylates repressive histone marks to promote androgen-receptor-dependent transcription*. Nature, 2005. 437(7057): p. 436-9; Kahl, P., et al., *Androgen receptor coactivators lysine-specific histone demethylase 1 and four and a half LIM domain protein 2 predict risk of prostate cancer recurrence*. Cancer Res, 2006. 66(23): p. 11341-7). This suggests the substrate specificity of LSD1 can be determined by associated factors, thereby regulating alternative gene expressions in a context dependent manner. In addition to histone proteins, LSD1 may demethylate non-histone proteins. These include p53 (Huang, J., et al., *p53 is regulated by the lysine demethylase LSD1*. Nature, 2007. 449(7158): p. 105-8), E2F (Kontaki, H. and I. Talianidis, *Lysine methylation regulates E2F1-induced cell death*. Mol Cell, 2010. 39(1): p. 152-60), STAT3 (Yang, J., et al., *Reversible methylation of promoter-bound STAT3 by histone-modifying enzymes*. Proc Natl Acad Sci USA, 2010. 107(50): p. 21499-504), Tat (Sakane, N., et al., *Activation of HIV transcription by the viral Tat protein requires a demethylation step mediated by lysine-specific demethylase 1 (LSD1/KDM1)*. PLoS Pathog, 2011. 7(8): p. e1002184), and myosin phosphatase target subunit 1 (MYPT1) (Cho, H. S., et al., *Demethylation of RB regulator MYPT1 by histone demethylase LSD1 promotes cell cycle progression in cancer cells*. Cancer Res, 2011. 71(3): p. 655-60). The lists of non-histone substrates are growing with technical advances in functional proteomics studies. These suggest additional oncogenic roles of LSD1 beyond regulating chromatin remodeling. LSD1 also associates with other epigenetic regulators, such as DNA methyltransferase 1 (DNMT1) (Wang, J., et al., *The lysine demethylase LSD1 (KDM1) is required for maintenance of global DNA methylation*. Nat Genet, 2009. 41(1): p. 125-9) and histone deacetylases (HDACs) complexes (Hakimi, M. A., et al., *A core-BRAF35 complex containing histone deacetylase mediates repression of neuronal-specific genes*. Proc Natl Acad Sci USA, 2002. 99(11): p. 7420-5; Lee, M. G., et al., *Functional interplay between histone demethylase and deacetylase enzymes*. Mol Cell Biol, 2006. 26(17): p. 6395-402; You, A., et al., *CoREST is an integral component of the CoREST-human histone deacetylase complex*. Proc Natl Acad Sci USA, 2001. 98(4): p. 1454-8). These associations augment the activities of DNMT or HDACs. LSD1 inhibitors may therefore potentiate the effects of HDAC or DNMT inhibitors. Indeed, preclinical studies have shown such potential already (Singh, M. M., et al., *Inhibition of LSD1 sensitizes glioblastoma cells to histone deacetylase inhibitors*. Neuro Oncol, 2011. 13(8): p. 894-903; Han, H., et al., *Synergistic re-activation of epigenetically silenced genes by combinatorial inhibition of DNMTs and LSD1 in cancer cells*. PLoS One, 2013. 8(9): p. e75136).

LSD1 has been reported to contribute to the a variety of biological processes, including cell proliferation, epithelial-mesenchymal transition (EMT), and stem cell biology (both embryonic stem cells and cancer stem cells) or self-renewal and cellular transformation of somatic cells (Chen, Y., et al., *Lysine-specific histone demethylase 1 (LSD1): A potential molecular target for tumor therapy*. Crit Rev Eukaryot Gene Expr, 2012. 22(1): p. 53-9; Sun, G., et al., *Histone demethylase LSD1 regulates neural stem cell proliferation*. Mol Cell Biol, 2010. 30(8): p. 1997-2005; Adamo, A., M. J. Barrero, and J. C. Izpisua Belmonte, *LSD1 and pluripotency: a new player in the network*. Cell Cycle, 2011. 10(19): p. 3215-6; Adamo, A., et al., *LSD1 regulates the balance between self-renewal and differentiation in human embryonic stem cells*. Nat Cell Biol, 2011. 13(6): p. 652-9). In particular, cancer stem cells or cancer initiating cells have some pluripotent stem cell properties that contribute the heterogeneity of cancer cells. This feature may render cancer cells more resistant to conventional therapies, such as chemotherapy or radiotherapy, and then develop recurrence after treatment (Clevers, H., *The cancer stem cell: premises, promises and challenges*. Nat Med, 2011. 17(3): p. 313-9; Beck, B. and C. Blanpain, *Unravelling cancer stem cell potential*. Nat Rev Cancer, 2013. 13(10): p. 727-38). LSD1 was reported to maintain an undifferentiated tumor initiating or cancer stem cell phenotype in a spectrum of cancers (Zhang, X., et al., *Pluripotent Stem Cell Protein Sox2 Confers Sensitivity to LSD1 Inhibition in Cancer Cells*. Cell Rep, 2013. 5(2): p. 445-57; Wang, J., et al., *Novel histone demethylase LSD1 inhibitors selectively target cancer cells with pluripotent stem cell properties*. Cancer Res, 2011. 71(23): p. 7238-49). Acute myeloid leukemias (AMLs) are an example of neoplastic cells that retain some of their less differentiated stem cell like phenotype or leukemia stem cell (LSC) potential. Analysis of AML cells including gene expression arrays and chromatin immunoprecipitation with next generation sequencing (ChIP-Seq) revealed that LSD1 may regulate a subset of genes involved in multiple oncogenic programs to maintain LSC (Harris, W. J., et al., *The histone demethylase KDM1A sustains the oncogenic potential of MLL-AF9 leukemia stem cells*. Cancer Cell, 2012. 21(4): p. 473-87; Schenk, T., et al., *Inhibition of the LSD1 (KDM1A) demethylase reactivates the all-trans-retinoic acid differentiation pathway in acute myeloid leukemia*. Nat Med, 2012. 18(4): p. 605-11). These findings suggest potential therapeutic benefit of LSD1 inhibitors targeting cancers having stem cell properties, such as AMLs.

Overexpression of LSD1 is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Over-expression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6(1): p. 75; Sareddy, G. R., et al., *KDM1 is a novel therapeutic target for the treatment of gliomas*. Oncotarget, 2013. 4(1): p. 18-28; Ding, J., et al., *LSD1-mediated epigenetic modification contributes to proliferation and metastasis of colon cancer*. Br J Cancer, 2013. 109(4): p. 994-1003; Bennani-Baiti, I. M., et al., *Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma*. Hum Pathol, 2012. 43(8): p. 1300-7; Schulte, J. H., et al., *Lysine-specific demethylase 1 is strongly expressed in poorly differentiated neuroblastoma: implications for therapy*. Cancer Res, 2009. 69(5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70(8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54(3): p. 499-503.

Recently, the induction of CD86 expression by inhibiting LSD1 activity was reported (Lynch, J. T., et al., *CD86 expression as a surrogate cellular biomarker for pharmacological inhibition of the histone demethylase lysine-specific demethylase 1*. Anal Biochem, 2013. 442(1): p. 104-6). CD86 expression is a marker of maturation of dendritic cells (DCs) which are involved in antitumor immune response. Notably, CD86 functions as a co-stimulatory factor to activate T cell proliferation (Greaves, P. and J. G. Gribben, *The role of B7 family molecules in hematologic malignancy*. Blood, 2013. 121(5): p. 734-44; Chen, L. and D. B. Flies, *Molecular mechanisms of T cell co-stimulation and co-inhibition*. Nat Rev Immunol, 2013. 13(4): p. 227-42).

In addition to playing a role in cancer, LSD1 activity has also been associated with viral pathogenesis. Particularly, LSD1 activity appears to be linked with viral replications and expressions of viral genes. For example, LSD1 functions as a co-activator to induce gene expression from the viral immediate early genes of various type of herpes virus including herpes simplex virus (HSV), varicella zoster virus (VZV), and β-herpesvirus human cytomegalovirus (Liang, Y., et al., *Targeting the JMJD2 histone demethylases to epigenetically control herpesvirus infection and reactivation from latency*. Sci Transl Med, 2013. 5(167): p. 167ra5; Liang, Y., et al., *Inhibition of the histone demethylase LSD1 blocks alpha-herpesvirus lytic replication and reactivation from latency*. Nat Med, 2009. 15(11): p. 1312-7). In this setting, a LSD1 inhibitor showed antiviral activity by blocking viral replication and altering virus associated gene expression.

Recent studies have also shown that the inhibition of LSD1 by either genetic depletion or pharmacological intervention increased fetal globin gene expression in erythroid cells (Shi, L., et al., *Lysine-specific demethylase 1 is a therapeutic target for fetal hemoglobin induction*. Nat Med, 2013. 19(3): p. 291-4; Xu, J., et al., *Corepressor-dependent silencing of fetal hemoglobin expression by BCL11A*. Proc Natl Acad Sci USA, 2013. 110(16): p. 6518-23). Inducing fetal globin gene would be potentially therapeutically beneficial for the disease of β-globinopathies, including β-thalassemia and sickle cell disease where the production of normal β-globin, a component of adult hemoglobin, is impaired (Sankaran, V. G. and S. H. Orkin, *The switch from fetal to adult hemoglobin*. Cold Spring Harb Perspect Med, 2013. 3(1): p. a011643; Bauer, D. E., S. C. Kamran, and S. H. Orkin, *Reawakening fetal hemoglobin: prospects for new therapies for the beta-globin disorders*. Blood, 2012. 120 (15): p. 2945-53). Moreover, LSD1 inhibition may potentiate other clinically used therapies, such as hydroxyurea or azacitidine. These agents may act, at least in part, by increasing γ-globin gene expression through different mechanisms.

In summary, LSD1 contributes to tumor development by altering epigenetic marks on histones and non-histone proteins. Accumulating data have validated that either genetic depletion or pharmacological intervention of LSD1 normalizes altered gene expressions, thereby inducing differentiation programs into mature cell types, decreasing cell proliferation, and promoting apoptosis in cancer cells. Therefore, LSD1 inhibitors alone or in combination with established therapeutic drugs would be effective to treat the diseases associated with LSD1 activity.

SUMMARY OF THE INVENTION

The present invention is directed to, inter alia, a compound of Formula I:

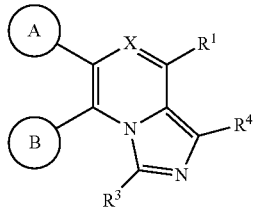

I or a pharmaceutically acceptable salt thereof, wherein constituent variables are defined herein.

The present invention is further directed to a pharmaceutical composition comprising a compound of Formula I and at least one pharmaceutically acceptable carrier.

The present invention is further directed to a method of inhibiting LSD1 comprising contacting the LSD1 with a compound of Formula I.

The present invention is further directed to a method of treating an LSD1-mediated disease in a patient comprising administering to the patient a therapeutically effective amount of a compound of Formula I.

DETAILED DESCRIPTION

The present invention provides, inter alia, LSD1-inhibiting compounds such as a compound of Formula I:

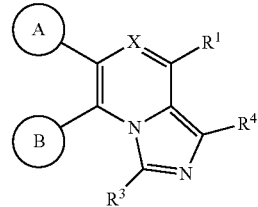

I or a pharmaceutically acceptable salt thereof, wherein:

X is N or $CR^X$;

Ring A is $C_{6-10}$ aryl or 5-10 membered heteroaryl comprising (or having) carbon and 1, 2, 3, or 4 heteroatoms selected from N, O, and S, wherein said $C_{6-10}$ aryl and 5-10 membered heteroaryl are each optionally substituted by 1, 2, 3, or 4 substituents independently selected from $R^A$;

Ring B is $C_{6-10}$ aryl; 5-10 membered heteroaryl comprising (or having) carbon and 1, 2, 3 or 4 heteroatoms selected from N, O, and S; $C_{3-10}$ cycloalkyl; or 4-10 membered heterocycloalkyl comprising (or having) carbon and 1, 2, 3 or 4 heteroatoms selected from N, O, and S; wherein said $C_{6-10}$ aryl, 5-10 membered heteroaryl, $C_{3-10}$ cycloalkyl, and 4-10 membered heterocycloalkyl are each optionally substituted by 1, 2, 3, or 4 substituents independently selected from $R^B$;

$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^3$ is H, halo, $C_{1-6}$ alkyl, $C_{2-6}$ alkenyl, $C_{2-6}$ alkynyl, $C_{1-6}$ haloalkyl, $Cy^2$, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted by 1, 2, or 3 substituents selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^4$ is $Cy^3$, H, halo, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}\ S(O)R^{b2}$, $NR^{c2}\ S(O)_2R^{b2}$, $NR^{c2}\ S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}\ S(O)R^{b4}$, $NR^{c4}\ S(O)_2R^{b4}$, $NR^{c4}\ S(O)_2NR^{c4}R^{d4}$, $S(O)R^{b4}$ $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}\ S(O)R^{b4}$, $NR^{c4}\ S(O)_2R^{b4}$, $NR^{c4}\ S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^4$, halo, $C_{1-6}$ alkyl, $C_{2-6}$ alkenyl, $C_{2-6}$ alkynyl, $C_{1-6}$ haloalkyl, =O, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}\ S(O)R^{b5}$, $NR^{c5}S(O)_2R^{b5}$, $NR^{c5}\ S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, and $C_{2-6}$ alkynyl are each optionally substituted by 1, 2, or 3 substituents independently selected from $Cy^4$, halo, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}\ S(O)R^{b5}$, $NR^{c5}\ S(O)_2R^{b5}$, $NR^{c5}\ S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

$R^X$ is H, halo, $C_{1-6}$ alkyl, $C_{2-6}$ alkenyl, $C_{2-6}$ alkynyl, $C_{1-6}$ haloalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $NR^{c8}C(=NR^{e8})NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, or $S(O)_2NR^{c8}R^{d8}$;

each $Cy^1$, $Cy^3$, $Cy^4$, and $Cy^5$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $Cy^2$ is independently selected from phenyl, $C_{3-7}$ cycloalkyl, 5-6 membered heteroaryl, and 4-7 membered heterocycloalkyl, each of which is optionally substituted with 1, 2, or 3 substituents independently selected from $R^{Cy}$;

each $R^{Cy}$ is selected from halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, oxo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-4}$ alkyl, $C_{1-4}$ haloalkyl, $C_{1-4}$ cyanoalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^{a1}$ is independently selected from H, $C_{1-6}$ alkyl, $C_{2-6}$ alkenyl, $C_{2-6}$ alkynyl, and $Cy^5$, wherein said $C_{1-6}$ alkyl, $C_{2-6}$ alkenyl, and $C_{2-6}$ alkynyl are each optionally substituted with 1, 2, or 3 substituents independently selected from $Cy^5$, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$;

each $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})$ NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

each R$^{a7}$, R$^{b7}$, R$^{c7}$, and R$^{d7}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

or any R$^{c7}$ and R$^{d7}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$cycloalkyl, 4-7 membered heterocycloalkyl, C$_{6-10}$ aryl, 5-6 membered heteroaryl, C$_{1-6}$ haloalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$, wherein said C$_{1-6}$ alkyl, C$_{3-7}$ cycloalkyl, 4-7 membered heterocycloalkyl, C$_{6-10}$ aryl, and 5-6 membered heteroaryl are each optionally substituted by 1, 2, or 3 substituents independently selected from halo, C$_{1-4}$ alkyl, C$_{1-4}$ haloalkyl, C$_{1-4}$ cyanoalkyl, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

each R$^{a8}$, R$^{b8}$, R$^{c8}$, and R$^{d8}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl are each optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

each R$^{e1}$, R$^{e2}$, R$^{e3}$, R$^{e4}$, R$^{e5}$, R$^{e6}$, R$^{e7}$, and R$^{e8}$, is independently selected from H, C$_{1-4}$ alkyl, and CN.

In some embodiments:

X is N or CR$^X$;

Ring A is C$_{6-10}$ aryl optionally substituted by 1, 2, 3, or 4 substituents independently selected from R$^A$;

Ring B is C$_{6-10}$ aryl; 5-10 membered heteroaryl comprising (or having) carbon and 1, 2, 3 or 4 heteroatoms selected from N, O, and S; C$_{3-10}$ cycloalkyl; or 4-10 membered heterocycloalkyl comprising (or having) carbon and 1, 2, 3 or 4 heteroatoms selected from N, O, and S; wherein said C$_{6-10}$ aryl, 5-10 membered heteroaryl, C$_{3-10}$ cycloalkyl, and 4-10 membered heterocycloalkyl are each optionally substituted by 1, 2, 3, or 4 substituents independently selected from R$^B$;

R$^1$ is OR$^{a1}$ or Cy$^1$;

R$^3$ is H

R$^4$ is H;

each R$^A$ is independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, and C$_{2-6}$ alkynyl are each optionally substituted by 1, 2, or 3, substituents independently selected from halo, C$_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$;

each R$^B$ is independently selected from Cy$^4$, halo, C$_{1-6}$ alkyl, C$_{2-6}$ alkenyl, C$_{2-6}$ alkynyl, C$_{1-6}$ haloalkyl, =O, CN, NO$_2$, OR$^{a5}$, SR$^{a5}$, C(O)R$^{b5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said C$_{1-6}$ alkyl, C$_{2-6}$ alkenyl, and C$_{2-6}$ alkynyl are each optionally substituted by 1, 2, or 3 substituents independently selected from Cy$^4$, halo, C$_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

R$^X$ is H;

each Cy$^1$, Cy$^4$ and Cy$^5$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, or 4 substituents independently selected from R$^{Cy}$;

each R$^{Cy}$ is selected from halo, C$_{1-4}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, (4-7 membered heterocycloalkyl)-C$_{1-4}$ alkyl-, oxo, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, C(=NR$^{e6}$)NR$^{c6}$R$^{d6}$, NR$^{c6}$C(=NR$^{e6}$)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$, wherein said C$_{1-4}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, (5-6 membered heteroaryl)-C$_{1-4}$ alkyl-, and (4-7 membered heterocycloalkyl)-C$_{1-4}$ alkyl- are each optionally substituted by 1, 2, or 3 substituents independently selected from C$_{1-4}$ alkyl, C$_{1-4}$ haloalkyl, C$_{1-4}$ cyanoalkyl, halo, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, C(=NR$^{e6}$)NR$^{c6}$R$^{d6}$, NR$^{c6}$C(=NR$^{e6}$)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, and S(O)$_2$NR$^{c6}$R$^{d6}$;

each R$^{a1}$ is independently selected from C$_{1-6}$ alkyl optionally substituted with 1, 2, or 3 substituents independently selected from Cy$^5$;

each R$^{a4}$, R$^{b4}$, R$^{c4}$, and R$^{d4}$ is independently selected from H, C$_{1-6}$ alkyl, C$_{1-4}$ haloalkyl, C$_{2-6}$ alkenyl, and C$_{2-6}$ alkynyl, wherein said C$_{1-6}$ alkyl, C$_{2-6}$ alkenyl, and C$_{2-6}$ alkynyl are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)

OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from C$_{1-6}$ alkyl, C$_{1-6}$ haloalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

each R$^{a5}$, R$^{b5}$, R$^{c5}$, and R$^{d5}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

or any R$^{c5}$ and R$^{d5}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$, wherein said C$_{1-6}$ alkyl, C$_{3-7}$ cycloalkyl, 4-7 membered heterocycloalkyl, C$_{6-10}$ aryl, and 5-6 membered heteroaryl are each optionally substituted by 1, 2, or 3 substituents independently selected from halo, C$_{1-4}$ alkyl, C$_{1-4}$ haloalkyl, C$_{1-4}$ cyanoalkyl, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

each R$^{a6}$, R$^{b6}$, R$^{c6}$, and R$^{d6}$ is independently selected from H, C$_{1-6}$ alkyl, C$_{1-4}$ haloalkyl, C$_{2-6}$ alkenyl, and C$_{2-6}$ alkynyl, wherein said C$_{1-6}$ alkyl, C$_{2-6}$ alkenyl, and C$_{2-6}$ alkynyl are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, NR$^{c8}$C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

or any R$^{c6}$ and R$^{d6}$ together with the N atom to which they are attached form a 4-, 5-, 6-, or 7-membered heterocycloalkyl group optionally substituted with 1, 2, or 3 substituents independently selected from C$_{1-6}$ alkyl, C$_{1-6}$ haloalkyl, halo, CN, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)NR$^{c8}$R$^{d8}$, NR$^{c8}$C(O)OR$^{a8}$, C(=NR$^{e8}$)NR$^{c8}$R$^{d8}$, S(O)R$^{b8}$, S(O)NR$^{c8}$R$^{d8}$, S(O)$_2$R$^{b8}$, NR$^{c8}$S(O)$_2$R$^{b8}$, NR$^{c8}$S(O)$_2$NR$^{c8}$R$^{d8}$, and S(O)$_2$NR$^{c8}$R$^{d8}$;

each R$^{a8}$, R$^{b8}$, R$^{c8}$, and R$^{d8}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl are each optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

each R$^{e5}$, R$^{e6}$, and R$^{e8}$ is independently selected from H, C$_{1-4}$ alkyl, and CN.

In some embodiments:

X is N or CR$^X$;

Ring A is C$_{6-10}$ aryl optionally substituted by 1, 2, 3, or 4 substituents independently selected from R$^A$;

Ring B is C$_{6-10}$ aryl; 5-10 membered heteroaryl comprising (or having) carbon and 1, 2, 3 or 4 heteroatoms selected from N, O, and S; C$_{3-10}$ cycloalkyl; or 4-10 membered heterocycloalkyl comprising (or having) carbon and 1, 2, 3 or 4 heteroatoms selected from N, O, and S; wherein said C$_{6-10}$ aryl, 5-10 membered heteroaryl, C$_{3-10}$ cycloalkyl, and 4-10 membered heterocycloalkyl are each optionally substituted by 1, 2, 3, or 4 substituents independently selected from R$^B$;

R$^1$ is OR$^{a1}$;

R$^3$ is H

R$^4$ is H;

each R$^A$ is independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, and C$_{2-6}$ alkynyl are each optionally substituted by 1, 2, or 3, substituents independently selected from halo, C$_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$;

each R$^B$ is independently selected from Cy$^4$, halo, C$_{1-6}$ alkyl, C$_{2-6}$ alkenyl, C$_{2-6}$ alkynyl, C$_{1-6}$ haloalkyl, =O, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said C$_{1-6}$ alkyl, C$_{2-6}$ alkenyl, and C$_{2-6}$ alkynyl are each optionally substituted by 1, 2, or 3 substituents independently selected from Cy$^4$, halo, C$_{1-6}$ haloalkyl, CN, NO$_2$, OR$^{a5}$, SR$^{a5}$, C(O)R$^{b5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$) NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

R$^X$ is H;

each Cy$^4$ and Cy$^5$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, or 4 substituents independently selected from R$^{Cy}$;

each R$^{Cy}$ is selected from halo, C$_{1-4}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, oxo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})$ $NR^{c6}R^{d6}$, $NR^{c6}R^{d6}$, $NR^{c6}C(O)R^{b6}$, $NR^{c8}C(O)OR^{a8}$, $NR^{c6}C(O)NR^{c6}R^{d6}$, $NR^{c6}S(O)R^{b6}$, $NR^{c6}S(O)_2R^{b6}$, $NR^{c6}S(O)_2$ $NR^{c6}R^{d6}$, $S(O)R^{b6}$, $S(O)NR^{c6}R^{d6}$, $S(O)_2R^{b6}$, and $S(O)_2$ $NR^{c6}R^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-4}$ alkyl, $C_{1-4}$ haloalkyl, $C_{1-4}$ cyanoalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c8}C$ $(=NR^{e6})NR^{c6}R^{d6}$, $NR^{c6}R^{d6}$, $NR^{c8}C(O)R^{b6}$, $NR^{c8}C(O)$ $OR^{a8}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^{a1}$ is independently selected from $C_{1-6}$ alkyl optionally substituted with 1, 2, or 3 substituents independently selected from $Cy^5$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)$ $OR^{a8}$, $C(=NR^{e8})NR^{c8}R^{d8}$, $NR^{c8}C(=NR^{e8})NR^{c8}R^{d8}$, $S(O)$ $R^{b8}$, $S(O)NR^{c8}R^{d8}$, $S(O)_2R^{b8}$, $NR^{c8}S(O)_2R^{b8}$, $NR^{c8}S(O)_2$ $NR^{c8}R^{d8}$, and $S(O)_2NR^{c8}R^{d8}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C$ $(O)R^{b8}$, $NR^{c8}C(O)NR^{c8}R^{d8}$, $NR^{c8}C(O)OR^{a8}$, $C(=NR^{e8})$ $NR^{c8}R^{d8}$, $NR^{c8}C(=NR^{e8})NR^{c8}R^{d8}$, $S(O)R^{b8}$, $S(O)$ $NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)$ $NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2$ $NR^{c8}R^{d8}$, and $S(O)_2NR^{c8}R^{d8}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)$ $NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})$ $NR^{c8}R^{d8}$, $S(O)R^{b8}$, $S(O)NR^{c8}R^{d8}$, $S(O)_2R^{b8}$, $NR^{c8}S(O)_2$ $R^{b8}$, $NR^{c8}S(O)_2NR^{c8}R^{d8}$, and $S(O)_2NR^{c8}R^{d8}$, wherein said $C_{1-6}$ alkyl, $C_{3-7}$cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)$ $R^{b8}$, $OC(O)NR^{c8}R^{d8}$, $NR^{c8}R^{d8}$, $NR^{c8}C(O)R^{b8}$, $NR^{c8}C(O)$ $NR^{c8}R^{d8}$, $NR^{c8}C(O)OR^{a8}$, $C(=NR^{e8})NR^{c8}R^{d8}$, $NR^{c8}C$ $(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)$ $OR^{a8}$, $C(=NR^{e8})NR^{c8}R^{d8}$, $NR^{c8}C(=NR^{e8})NR^{c8}R^{d8}$, $S(O)$ $R^{b8}$, $S(O)NR^{c8}R^{d8}$, $S(O)_2R^{b8}$, $NR^{c8}S(O)_2R^{b8}$, $NR^{c8}S(O)_2$ $NR^{c8}R^{d8}$, and $S(O)_2NR^{c8}R^{d8}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C$ $(O)R^{b8}$, $NR^{c8}C(O)NR^{c8}R^{d8}$, $NR^{c8}C(O)OR^{a8}$, $C(=NR^{e8})$ $NR^{c8}R^{d8}$, $NR^{c8}C(=NR^{e8})NR^{c8}R^{d8}$, $S(O)R^{b8}$, $S(O)$ $NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a8}$, $R^{b8}$, $R^{c8}$, and $R^{d8}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$, $R^{e6}$, and $R^{e8}$ is independently selected from H, $C_{1-4}$ alkyl, and CN.

In some embodiments:

X is $CR^X$;

Ring A is phenyl optionally substituted by 1 or 2 substituents independently selected from $R^A$;

Ring B is phenyl; 5-10 membered heteroaryl comprising (or having) carbon and 1, 2, 3 or 4 heteroatoms selected from N, O, and S; $C_{3-7}$ cycloalkyl; or 4-10 membered heterocycloalkyl comprising (or having) carbon and 1, 2, 3 or 4 heteroatoms selected from N, O, and S; wherein said phenyl, 5-10 membered heteroaryl, $C_{3-7}$cycloalkyl, and 4-10 membered heterocycloalkyl are each optionally substituted by 1, 2, 3, or 4 substituents independently selected from $R^B$;

$R^1$ is $OR^{a1}$;

$R^3$ is H $R^4$ is H;

each $R^A$ is independently selected from halo, CN, and $NO_2$;

each $R^B$ is independently selected from $Cy^4$, halo, $C_{1-6}$ alkyl, =O, and $C(O)OR^{a5}$, wherein said $C_{1-6}$ alkyl is optionally substituted by $Cy^4$;

$R^X$ is H;

each $Cy^4$ is independently selected from $C_{3-7}$ cycloalkyl and 4-7 membered heterocycloalkyl, each of which is optionally substituted with 1 or 2 substituents independently selected from $R^{Cy}$;

each $Cy^5$ is independently selected from 4-7 membered heterocycloalkyl optionally substituted with 1 or 2 substituents independently selected from $R^{Cy}$;

each $R^{Cy}$ is selected from halo, $C_{1-4}$ alkyl, $C_{1-4}$ haloalkyl, $C_{1-4}$ cyanoalkyl, $C_{2-6}$ alkenyl, $C_{2-6}$ alkynyl, oxo, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $S(O)_2R^{b6}$, and $S(O)_2NR^{c6}R^{d6}$, wherein said $C_{1-4}$ alkyl, $C_{2-6}$ alkenyl, and $C_{2-6}$ alkynyl are each optionally substituted by 1 or 2 substituents independently selected from halo, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $S(O)_2R^{b6}$, and $S(O)_2NR^{c6}R^{d6}$;

each $R^{a1}$ is independently selected from $C_{1-3}$ alkyl optionally substituted with 1 or 2 substituents independently selected from $Cy^5$;

each $R^{a5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)$ $OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a8}$, $R^{b8}$, $R^{c8}$, and $R^{d8}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e8}$ is independently selected from H, $C_{1-4}$ alkyl, and CN.

In some embodiments, X is N.

In some embodiments, X is $CR^X$.

In some embodiments, Ring A is $C_{6-10}$ aryl optionally substituted by 1, 2, 3, or 4 substituents independently selected from $R^A$.

In some embodiments, Ring A is phenyl optionally substituted by 1 or 2 substituents independently selected from $R^A$.

In some embodiments, Ring A is phenyl optionally substituted by 1 or 2 substituents independently selected from halo, CN, and $NO_2$.

In some embodiments, Ring B is phenyl; 5-10 membered heteroaryl comprising carbon and 1, 2, 3 or 4 heteroatoms selected from N, O, and S; $C_{3-7}$ cycloalkyl; or 4-10 membered heterocycloalkyl comprising carbon and 1, 2, 3 or 4 heteroatoms selected from N, O, and S; wherein said phenyl, 5-10 membered heteroaryl, $C_{3-7}$ cycloalkyl, and 4-10 membered heterocycloalkyl are each optionally substituted by 1, 2, or 3 substituents independently selected from $R^B$.

In some embodiments, Ring B is phenyl, pyrazolyl, cyclohexenyl, dihydropyridinyl, 1H-indazolyl, 2,3-dihydro-1H-indolyl, 3,4-dihydro-2H-1,4-benzoxazinyl, 2,3-dihydro-1,4-benzodioxinyl, 2,3-dihydro-1,3-benzoxazolyl, 1,2,3,4-tetrahydroquinolinyl, 2,3-dihydro-benzimidazolyl, 1H-pyrazolo[3,4-b]pyridinyl, 1H-benzimidazolyl, 3,4-dihydro-2H-pyrido[3,2-b][1,4]oxazinyl, quinolinyl, 1,3-benzothiazolyl, pyridinyl, 1,5-naphthyridinyl, quinoxalinyl, 2,3-dihydrooxazolo[4,5-b]pyridinyl, 3H-imidazo[4,5-b]pyridinyl, furo[3,2-b]pyridinyl, 3,4-dihydro-2H-pyrano[2,3-b]pyridinyl, 2,3-dihydro-[1,4]dioxino[2,3-b]pyridinyl, 1H-pyrrolo[2,3-b]pyridinyl, 2,3-dihydro-1H-indenyl, 1,4-dihydro-2H-3,1-benzoxazinyl, 3H-[1,2,3]triazolo[4,5-b]pyridinyl, 2,3-dihydro-1H-isoindolyl, imidazo[4,5-b]pyridinyl, or pyrimidinyl, each optionally substituted by 1, 2, or 3 substituents independently selected from $C_{3-7}$ cycloalkyl, 5-6 membered heterocycloalkyl, halo, $C_{1-6}$ alkyl, $C_{1-6}$ haloalkyl, =O, CN, $OR^{a5}$, $NR^{c5}C(O)OR^{a5}$, $NR^{c5}R^{d5}$, $C(O)NR^{c5}R^{d5}$, and $C(O)OR^{a5}$, wherein said $C_{1-6}$ alkyl is optionally substituted by 5-6 membered heterocycloalkyl, CN, $OR^{a5}$, $NR^{c5}C(O)OR^{a5}$, or $NR^{c5}C(O)NR^{c5}R^{d5}$.

In some embodiments, Ring B is phenyl, pyrazolyl, cyclohexenyl, dihydropyridinyl, 1H-indazolyl, 2,3-dihydro-1H-indolyl, 3,4-dihydro-2H-1,4-benzoxazinyl, 2,3-dihydro-1,4-benzodioxinyl, each optionally substituted by 1, 2, or 3 substituents independently selected from $C_{3-7}$ cycloalkyl, 5-6 membered heterocycloalkyl, halo, $C_{1-6}$ alkyl, =O, and C(O)OR$^5$, wherein said $C_{1-6}$ alkyl is optionally substituted by 5-6 membered heterocycloalkyl.

In some embodiments, R$^1$ is OR$^{a1}$ or Cy$^1$.

In some embodiments, R$^1$ is OR$^{a1}$ or 4-10 membered heterocycloalkyl.

In some embodiments, R$^1$ is OR$^{a1}$.

In some embodiments, R$^1$ is (i) $C_{1-6}$ alkyl substituted with NR$^{c1}$R$^{d1}$ or (ii) NR$^{c1}$R$^{d1}$, wherein R$^{c1}$ is H and R$^{d1}$ is substituted with NR$^{c8}$R$^{d8}$; or R$^{c1}$ and R$^{d1}$ together with the N atom to which they are attached form a 4-, 5-, 6-, or 7-membered heterocycloalkyl group substituted with NR$^{c8}$R$^{d8}$.

In some embodiments, R$^1$ is independently selected from pyrrolidinylmethoxy optionally substituted by methyl; piperidinylmethoxy optionally substituted by methyl, ethyl, 2-hydroxyethyl, 2-cyanoethyl, 2-hydroxypropyl, 2-methoxyethyl, or 2-hydroxy-2-methylpropyl; 4-(dimethylamino)piperidinyl; and 3-(dimethylamino)pyrrolidinyl.

In some embodiments, R$^1$ is 3-piperidinylmethoxy, 3-pyrrolidinylmethoxy or 1-piperidinyl, 1-pyrrolidinyl, each of which is optionally substituted with a member selected from methyl, ethyl, 2-hydroxyethyl, 2-cyanoethyl, 2-hydroxypropyl, 2-methoxyethyl, 2-hydroxy-2-methylpropyl or 4-(dimethylamino).

In some embodiments, R$^1$ is 3-piperidinylmethoxy, 3-pyrrolidinylmethoxy, 1-piperidinyl, 1-pyrrolidinyl, 1-methylpiperidin-3-yl-methoxy, 1-(2-hydoxyethyl)piperidin-3-yl, 1-(2-cyanoethyl)piperidin-3-yl, 1-(2-hydoxypropyl)piperidin-3-yl, 1-(2-methoxyethyl)piperidin-3-yl, 1-(2-hydoxy-2-methylpropyl)piperidin-3-yl, 4-(dimethylamino)piperidin-1-yl, or 1-ethylpiperidin-3-yl-methoxy, 3-(dimethylamino)pyrrolidin-1-yl.

In some embodiments, R$^1$ is pyrrolidinylmethoxy optionally substituted by methyl.

In some embodiments, R$^3$ is H.

In some embodiments, R$^4$ is H.

In some embodiments, each R$^4$ is independently selected from halo, $C_{1-6}$ alkyl, $C_{2-6}$ alkenyl, $C_{2-6}$ alkynyl, $C_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, each R$^4$ is independently selected from halo, CN, and NO$_2$.

In some embodiments, R$^4$ is CN.

In some embodiments, R$^B$ is independently selected from Cy$^4$, halo, CN, $C_{1-6}$ alkyl, $C_{1-6}$ haloalkyl, =O, OR$^{a5}$, NR$^{c5}$C(O)OR$^{a5}$, NR$^{c5}$R$^{d5}$, C(O)NR$^{c5}$R$^{d5}$, and C(O)OR$^{a5}$, wherein said $C_{1-6}$ alkyl is optionally substituted by Cy$^4$, CN, OR$^{a5}$, NR$^{c5}$C(O)OR$^{a5}$, or NR$^{c5}$C(O)NR$^{c5}$R$^{d5}$.

In some embodiments, each R$^B$ is independently selected from Cy$^4$, halo, $C_{1-6}$ alkyl, =O, and C(O)OR$^{a5}$, wherein said $C_{1-6}$ alkyl is optionally substituted by Cy$^4$.

In some embodiments, R$^B$ is independently selected from $C_{3-7}$ cycloalkyl, 5-6 membered heterocycloalkyl, halo, $C_{1-4}$ alkyl wherein said $C_{1-4}$ alkyl is optionally substituted by CN, OH, N($C_{1-4}$ alkyl)C(O)O($C_{1-4}$ alkyl), —O—($C_{1-4}$ alkyl) or N($C_{1-4}$ alkyl)C(O)N($C_{1-4}$ alkyl)$_2$; $C_{1-6}$ haloalkyl, =O, C(O)O($C_{1-4}$ alkyl), OH, $C_{1-4}$ alkoxy, N($C_{1-4}$ alkyl)C(O)O($C_{1-4}$ alkyl), CN, NH$_2$, NH($C_{1-4}$ alkyl), C(O)NH($C_{1-4}$ alkyl), and (5-6 membered heterocycloalkyl)-$C_{1-4}$ alkyl- wherein said (5-6 membered heterocycloalkyl)-$C_{1-4}$ alkyl- is optionally substituted by $C_{1-4}$ alkyl.

In some embodiments, each R$^B$ is independently selected from $C_{3-7}$ cycloalkyl, 5-6 membered heterocycloalkyl, halo, $C_{1-4}$ alkyl, =O, C(O)O($C_{1-4}$ alkyl), and (5-6 membered heterocycloalkyl)-$C_{1-4}$ alkyl- wherein said (5-6 membered heterocycloalkyl)-$C_{1-4}$ alkyl- is optionally substituted by $C_{1-4}$ alkyl.

In some embodiments, R$^B$ is independently selected from cyclobutyl, morpholino, chloro, fluoro, methyl, ethyl, 2-propyl, cyclopropyl, difluoromethyl, =O, t-butoxycarbonyl, morpholinomethyl, morpholinoethyl, hydroxymethyl, methoxy, —N(CH$_3$)C(O)O(CH$_3$), —CH$_2$—N(CH$_3$)C(O)O(CH$_3$), 2-oxopyrrolidinyl, CN, NH$_2$, OH, 1-hydroxy-1-methylethyl, dimethylamino, —CH$_2$—N(CH$_3$)C(O)N(CH$_3$)$_2$, difluoromethoxy, ethoxy, methoxymethyl, 1-hydroxyethyl, 1-cyano-1-methylethyl, C(O)NH(CH$_3$) and 4-methyl-piperazinylmethyl.

In some embodiments, each R$^B$ is independently selected from cyclobutyl, morpholino, chloro, fluoro, methyl, ethyl, =O, t-butoxycarbonyl, morpholinomethyl, morpholinoethyl, and 4-methyl-piperazinylmethyl.

In some embodiments, R$^X$ is H.

In some embodiments, each Cy$^1$, Cy$^3$, Cy$^4$, and Cy$^5$ is independently selected from phenyl, $C_{3-7}$ cycloalkyl, 5-6 membered heteroaryl, and 4-7 membered heterocycloalkyl, each of which is optionally substituted with 1, 2, 3, or 4 substituents independently selected from R$^{Cy}$.

In some embodiments, each Cy$^4$ is independently selected from $C_{3-7}$ cycloalkyl and 4-7 membered heterocycloalkyl, each of which is optionally substituted with 1 or 2 substituents independently selected from R$^{Cy}$.

In some embodiments, Cy$^4$ is independently selected from cyclobutyl, morpholino, 2-oxopyrrolidinyl and piperazinyl, each of which is optionally substituted with $C_{1-4}$ alkyl.

In some embodiments, each Cy$^4$ is independently selected from cyclobutyl, morpholino, and piperazinyl, each of which is optionally substituted with $C_{1-4}$ alkyl.

In some embodiments, Cy$^5$ is independently selected from 4-10 membered heterocycloalkyl optionally substituted with 1 or 2 substituents independently selected from R$^{Cy}$.

In some embodiments, Cy$^5$ is independently selected from pyrrolidinyl and piperidinyl, each of which is optionally substituted with 1 or 2 substituents independently selected from R$^{Cy}$.

In some embodiments, R$^{Cy}$ is independently selected from $C_{1-4}$ alkyl, oxo, and NR$^{c6}$R$^{d6}$, wherein said $C_{1-4}$ alkyl is optionally substituted with 1 or 2 substituents independently selected from CN and OR$^{a6}$.

In some embodiments, R$^{Cy}$ is methyl, ethyl, 2-hydroxyethyl, 2-cyanoethyl, 2-hydroxypropyl, 2-methoxyethyl, 2-hydroxy-2-methylpropyl, or (dimethyl)amino.

In some embodiments, each R$^{a1}$ is independently selected from $C_{1-6}$ alkyl optionally substituted with 1, 2, or 3 substituents independently selected from Cy$^5$.

In some embodiments, each R$^{a1}$ is independently selected from $C_{1-3}$ alkyl optionally substituted with 1 or 2 substituents independently selected from Cy$^5$.

In some embodiments, R$^{a1}$ is independently selected from (pyrrolidinyl)methyl which is optionally substituted on the pyrrolidinyl moiety by a methyl group-; and (piperidinyl)methyl-which is optionally substituted on the piperidinyl moiety by methyl, ethyl, 2-hydroxyethyl, 2-cyanoethyl, 2-hydroxypropyl, 2-methoxyethyl, or 2-hydroxy-2-methylpropyl.

In some embodiments, each $R^{a1}$ is independently selected from (pyrrolidinyl)methyl-which is optionally substituted on the pyrrolidinyl moiety by a methyl group.

In some embodiments, the compounds of the invention have Formula IIa:

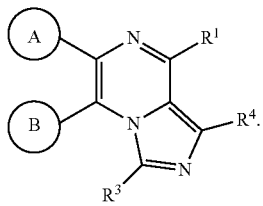

IIa

In some embodiments, the compounds of the invention have Formula IIb:

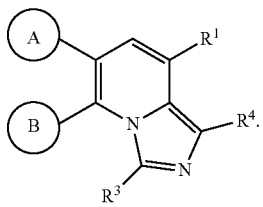

IIb

In some embodiments, the compounds of the invention have Formula IIIa:

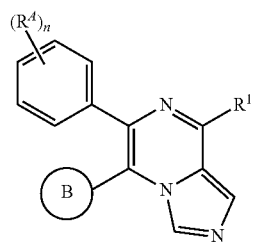

IIIa wherein n is 0, 1, 2, 3, or 4.

In some embodiments, the compounds of the invention have Formula IIIb:

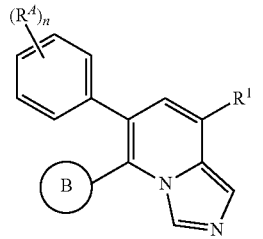

IIIb wherein n is 0, 1, 2, 3, or 4.

In some embodiments, the compounds of the invention have Formula IVa:

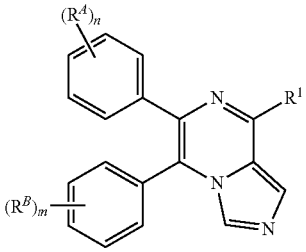

IVa wherein:
n is 0, 1, 2, 3, or 4; and
m is 0, 1, 2, 3, or 4.

In some embodiments, the compounds of the invention have Formula IVb:

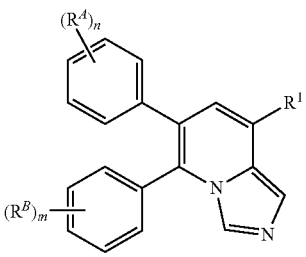

IVb wherein:
n is 0, 1, 2, 3, or 4; and
m is 0, 1, 2, 3, or 4.

In some embodiments, the compounds of the invention have Formula Va:

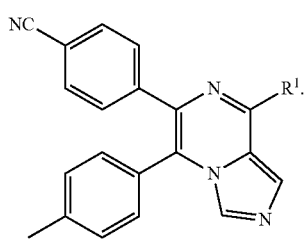

Va

In some embodiments, the compounds of the invention have Formula Vb:

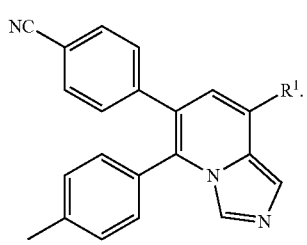

Vb

In some embodiments, the compounds of the invention have Formula VIa or VIb:

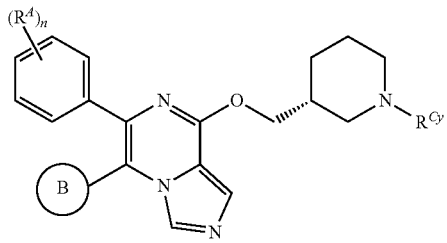
VIa

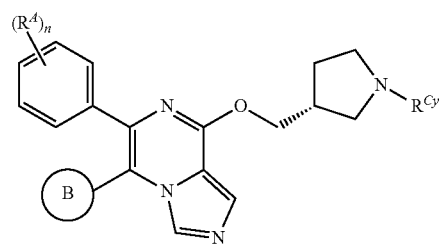
VIb wherein n is 0, 1, 2, 3, or 4.

In some embodiments, the compounds of the invention have Formula VIIa or VIIb:

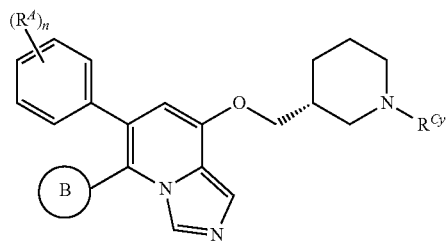
VIIa

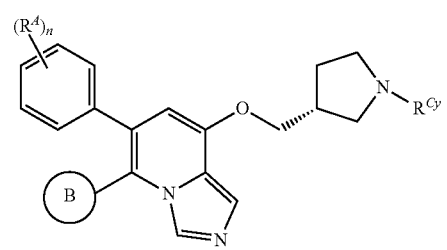
VIIb wherein n is 0, 1, 2, 3, or 4.

In some embodiments, the compounds of the invention have Formula VIIIa or VIIIb:

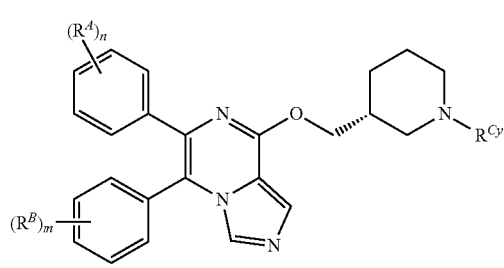
VIIIa

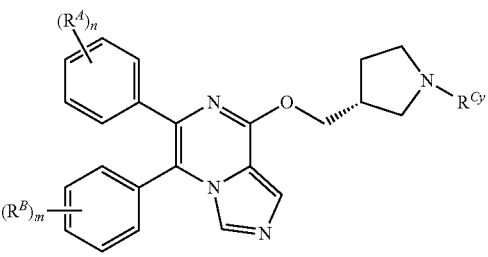
VIIIb wherein:
n is 0, 1, 2, 3, or 4; and
m is 0, 1, 2, 3, or 4.

In some embodiments, the compounds of the invention have Formula IXa or IXb:

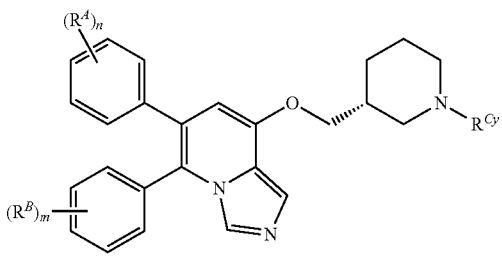
IXa

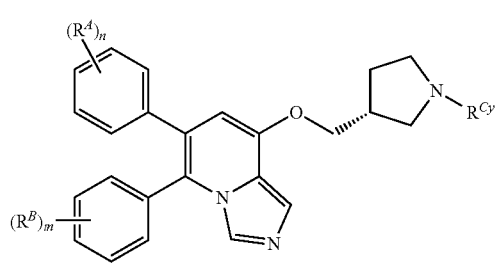
IXb wherein:
n is 0, 1, 2, 3, or 4; and
m is 0, 1, 2, 3, or 4.

In some embodiments, the compounds of the invention have Formula Xa or Xb:

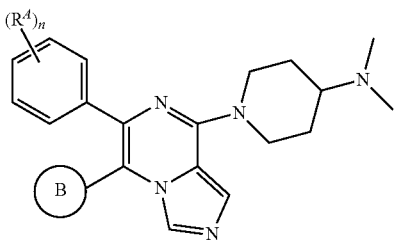
Xa

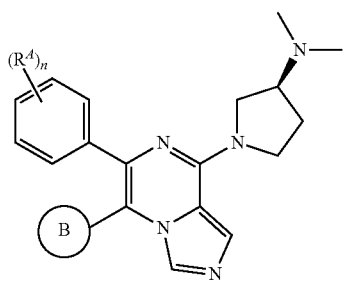
Xb wherein n is 0, 1, 2, 3, or 4.

In some embodiments, the compounds of the invention have Formula XIa or XIb:

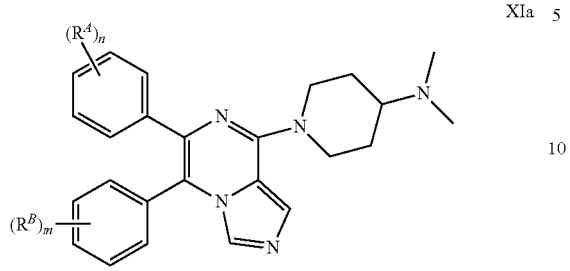
XIa

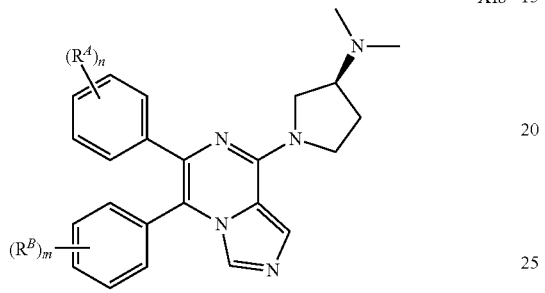
XIb or a pharmaceutically acceptable salt thereof, wherein:
n is 0, 1, 2, 3, or 4; and
m is 0, 1, 2, 3, or 4.

In certain embodiments of Formulas I, IIa, IIb, IIIa, IIIb, IVa, IVb, Va, Vb, VIa, VIb, VIIa, VIIb, VIIIa, VIIIb, IXa, and IXb, $R^{cy}$ is methyl, ethyl, 2-hydroxyethyl, 2-cyanoethyl, 2-hydroxypropyl, 2-methoxyethyl, 2-hydroxy-2-methylpropyl or (dimethyl)amino.

In some embodiments, the group:

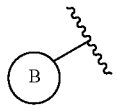

as in any of the formulas described herein, is independently selected from the following Formulae (B-1) to (B-30):

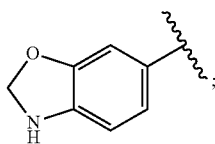
(B-1)

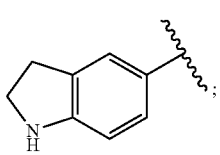
(B-2)

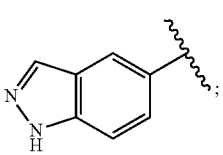
(B-3)

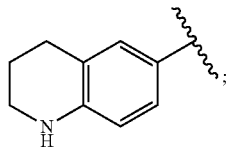
(B-4)

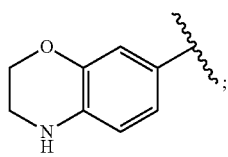
(B-5)

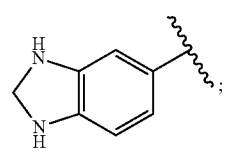
(B-6)

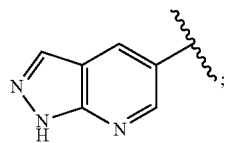
(B-7)

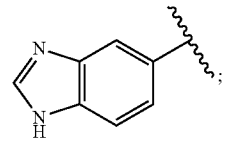
(B-8)

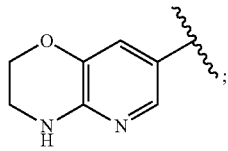
(B-9)

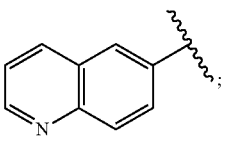
(B-10)

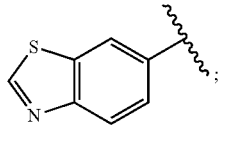
(B-11)

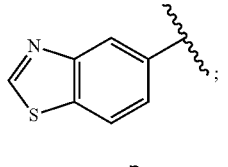
(B-12)

(B-13)

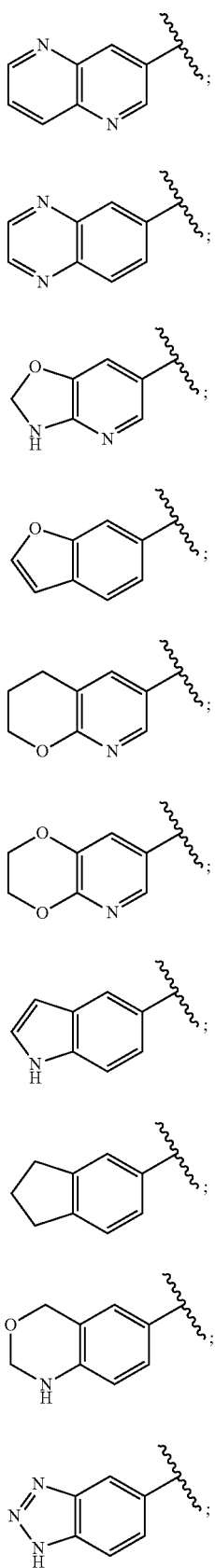
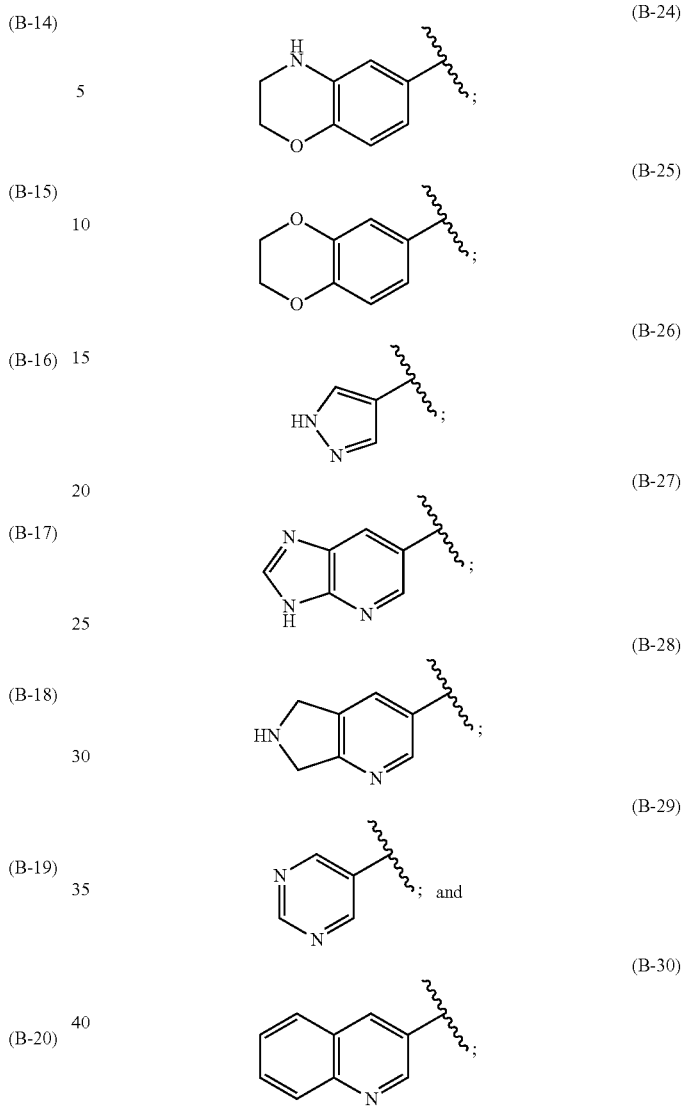

wherein any one of the groups of Formulae (B-1) to (B-30) is optionally substituted with 1, 2, 3, or 4 substituents independently selected from $R^B$.

In some embodiments, n is 0, 1, or 2.
In some embodiments, n is 1.
In some embodiments, m is 0, 1, or 2.
In some embodiments, m is 1.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a monovalent substituent, or two hydrogen atoms are replaced with a divalent substituent like a terminal oxo group. It is to be understood that substitution at a given atom is limited by valency.

Throughout the definitions, the term "$C_{i\text{-}j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms. In some embodiments, the alkylamino group is —NH($C_{1-4}$ alkyl) such as, for example, methylamino, ethylamino, or propylamino.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "aryl-$C_{i-j}$ alkyl," employed alone or in combination with other terms, refers to an alkyl group substituted by an aryl group. An example of a aryl-$C_{i-j}$ alkyl group is benzyl.

As used herein, the term "carbonyl", employed alone or in combination with other terms, refers to a —C(O)— group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e. having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl.

As used herein, the term "$C_{i-j}$ cycloalkyl-$C_{i-j}$ alkyl," employed alone or in combination with other terms, refers to an alkyl group substituted by a cycloalkyl group. An example of a $C_{i-j}$ cycloalkyl-$C_{i-j}$ alkyl group is cyclopropylmethyl.

As used herein, "$C_{i-j}$ haloalkoxy," employed alone or in combination with other terms, refers to a group of formula —O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocyclic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, indazole, benzothiophene, benzofuran, benzisoxazole, imidazo[1,2-b]thiazole, purine, triazine, and the like.

A 5-membered heteroaryl is a heteroaryl group having five ring-forming atoms wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heteroaryl-$C_{i-j}$ alkyl," employed alone or in combination with other terms, refers to an alkyl group substituted by a heteroaryl group. An example of a heteroaryl-$C_{i-j}$ alkyl group is pyridylmethyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, the heterocycloalkyl is 5- to 10-membered, 4- to 10-membered, 4- to 7-membered, 5-membered, or 6-membered. Examples of heterocycloalkyl groups include 1,2,3,4-tetrahydro-quinoline, dihydrobenzofuran, dihydropyridine, azetidine, azepane, pyrrolidine, piperidine, piperazine, morpholine, thiomorpholine, and pyran. In some embodiments, the heterocycloalkyl group is 2-oxo-2,3-dihydro-1H-indol-5-yl, 3,4-dihydro-2H-1,4-benzoxazinyl, or 2,3-dihydro-1,4-benzodioxinyl.

As used herein, the term "heterocycloalkyl-$C_{i-j}$ alkyl," employed alone or in combination with other terms, refers to an alkyl group substituted by a heterocycloalkyl group. An example of a heterocycloalkyl-$C_{i-j}$ alkyl group is pyrrolidinylmethyl.

As used herein, the term "oxo" refers to an =O group.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N, N-diisopropylethylamine); DMF (N, N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); IPA (isopropyl alcohol); LCMS (liquid chromatography mass spectrometry); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); μL (microliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4th Ed., Wiley & Sons, Inc., New York (2006), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of formula 9 can be synthesized as shown in Scheme 1. A selective coupling of the iodide in compound 1 with compounds of formula 2 under standard cross coupling conditions, such as standard Suzuki coupling conditions [e.g., M is boronic acid or ester, in the presence of a palladium catalyst and a suitable base such as potassium carbonate], or Negishi coupling conditions [e.g., M is Zn-halo, in the presence of a palladium catalyst] can give compounds of formula 3. The phenol group in compound 3 can undergo Mitsunobu reaction [e.g., in the presence of diethyl azodicarboxylate (DEAD) and triphenylphospine (Ph$_3$P)] with an appropriate alcohol R$^{a1}$—OH to give the ether compound of formula 4. Selective cyanation of compound 4 using Zn(CN)$_2$ under standard palladium catalysis conditions can deliver a pyridyl cyanide of formula 5. Reduction of the cyanide with a suitable reducing agent such as diisobutylaluminium hydride (DIBAL), lithium aluminium hydride (LAH), or BH$_3$ can afford the amine 6 (R$^4$=H). Alternatively, addition of a Grignard reagent R$^4$MgBr to the cyanide in compound 5, followed by NaBH$_4$ reduction can afford the amine 6 with R$^4$ as a non-hydrogen moiety. Acylation of the amine 6 using an appropriate acid chloride R$^3$COCl or equivalent can generate an amide intermediate, which can undergo cyclization upon treatment with phosphoryl chloride (POCl$_3$) to provide a bicyclic imidazole derivative of formula 7. Finally, the aryl chloride 7 can react with an appropriate boronic acid or ester of formula 8 under standard Suzuki coupling conditions to provide compounds of formula 9.

Scheme 1

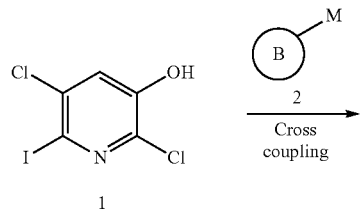

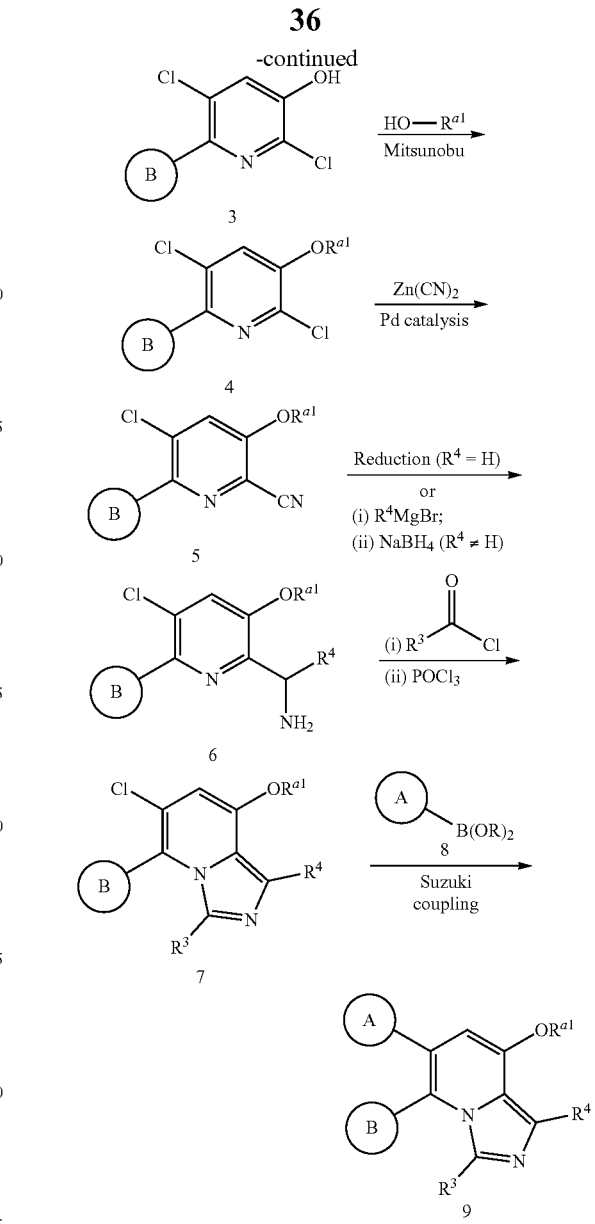

Compounds of formula 15 can be synthesized as shown in Scheme 2 starting from compound 3 which can be prepared as described in Scheme 1. The phenol derivative 3 can be converted to a triflate (Tf) of formula 10 using triflic anhydride (Tf$_2$O) with an appropriate base such as pyridine. The triflate of compound 10 can react with R$^1$-M under standard cross coupling conditions, such as standard Suzuki coupling conditions (where M is a boronic acid or ester, with palladium catalysis), standard Sonogashira coupling conditions (M-R$^1$ is a terminal alkyne, with palladium catalysis), standard Negishi coupling conditions (M is ZnCl, ZnBr or ZnI, with palladium catalysis) or standard Buchwald amination conditions (M-R$^1$ is an amine, with palladium catalysis) to give a compound of formula 11. Cyanation of compound 11 using Zn(CN)$_2$ under standard palladium catalysis conditions can deliver a cyanopyridine derivative of formula 12. Transformation of the cyano group in compound 12 to an amine can be achieved by Grignard addition of R$^4$MgBr (wherein R$^4$ is not hydrogen) to the cyano group, followed by NaBH$_4$ reduction to give the amine of formula 13. Alternatively, if $R^4$ is hydrogen, direct reduction of the cyano group in compound 12 using a reducing reagent such as, but not limited to, $LiAlH_4$ can afford the amine 13. Acylation of the amine 13 using an appropriate acid chloride $R^3COCl$ or equivalent can generate an amide intermediate, which can undergo cyclization upon treatment with $POCl_3$ to provide a bicyclic imidazole derivative of formula 14. Finally, the aryl chloride 14 can react with an appropriate boronic ester or acid of formula 8 under standard Suzuki coupling conditions to provide the compound of formula 15.

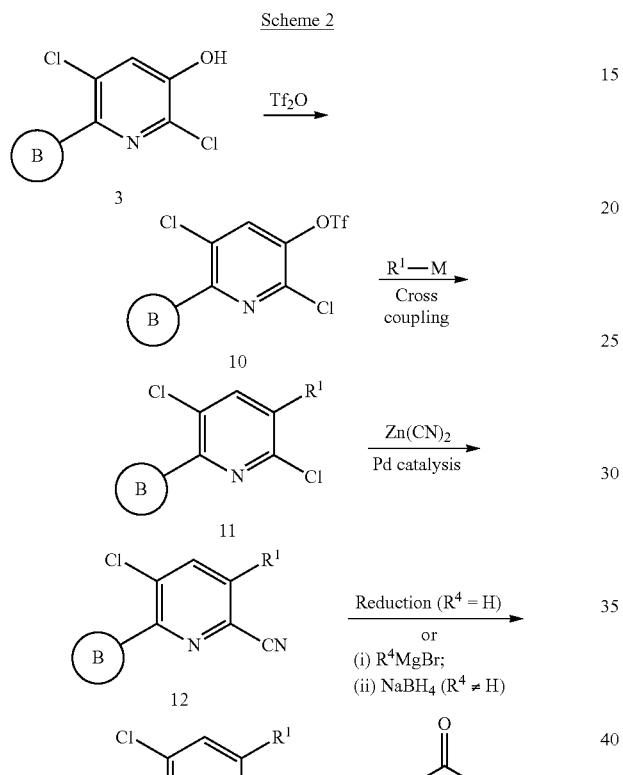

available aminopyrazine 16. Installation of ring B can be achieved by selective coupling of the bromide in compound 16 with compound 2 using standard cross coupling conditions as described in Scheme 1 to give compounds of formula 17. Bromination of the aminopyrazine derivative 17 with N-bromosuccinibide (NBS) or equivalent can give compounds of formula 18. Conversion of the amine group in compound 18 to a hydroxyl group to give compound 19 can be achieved in the presence of $NaNO_2$ under acidic conditions such as $H_2SO_4$. The newly formed hydroxyl group can be protected with a suitable protecting group (PG) such as methyl or benzyl by reacting with methyl iodide or benzyl chloride in the presence of a suitable base such as $K_2CO_3$ to give compound 20. Selective cyanation of the bromide in compound 20 using $Zn(CN)_2$ under standard palladium catalysis conditions can deliver a cyanopyrazine derivative of formula 21. Conversion of the cyano group in compound 21 to an amine can be achieved by Grignard addition of $R^4MgBr$ (wherein $R^4$ is not hydrogen) to the cyano group, followed by $NaBH_4$ reduction to give the amine of formula 22. Alternatively, if $R^4$ is hydrogen, direct reduction of the cyano group in compound 21 using a reducing reagent such as, but not limited to, $LiAlH_4$ can afford the amine 22. Acylation of the amine 22 using an appropriate acid chloride $R^3COCl$ or equivalent can generate an amide intermediate, which can undergo cyclization upon treatment with $POCl_3$ to provide a bicyclic imidazole derivative of formula 23. The aryl chloride 23 can react with an appropriate boronic ester or acid of formula 8 under standard Suzuki coupling conditions to provide the compound of formula 24. Removal of the protecting group PG in compound 24, followed by reacting with $Tf_2O$ can give the triflate of formula 25. The triflate of compound 25 can react with $R^1$-M under standard cross coupling conditions as described in Scheme 2 to give the compound of formula 26.

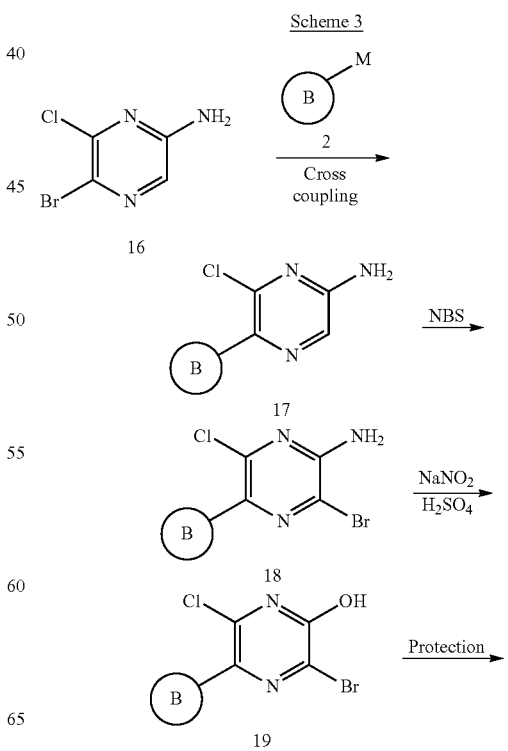

Compounds of formula 26 can be prepared using procedures as shown in Scheme 3 starting from the commercially

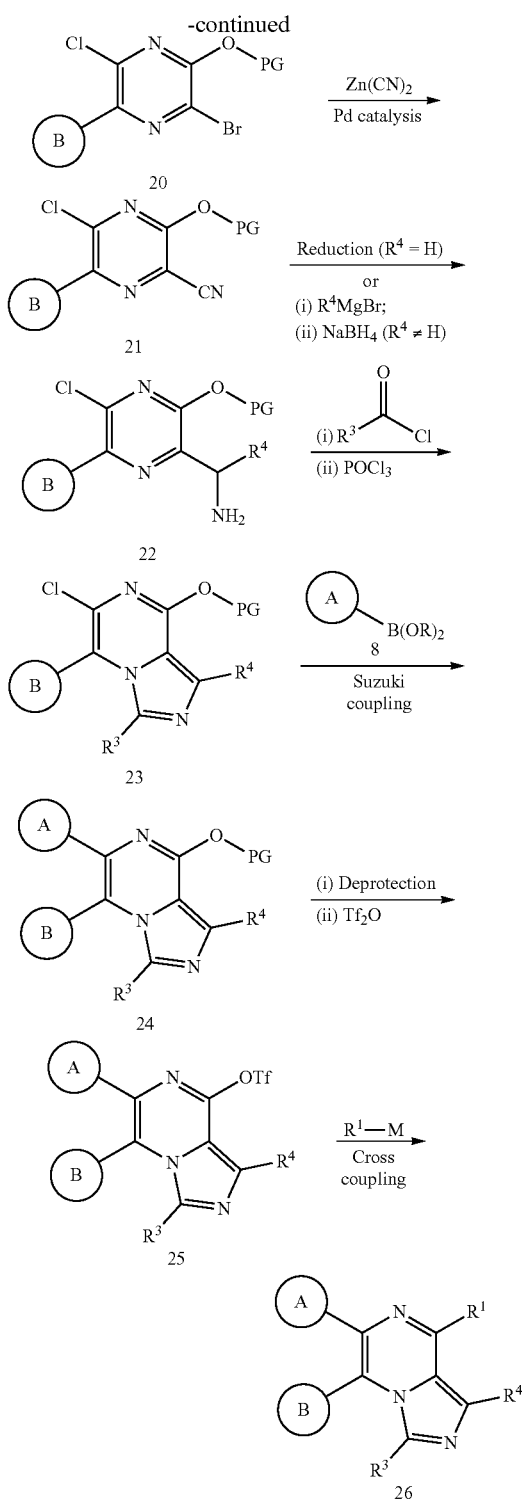

Methods of Use

Compounds of the invention are LSD1 inhibitors and, thus, are useful in treating diseases and disorders associated with activity of LSD1. For the uses described herein, any of the compounds of the invention, including any of the embodiments thereof, may be used.

In some embodiments, the compounds of the invention are selective for LSD1 over LSD2, meaning that the compounds bind to or inhibit LSD1 with greater affinity or potency, compared to LSD2. In general, selectivity can be at least about 5-fold, at least about 10-fold, at least about 20-fold, at least about 50-fold, at least about 100-fold, at least about 200-fold, at least about 500-fold or at least about 1000-fold.

As inhibitors of LSD1, the compounds of the invention are useful in treating LSD1-mediated diseases and disorders. The term "LSD1-mediated disease" or "LSD1-mediated disorder" refers to any disease or condition in which LSD1 plays a role, or where the disease or condition is associated with expression or activity of LSD1. The compounds of the invention can therefore be used to treat or lessen the severity of diseases and conditions where LSD1 is known to play a role.

Diseases and conditions treatable using the compounds of the invention include generally cancers, inflammation, autoimmune diseases, viral induced pathogenesis, beta-globinopathies, and other diseases linked to LSD1 activity.

Cancers treatable using compounds according to the present invention include, for example, hematological cancers, sarcomas, lung cancers, gastrointestinal cancers, genitourinary tract cancers, liver cancers, bone cancers, nervous system cancers, gynecological cancers, and skin cancers.

Example hematological cancers include, for example, lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Example sarcomas include, for example, chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Example lung cancers include, for example, non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Example gastrointestinal cancers include, for example, cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Example genitourinary tract cancers include, for example, cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Example liver cancers include, for example, hepatoma (hepatocellular carcinoma), cholangiocarcinoma, hepatoblastoma, angiosarcoma, hepatocellular adenoma, and hemangioma.

Example bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Example nervous system cancers include, for example, cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Example gynecological cancers include, for example, cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Example skin cancers include, for example, melanoma, basal cell carcinoma, squamous cell carcinoma, Kaposi's sarcoma, moles dysplastic nevi, lipoma, angioma, dermatofibroma, and keloids.

The compounds of the invention can further be used to treat cancer types where LSD1 may be overexpressed including, for example, breast, prostate, head and neck, laryngeal, oral, and thyroid cancers (e.g., papillary thyroid carcinoma).

The compounds of the invention can further be used to treat genetic disorders such as Cowden syndrome and Bannayan-Zonana syndrome.

The compounds of the invention can further be used to treat viral diseases such as herpes simplex virus (HSV), varicella zoster virus (VZV), human cytomegalovirus, hepatitis B virus (HBV), and adenovirus.

The compounds of the invention can further be used to treat beta-globinopathies including, for example, beta-thalassemia and sickle cell anemia.

As used herein, the term "contacting" refers to the bringing together of indicated moieties in an in vitro system or an in vivo system. For example, "contacting" a LSD1 protein with a compound of the invention includes the administration of a compound of the present invention to an individual or patient, such as a human, having a LSD1 protein, as well as, for example, introducing a compound of the invention into a sample containing a cellular or purified preparation containing the LSD1 protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e. arresting further development of the pathology and/or symptomatology) or ameliorating the disease; for example, ameliorating a disease, condition or disorder in an individual who is experiencing or displaying the pathology or symptomatology of the disease, condition or disorder (i.e. reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, JAK, PIM, PI3K inhibitors for treatment of LSD1-mediated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, agonists or antagonists of nuclear receptors, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

For treating beta-thalassemia or sickle cell disease, the compound of the invention can be administered in combination with one or more additional agents such as Hydrea® (hydroxyurea).

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating LSD1 in tissue samples, including human, and for identifying LSD1 ligands by inhibition binding of a labeled compound. Accordingly, the present invention includes LSD1 assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind LSD1 by monitoring its concentration variation when contacting with LSD1, through tracking of the labeling. For example, a test compound (labeled) can be evaluated for its ability to reduce binding of another compound which is known to bind to LSD1 (i.e., standard compound). Accordingly, the ability of a test compound to compete with the standard compound for binding to LSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of LSD1 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples.

Typical preparative reverse-phase high performance liquid chromatography (RP-HPLC) column conditions are as follows:

pH=2 purifications: Waters Sunfire™ $C_{18}$ 5 µm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Examples

Example 1

4-{5-(4-methylphenyl)-8-[(3R)-pyrrolidin-3-yl-methoxy]imidazo[1,5-a]pyridin-6-yl}benzonitrile

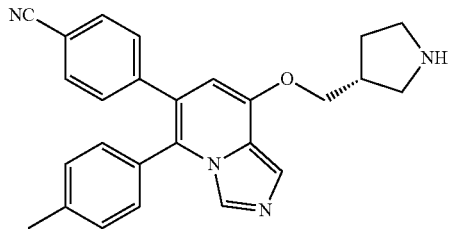 [SMILES: Cc1ccc(-c2c(-c3ccc(C#N)cc3)cc(OC[C@@H]3CCNC3)c3cncn23)cc1]

Step 1: 2,5-dichloro-6-(4-methylphenyl)pyridin-3-ol

A reaction vessel containing a mixture of 2,5-dichloro-6-iodopyridin-3-ol (3.5 g, 12 mmol), palladium acetate (271 mg, 1.21 mmol), tri-o-tolylphosphine (735 mg, 2.41 mmol), sodium carbonate (3.2 g, 30.2 mmol), and (4-methylphenyl) boronic acid (2.0 g, 14 mmol) in 1,4-dioxane (20 mL) and water (2 mL) was evacuated then filled with nitrogen. The resulting mixture was heated to 80° C. and stirred for 2 h. The reaction mixture was cooled to room temperature and passed through a short pad of celite and rinsed with EtOAc. The filtrate was concentrated and the residue was purified on a silica gel column eluting with 0 to 75% EtOAc/Hexanes to give the desired product (3.0 g, 98%) as a light yellow solid. LC-MS calculated for $C_{12}H_{10}Cl_2NO$ (M+H)$^+$: m/z=254.0. found 254.1.

Step 2: tert-butyl (3R)-3-({[2,5-dichloro-6-(4-methylphenyl)pyridin-3-yl]oxy}methyl)pyrrolidine-1-carboxylate

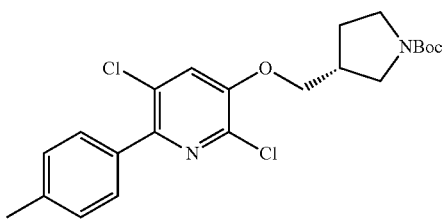 [SMILES: Cc1ccc(-c2nc(Cl)c(OC[C@@H]3CCN(C(=O)OC(C)(C)C)C3)cc2Cl)cc1]

To a solution of 2,5-dichloro-6-(4-methylphenyl)pyridin-3-ol (3.0 g, 11.8 mmol), tert-butyl (3R)-3-(hydroxymethyl) pyrrolidine-1-carboxylate (2.85 g, 14.2 mmol), and triphenylphosphine (6.19 g, 23.6 mmol) in toluene (50 mL) at room temperature was added diisopropyl azodicarboxylate (4.65 mL, 23.6 mmol) dropwise. The resulting mixture was stirred at room temperature overnight and then concentrated. The residue was purified on a silica gel column eluting with 0 to 75% EtOAc/Hexanes to give the desired product (4.9 g, 95%) as a white solid. LC-MS calculated for $C_{18}H_{19}Cl_2N_2O_3$ (M-$^t$Bu+2H)$^+$: m/z=381.1. found 381.1.

Step 3: tert-butyl (3R)-3-({[5-chloro-2-cyano-6-(4-methylphenyl)pyridin-3-yl]oxy}methyl)-pyrrolidine-1-carboxylate

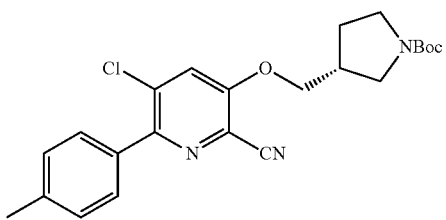 [SMILES: Cc1ccc(-c2nc(C#N)c(OC[C@@H]3CCN(C(=O)OC(C)(C)C)C3)cc2Cl)cc1]

A reaction vessel containing a mixture of tert-butyl (3R)-3-({[2,5-dichloro-6-(4-methylphenyl)pyridin-3-yl] oxy}methyl)pyrrolidine-1-carboxylate (2.00 g, 4.57 mmol), [1,1'-bis(diphenylphosphino)ferrocene]dichloropalladium (II) complexed with dichloromethane (1:1) (200 mg, 0.2 mmol), zinc cyanide (215 mg, 1.83 mmol), and zinc (150 mg, 2.29 mmol) in N,N-dimethylformamide (30 mL) was evacuated then filled with nitrogen. The resulting mixture was heated to 85° C. and stirred for 5 h. The reaction mixture was cooled to room temperature then filtered and washed with EtOAc. The filtrate was washed with water and brine. The organic layer was dried over $Na_2SO_4$ and concentrated. The residue was purified on a silica gel column eluting with 0 to 35% EtOAc/Hexanes to give the desired product (1.1 g, 65%). LC-MS calculated for $C_{19}H_{19}ClN_3O_3$ (M-$^t$Bu+2H)$^+$: m/z=372.1. found 372.1.

Step 4: Acetic Formic Anhydride

A mixture of acetic anhydride (3.0 mL, 32 mmol) and formic acid (1.2 mL, 32 mmol) was heated to 55° C. and stirred for 2 h. The mixture was cooled to room temperature and the crude product was used directly in the next step.

Step 5: 6-chloro-5-(4-methylphenyl)-8-[(3R)-pyrrolidin-3-ylmethoxy]imidazo[1,5-a]pyridine

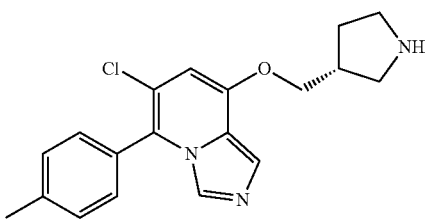 [SMILES: Cc1ccc(-c2c(Cl)cc(OC[C@@H]3CCNC3)c3cncn23)cc1]

To a solution of tert-butyl (3R)-3-({[5-chloro-2-cyano-6-(4-methylphenyl)pyridin-3-yl]oxy}methyl)pyrrolidine-1-carboxylate (1.00 g, 2.34 mmol) in tetrahydrofuran (5.0 mL) at 0° C. was added 2.0 M borane-dimethyl sulfide complex in THF (3.5 mL, 7.0 mmol) dropwise. The resulting solution was then warmed up to room temperature and stirred overnight. The reaction mixture was quenched with saturated NaHCO$_3$ aqueous solution then extracted with DCM. The combined extracts were washed with brine then dried over Na$_2$SO$_4$ and concentrated. The residue was purified on a silica gel column eluting with 0 to 10% MeOH/DCM to give the desired intermediate (800 mg). The intermediate was dissolved in methylene chloride (5.0 mL) then acetic formic anhydride (919 µL, 11.7 mmol) was added. The resulting mixture was stirred at room temperature overnight then concentrated. The residue was dissolved in methylene chloride (5.0 mL) then phosphoryl chloride (220 µL, 2.3 mmol) was added. The mixture was heated to 40° C. and stirred for 5 h. The reaction mixture was cooled to room temperature and the volatiles were removed under vacuum and the residue was purified on a silica gel column eluting with 0 to 8% MeOH/DCM then 10% MeOH & 1% Et3N in DCM to give the desired product (602 mg, 75%). LC-MS calculated for C$_{19}$H$_{21}$ClN$_3$O (M+H)$^+$: m/z=342.1. found 342.1.

Step 6: 4-{5-(4-methylphenyl)-8-[(3R)-pyrrolidin-3-ylmethoxy]imidazo[1,5-a]pyridin-6-yl}benzonitrile A reaction vessel containing a mixture of 6-chloro-5-(4-methylphenyl)-8-[(3R)-pyrrolidin-3-ylmethoxy]imidazo[1,5-a]pyridine (30 mg, 0.086 mmol), (4-cyanophenyl)boronic acid (20 mg, 0.13 mmol), sodium carbonate (28 mg, 0.26 mmol), and [1,1'-bis(di-cyclohexylphosphino)ferrocene]-dichloropalladium(II) (13 mg, 0.018 mmol) in tert-butyl alcohol (1.5 mL) and water (0.5 mL) was evacuated then filled with nitrogen. The resulting mixture was heated to 90° C. and stirred for 2 h. The reaction mixture was then cooled to room temperature, filtered and then purified by prep HPLC (pH=2, acetonitrile/water+TFA) to give the product as the TFA salt. LC-MS calculated for C$_{26}$H$_{25}$N$_4$O (M+H)$^+$: m/z=409.2. found 409.2. $^1$H NMR (500 MHz, DMSO) δ 8.85 (s, 1H), 8.04 (s, 1H), 7.76-7.71 (m, 3H), 7.38 (d, J=8.4 Hz, 2H), 7.25 (s, 4H), 6.47 (s, 1H), 4.34-4.19 (m, 2H), 3.51-3.39 (m, 1H), 3.36-3.17 (m, 2H), 3.12-3.04 (m, 1H), 2.90-2.80 (m, 1H), 2.33 (s, 3H), 2.20-2.10 (m, 1H), 1.86-1.76 (m, 1H).

Example 2

6-(4-fluorophenyl)-5-(4-methylphenyl)-8-[(3R)-pyrrolidin-3-ylmethoxy]imidazo[1,5-a]pyridine

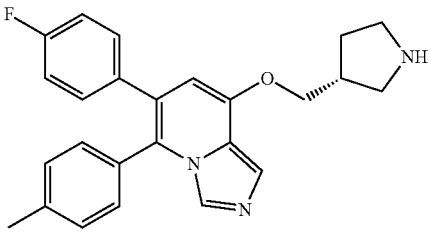 [SMILES: Cc1ccc(-c2c(-c3ccc(F)cc3)cc(OC[C@@H]3CCNC3)c3cncn23)cc1]

This compound was prepared using procedures analogous to those described for Example 1 with 4-fluorophenylboronic acid replacing (4-cyanophenyl)boronic acid in Step 6. The product was purified by prep HPLC (pH=2, acetonitrile/water+TFA) to give the compound as the TFA salt. LC-MS calculated for C$_{25}$H$_{25}$FN$_3$O (M+H)$^+$: m/z=402.2. found 402.2.

Example 3

5-(4-methylphenyl)-6-(4-nitrophenyl)-8-[(3R)-pyrrolidin-3-ylmethoxy]imidazo[1,5-a]pyridine

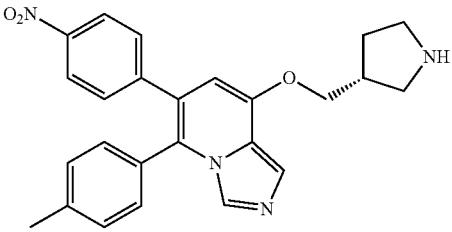 [SMILES: Cc1ccc(-c2c(-c3ccc([N+](=O)[O-])cc3)cc(OC[C@@H]3CCNC3)c3cncn23)cc1]

This compound was prepared using procedures analogous to those described for Example 1 with 4-nitrophenylboronic acid replacing (4-cyanophenyl)boronic acid in Step 6. The product was purified by prep HPLC (pH=2, acetonitrile/water+TFA) to give the compound as the TFA salt. LC-MS calculated for C$_{25}$H$_{25}$N$_4$O$_3$ (M+H)$^+$: m/z=429.2. found 429.2.

Example 4

2-fluoro-4-{5-(4-methylphenyl)-8-[(3R)-pyrrolidin-3-ylmethoxy]imidazo[1,5-a]pyridin-6-yl}benzonitrile

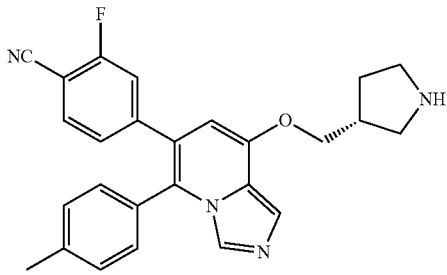 [SMILES: Cc1ccc(-c2c(-c3ccc(C#N)c(F)c3)cc(OC[C@@H]3CCNC3)c3cncn23)cc1]

This compound was prepared using procedures analogous to those described for Example 1 with (4-cyano-3-fluorophenyl)boronic acid replacing (4-cyanophenyl)boronic acid in Step 6. The product was purified by prep HPLC (pH=2, acetonitrile/water+TFA) to give the compound as the TFA salt. LC-MS calculated for $C_{26}H_{24}FN_4O$ $(M+H)^+$: m/z=427.2. found 427.1.

Example 5

3-fluoro-4-{5-(4-methylphenyl)-8-[(3R)-pyrrolidin-3-ylmethoxy]imidazo[1,5-a]pyridin-6-yl}benzonitrile

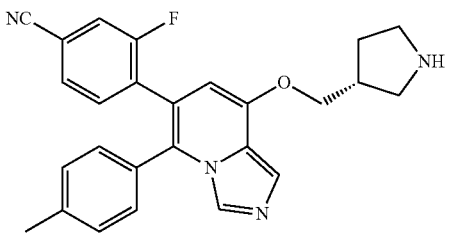 [SMILES: Cc1ccc(-c2c(-c3ccc(C#N)cc3F)cc(OC[C@@H]3CCNC3)c3cncn23)cc1]

This compound was prepared using procedures analogous to those described for Example 1 with (4-cyano-2-fluorophenyl)boronic acid replacing (4-cyanophenyl)boronic acid in Step 6. The product was purified by prep HPLC (pH=2, acetonitrile/water+TFA) to give the compound as the TFA salt. LC-MS calculated for $C_{26}H_{24}FN_4O$ $(M+H)^+$: m/z=427.2. found 427.2.

Example 6

4-{5-(4-chlorophenyl)-8-[(3R)-pyrrolidin-3-ylmethoxy]imidazo[1,5-a]pyridin-6-yl}benzonitrile

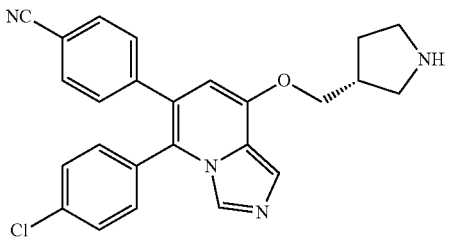 [SMILES: N#Cc1ccc(-c2cc(OC[C@@H]3CCNC3)c3cncn3c2-c2ccc(Cl)cc2)cc1]

Step 1: 5-bromo-6-chloro-2-iodopyridin-3-ol

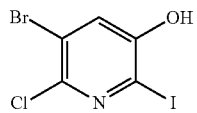

To a mixture of 5-bromo-6-chloropyridin-3-ol (2.0 g, 9.6 mmol) and sodium carbonate (2.1 g, 20. mmol) in water (14 mL) at room temperature was added iodine (2.4 g, 9.6 mmol). The resulting mixture was stirred at room temperature for 1 h then poured into HCl solution (2N in water, 10 mL, 20 mmol). The off-white precipitate was collected via filtration then washed with water and dried to give the desired product (3.17 g, 99%) which was used in the next step without further purification. LC-MS calculated for $C_5H_3BrClINO$ $(M+H)^+$: m/z=333.8. found 333.8.

Step 2: tert-butyl (3R)-3-{[(5-bromo-6-chloro-2-iodopyridin-3-yl)oxy]methyl}pyrrolidine-1-carboxylate

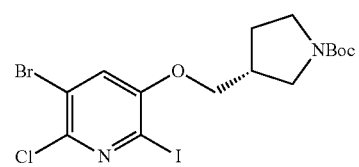 [SMILES: CC(C)(C)OC(=O)N1CC[C@@H](COc2cc(Br)c(Cl)nc2I)C1]

To a suspension of 5-bromo-6-chloro-2-iodopyridin-3-ol (3.17 g, 9.48 mmol), tert-butyl (3R)-3-(hydroxymethyl)pyrrolidine-1-carboxylate (2.03 g, 10.1 mmol) and triphenylphosphine (7.0 g, 27 mmol) in toluene (30 mL) at room temperature was added dropwise diisopropyl azodicarboxylate (2.2 mL, 11 mmol). The resulting mixture was stirred at room temperature for 2 h then concentrated. The residue was purified on a silica gel column eluting with 0 to 50% EtOAc/Hexanes to give the desired product (4.9 g, quant.). LC-MS calculated for $C_{11}H_{12}BrClIN_2O_3$ $(M-^tBu+2H)^+$: m/z=460.9. found 460.9.

Step 3: tert-butyl (3R)-3-{[(5-bromo-6-chloro-2-cyanopyridin-3-yl)oxy]methyl}pyrrolidine-1-carboxylate

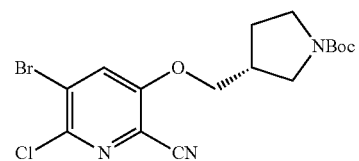 [SMILES: CC(C)(C)OC(=O)N1CC[C@@H](COc2cc(Br)c(Cl)nc2C#N)C1]

A mixture of tert-butyl (3R)-3-{[(5-bromo-6-chloro-2-iodopyridin-3-yl)oxy]methyl}pyrrolidine-1-carboxylate (4.9 g, 9.5 mmol) and copper cyanide (1.1 g, 12 mmol) in pyridine (30 mL) was heated to 90° C. and stirred for 1 hour. The reaction mixture was cooled to room temperature then concentrated. The residue was purified on a silica gel column eluting with 0 to 40% EtOAc/Hexanes to give the desired product (3.9 g, quant.). LC-MS calculated for $C_{12}H_{11}BrClN_3O_3$ $(M-^tBu+2H)^+$: m/z=360.0. found 360.0.

Step 4: tert-butyl (3R)-3-{[(6-bromo-5-chloroimidazo[1,5-a]pyridin-8-yl)oxy]methyl}-pyrrolidine-1-carboxylate

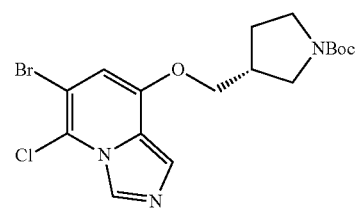 [SMILES: CC(C)(C)OC(=O)N1CC[C@@H](COc2cc(Br)c(Cl)n3cncc23)C1]

To a solution of tert-butyl (3R)-3-{[(5-bromo-6-chloro-2-cyanopyridin-3-yl)oxy]methyl}pyrrolidine-1-carboxylate (3.90 g, 9.36 mmol) in methylene chloride (50 mL) at −78° C. was added diisobutylaluminum hydride (1.0 M in DCM, 47 mL, 47 mmol). The resulting mixture was stirred at 78° C. for 2 h then quenched with saturated NH$_4$Cl aqueous solution. The mixture was warmed to room temperature then diluted with saturated sodium potassium tartrate and stirred at room temperature overnight. The layers were separated and the aqueous layer was extracted with DCM. The combined organic layers were dried over Na$_2$SO$_4$ then concentrated. The residue was dissolved in methylene chloride (30 mL) then acetic formic anhydride (3.7 mL, 47 mmol) was added. The resulting mixture was stirred at room temperature for 2 h. The volatiles were removed under vacuum and the residue was dissolved in methylene chloride (30 mL) then phosphoryl chloride (1.0 mL, 11 mmol) was added. The mixture was stirred at 40° C. for 1.5 h then cooled to room temperature and triethylamine (1.6 mL, 11 mmol) was added. The mixture was stirred at room temperature for 10 min then concentrated. The residue was purified on a silica gel column eluting with 0 to 5% MeOH/DCM to give the desired product (2.8 g, 69%). LC-MS calculated for C$_{17}$H$_{22}$BrClN$_3$O$_3$ (M+H)$^+$: m/z=430.1. found 430.1.

Step 5: tert-butyl (3R)-3-({[5-chloro-6-(4-cyanophenyl)imidazo[1,5-a]pyridin-8-yl]oxy}-methyl)pyrrolidine-1-carboxylate

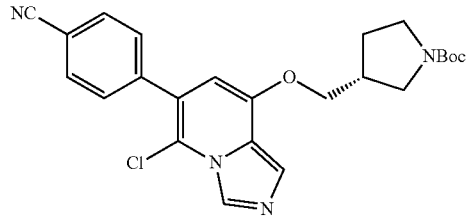 [SMILES: CC(C)(C)OC(=O)N1CC[C@@H](COc2cc(-c3ccc(C#N)cc3)c(Cl)n3cncc23)C1]

A reaction vessel containing a mixture of tert-butyl (3R)-3-{[(6-bromo-5-chloroimidazo[1,5-a]pyridin-8-yl)oxy]methyl}pyrrolidine-1-carboxylate (1.8 g, 4.2 mmol), (4-cyanophenyl)boronic acid (0.8 g, 5.4 mmol), palladium acetate (94 mg, 0.42 mmol), tri-o-tolylphosphine (250 mg, 0.84 mmol), and sodium carbonate (1.3 g, 12 mmol) in 1,4-dioxane (8 mL) and water (2 mL) was evacuated then filled with nitrogen. The resulting mixture was stirred at 80° C. for 1 hour then cooled to room temperature and concentrated. The residue was purified on a silica gel column eluting with 0 to 80% EtOAc/Hexanes to give the desired product (0.9 g, 47%). LC-MS calculated for C$_{24}$H$_{26}$ClN$_4$O$_3$ (M+H)$^+$: m/z=453.2. found 453.1.

Step 6: 4-{5-(4-chlorophenyl)-8-[(3R)-pyrrolidin-3-ylmethoxy]imidazo[1,5-a]pyridin-6-yl}benzonitrile A reaction vessel containing a mixture of tert-butyl (3R)-3-({[5-chloro-6-(4-cyanophenyl)imidazo[1,5-a]pyridin-8-yl]oxy}methyl)pyrrolidine-1-carboxylate (8 mg, 0.02 mmol), (4-chlorophenyl)boronic acid (4.1 mg, 0.026 mmol), sodium carbonate (3.7 mg, 0.035 mmol) and [1,1'-bis(dicyclohexylphosphino)ferrocene]-dichloropalladium(II) (1.3 mg, 0.0018 mmol) in tert-butyl alcohol (0.4 mL) and water (0.4 mL) was evacuated then filled with nitrogen. The resulting mixture was stirred at 90° C. for 1 h then cooled to room temperature, diluted with EtOAc and washed with water and brine. The organic layer was dried over Na$_2$SO$_4$ then concentrated. The residue was dissolved in methylene chloride (1 mL) and trifluoroacetic acid (0.5 mL) was added. The resulting mixture was stirred at room temperature for 1 h then concentrated. The residue was dissolved in acetonitrile then purified by prep HPLC (pH=2, acetonitrile/water+TFA) to give the desired product as the TFA salt. LC-MS calculated for C$_{25}$H$_{22}$ClN$_4$O (M+H)$^+$: m/z=429.1. found 429.1.

Example 7

4-{5-(1-cyclobutyl-1H-pyrazol-4-yl)-8-[(3R)-pyrrolidin-3-ylmethoxy]imidazo[1,5-a]pyridin-6-yl}benzonitrile

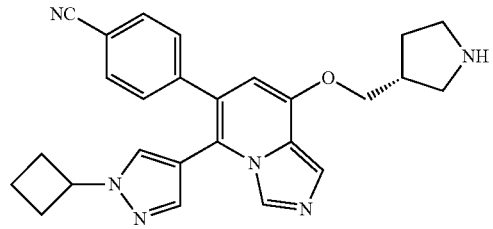 [SMILES: N#Cc1ccc(-c2cc(OC[C@@H]3CCNC3)c3cncn3c2-c2cnn(C3CCC3)c2)cc1]

A mixture of tert-butyl (3R)-3-({[5-chloro-6-(4-cyanophenyl)imidazo[1,5-a]pyridin-8-yl]oxy}methyl)pyrrolidine-1-carboxylate (Example 6, Step 5: 10 mg, 0.02 mmol), 1-cyclobutyl-4-(4,4,5,5-tetramethyl-1,3,2-dioxaborolan-2-yl)-1H-pyrazole (8.2 mg, 0.033 mmol), dichloro(bis{di-tert-butyl[4-(dimethylamino)phenyl]phosphoranyl})palladium (0.2 mg, 0.0002 mmol) and cesium fluoride (9.0 mg, 0.060 mmol) in tert-butyl alcohol (0.8 mL) and water (0.2 mL) was evacuated and filled with nitrogen. The mixture was stirred at 90° C. for 2 h then cooled to room temperature and filtered. The filtrate was concentrated and the residue was dissolved in methylene chloride (1 mL) then trifluoroacetic acid (0.5 mL) was added. The mixture was stirred at room temperature for 1 h then concentrated. The residue was dissolved in methanol then purified by prep HPLC (pH=2, acetonitrile/water+TFA) to give the desired product as the TFA salt. LC-MS calculated for C$_{26}$H$_{27}$N$_6$O (M+H)$^+$: m/z=439.2. found 439.2.

Example 8

4-{5-(2-fluoro-4-methylphenyl)-8-[(3R)-pyrrolidin-3-ylmethoxy]imidazo[1,5-a]pyridin-6-yl}benzonitrile

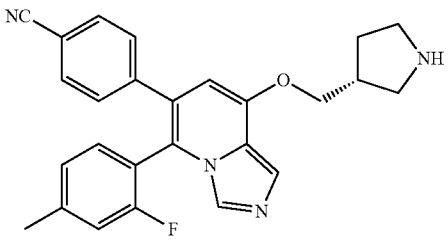 [SMILES: Cc1ccc(-c2c(-c3ccc(C#N)cc3)cc(OC[C@@H]3CCNC3)c3cncn23)c(F)c1]

This compound was prepared using procedures analogous to those for Example 7 with (2-fluoro-4-methylphenyl) boronic acid replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{26}H_{24}FN_4O$ (M+H)$^+$: m/z=427.2. found 427.2.

Example 9

4-{5-(4-ethylcyclohex-1-en-1-yl)-8-[(3R)-pyrrolidin-3-ylmethoxy]imidazo[1,5-a]pyridin-6-yl}benzonitrile

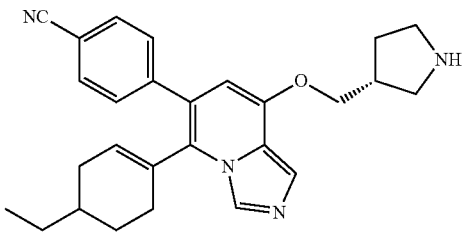 [SMILES: CCC1CC=C(c2c(-c3ccc(C#N)cc3)cc(OC[C@@H]3CCNC3)c3cncn23)CC1]

To a solution of tert-butyl (3R)-3-({[5-chloro-6-(4-cyanophenyl)imidazo[1,5-a]pyridin-8-yl]oxy}methyl)pyrrolidine-1-carboxylate (Example 6, Step 5, 10 mg, 0.02 mmol) in methylene chloride (0.4 mL) was added trifluoroacetic acid (0.2 mL, 2 mmol). The resulting mixture was stirred at room temperature for 1 h then concentrated. A mixture of the above residue, (4-ethylcyclohex-1-en-1-yl)boronic acid (5.1 mg, 0.033 mmol), cesium fluoride (10. mg, 0.066 mmol) and dichloro(bis{di-tert-butyl[4-(dimethylamino)phenyl]phosphoranyl})palladium (1.6 mg, 0.0022 mmol) in tert-butyl alcohol (0.8 mL) and water (0.2 mL) was evacuated then filled with nitrogen. The resulting mixture was stirred at 90° C. for 2 h then cooled to room temperature and filtered. The filtrate was purified by prep HPLC (pH=2, acetonitrile/water+TFA) to give the desired product as the TFA salt. LC-MS calculated for $C_{27}H_{31}N_4O$ (M+H)$^+$: m/z=427.2. found 427.2.

Example 10 tert-butyl 4-{6-(4-cyanophenyl)-8-[(3R)-pyrrolidin-3-ylmethoxy]imidazo[1,5-a]pyridin-5-yl}-3,6-dihydropyridine-1(2H)-carboxylate

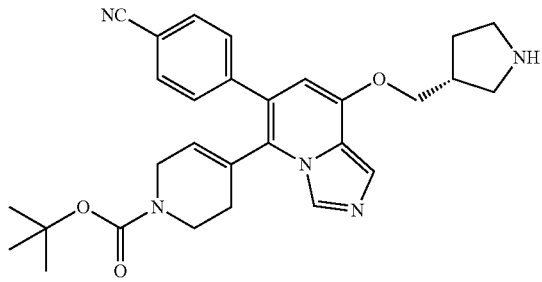 [SMILES: CC(C)(C)OC(=O)N1CC=C(c2c(-c3ccc(C#N)cc3)cc(OC[C@@H]3CCNC3)c3cncn23)CC1]

This compound was prepared using procedures analogous to those for Example 9 with tert-butyl 4-(4,4,5,5-tetramethyl-1,3,2-dioxaborolan-2-yl)-3,6-dihydropyridine-1(2H)-carboxylate replacing (4-ethylcyclohex-1-en-1-yl)boronic acid. The product was purified by prep HPLC (pH=2, acetonitrile/water+TFA) to give the compound as the TFA salt. LC-MS calculated for $C_{29}H_{34}N_5O_3$ (M+H)$^+$: m/z=500.3. found 500.2.

Example 11

4-{5-(1-methyl-1H-indazol-5-yl)-8-[(3R)-pyrrolidin-3-ylmethoxy]imidazo[1,5-a]pyridin-6-yl}benzonitrile

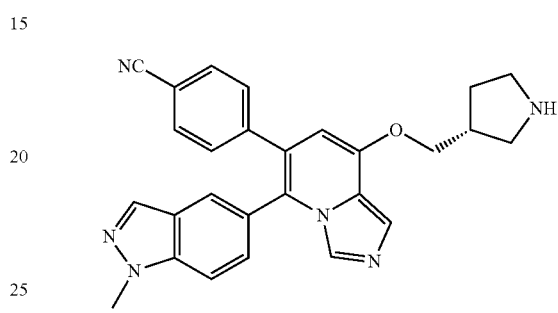

This compound was prepared using procedures analogous to those for Example 9 with (1-methyl-1H-indazol-5-yl)boronic acid replacing (4-ethylcyclohex-1-en-1-yl)boronic acid. The product was purified by prep HPLC (pH=2, acetonitrile/water+TFA) to give the compound as the TFA salt. LC-MS calculated for $C_{27}H_{25}N_6O$ (M+H)$^+$: m/z=449.2. found 449.2.

Example 12

4-{5-(1-methyl-2-oxo-2,3-dihydro-1H-indol-5-yl)-8-[(3R)-pyrrolidin-3-ylmethoxy]imidazo-[1,5-a]pyridin-6-yl}benzonitrile

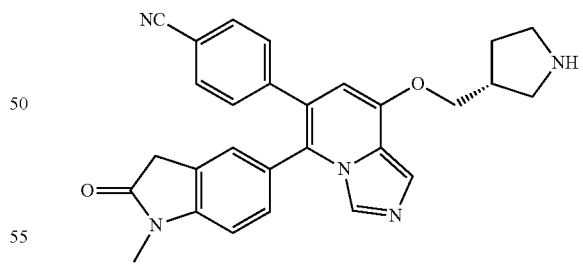

This compound was prepared using procedures analogous to those for Example 9 with 1-methyl-5-(4,4,5,5-tetramethyl-1,3,2-dioxaborolan-2-yl)-1,3-dihydro-2H-indol-2-one replacing (4-ethylcyclohex-1-en-1-yl)boronic acid. The product was purified by prep HPLC (pH=2, acetonitrile/water+TFA) to give the compound as the TFA salt. LC-MS calculated for $C_{28}H_{26}N_5O_2$ (M+H)$^+$: m/z=464.2. found 464.1.

Example 13

4-{5-(4-morpholin-4-ylphenyl)-8-[(3R)-pyrrolidin-3-ylmethoxy]imidazo[1,5-a]pyridin-6-yl}benzonitrile

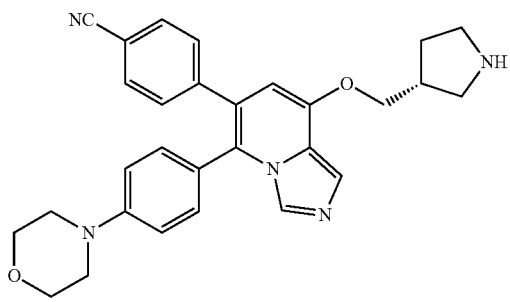 [SMILES: N#Cc1ccc(-c2cc(OC[C@@H]3CCNC3)c3cncn3c2-c2ccc(N3CCOCC3)cc2)cc1]

This compound was prepared using procedures analogous to those for Example 7 with (4-morpholin-4-ylphenyl)boronic acid replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{29}H_{30}N_5O_2$ (M+H)$^+$: m/z=480.2. found 480.2.

Example 14

4-{5-(4-methyl-3,4-dihydro-2H-1,4-benzoxazin-7-yl)-8-[(3R)-pyrrolidin-3-ylmethoxy]imidazo[1,5-a]pyridin-6-yl}benzonitrile

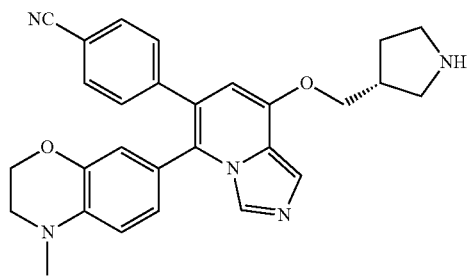 [SMILES: CN1CCOc2cc(-c3c(-c4ccc(C#N)cc4)cc(OC[C@@H]4CCNC4)c4cncn34)ccc21]

This compound was prepared using procedures analogous to those for Example 7 with 4-methyl-7-(4,4,5,5-tetramethyl-1,3,2-dioxaborolan-2-yl)-3,4-dihydro-2H-1,4-benzoxazine replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{28}H_{28}N_5O_2$ (M+H)$^+$: m/z=466.2. found 466.3.

Example 15

4-{5-(4-methyl-3,4-dihydro-2H-1,4-benzoxazin-6-yl)-8-[(3R)-pyrrolidin-3-ylmethoxy]imidazo[1,5-a]pyridin-6-yl}benzonitrile

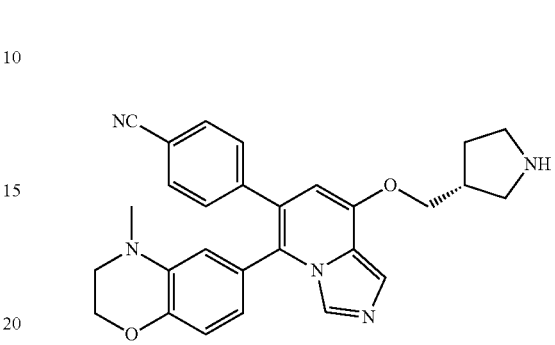

This compound was prepared using procedures analogous to those for Example 7 with (4-methyl-3,4-dihydro-2H-1,4-benzoxazin-6-yl)boronic acid replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{28}H_{28}N_5O_2$ (M+H)$^+$: m/z=466.2. found 466.2.

Example 16

4-{5-(2,3-dihydro-1,4-benzodioxin-6-yl)-8-[(3R)-pyrrolidin-3-ylmethoxy]imidazo[1,5-a]pyridin-6-yl}benzonitrile

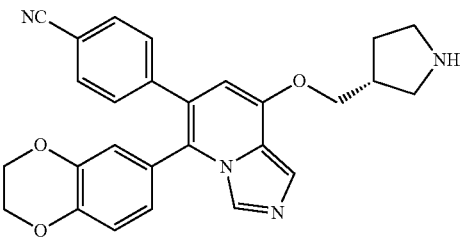 [SMILES: N#Cc1ccc(-c2cc(OC[C@@H]3CCNC3)c3cncn3c2-c2ccc3c(c2)OCCO3)cc1]

This compound was prepared using procedures analogous to those for Example 7 with 2,3-dihydro-1,4-benzodioxin-6-ylboronic acid replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{27}H_{25}N_4O_3$ (M+H)$^+$: m/z=453.2. found 453.1.

Example 17

4-{5-[4-(morpholin-4-ylmethyl)phenyl]-8-[(3R)-pyrrolidin-3-ylmethoxy]imidazo[1,5-a]pyridin-6-yl}benzonitrile

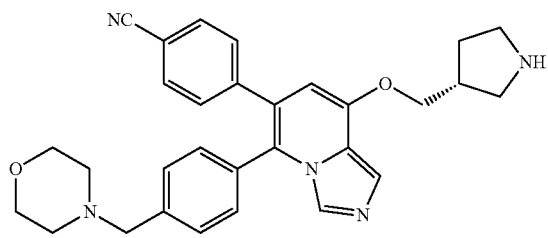 [SMILES: N#Cc1ccc(-c2cc(OC[C@@H]3CCNC3)c3cncn3c2-c2ccc(CN3CCOCC3)cc2)cc1]

This compound was prepared using procedures analogous to those for Example 7 with 4-[4-(4,4,5,5-tetramethyl-1,3,2-dioxaborolan-2-yl)benzyl]morpholine (Frontier, cat#M1236) replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{30}H_{32}N_5O_2$ (M+H)$^+$: m/z=494.3. found 494.2.

Example 18

4-{5-[4-(2-morpholin-4-ylethyl)phenyl]-8-[(3R)-pyrrolidin-3-ylmethoxy]imidazo[1,5-a]pyridin-6-yl}benzonitrile

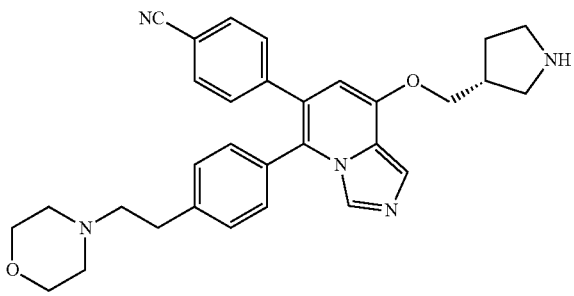 [SMILES: N#Cc1ccc(-c2cc(OC[C@@H]3CCNC3)c3cncn3c2-c2ccc(CCN3CCOCC3)cc2)cc1]

This compound was prepared using procedures analogous to those for Example 7 with [4-(2-morpholin-4-ylethyl)phenyl]boronic acid replacing 1-cyclobutyl-4-(4,4,5,5-tetramethyl-1,3,2-dioxaborolan-2-yl)-1H-pyrazole. The product was purified by prep HPLC (pH=2, acetonitrile/water+TFA) to give the compound as the TFA salt. LC-MS calculated for $C_{31}H_{34}N_5O_2$ (M+H)$^+$: m/z=508.3. found 508.3.

Example 19

4-{5-{4-[(4-methylpiperazin-1-yl)methyl]phenyl}-8-[(3R)-pyrrolidin-3-ylmethoxy]imidazo-[1,5-a]pyridin-6-yl}benzonitrile

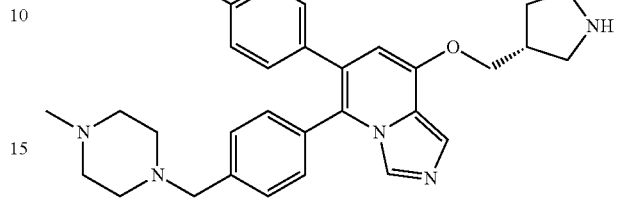

Step 1: tert-butyl (3R)-3-({[6-(4-cyanophenyl)-5-(4-formylphenyl)imidazo[1,5-a]pyridin-8-yl]oxy}methyl)pyrrolidine-1-carboxylate

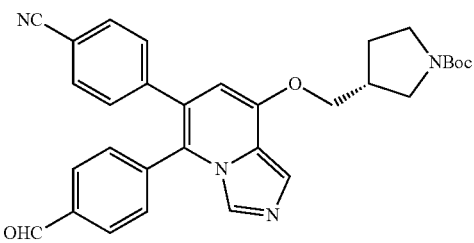 [SMILES: CC(C)(C)OC(=O)N1CC[C@@H](COc2cc(-c3ccc(C#N)cc3)c(-c3ccc(C=O)cc3)n3cncc23)C1]

A mixture of tert-butyl (3R)-3-({[5-chloro-6-(4-cyanophenyl)imidazo[1,5-a]pyridin-8-yl]oxy}methyl)pyrrolidine-1-carboxylate (Example 6, Step 5, 70 mg, 0.2 mmol), 4-(4,4,5,5-tetramethyl-1,3,2-dioxaborolan-2-yl)benzaldehyde (54 mg, 0.23 mmol), dichloro(bis{di-tert-butyl[4-(dimethylamino)phenyl]phosphoranyl})palladium (11 mg, 0.015 mmol) and cesium fluoride (70. mg, 0.46 mmol) in tert-butyl alcohol (1.6 mL) and water (0.4 mL) was evacuated then filled with nitrogen. The resulting mixture was stirred at 90° C. for 2 h then cooled to room temperature and diluted with EtOAc, washed with water and brine. The organic layer was dried over $Na_2SO_4$ and concentrated. The residue was purified on a silica gel column. LC-MS calculated for $C_{31}H_{31}N_4O_4$ (M+H)$^+$: m/z=523.2. found 523.2.

Step 2: 4-{5-{4-[(4-methylpiperazin-1-yl)methyl]phenyl}-8-[(3R)-pyrrolidin-3-ylmethoxy]imidazo[1,5-a]pyridin-6-yl}benzonitrile A solution of tert-butyl (3R)-3-({[6-(4-cyanophenyl)-5-(4-formylphenyl)imidazo[1,5-a]pyridin-8-yl]oxy}methyl)pyrrolidine-1-carboxylate (10 mg, 0.02 mmol), 1-methylpiperazine (4.2 µL, 0.038 mmol) in methylene chloride (1 mL) was stirred at room temperature for 30 min then sodium triacetoxyborohydride (12 mg, 0.057 mmol) was added. The resulting mixture was stirred at room temperature overnight then diluted with DCM and washed with saturated NaHCO$_3$ solution and brine. The organic layer was dried over $Na_2SO_4$ and concentrated. The residue was dissolved in methylene chloride (1 mL) then trifluoroacetic acid (0.3 mL) was added. The mixture was stirred at room temperature for 1 h then concentrated. The residue was dissolved in methanol and purified by prep HPLC (pH=2, acetonitrile/water+TFA) to give the desired product as the TFA salt. LC-MS calculated for $C_{31}H_{35}N_6O$ (M+H)$^+$: m/z=507.3. found 507.3.

Example 20

4-(5-(4-methylphenyl)-8-{[(3R)-1-methylpyrrolidin-3-yl]methoxy}imidazo[1,5-a]pyridin-6-yl)benzonitrile

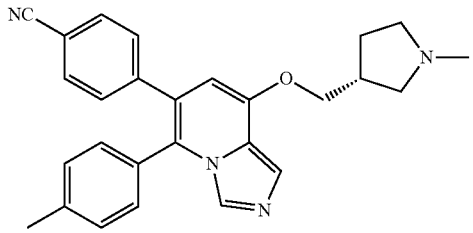

To a solution of 4-{5-(4-methylphenyl)-8-[(3R)-pyrrolidin-3-ylmethoxy]imidazo[1,5-a]pyridin-6-yl}benzonitrile (Example 1: 90 mg, 0.2 mmol) in methylene chloride (3 mL) was added formaldehyde (37 wt % in water, 200 μL, 2 mmol). The resulting mixture was stirred at room temperature for 30 min then sodium triacetoxyborohydride (140 mg, 0.66 mmol) was added. The mixture was stirred at room temperature overnight then diluted with DCM and washed with saturated NaHCO$_3$ and brine. The organic layer was dried over Na$_2$SO$_4$ and concentrated. The residue was dissolved in acetonitrile and purified by prep HPLC (pH=2, acetonitrile/water+TFA) to give the desired product as the TFA salt. LC-MS calculated for $C_{27}H_{27}N_4O$ (M+H)$^+$: m/z=423.2. found 423.3.

Example 21

4-(5-(3-methyl-2-oxo-2,3-dihydro-1,3-benzoxazol-6-yl)-8-{[(3R)-1-methylpiperidin-3-yl]methoxy}imidazo[1,5-a]pyrazin-6-yl)benzonitrile

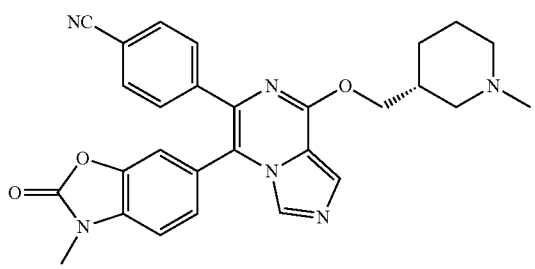 [SMILES: CN1CCC[C@@H](COc2nc(-c3ccc(C#N)cc3)c(-c3ccc4c(c3)oc(=O)n4C)n3cncc23)C1]

Step 1: 5-bromo-6-chloropyrazin-2-ol

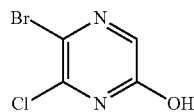

Sodium nitrite (3.6 g, 53 mmol) was added to a solution of 5-bromo-6-chloropyrazin-2-amine [Synnovator Inc, cat#PBN20120512] (10 g, 50 mmol) in sulfuric acid (70. mL) at 0° C. The resulting reaction mixture was stirred at 0° C. for 1 h then ice was slowly added to quench the reaction. The resulting precipitate was collected via filtration, washed with water then dried to give the desired product as off white solid. LC-MS calculated for $C_4H_3BrClN_2O$ (M+H)$^+$: m/z=208.9. found 208.9.

Step 2: 5-bromo-6-chloro-1-(4-methoxybenzyl)pyrazin-2(1H)-one

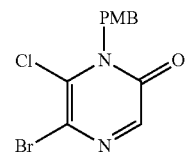

A mixture of calcium hydride powder (800 mg, 20 mmol) and 5-bromo-6-chloropyrazin-2-ol (4 g, 20 mmol) in N,N-dimethylformamide (50 mL) was stirred at 70° C. for 1 h then cooled to room temperature and 4-methoxyphenyl methylbromide (3.0 mL, 21 mmol) was added. The resulting mixture was stirred at 90° C. overnight then cooled to room temperature and diluted with EtOAc, washed with water and brine. The organic layer was dried over Na$_2$SO$_4$, filtered and concentrated. The residue was purified by flash chromatography eluting with 0 to 60% DCM in hexanes to give the desired product. $^1$H NMR (500 MHz, DMSO) δ 7.99 (s, 1H), 7.28-7.18 (m, 2H), 6.93-6.83 (m, 2H), 5.29 (s, 2H), 3.73 (s, 3H).

Step 3: 5-bromo-6-chloro-7-(4-methoxybenzyl)imidazo[1,5-a]pyrazin-8(7H)-one

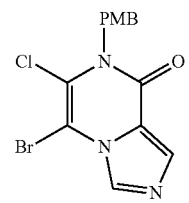

To a suspension of sodium hydride (60 wt % in mineral oil, 1.0 g, 25 mmol) in THF (100 mL) was added a THF (50 mL) solution of 5-bromo-6-chloro-1-(4-methoxybenzyl)pyrazin-2(1H)-one (5.6 g, 17 mmol) and p-tolylsulfonylmethyl isocyanide (3.5 g, 18 mmol) at 0° C. The resulting mixture was stirred at 0° C. for 30 min, then warmed to room temperature and stirring continued for 1 h. The mixture was diluted with EtOAc then washed with water and brine. The organic layer was dried over Na$_2$SO$_4$, filtered and concentrated. The residue was purified by flash chromatography on a silica gel column eluting with 0 to 40% EtOAc in DCM to give the desired product. LC-MS calculated for $C_{14}H_{12}BrClN_3O_2$ (M+H)$^+$: m/z=368.0. found 368.0.

Step 4: 5-bromo-6-chloroimidazo[1,5-a]pyrazin-8-ol

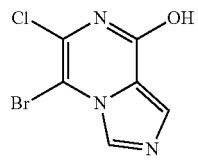 [SMILES: Oc1nc(Cl)c(Br)n2cncc12]

Trifluoromethanesulfonic acid (2 mL, 30 mmol) was added to a mixture of 5-bromo-6-chloro-7-(4-methoxybenzyl)imidazo[1,5-a]pyrazin-8(7H)-one (2.3 g, 6.2 mmol) in trifluoroacetic acid (13 mL, 160 mmol)/anisole (5 mL, 50 mmol). The reaction mixture was stirred at room temperature for 1 h then warmed to 40° C. and the stirring continued for 1 h. The mixture was cooled to room temperature then concentrated. The residue was titurated with diethyl ether and the solid was collected via filtration then washed with pH=1 aqueous HCl solution, ether and dried to give the desired product as a white solid. LC-MS calculated for $C_6H_4BrClN_3O$ $(M+H)^+$: m/z=247.9. found 247.9.

Step 5: tert-butyl (3R)-3-{[(5-bromo-6-chloroimidazo[1,5-a]pyrazin-8-yl)oxy]methyl}piperidine-1-carboxylate

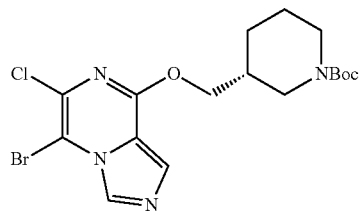

To a mixture of 5-bromo-6-chloroimidazo[1,5-a]pyrazin-8-ol (400 mg, 2 mmol), tert-butyl (3R)-3-(hydroxymethyl)piperidine-1-carboxylate (520 mg, 2.4 mmol) [Synnovator, cat#PB00890: 2.3 g, 11 mmol], and triphenylphosphine (1.06 g, 4.02 mmol) in toluene (8 mL) was added diethyl azodicarboxylate (600 µL, 3.8 mmol) dropwise at 0° C. The resulting mixture was warmed to room temperature and then stirred for 2 h. The mixture was diluted with ethyl acetate, washed with saturated $NaHCO_3$, water and brine. The organic layer was dried over $Na_2SO_4$, filtered and concentrated. The residue was purified by flash chromatography on a silica gel column eluting with 0 to 40% EtOAc in DCM to give the desired product. LC-MS calculated for $C_{13}H_{15}BrClN_4O_3$ $(M-^tBu+H)^+$: m/z=389.0. found 389.0.

Step 6: 5-bromo-6-chloro-8[(3R)-piperidin-3-yl-methoxy]imidazo[1,5-a]pyrazine

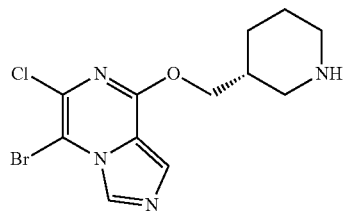 [SMILES: Clc1nc(OC[C@@H]2CCCNC2)c2cncn2c1Br]

4.0 M Hydrogen chloride in 1,4-dioxane (2 mL, 8 mmol) was added to a methylene chloride (1.0 mL) solution of tert-butyl (3R)-3-{[(5-bromo-6-chloroimidazo[1,5-a]pyrazin-8-yl)oxy]methyl}piperidine-1-carboxylate (340 mg, 0.76 mmol). The resulting mixture was stirred at room temperature for 30 min and the precipitate was collected via filtration then dried to give the desired product, which was used in the next step without further purification. LC-MS calculated for $C_{12}H_{15}BrClN_4O$ $(M+H)^+$: m/z=345.0. found 345.0.

Step 7: 5-bromo-6-chloro-8-{[(3R)-1-methylpiperidin-3-yl]methoxy}imidazo[1,5-a]pyrazine

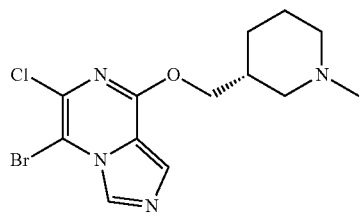 [SMILES: CN1CCC[C@@H](COc2nc(Cl)c(Br)n3cncc23)C1]

7.0 M Formaldehyde in water (1 mL, 8 mmol) was added to a methylene chloride (5 mL) solution of 5-bromo-6-chloro-8-[(3R)-piperidin-3-ylmethoxy]imidazo[1,5-a]pyrazine hydrochloride (crude product from Step 6: 400 mg, 1 mmol) and N,N-diisopropylethylamine (360 µL, 2.1 mmol). The resulting mixture was stirred at room temperature for 30 min then sodium triacetoxyborohydride (440 mg, 2.1 mmol) was added. The reaction mixture was stirred at room temperature for 1 h then diluted with methylene chloride, washed with 1N NaOH, water and brine. The organic layer was dried over $Na_2SO_4$, filtered and concentrated to provide the desired product, which was used in the next step without further purification. LC-MS calculated for $C_{13}H_{17}BrClN_4O$ $(M+H)^+$: m/z=359.0. found 359.0. $^1H$ NMR (400 MHz, $CD_3OD$) δ 8.60 (s, 1H), 7.99 (s, 1H), 4.56 (dd, J=11.1, 4.9 Hz, 1H), 4.44 (dd, J=11.1, 7.0 Hz, 1H), 3.77-3.64 (m, 1H), 3.59-3.49 (m, 1H), 3.03-2.94 (m, 2H), 2.93 (s, 3H), 2.52-2.36 (m, 1H), 2.15-1.95 (m, 2H), 1.95-1.80 (m, 1H), 1.56-1.39 (m, 1H).

Step 8: 3-methyl-6-(4,4,5,5-tetramethyl-1,3,2-dioxaborolan-2-yl)-1,3-benzoxazol-2(3H)-one

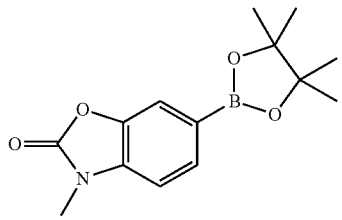

A mixture of [1,1'-bis(diphenylphosphino)ferrocene]dichloropalladium(II), complex with dichloromethane (1:1) (300 mg, 0.3 mmol), 6-bromo-3-methyl-1,3-benzoxazol-2(3H)-one (1.5 g, 6.6 mmol) [Acros, cat#432710050], 4,4,5,5,4',4',5',5'-octamethyl-[2,2']bi[[1,3,2]dioxaborolanyl] (2.5 g, 9.9 mmol) and potassium acetate (2 g, 20 mmol) in 1,4-dioxane (50 mL) was purged with nitrogen then stirred at 90° C. overnight. The reaction mixture was cooled to room temperature then diluted with EtOAc, washed with water and brine. The organic layer was dried over $Na_2SO_4$, filtered and concentrated. The residue was purified by flash chromatography on a silica gel column eluting with 0 to 25% EtOAc in hexanes to give the desired product. LC-MS calculated for $C_{14}H_{19}BNO_4$ (M+H)$^+$: m/z=276.1. found 276.2.

Step 9: 4-(5-(3-methyl-2-oxo-2,3-dihydro-1,3-benzoxazol-6-yl)-8-{[(3R)-1-methylpiperidin-3-yl]methoxy}imidazo[1,5-a]pyrazin-6-yl)benzonitrile A mixture of 5-bromo-6-chloro-8-{[(3R)-1-methylpiperidin-3-yl]methoxy}imidazo[1,5-a]pyrazine (20 mg, 0.06 mmol), 3-methyl-6-(4,4,5,5-tetramethyl-1,3,2-dioxaborolan-2-yl)-1,3-benzoxazol-2(3H)-one (18 mg, 0.067 mmol), tetrakis(triphenylphosphine)palladium(0) (3 mg, 0.003 mmol), and potassium carbonate (23 mg, 0.17 mmol) in 1,4-dioxane (620 µL) and water (100 µL) was purged with nitrogen then stirred at 100° C. for 2 hours. The reaction mixture was cooled to room temperature then (4-cyanophenyl)boronic acid (12 mg, 0.083 mmol), cesium carbonate (36 mg, 0.11 mmol), dichloro[1,1'-bis(dicyclohexylphosphino)ferrocene]palladium(II) (4 mg, 0.006 mmol) and tert-Butyl alcohol (0.5 mL) were added. The mixture was purged with nitrogen and stirred at 90° C. for 1 hour. After cooling to room temperature, the reaction mixture was diluted with methanol, filtered then purified by prep-HPLC (pH=2, acetonitrile/water+TFA) to give the desired product as the TFA salt. LC-MS calculated for $C_{28}H_{27}N_6O_3$ (M+H)$^+$: m/z=495.2. found 495.2. $^1$H NMR (500 MHz, CD$_3$OD) δ 8.30 (s, 1H), 8.03 (s, 1H), 7.63-7.52 (m, 4H), 7.42 (s, 1H), 7.29 (s, 2H), 4.66 (dd, J=11.1, 5.0 Hz, 1H), 4.54 (dd, J=11.1, 6.9 Hz, 1H), 3.81-3.69 (m, 1H), 3.62-3.48 (m, 1H), 3.45 (s, 3H), 3.03-2.95 (m, 2H), 2.94 (s, 3H), 2.55-2.42 (m, 1H), 2.13-1.99 (m, 2H), 1.93-1.80 (m, 1H), 1.57-1.43 (m, 1H).

Example 22

4-(5-(1-methyl-2-oxo-2,3-dihydro-1H-indol-5-yl)-8-{[(3R)-1-methylpiperidin-3-yl]methoxy}imidazo[1,5-a]pyrazin-6-yl)benzonitrile

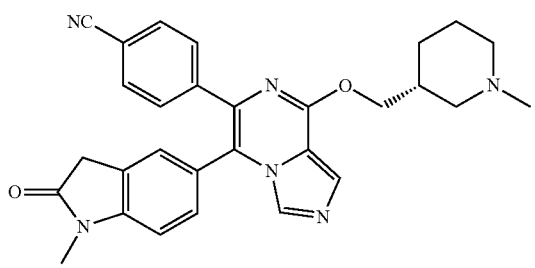 [SMILES: CN1CCC[C@@H](COc2nc(-c3ccc(C#N)cc3)c(-c3ccc4c(c3)CC(=O)N4C)n3cncc23)C1]

Step 1: 1-methyl-5-(4,4,5,5-tetramethyl-1,3,2-dioxaborolan-2-yl)-1,3-dihydro-2H-indol-2-one

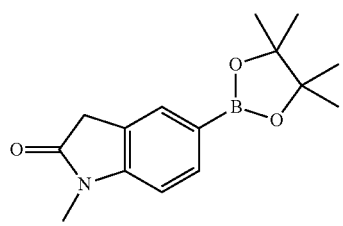 [SMILES: CN1C(=O)Cc2cc(B3OC(C)(C)C(C)(C)O3)ccc21]

A mixture of 5-bromo-1-methyl-1,3-dihydro-2H-indol-2-one (1 g, 4 mmol) [Maybridge, cat#10430564], 4,4,5,5,4',4',5',5'-octamethyl-[2,2']bi[[1,3,2]dioxaborolanyl] (1.7 g, 6.6 mmol), [1,1'-bis(diphenylphosphino)ferrocene]dichloropalladium(II) complexed with dichloromethane (1:1) (200 mg, 0.2 mmol) and potassium acetate (1.3 g, 13 mmol) in 1,4-dioxane (40 mL) was purged with nitrogen and then stirred at 90° C. overnight. After cooling to room temperature, the reaction mixture was concentrated. The residue was purified by flash chromatography eluting with 0 to 25% EtOAc in hexanes to give the desired product. LC-MS calculated for $C_{15}H_{21}BNO_3$ (M+H)$^+$: m/z=274.1. found 274.1.

Step 2: 4-(5-(1-methyl-2-oxo-2,3-dihydro-1H-indol-5-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 1-methyl-5-(4,4,5,5-tetramethyl-1,3,2-dioxaborolan-2-yl)-1,3-dihydro-2H-indol-2-one replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{29}H_{29}N_6O_2$ (M+H)$^+$: m/z=493.2. found 493.2. $^1$H NMR (500 MHz, CD$_3$OD) δ 8.38-8.28 (m, 1H), 8.09-8.00 (m, 1H), 7.63-7.56 (m, 4H), 7.44-7.39 (m, 1H), 7.34 (d, J=7.9 Hz, 1H), 7.10 (d, J=8.1 Hz, 1H), 4.71-4.63 (m, 1H), 4.58-4.51 (m, 1H), 3.80-3.72 (m, 1H), 3.65-3.51 (m, 3H), 3.26 (s, 3H), 3.05-2.95 (m, 2H), 2.94 (s, 3H), 2.57-2.43 (m, 1H), 2.13-2.01 (m, 2H), 1.99-1.80 (m, 1H), 1.58-1.44 (m, 1H).

Example 23

4-(5-(1-methyl-1H-indazol-5-yl)-8-{[(3R)-1-methylpiperidin-3-yl]methoxy}imidazo[1,5-a]pyrazin-6-yl)benzonitrile

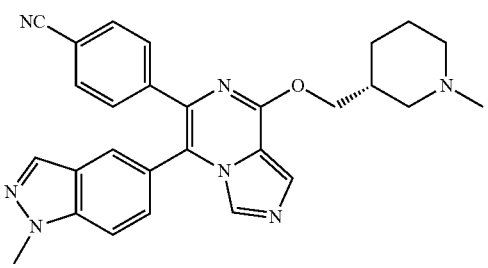 [SMILES: CN1CCC[C@@H](COc2nc(-c3ccc(C#N)cc3)c(-c3ccc4c(cnn4C)c3)n3cncc23)C1]

The title compound was prepared using procedures analogous to those described in Example 21, Step 9 with 1-methyl-5-(4,4,5,5-tetramethyl-1,3,2-dioxaborolan-2-yl)-1H-indazole [Astatech, cat#64501] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{28}N_7O$ (M+H)$^+$: m/z=478.2. found 478.2. $^1$H NMR (400 MHz, CD$_3$OD) δ 8.07 (s, 1H), 7.97 (s, 1H), 7.91 (s, 1H), 7.84 (s, 1H), 7.75 (d, J=8.6 Hz, 1H), 7.59-7.50 (m, 4H), 7.47 (d, J=8.7 Hz, 1H), 4.57 (dd, J=10.9, 5.8 Hz, 1H), 4.48 (dd, J=10.7, 7.3 Hz, 1H), 2.32-2.27 (m, 1H), 4.15 (s, 3H), 3.14-3.05 (m, 1H), 2.93-2.82 (m, 1H), 2.35 (s, 3H), 2.12-1.89 (m, 3H), 1.86-1.77 (m, 1H), 1.76-1.63 (m, 1H), 1.32-1.14 (m, 1H).

Example 24

4-(5-(1-methyl-2-oxo-1,2,3,4-tetrahydroquinolin-6-yl)-8-{[(3R)-1-methylpiperidin-3-yl]methoxy}imidazo[1,5-a]pyrazin-6-yl)benzonitrile

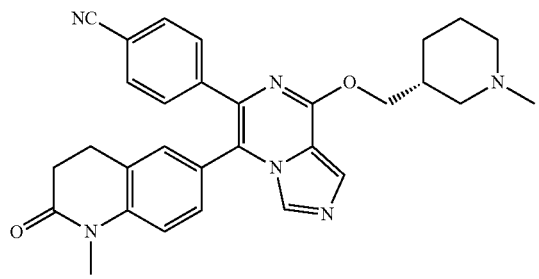

Step 1: 6-bromo-1-methyl-3,4-dihydroquinolin-2(1H)-one

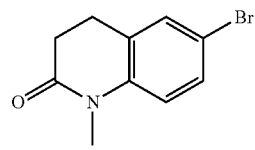

To a mixture of 6-bromo-3,4-dihydroquinolin-2(1H)-one (0.4 g, 2 mmol) [Matrix Scientific, cat#3279-90-1] and potassium carbonate (240 mg, 1.8 mmol) in acetone (8 mL) was added methyl iodide (0.44 mL, 7.1 mmol). The reaction mixture was stirred at 80° C. overnight then cooled to room temperature and concentrated. The residue was dissolved in EtOAc then washed with water and brine. The organic layer was dried over $Na_2SO_4$, filtered and concentrated. The residue was used in the next step without further purification. LC-MS calculated for $C_{10}H_{11}BrNO$ $(M+H)^+$: m/z=240.0. found 240.0.

Step 2: 1-methyl-6-(4,4,5,5-tetramethyl-1,3,2-dioxaborolan-2-yl)-3,4-dihydroquinolin-2(1H)-one

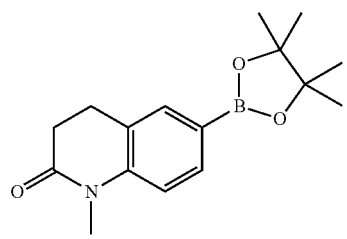 [SMILES: CN1C(=O)CCc2cc(B3OC(C)(C)C(C)(C)O3)ccc21]

A mixture of 6-bromo-1-methyl-3,4-dihydroquinolin-2(1H)-one (0.4 g, 2 mmol), 4,4,5,5,4',4',5',5'-Octamethyl-[2,2']bi[[1,3,2]dioxaborolanyl] (630 mg, 2.5 mmol), [1,1'-Bis(diphenylphosphino)ferrocene]dichloropalladium(II) complexed with dichloromethane (1:1) (70 mg, 0.08 mmol) and potassium acetate (490 mg, 5.0 mmol) in 1,4-dioxane (20 mL) was purged with nitrogen and stirred at 90° C. overnight. After cooling to room temperature, the reaction mixture was concentrated. The residue was purified by flash chromatography eluting with 0 to 35% EtOAc in Hexanes to give the desired product. LC-MS calculated for $C_{16}H_{23}BNO_3$ $(M+H)^+$: m/z=288.2. found 288.1.

Step 3: 4-(5-(1-methyl-2-oxo-1,2,3,4-tetrahydroquinolin-6-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 1-methyl-6-(4,4,5,5-tetramethyl-1,3,2-dioxaborolan-2-yl)-3,4-dihydroquinolin-2(1H)-one replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{30}H_{31}N_6O_2$ $(M+H)^+$: m/z=507.2. found 507.3. $^1$H NMR (400 MHz, $CD_3OD$) δ 8.04 (s, 1H), 7.83 (s, 1H), 7.62-7.59 (m, 4H), 7.39-7.32 (m, 2H), 7.27 (d, J=8.2 Hz, 1H), 4.56 (dd, J=10.9, 5.8 Hz, 1H), 4.46 (dd, J=10.8, 7.3 Hz, 1H), 3.41 (s, 3H), 3.12-3.07 (m, 1H), 2.99-2.84 (m, 3H), 2.75-2.64 (m, 2H), 2.35 (s, 3H), 2.33-2.28 (m, 1H), 2.13-1.89 (m, 3H), 1.87-1.78 (m, 1H), 1.76-1.67 (m, 1H), 1.29-1.16 (m, 1H).

Example 25

4-(5-(4-methyl-3-oxo-3,4-dihydro-2H-1,4-benzoxazin-7-yl)-8-{[(3R)-1-methylpiperidin-3-yl]methoxy}imidazo[1,5-a]pyrazin-6-yl)benzonitrile

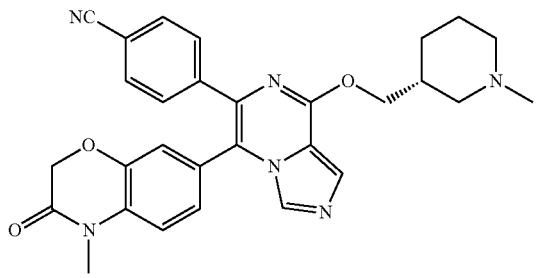 [SMILES: CN1CCC[C@@H](COc2nc(-c3ccc(C#N)cc3)c(-c3ccc4c(c3)OCC(=O)N4C)n3cncc23)C1]

Step 1: 4-methyl-7-(4,4,5,5-tetramethyl-1,3,2-dioxaborolan-2-yl)-2H-1,4-benzoxazin-3(4H)-one

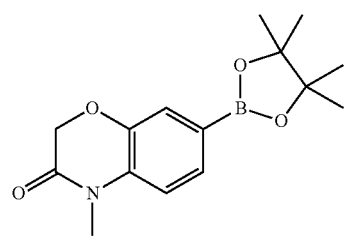 [SMILES: CN1C(=O)COc2cc(B3OC(C)(C)C(C)(C)O3)ccc21]

To a mixture of 7-(4,4,5,5-tetramethyl-1,3,2-dioxaborolan-2-yl)-2H-1,4-benzoxazin-3(4H)-one (0.3 g, 1 mmol) [Ark Pharma, cat#AK-37869] and potassium carbonate (150 mg, 1.1 mmol) in acetone (5 mL) was added methyl iodide (0.20 mL, 3.3 mmol). The resulting mixture was stirred at 80° C. overnight then cooled to room temperature and concentrated. The residue was dissolved in EtOAc, washed with water and brine. The organic layer was dried over Na$_2$SO$_4$, filtered and concentrated. The residue was used in the next step without further purification. LC-MS calculated for C$_{15}$H$_{21}$BNO$_4$ (M+H)$^+$: m/z=290.2. found 290.1.

Step 2: 4-(5-(4-methyl-3-oxo-3,4-dihydro-2H-1,4-benzoxazin-7-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 4-methyl-7-(4,4,5,5-tetramethyl-1,3,2-dioxaborolan-2-yl)-2H-1,4-benzoxazin-3(4H)-one replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for C$_{29}$H$_{29}$N$_6$O$_3$ (M+H)$^+$: m/z=509.2. found 509.2. $^1$H NMR (400 MHz, CD$_3$OD) δ 8.06 (s, 1H), 7.82 (d, J=7.2 Hz, 1H), 7.64-7.58 (m, 4H), 7.29 (d, J=8.7 Hz, 1H), 7.17-7.09 (m, 2H), 4.70 (s, 2H), 4.55 (dd, J=10.9, 5.9 Hz, 1H), 4.46 (dd, J=10.9, 7.3 Hz, 1H), 2.31-2.26 (m, 1H), 3.42 (s, 3H), 3.12-3.03 (m, 1H), 2.92-2.81 (m, 1H), 2.34 (s, 3H), 2.12-1.88 (m, 3H), 1.86-1.76 (m, 1H), 1.76-1.63 (m, 1H), 1.32-1.13 (m, 1H).

Example 26

4-(5-(1,3-dimethyl-2-oxo-2,3-dihydro-1H-benzimidazol-5-yl)-8-{[(3R)-1-methylpiperidin-3-yl]methoxy}imidazo[1,5-a]pyrazin-6-yl)benzonitrile

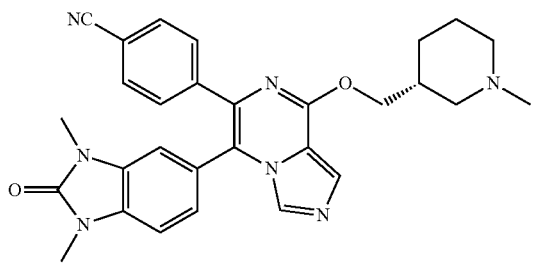 [SMILES: CN1CCC[C@@H](COc2nc(-c3ccc(C#N)cc3)c(-c3ccc4c(c3)n(C)c(=O)n4C)n3cncc23)C1]

Step 1: 5-bromo-1,3-dimethyl-1,3-dihydro-2H-benzimidazol-2-one

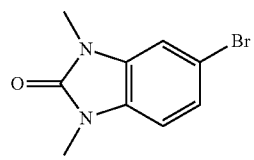

A mixture of 5-bromo-1,3-dihydro-2H-benzimidazol-2-one (0.40 g, 1.9 mmol) [Combi-Blocks, cat#HI-1532], methyl iodide (0.58 mL, 9.4 mmol) and potassium carbonate (520 mg, 3.8 mmol) in acetone (3 mL) was heated at 80° C. for 3 h then cooled to room temperature and diluted with EtOAc. The mixture was washed with water and brine. The organic layer was dried over Na$_2$SO$_4$, filtered and concentrated. The residue was used in the next step without further purification. LC-MS calculated for C$_9$H$_{10}$BrN$_2$O (M+H)$^+$: m/z=241.0. found 241.0.

Step 2: 1,3-dimethyl-5-(4,4,5,5-tetramethyl-1,3,2-dioxaborolan-2-yl)-1,3-dihydro-2H-benzimidazol-2-one

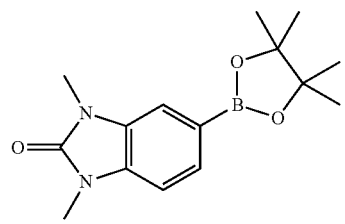 [SMILES: Cn1c(=O)n(C)c2cc(B3OC(C)(C)C(C)(C)O3)ccc21]

A mixture of 5-bromo-1,3-dimethyl-1,3-dihydro-2H-benzimidazol-2-one (crude product from Step 1), 4,4,5,5,4',4',5',5'-Octamethyl-[2,2']bi[[1,3,2]dioxaborolanyl] (680 mg, 2.7 mmol), [1,1'-bis(diphenylphosphino)ferrocene]dichloropalladium(II) complexed with dichloromethane (1:1) (70 mg, 0.09 mmol) and potassium acetate (520 mg, 5.4 mmol) in 1,4-dioxane (20 mL) was purged with nitrogen and stirred at 90° C. overnight. After cooling to room temperature, the reaction mixture was concentrated. The residue was purified by flash chromatography eluting with 0 to 4% MeOH in DCM to give the desired product. LC-MS calculated for C$_{15}$H$_{22}$BN$_2$O$_3$ (M+H)$^+$: m/z=289.2. found 289.2.

Step 3: 4-(5-(1,3-dimethyl-2-oxo-2,3-dihydro-1H-benzimidazol-5-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 1,3-dimethyl-5-(4,4,5,5-tetramethyl-1,3,2-dioxaborolan-2-yl)-1,3-dihydro-2H-benzimidazo 1-2-one replacing 3-methyl-6-(4,4,5,5-tetramethyl-1,3,2-dioxaborolan-2-yl)-1,3-benzoxazol-2(3H)-one. The reaction mixture was purified by prep-HPLC (pH=10, acetonitrile/water+NH$_4$OH) to give the desired product. LC-MS calculated for C$_{29}$H$_{30}$N$_7$O$_2$ (M+H)$^+$: m/z=508.2. found 508.2.

Example 27

4-[8-{[(3R)-1-methylpiperidin-3-yl]methoxy}-5-(1-methyl-1H-pyrazolo[3,4-b]pyridin-5-yl)imidazo[1,5-a]pyrazin-6-yl]benzonitrile

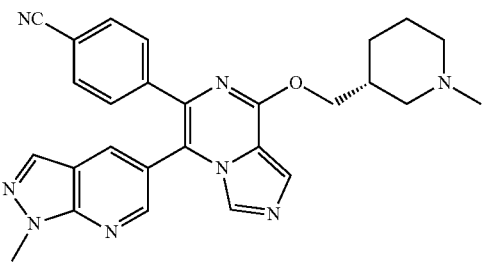

The title compound was prepared using procedures analogous to those described in Example 21, Step 9 with 1-methyl-5-(4,4,5,5-tetramethyl-1,3,2-dioxaborolan-2-yl)-1H-pyrazolo[3,4-b]pyridine [Advanced ChemBlocks Inc, cat#I-9516] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{27}H_{27}N_8O$ (M+H)$^+$: m/z=479.2. found 479.3. $^1$H NMR (500 MHz, CD$_3$OD) δ 8.47-8.41 (m, 2H), 8.25 (s, 1H), 8.16 (s, 1H), 8.01 (s, 1H), 7.61-7.48 (m, 4H), 4.67 (dd, J=10.9, 5.0 Hz, 1H), 4.59-4.50 (m, 1H), 4.14 (s, 3H), 3.80-3.70 (m, 1H), 3.59-3.51 (m, 1H), 3.04-2.95 (m, 2H), 2.94 (s, 3H), 2.55-2.43 (m, 1H), 2.14-2.00 (m, 2H), 1.94-1.79 (m, 1H), 1.59-1.45 (m, 1H).

Example 28

4-(5-(1-methyl-1H-benzimidazol-5-yl)-8-{[(3R)-1-methylpiperidin-3-yl]methoxy}imidazo[1,5-a]pyrazin-6-yl)benzonitrile

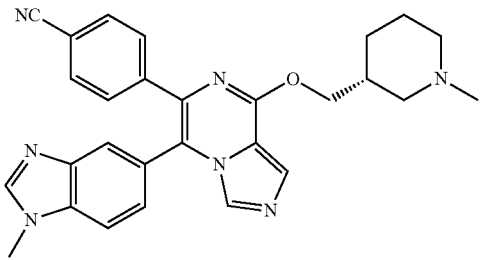 [SMILES: CN1CCC[C@@H](COc2nc(-c3ccc(C#N)cc3)c(-c3ccc4c(c3)ncn4C)n3cncc23)C1]

The title compound was prepared using procedures analogous to those described in Example 21, Step 9 with (1-methyl-1H-benzimidazol-5-yl)boronic acid [Combi-Blocks, cat# FA-4841] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{28}N_7O$ (M+H)$^+$: m/z=478.2. found 478.2.

Example 29

4-(5-(4-methyl-3,4-dihydro-2H-pyrido[3,2-b][1,4]oxazin-7-yl)-8-{[(3R)-1-methylpiperidin-3-yl]methoxy}imidazo[1,5-a]pyrazin-6-yl)benzonitrile

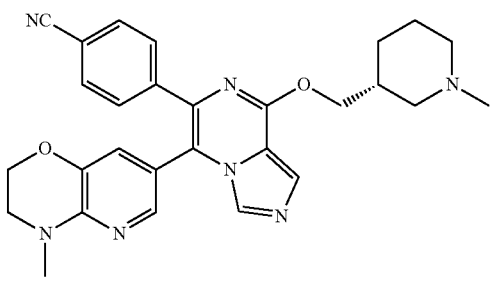 [SMILES: CN1CCC[C@@H](COc2nc(-c3ccc(C#N)cc3)c(-c3cnc4c(c3)OCCN4C)n3cncc23)C1]

Step 1: 4-methyl-7-(4,4,5,5-tetramethyl-1,3,2-dioxaborolan-2-yl)-3,4-dihydro-2H-pyrido[3,2-b][1,4]oxazine

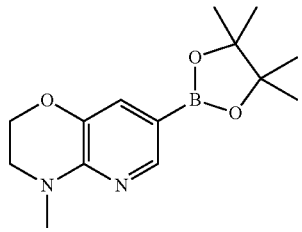 [SMILES: CN1CCOc2cc(B3OC(C)(C)C(C)(C)O3)cnc21]

A mixture of 7-bromo-4-methyl-3,4-dihydro-2H-pyrido[3,2-b][1,4]oxazine (300 mg, 1 mmol) [Maybridge, cat#CC62010], 4,4,5,5,4',4',5',5'-octamethyl-[2,2']bi[[1,3,2]dioxaborolanyl] (660 mg, 2.6 mmol), potassium acetate (380 mg, 3.9 mmol), [1,1'-bis(diphenylphosphino)ferrocene]dichloropalladium(II) complexed with dichloromethane (1:1) (50 mg, 0.06 mmol) in 1,4-dioxane (10 mL, 100 mmol) was purged with nitrogen then heated to 90° C. and stirred overnight. The reaction mixture was cooled to room temperature then concentrated. The residue was purified by flash chromatography on a silica gel column eluting with 0 to 40% EtOAc/DCM to give the desired product. LC-MS calculated for $C_{14}H_{22}BN_2O_3$ (M+H)$^+$: m/z=277.2. found 277.1.

Step 2: 4-(5-(4-methyl-3,4-dihydro-2H-pyrido[3,2-b][1,4]oxazin-7-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 4-methyl-7-(4,4,5,5-tetramethyl-1,3,2-dioxaborolan-2-yl)-3,4-dihydro-2H-pyrido[3,2-b][1,4]oxazine replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{30}N_7O_2$ (M+H)$^+$: m/z=496.2. found 496.2.

Example 30

4-(5-(5-fluoro-3-methyl-2-oxo-2,3-dihydro-1,3-benzoxazol-6-yl)-8-{[(3R)-1-methylpiperidin-3-yl]methoxy}imidazo[1,5-a]pyrazin-6-yl)benzonitrile

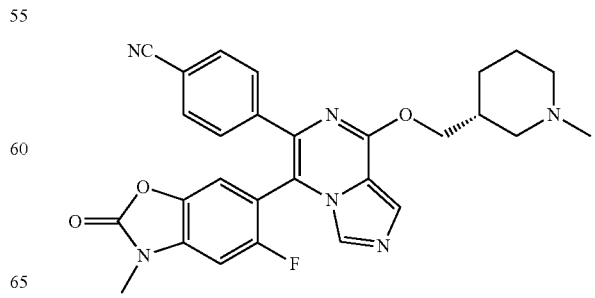

Step 1: 6-bromo-5fluoro-1,3-benzoxazol-2(3H)-one

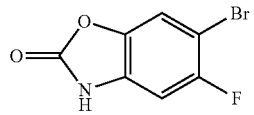

To a mixture of 2-amino-5-bromo-4-fluorophenol (0.3 g, 1 mmol) [Synquest Labs, cat#4656-B-15] and triethylamine (1.0 mL, 7.3 mmol) in tetrahydrofuran (20 mL) at 0° C. was added triphosgene (0.52 g, 1.7 mmol). The mixture was stirred for 1 h, then 1.0 M sodium hydroxide in water (2.9 mL, 2.9 mmol) was added to the reaction mixture. The mixture was stirred at room temperature for another hour then diluted with EtOAc, washed with water and brine. The organic layer was dried over $Na_2SO_4$ and the solvents were removed under reduced pressure. The residue was used for next step directly without purification.

Step 2: 6-bromo-5fluoro-3-methyl-1,3-benzoxazol-2(3H)-one

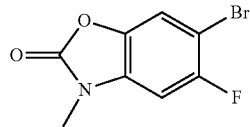

A mixture of 6-bromo-5-fluoro-1,3-benzoxazol-2(3H)-one (crude product from Step 1), potassium carbonate (0.4 g, 3 mmol) and methyl iodide (0.2 mL, 3 mmol) in acetone (5 mL) was heated at 80° C. overnight. The reaction mixture was cooled to room temperature then concentrated. The residue was dissolved in EtOAc then washed with water and brine. The organic layer was dried over $Na_2SO_4$, filtered then concentrated. The residue was purified by flash chromatography on a silica gel column eluting with 0 to 25% EtOAc in Hexanes. LC-MS calculated for $C_8H_6BrFNO_2$ (M+H)$^+$: m/z=246.0. found 245.9.

Step 3: 5-fluoro-3-methyl-6-(4,4,5,5-tetramethyl-1,3,2-dioxaborolan-2-yl)-1,3-benzoxazol-2(3H)-one

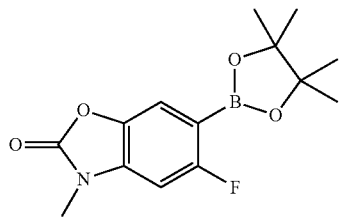 [SMILES: Cn1c(=O)oc2cc(B3OC(C)(C)C(C)(C)O3)c(F)cc21]

A mixture of 6-bromo-5-fluoro-3-methylbenzo[d]oxazol-2(3H)-one (290 mg, 1.2 mmol), 4,4,5,5,4',4',5',5'-Octamethyl-[2,2']bi[[1,3,2]dioxaborolanyl] (450 mg, 1.8 mmol), [1,1'-Bis(diphenylphosphino)ferrocene]dichloropalladium (II) complex with dichloromethane (1:1) (50 mg, 0.06 mmol), potassium acetate (350 mg, 3.5 mmol) in 1,4-dioxane (10 mL) was purged with nitrogen and heated at 90° C. for 5 h. After cooling to room temperature, the reaction mixture was concentrated and the residue was purified by column chromatography eluting with 0 to 30% EtOAc in hexanes to give the desired product. LC-MS calculated for $C_{14}H_{18}BFNO_4$ (M+H)$^+$: m/z=294.1. found 294.1.

Step 4: 4-(5-(5-fluoro-3-methyl-2-oxo-2,3-dihydro-1,3-benzoxazol-6-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 5-fluoro-3-methyl-6-(4,4,5,5-tetramethyl-1,3,2-dioxaborolan-2-yl)-1,3-benzoxazol-2(3H)-one replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{26}FN_6O_3$ (M+H)$^+$: m/z=513.2. found 513.2.

Example 31

4-(8-{[(3R)-1-methylpiperidin-3-yl]methoxy}-5-quinolin-6-ylimidazo[1,5-a]pyrazin-6-yl)benzonitrile

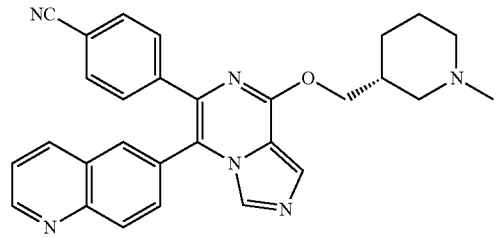 [SMILES: CN1CCC[C@@H](COc2nc(-c3ccc(C#N)cc3)c(-c3ccc4ncccc4c3)n3cncc23)C1]

The title compound was prepared using procedures analogous to those described in Example 21, Step 9 with 6-(4,4,5,5-tetramethyl-1,3,2-dioxaborolan-2-yl)quinoline [Sigma-Aldrich, cat#641618] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{29}H_{27}N_6O$ (M+H)$^+$: m/z=475.2. found 475.2.

Example 32

4-(5-(1,3-dimethyl-1H-indazol-5-yl)-8-{[(3R)-1-methylpiperidin-3-yl]methoxy}imidazo[1,5-a]pyrazin-6-yl)benzonitrile

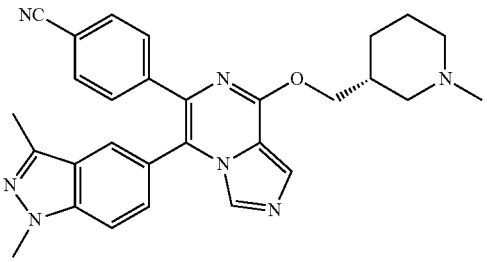

Step 1: 3-methyl-5-(4,4,5,5-tetramethyl-1,3,2-dioxaborolan-2-yl)-1H-indazole

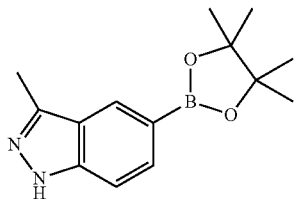 [SMILES: Cc1n[nH]c2ccc(B3OC(C)(C)C(C)(C)O3)cc12]

A mixture of (3-methyl-1H-indazol-5-yl)boronic acid (50 mg, 0.3 mmol) [Oakwood Chemical, cat#092597], 2,3-dimethyl-2,3-butanediol (50. mg, 0.43 mmol), 4.0 M Hydrogen chloride in dioxane (0.1 mL, 0.6 mmol) and magnesium sulfate (200 mg, 2 mmol) was stirred at room temperature overnight. The reaction mixture was filtered and concentrated. The residue was used in the next step without further purification.

Step 2: 1,3-dimethyl-5-(4,4,5,5-tetramethyl-1,3,2-dioxaborolan-2-yl)-1H-indazole

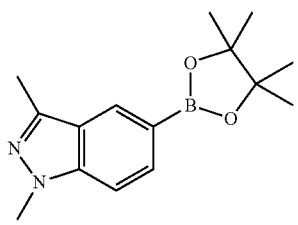 [SMILES: Cc1nn(C)c2ccc(B3OC(C)(C)C(C)(C)O3)cc12]

3-Methyl-5-(4,4,5,5-tetramethyl-1,3,2-dioxaborolan-2-yl)-1H-indazole (crude product from Step 1) was dissolved in acetone (2 mL) then potassium carbonate (100 mg, 0.8 mmol) and methyl iodide (40 µL, 0.6 mmol) were added. The resulting mixture was stirred at 75° C. for 7 h then cooled to room temperature and concentrated. The residue was purified by flash chromatography eluting with 0 to 5% MeOH in DCM to afford desired product. LC-MS calculated for $C_{15}H_{22}BN_2O_2$ (M+H)$^+$: m/z=273.2. found 273.2.

Step 3: 4-(5-(1,3-dimethyl-1H-indazol-5-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 1,3-dimethyl-5-(4,4,5,5-tetramethyl-1,3,2-dioxaborolan-2-yl)-1H-indazole replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{29}H_{30}N_7O$ (M+H)$^+$: m/z=492.2. found 492.2.

Example 33

4-(5-(1,3-benzothiazol-6-yl)-8-{[(3R)-1-methylpiperidin-3-yl]methoxy}imidazo[1,5-a]pyrazin-6-yl)benzonitrile

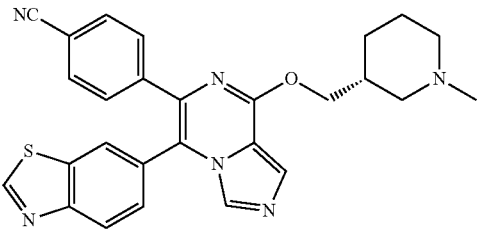 [SMILES: CN1CCC[C@@H](COc2nc(-c3ccc(C#N)cc3)c(-c3ccc4ncsc4c3)n3cncc23)C1]

The title compound was prepared using procedures analogous to those described in Example 21, Step 9 with 6-(4,4,5,5-tetramethyl-1,3,2-dioxaborolan-2-yl)-1,3-benzothiazole [Combi-Blocks, cat#PN-6022] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{27}H_{25}N_6OS$ (M+H)$^+$: m/z=481.2. found 481.2.

Example 34

(R)-4-(5-(benzo[d]thiazol-5-yl)-8-((1-methylpiperidin-3-yl)methoxy)imidazo[1,5-a]pyrazin-6-yl)benzonitrile

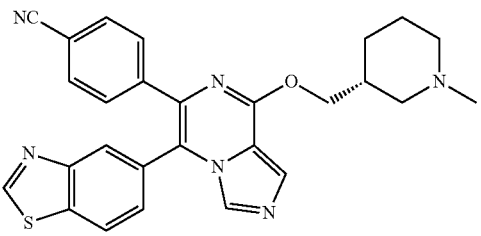 [SMILES: CN1CCC[C@@H](COc2nc(-c3ccc(C#N)cc3)c(-c3ccc4scnc4c3)n3cncc23)C1]

The title compound was prepared using procedures analogous to those described in Example 21, Step 9 with 5-(4,4,5,5-tetramethyl-1,3,2-dioxaborolan-2-yl)-1,3-benzothiazole [Combi-Blocks, cat#PN-8787] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product. LC-MS calculated for $C_{27}H_{25}N_6OS$ (M+H)$^+$: m/z=481.2. found 481.1.

Example 35

4-(5-(2-methyl-1,3-benzothiazol-5-yl)-8-{[(3R)-1-methylpiperidin-3-yl]methoxy}imidazo[1,5-a]pyrazin-6-yl)benzonitrile

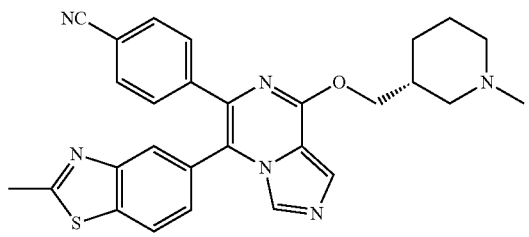

The title compound was prepared using procedures analogous to those described in Example 21, Step 9 with (2-methyl-1,3-benzothiazol-5-yl)boronic acid [Combi-Blocks, cat#BB-5679] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{27}N_6OS$ (M+H)$^+$: m/z=495.2. found 495.1.

Example 36

2-fluoro-4-[8-{[(3R)-1-methylpiperidin-3-yl]methoxy}-5-(1-methyl-1H-pyrazolo[3,4-b]pyridin-5-yl)imidazo[1,5-a]pyrazin-6-yl]benzonitrile

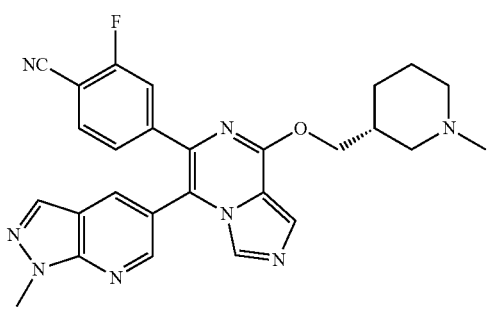 [SMILES: CN1CCC[C@@H](COc2nc(-c3ccc(C#N)c(F)c3)c(-c3cnc4c(cnn4C)c3)n3cncc23)C1]

The title compound was prepared using procedures analogous to those described in Example 21, Step 9 with 1-methyl-5-(4,4,5,5-tetramethyl-1,3,2-dioxaborolan-2-yl)-1H-pyrazolo[3,4-b]pyridine [Advanced ChemBlocks Inc, cat#I-9516] replacing 3-methyl-6-(4,4,5,5-tetramethyl-1,3,2-dioxaborolan-2-yl)-1,3-benzoxazol-2(3H)-one, and with (4-cyano-3-fluorophenyl)boronic acid [Combi-Blocks, PN-3408] replacing (4-cyanophenyl)boronic acid. The reaction mixture was purified by prep-HPLC (pH=2, acetonitrile/water+TFA) to give the desired product as the TFA salt. LC-MS calculated for $C_{27}H_{26}FN_8O$ (M+H)$^+$: m/z=497.2. found 497.1.

Example 37

4-[8-{[(3R)-1-(2-hydroxyethyl)piperidin-3-yl]methoxy}-5-(1-methyl-1H-pyrazolo[3,4-b]pyridin-5-yl)imidazo[1,5-a]pyrazin-6-yl]benzonitrile

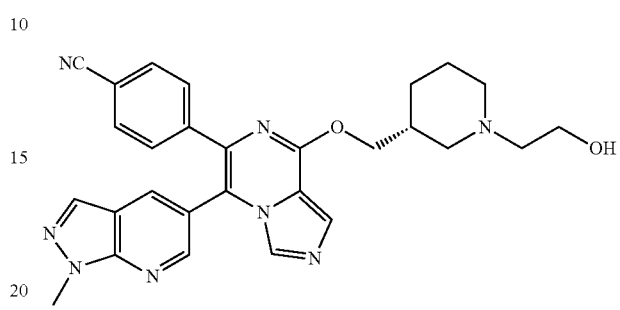

Step 1: tert-butyl (3R)-3-({[6-(4-cyanophenyl)-5-(1-methyl-1H-pyrazolo[3,4-b]pyridin-5-yl)imidazo[1,5-a]pyrazin-8-yl]oxy}methyl)piperidine-1-carboxylate

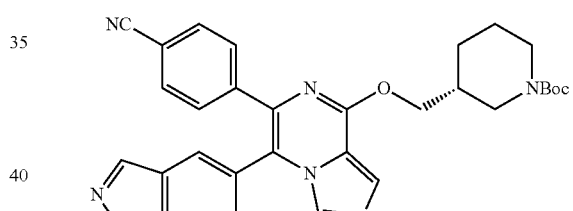

A mixture of tert-butyl (3R)-3-{[(5-bromo-6-chloroimidazo[1,5-a]pyrazin-8-yl)oxy]methyl}piperidine-1-carboxylate (Example 21, Step 5: 140 mg, 0.31 mmol), 1-methyl-5-(4,4,5,5-tetramethyl-1,3,2-dioxaborolan-2-yl)-1H-pyrazolo[3,4-b]pyridine (98 mg, 0.38 mmol) [Advanced ChemBlocks Inc, cat#I-9516], tetrakis(triphenylphosphine)palladium(0) (20 mg, 0.02 mmol) and potassium carbonate (130 mg, 0.94 mmol) in 1,4-dioxane (3.5 mL) and water (0.7 mL) was purged with nitrogen and then stirred at 100° C. for 2 hours. After cooling to room temperature, (4-cyanophenyl)boronic acid (69 mg, 0.47 mmol), dichloro[1,1'-bis(dicyclohexylphosphino)ferrocene]palladium(II) (20 mg, 0.03 mmol), and cesium carbonate (200 mg, 0.63 mmol) and tert-butyl alcohol (3 mL) were added the reaction mixture. The resulting mixture was purged with nitrogen and stirred at 90° C. for 1 hour. After cooling to room temperature, the mixture was concentrated and purified by flash chromatography eluting with 0 to 5% MeOH in DCM to give the desired product. LC-MS calculated for $C_{31}H_{32}N_8O_3$ (M+H)$^+$: m/z=565.2. found 565.3.

Step 2: 4-{5-(1-methyl-1H-pyrazolo[3,4-b]pyridin-5-yl)-8-[(3R)-piperidin-3-ylmethoxy]imidazo[1,5-c]pyrazin-6-yl}benzonitrile

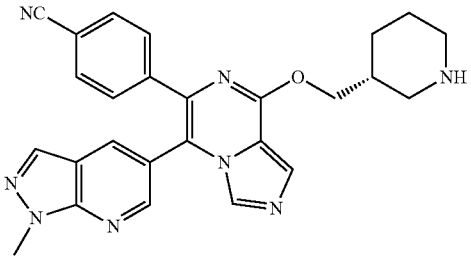

4.0 M Hydrogen chloride in dioxane (0.5 mL, 2 mmol) was added to a DCM (2 mL) solution of tert-butyl (3R)-3-({[6-(4-cyanophenyl)-5-(1-methyl-1H-pyrazolo[3,4-b]pyridin-5-yl) imidazo[1,5-a]pyrazin-8-yl]oxy}methyl)piperidine-1-carboxylate (0.2 mmol). The resulting mixture was stirred at room temperature for 30 min then concentrated. The residue was used in the next step without further purification. LC-MS calculated for $C_{26}H_{25}N_8O$ (M+H)$^+$: m/z=465.2. found 465.2.

Step 3: 4-[8-{[(3R)-1-(2-hydroxyethyl)piperidin-3-yl]methoxy}-5-(1-methyl-M-pyrazolo[3,4-b]pyridin-5-yl)imidazo[1,5-a]pyrazin-6-yl]benzonitrile 2-Bromoethanol (7 μL, 0.1 mmol) was added to a THF (1 mL) solution of 4-{5-(1-methyl-1H-pyrazolo[3,4-b]pyridin-5-yl)-8-[(3R)-piperidin-3-ylmethoxy]imidazo[1,5-a]pyrazin-6-yl}benzonitrile hydrochloride (10 mg, 0.02 mmol) and potassium carbonate (30 mg, 0.2 mmol). Then the reaction mixture was stirred at 45° C. for 2 h then cooled to room temperature, diluted with methanol and purified by prep-HPLC (pH=2, acetonitrile/water+TFA) to give the desired product as the TFA salt. LC-MS calculated for $C_{28}H_{29}N_8O_2$ (M+H)$^+$: m/z=509.2. found 509.2.

Example 38

4-[8-{[(3R)-1-(2-cyanoethyl)piperidin-3-yl]methoxy}-5-(1-methyl-1H-pyrazolo[3,4-b]pyridin-5-yl)imidazo[1,5-a]pyrazin-6-yl]benzonitrile

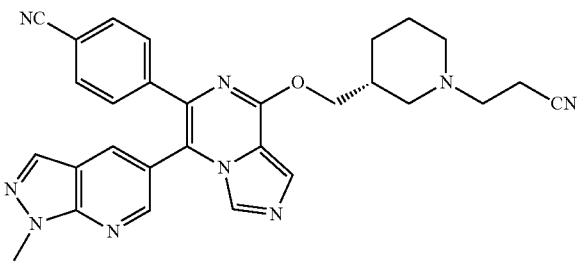 [SMILES: Cn1ncc2cc(-c3c(-c4ccc(C#N)cc4)nc(OC[C@@H]4CCCN(CCO)C4)c4cncn34)cnc21]

2-Propenenitrile (2.0 μL, 0.030 mmol) was added to a DMF (1 mL) solution of 4-{5-(1-methyl-1H-pyrazolo[3,4-b]pyridin-5-yl)-8-[(3R)-piperidin-3-ylmethoxy]imidazo[1,5-a]pyrazin-6-yl}benzonitrile hydrochloride (Example 37, Step 2: 10 mg, 0.02 mmol) and 1,8-diazabicyclo[5.4.0]undec-7-ene (9 μL, 0.06 mmol). The mixture was stirred at room temperature overnight then diluted with methanol and purified by prep-HPLC (pH=2, acetonitrile/water+TFA) to give the desired product as the TFA salt. LC-MS calculated for $C_{29}H_{28}N_9O$ (M+H)$^+$: m/z=518.2. found 518.2.

Example 39

4-[8-{[(3R)-1-(2-hydroxypropyl)piperidin-3-yl]methoxy}-5-(1-methyl-1H-pyrazolo[3,4-b]pyridin-5-yl)imidazo[1,5-a]pyrazin-6-yl]benzonitrile

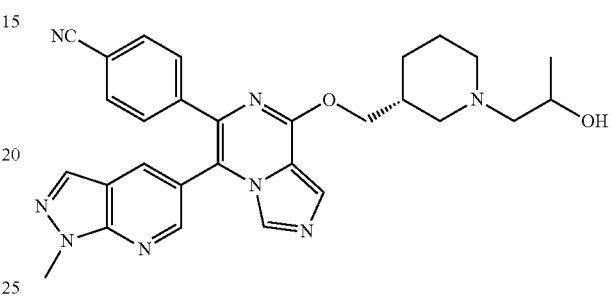

The title compound was prepared using procedures analogous to those described in Example 37, Step 3 with 1-bromopropan-2-ol replacing 2-bromoethanol. The reaction mixture was purified by prep-HPLC (pH=2, acetonitrile/water+TFA) to give the desired product (a mixture of two diastereomers) as the TFA salt. LC-MS calculated for $C_{29}H_{31}N_8O_2$ (M+H)$^+$: m/z=523.2. found 523.2.

Example 40

4-[8-{[(3R)-1-(2-methoxyethyl)piperidin-3-yl]methoxy}-5-(1-methyl-1H-pyrazolo[3,4-b]pyridin-5-yl)imidazo[1,5-a]pyrazin-6-yl]benzonitrile

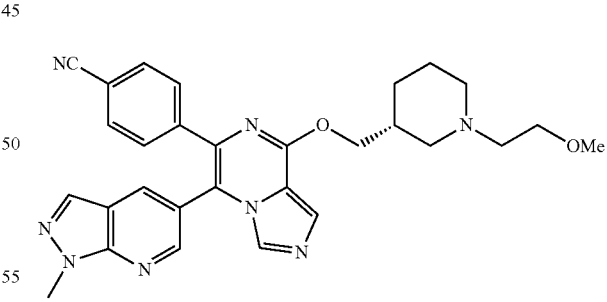

The title compound was prepared using procedures analogous to those described in Example 37, Step 3 with 1-bromo-2-methoxyethane replacing 2-bromoethanol. The reaction mixture was purified by prep-HPLC (pH=2, acetonitrile/water+TFA) to give the desired product as the TFA salt. LC-MS calculated for $C_{29}H_{31}N_8O_2$ (M+H)$^+$: m/z=523.2. found 523.3.

Example 41

4-[8-{[(3R)-1-(2-hydroxy-2-methylpropyl)piperidin-3-yl]methoxy}-5-(1-methyl-1H-pyrazolo[3,4-b]pyridin-5-yl)imidazo[1,5-a]pyrazin-6-yl]benzonitrile

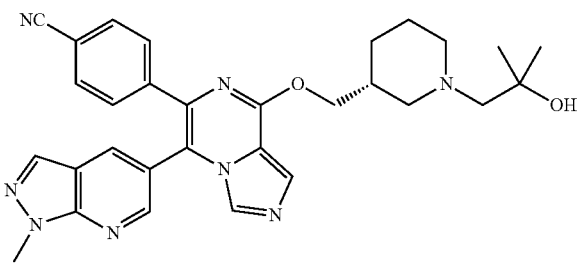 [SMILES: Cn1ncc2cc(-c3c(-c4ccc(C#N)cc4)nc(OC[C@@H]4CCCN(CC(C)(C)O)C4)c4cncn34)cnc21]

Oxirane, 2,2-dimethyl-(3 μL, 0.04 mmol) was added to a MeOH (1 mL) solution of 4-{5-(1-methyl-1H-pyrazolo[3,4-b]pyridin-5-yl)-8-[(3R)-piperidin-3-ylmethoxy]imidazo[1,5-a]pyrazin-6-yl}benzonitrile hydrochloride (Example 37, Step 2; 10 mg, 0.02 mmol), N,N-diisopropylethylamine (10 μL, 0.06 mmol), and the resulting mixture was allowed to stir at room temperature overnight. The reaction mixture was diluted with methanol then purified by prep-HPLC (pH=2, acetonitrile/water+TFA) to give the desired product as the TFA salt. LC-MS calculated for $C_{30}H_{33}N_8O_2$ (M+H)$^+$: m/z=537.2. found 537.2.

Example 42

4-(5-[3-(hydroxymethyl)-4-methylphenyl]-8-{[(3R)-1-methylpiperidin-3-yl]methoxy}imidazo[1,5-a]pyrazin-6-yl)benzonitrile

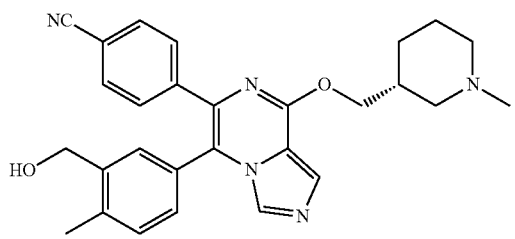 [SMILES: Cc1ccc(-c2c(-c3ccc(C#N)cc3)nc(OC[C@@H]3CCCN(C)C3)c3cncn23)cc1CO]

The title compound was prepared using procedures analogous to those described in Example 21, Step 9 with [2-methyl-5-(4,4,5,5-tetramethyl-1,3,2-dioxaborolan-2-yl)phenyl]methanol (Combi-Blocks, cat#FM-2080) replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{30}N_5O_2$ (M+H)$^+$: m/z=468.2. found 468.2.

Example 43

4-(5-(5-fluoro-6-methoxypyridin-3-yl)-8-{[(3R)-1-methylpiperidin-3-yl]methoxy}imidazo[1,5-a]pyrazin-6-yl)benzonitrile

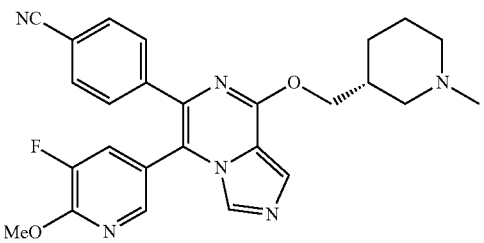 [SMILES: COc1ncc(-c2c(-c3ccc(C#N)cc3)nc(OC[C@@H]3CCCN(C)C3)c3cncn23)cc1F]

The title compound was prepared using procedures analogous to those described in Example 21, Step 9 with (5-fluoro-6-methoxypyridin-3-yl)boronic acid [Combi-Blocks, cat#BB-5725] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{26}H_{26}FN_6O_2$(M+H)$^+$: m/z=473.2. found 473.2.

Example 44

4-(5-[3-fluoro-4-(hydroxymethyl)-5-methylphenyl]-8-{[(3R)-1-methylpiperidin-3-yl]methoxy}imidazo[1,5-a]pyrazin-6-yl)benzonitrile

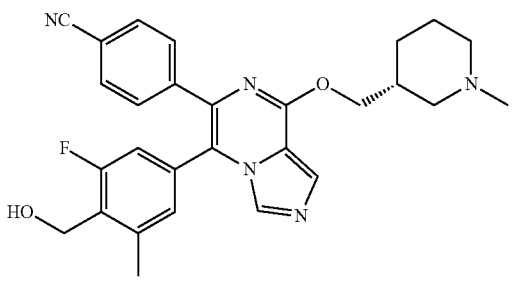 [SMILES: Cc1cc(-c2c(-c3ccc(C#N)cc3)nc(OC[C@@H]3CCCN(C)C3)c3cncn23)cc(F)c1CO]

Step 1: [2-fluoro-6-methyl-4-(4,4,5,5-tetramethyl-1,3,2-dioxaborolan-2-yl)phenyl]methanol

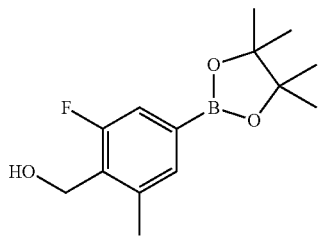 [SMILES: Cc1cc(B2OC(C)(C)C(C)(C)O2)cc(F)c1CO]

A mixture of (4-bromo-2-fluoro-6-methylphenyl)methanol (Oxchem, cat#AX8271172: 109 mg, 0.498 mmol), potassium acetate (150 mg, 1.5 mmol), [1,1'-bis(diphenylphosphino)ferrocene]dichloropalladium(II) complexed with dichloromethane (1:1) (20 mg, 0.02 mmol) and 4,4,5,5,4',4',5',5'-octamethyl-[2,2']bi[[1,3,2] dioxaborolanyl] (190 mg, 0.75 mmol) in 1,4-dioxane (2.3 mL) was purged with nitrogen then stirred at 100° C. overnight. The reaction mixture was cooled to room temperature, diluted with ethyl acetate, filtered through celite, then concentrated. The residue was used in the next step without further purification. LC-MS calculated for $C_{14}H_{19}BFO_2(M+H—H_2O)^+$: m/z=249.1. found 249.1.

Step 2: 4-(5-[3-fluoro-4-(hydroxymethyl)-5-methyl-phenyl]-8-{[(3R)-1-methylpiperidin-3-yl]methoxy}imidazo[1,5-a]pyrazin-6-yl)benzonitrile The title compound was prepared using procedures analogous to those described in Example 21, Step 9 with [2-fluoro-6-methyl-4-(4,4,5,5-tetramethyl-1,3,2-dioxaborolan-2-yl)phenyl]methanol replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{29}FN_5O_2$ $(M+H)^+$: m/z=486.2. found 486.3.

Example 45

4-(5-[4-(hydroxymethyl)-3-methylphenyl]-8-{[(3R)-1-methylpiperidin-3-yl]methoxy}imidazo[1,5-a]pyrazin-6-yl)benzonitrile

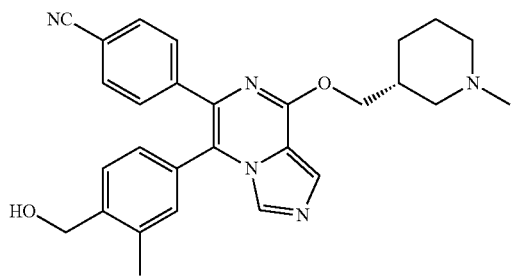 [SMILES: Cc1cc(-c2c(-c3ccc(C#N)cc3)nc(OC[C@@H]3CCCN(C)C3)c3cncn23)ccc1CO]

The title compound was prepared using procedures analogous to those described in Example 21, Step 9 with [4-(hydroxymethyl)-3-methylphenyl]boronic acid [Combi-Blocks, cat#BB-9056] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{30}N_5O_2$ $(M+H)^+$: m/z=468.2. found 468.2.

Example 46

Methyl[4-(6-(4-cyanophenyl)-8-{[(3R)-1-methylpiperidin-3-yl]methoxy}imidazo[1,5-a]pyrazin-5-yl)phenyl]methylcarbamate

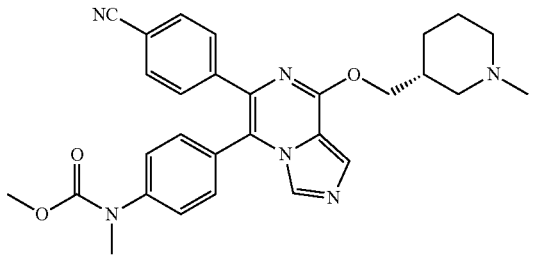

Step 1: methyl methyl[4-(4,4,5,5-tetramethyl-1,3,2-dioxaborolan-2-yl)phenyl]carbamate

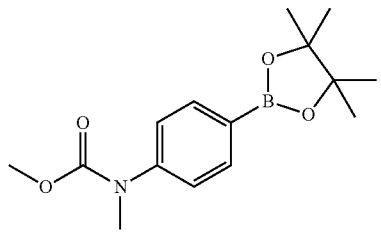

N-methyl-4-(4,4,5,5-tetramethyl-1,3,2-dioxaborolan-2-yl)aniline (100 mg, 0.45 mmol) [Ark Pharma, cat# AK-85506] was dissolved in methylene chloride (2.0 mL) then N,N-diisopropylethylamine (0.20 mL, 1.1 mmol) was added, followed by dropwise addition of methyl chloroformate (52 μL, 0.67 mmol). The resulting mixture was stirred at room temperature for 2 h then diluted with DCM and washed with 0.1 M HCl, water and brine. The organic layer was dried over $Na_2SO_4$, filtered and concentrated. The residue was used in the next step without further purification. LC-MS calculated for $C_{15}H_{23}BNO_4$ $(M+H)^+$: m/z=292.2. found 292.2.

Step 2: Methyl[4-(6-(4-cyanophenyl)-8-{[(3R)-1-methylpiperidin-3-yl]methoxy}imidazo[1,5-a]pyrazin-5-yl)phenyl]methylcarbamate The title compound was prepared using procedures analogous to those described in Example 21, Step 9 with methyl methyl[4-(4,4,5,5-tetramethyl-1,3,2-dioxaborolan-2-yl)phenyl]carbamate replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{29}H_{31}N_6O_3(M+H)^+$: m/z=511.2. found 511.2.

Example 47

4-(5-[3,5-difluoro-4-(hydroxymethyl)phenyl]-8-{[(3R)-1-methylpiperidin-3-yl]methoxy}imidazo[1,5-a]pyrazin-6-yl)benzonitrile

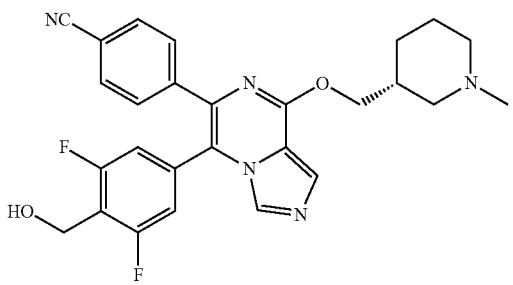 [SMILES: CN1CCC[C@@H](COc2nc(-c3ccc(C#N)cc3)c(-c3cc(F)c(CO)c(F)c3)n3cncc23)C1]

The title compound was prepared using procedures analogous to those described in Example 21, Step 9 with [3,5-difluoro-4-(hydroxymethyl)phenyl]boronic acid (Combi-Blocks, cat#BB-8390) replacing 3-methyl-6-(4,4,5,5-tetramethyl-1,3,2-dioxaborolan-2-yl)-1,3-benzoxazol-2 (3H)-one. The reaction mixture was purified by prep-HPLC (pH=2, acetonitrile/water+TFA) to give the desired product as the TFA salt. LC-MS calculated for $C_{27}H_{26}F_2N_5O_2$ (M+H)$^+$: m/z=490.2. found 490.2.

Example 48 methyl[4-(6-(4-cyanophenyl)-8-{[(3R)-1-methylpiperidin-3-yl]methoxy}imidazo[1,5-a]pyrazin-5-yl)-2-fluorobenzyl]methylcarbamate

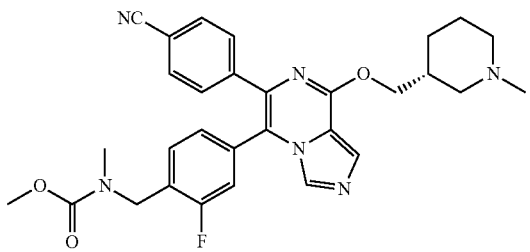

Step 1: 1-[2-fluoro-4-(4,4,5,5-tetramethyl-1,3,2-dioxaborolan-2-yl)phenyl]-N-methylmethanamine

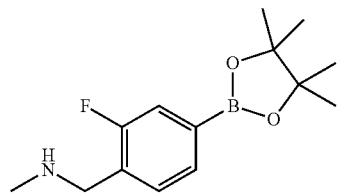

To a solution of 2.0 M methylamine in tetrahydrofuran (3 mL, 6 mmol) was added dropwise a solution of 2-[4-(bromomethyl)-3-fluorophenyl]-4,4,5,5-tetramethyl-1,3,2-dioxaborolane (Combi-Blocks, cat# PN-5654: 200 mg, 0.6 mmol) in tetrahydrofuran (10 mL). The reaction mixture was stirred at room temperature for 2 h, then concentrated. The crude product was used in the next step without further purification.

Step 2: methyl [2-fluoro-4-(4,4,5,5-tetramethyl-1,3,2-dioxaborolan-2-yl)benzyl]methylcarbamate

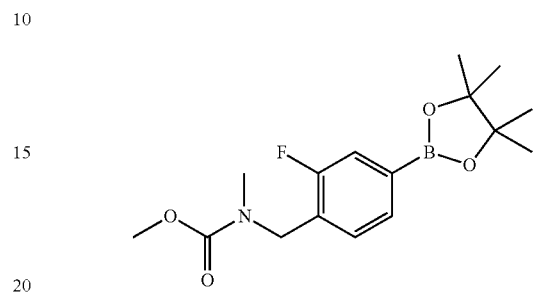

To a solution of 1-[2-fluoro-4-(4,4,5,5-tetramethyl-1,3,2-dioxaborolan-2-yl)phenyl]-N-methylmethanamine (40 mg, 0.2 mmol) and N,N-diisopropylethylamine (0.056 mL, 0.32 mmol) in methylene chloride (2 mL) was added methyl chloroformate (19 µL, 0.24 mmol). The reaction was stirred at room temperature for 2 h, then concentrated. The crude product was used in the next step without further purification. LC-MS calculated for $C_{16}H_{24}BFNO_4$ (M+H)$^+$: m/z=324.2. found 324.2.

Step 3: methyl [4-(6-(4-cyanophenyl)-8-{[(3R)-1-methylpiperidin-3-yl]methoxy}imidazo[1,5-a]pyrazin-5-yl)-2-fluorobenzyl]methylcarbamate The title compound was prepared using procedures analogous to those described in Example 21, Step 9 with methyl [2-fluoro-4-(4,4,5,5-tetramethyl-1,3,2-dioxaborolan-2-yl)benzyl]methylcarbamate replacing 3-methyl-6-(4,4,5,5-tetramethyl-1,3,2-dioxaborolan-2-yl)-1,3-benzoxazol-2 (3H)-one. The reaction mixture was purified by prep-HPLC (pH=2, acetonitrile/water+TFA) to give the desired product as the TFA salt. LC-MS calculated for $C_{30}H_{32}FN_6O_3$(M+H)$^+$: m/z=543.2. found 543.3.

Example 49 methyl[5-(6-(4-cyanophenyl)-8-{[(3R)-1-methylpiperidin-3-yl]methoxy}imidazo[1,5-a]pyrazin-5-yl)pyridin-2-yl]methylcarbamate

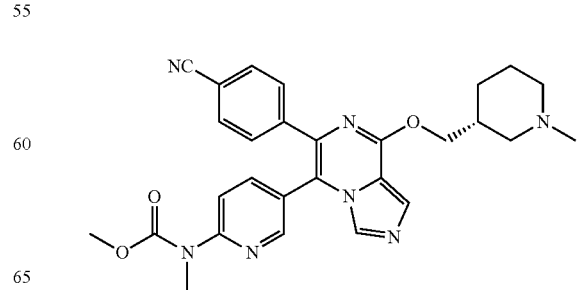

Step 1: methyl (5-bromopyridin-2-yl)methylcarbamate

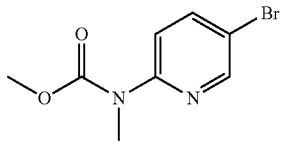

To a solution of 5-bromo-N-methylpyridin-2-amine (Combi-Blocks, cat# PY-1235: 138 mg, 0.738 mmol) in tetrahydrofuran (4 mL) was added cesium carbonate (288 mg, 0.885 mmol) and methyl chloroformate (285 μL, 3.69 mmol). The resulting mixture was heated for 12 h at 50° C., then diluted with ethyl acetate, filtered, and concentrated. The crude product was used without further purification. LC-MS calculated for $C_8H_{10}BrN_2O_2$ (M+H)$^+$: m/z=245.0. found 245.0.

Step 2: methyl methyl[5-(4,4,5,5-tetramethyl-1,3,2-dioxaborolan-2-yl)pyridin-2-yl]carbamate

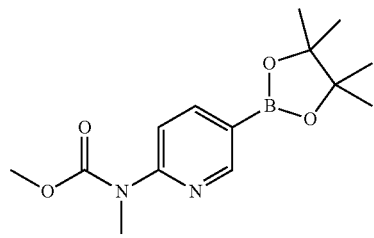

A mixture of methyl (5-bromopyridin-2-yl)methylcarbamate (0.227 g, 0.926 mmol), 4,4,5,5,4',4',5',5'-octamethyl-[2,2']bi[[1,3,2]dioxaborolanyl] (0.353 g, 1.39 mmol), potassium acetate (0.273 g, 2.78 mmol) and [1,1'-bis(diphenylphosphino)ferrocene]dichloropalladium (II) (34 mg, 0.046 mmol) in 1,4-dioxane (5 mL) was purged with nitrogen then stirred at 90° C. for 12 h. The resulting mixture was cooled to room temperature then diluted with EtOAc, filtered and concentrated. The residue was purified by flash chromatography eluting with 0 to 8% MeOH/DCM to give the desired product. LC-MS calculated for $C_{14}H_{22}BN_2O_4$ (M+H)$^+$: m/z=293.2. found 293.2.

Step 3: methyl[5-(6-(4-cyanophenyl)-8-{[(3R)-1-methylpiperidin-3-yl]methoxy}imidazo[1,5-a]pyrazin-5-yl)pyridin-2-yl]methylcarbamate The title compound was prepared using procedures analogous to those described in Example 21, Step 9 with methyl methyl[5-(4,4,5,5-tetramethyl-1,3,2-dioxaborolan-2-yl)pyridin-2-yl]carbamate replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{30}N_7O_3$(M+H)$^+$: m/z=512.2. found 512.3.

Example 50

4-[8-[4-(dimethylamino)piperidin-1-yl]-5-(1-methyl-1H-pyrazolo[3,4-b]pyridin-5-yl)imidazo[1,5-a]pyrazin-6-yl]benzonitrile

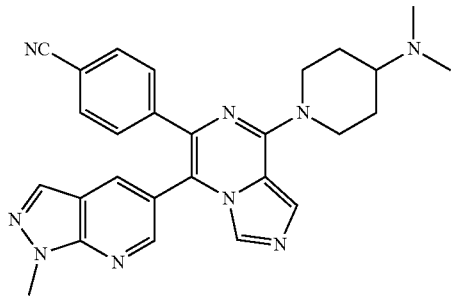 [SMILES: CN(C)C1CCN(c2nc(-c3ccc(C#N)cc3)c(-c3cnc4c(cnn4C)c3)n3cncc23)CC1]

Step 1: 1-(5-bromo-6-chloroimidazo[1,5-a]pyrazin-8-yl)-N,N-dimethylpiperidin-4-amine

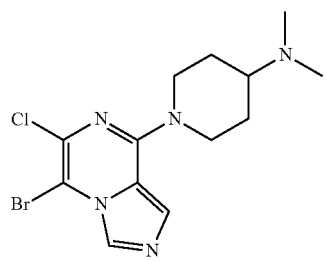 [SMILES: CN(C)C1CCN(c2nc(Cl)c(Br)n3cncc23)CC1]

To a solution of 5-bromo-6-chloroimidazo[1,5-a]pyrazin-8-ol (Example 21, Step 4: 200 mg, 0.8 mmol) in methylene chloride (4 mL) was added triethylamine (200 μL, 2 mmol) and 4-dimethylaminopyridine (10 mg, 0.08 mmol), followed by methanesulfonyl chloride (81 μL, 1.0 mmol) at 0° C. The resulting mixture was stirred at room temperature for 1 h then quenched with water. The organic layer was separated, dried over $Na_2SO_4$, filtered and concentrated. The residue was dissolved in acetonitrile (4 mL) then N,N-diisopropylethylamine (400 μL, 2 mmol) and N,N-dimethylpiperidin-4-amine (170 μL, 1.2 mmol) were added. The resulting mixture was stirred at 80° C. for 2 h then cooled to room temperature and diluted with DCM. The mixture was washed with 1N NaOH, water and brine. The organic layer was dried over $Na_2SO_4$, filtered and concentrated. The residue was purified by flash chromatography on a silica gel column eluting with 5 to 10% MeOH in DCM (5% triethylamine in DCM) to give the desired product. LC-MS calculated for $C_{13}H_{15}BrClN_5$ (M+H)$^+$: m/z=358.0. found 358.0. $^1$H NMR (400 MHz, CD$_3$OD) δ 8.55 (s, 1H), 8.07 (s, 1H), 4.84-4.72 (m, 2H), 3.67-3.51 (m, 2H), 3.32-3.17 (m, 1H), 2.92 (s, 6H), 2.30-2.14 (m, 2H), 1.91-1.72 (m, 2H).

Step 2: 4-[8-[4-(dimethylamino)piperidin-1-yl]-5-(1-methyl-1H-pyrazolo[3,4-b]pyridin-5-yl) imidazo[1,5-a]pyrazin-6-yl]benzonitrile A mixture of 1-(5-bromo-6-chloroimidazo[1,5-a]pyrazin-8-yl)-N,N-dimethylpiperidin-4-amine (30 mg, 0.08 mmol), 1-methyl-5-(4,4,5,5-tetramethyl-1,3,2-dioxaborolan-2-yl)-1H-pyrazolo[3,4-b]pyridine (Advanced ChemBlocks Inc, cat# I-9516: 20 mg, 0.08 mmol), tetrakis(triphenylphosphine)palladium(0) (10 mg, 0.008 mmol) and potassium carbonate (30 mg, 0.2 mmol) in 1,4-dioxane (910 μL) and water (200 μL) was purged with nitrogen and then stirred at 100° C. for 2 hours. The reaction mixture was cooled to room temperature then (4-cyanophenyl)boronic acid (18 mg, 0.12 mmol), dichloro[1,1'-bis(dicyclohexylphosphino)ferrocene]palladium(II) (6 mg, 0.008 mmol), cesium carbonate (50 mg, 0.2 mmol) and tert-butyl alcohol (0.7 mL) were added. The resulting mixture was purged with nitrogen and stirred at 90° C. for 1 hour. After cooling to room temperature, the reaction mixture was diluted with methanol then purified by prep-HPLC (pH=2, acetonitrile/water+TFA) to give the desired product as the TFA salt. LC-MS calculated for $C_{27}H_{28}N_9(M+H)^+$: m/z=478.2. found 478.2. $^1$H NMR (500 MHz, $CD_3OD$) δ 8.42 (d, J=2.0 Hz, 1H), 8.40 (d, J=2.0 Hz, 1H), 8.22 (s, 1H), 8.15 (s, 1H), 8.11 (s, 1H), 7.57-7.49 (m, 4H), 4.97-4.89 (m, 2H), 4.14 (s, 3H), 3.67-3.56 (m, 1H), 3.31-3.24 (m, 2H), 2.93 (s, 6H), 2.30-2.21 (m, 2H), 1.95-1.83 (m, 2H).

Example 51

4-[8-[4-(dimethylamino)piperidin-1-yl]-5-(3-methyl-2-oxo-2,3-dihydro-1,3-benzoxazol-6-yl)imidazo[1,5-a]pyrazin-6-yl]benzonitrile

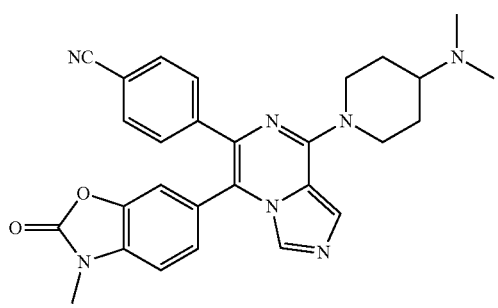 [SMILES: CN(C)C1CCN(c2nc(-c3ccc(C#N)cc3)c(-c3ccc4c(c3)oc(=O)n4C)n3cncc23)CC1]

The title compound was prepared using procedures analogous to those described in Example 50, Step 2 with 3-methyl-6-(4,4,5,5-tetramethyl-1,3,2-dioxaborolan-2-yl)-1,3-benzoxazol-2(3H)-one (Example 21, Step 8) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{28}N_7O_2(M+H)^+$: m/z=494.2. found 494.2. $^1$H NMR (400 MHz, $CD_3OD$) δ 8.38 (s, 1H), 8.22 (s, 1H), 7.60-7.53 (m, 4H), 7.40 (d, J=1.1 Hz, 1H), 7.32-7.20 (m, 2H), 4.95-4.87 (m, 2H), 3.70-3.53 (m, 1H), 3.46 (s, 3H), 3.35-3.32 (m, 2H), 2.94 (s, 6H), 2.31-2.22 (m, 2H), 2.01-1.80 (m, 2H).

Example 52

4-[8-[4-(dimethylamino)piperidin-1-yl]-5-(1-methyl-2-oxo-2,3-dihydro-1H-indol-5-yl)imidazo[1,5-a]pyrazin-6-yl]benzonitrile

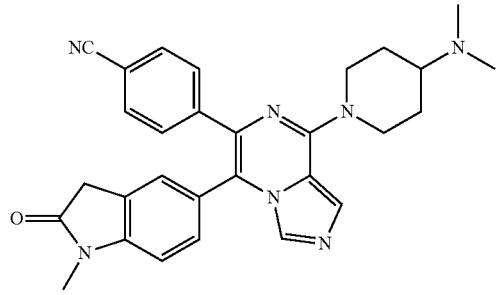 [SMILES: CN1C(=O)Cc2cc(-c3c(-c4ccc(C#N)cc4)nc(N4CCC(N(C)C)CC4)c4cncn34)ccc21]

The title compound was prepared using procedures analogous to those described in Example 50, Step 2 with 1-methyl-5-(4,4,5,5-tetramethyl-1,3,2-dioxaborolan-2-yl)-1,3-dihydro-2H-indol-2-one (Example 22, Step 1) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}N_7O$ $(M+H)^+$: m/z=492.3. found 492.2.

Example 53

4-[8-[4-(dimethylamino)piperidin-1-yl]-5-(6-methoxypyridin-3-yl)imidazo[1,5-a]pyrazin-6-yl]benzonitrile

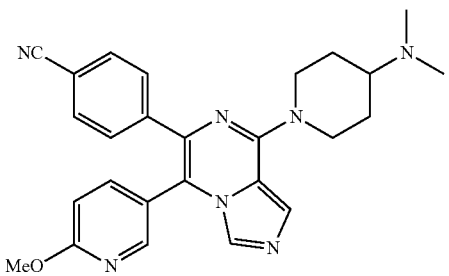 [SMILES: COc1ccc(-c2c(-c3ccc(C#N)cc3)nc(N3CCC(N(C)C)CC3)c3cncn23)cn1]

The title compound was prepared using procedures analogous to those described in Example 50, Step 2 with (6-methoxypyridin-3-yl)boronic acid [Aldrich, cat#637610] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{26}H_{28}N_7O$ $(M+H)^+$: m/z=454.2. found 454.2.

Example 54

4-{8-[4-(dimethylamino)piperidin-1-yl]-5-[6-(2-oxopyrrolidin-1-yl)pyridin-3-yl]imidazo[1,5-a]pyrazin-6-yl}benzonitrile

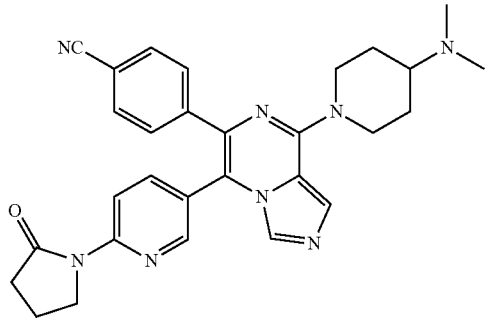 [SMILES: CN(C)C1CCN(c2nc(-c3ccc(C#N)cc3)c(-c3ccc(N4CCCC4=O)nc3)n3cncc23)CC1]

The title compound was prepared using procedures analogous to those described in Example 50, Step 2 with 1-[5-(4,4,5,5-tetramethyl-1,3,2-dioxaborolan-2-yl)pyridin-2-yl]pyrrolidin-2-one [JPM2 Pharma, cat#JPM2-00-744] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{31}N_8O$ (M+H)$^+$: m/z=507.3. found 507.2.

Example 55

4-[8-[4-(dimethylamino)piperidin-1-yl]-5-(1,5-naphthyridin-3-yl)imidazo[1,5-a]pyrazin-6-yl]benzonitrile

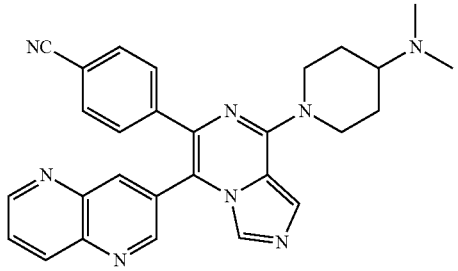 [SMILES: CN(C)C1CCN(c2nc(-c3ccc(C#N)cc3)c(-c3cnc4cccnc4c3)n3cncc23)CC1]

The title compound was prepared using procedures analogous to those described in Example 50, Step 2 with 3-(4,4,5,5-tetramethyl-1,3,2-dioxaborolan-2-yl)-1,5-naphthyridine [Adesis Inc, cat#3-141] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{27}N_8$ (M+H)$^+$: m/z=475.2. found 475.2.

Example 56

(R)-4-(8-((1-methylpiperidin-3-yl)methoxy)-5-(quinoxalin-6-yl)imidazo[1,5-a]pyridin-6-yl)benzonitrile

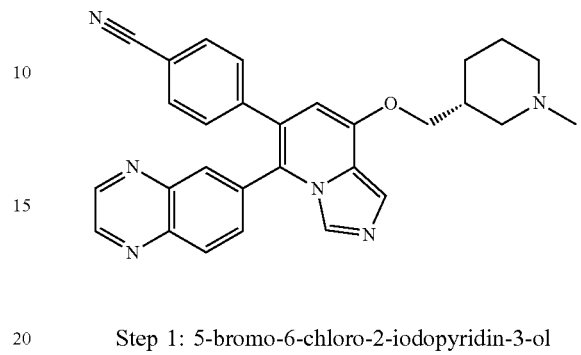

Step 1: 5-bromo-6-chloro-2-iodopyridin-3-ol

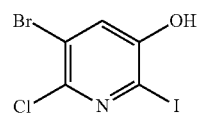

To a suspension of 5-bromo-6-chloropyridin-3-ol (Matrix, cat#057355: 10.00 g, 47.98 mmol) and sodium carbonate (11 g, 100 mmol) in water (200 mL) was added Iodine (12 g, 48 mmol) with stirring. The reaction mixture was stirred at room temperature for 1 hour then poured into a 2N HCl solution (100 mL). The precipitate was collected via filtration, washed with water and hexanes then dried to give the desired product (15.63 g, 97% yield), which was used in the next step without further purification. LC-MS calculated for $C_5H_3BrClINO$ (M+H)$^+$: m/z=333.8. found 333.8.

Step 2: (R)-tert-butyl 3-(((5-bromo-6-chloro-2-iodopyridin-3-yl)oxy)methyl)piperidine-1-carboxylate To a room temperature suspension of 5-bromo-6-chloro-2-iodopyridin-3-ol (5.45 g, 16.3 mmol), tert-butyl (3R)-3-(hydroxymethyl)piperidine-1-carboxylate (Synnovator, cat#PB00890: 3.72 g, 17.3 mmol), and triphenylphosphine (6.0 g, 23 mmol) in toluene (60 mL) was added dropwise diisopropyl azodicarboxylate (3.8 mL, 19 mmol) with stirring affording a dark red solution. The reaction was allowed to stir at room temperature for 1.5 hours. Once the reaction was deemed complete by LC-MS the reaction was concentrated under reduced pressure. The residue was purified by flash chromatography on a silica gel column eluting with 0-20% EtOAc/Hexanes to give the desired product with

Step 3: tert-butyl(3R)-3-{[(5-bromo-6-chloro-2-cyanopyridin-3-yl)oxy]methyl}piperidine-1-carboxylate

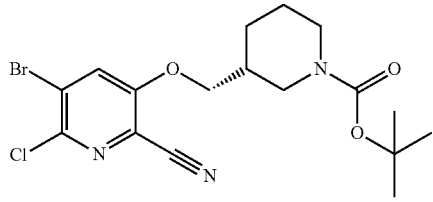

A mixture of tert-butyl (3R)-3-{[(5-bromo-6-chloro-2-iodopyridin-3-yl)oxy]methyl}piperidine-1-carboxylate (8.38 g, 15.8 mmol) and copper cyanide (1.7 g, 19 mmol) in pyridine (40. mL) was stirred at 80° C. for 1 hour. After cooling to room temperature, the reaction mixture was concentrated. The residue was purified by flash chromatography on a silica gel column eluting with 0 to 50% EtOAc/Hexanes to give the desired product in quantitative yield. LC-MS calculated for $C_{13}H_{14}BrClN_3O_3$ $(M-^tBu+2H)^+$: m/z=374.0. found 373.9.

Step 4: tert-butyl(3R)-3-({[2-(aminomethyl)-5-bromo-6-chloropyridin-3-yl]oxy}methyl) piperidine-1-carboxylate

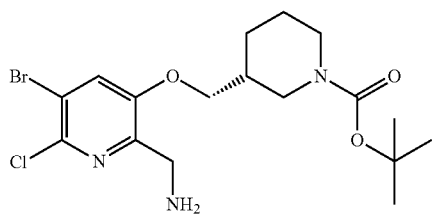

Tert-butyl (3R)-3-{[(5-bromo-6-chloro-2-cyanopyridin-3-yl)oxy]methyl}piperidine-1-carboxylate (6.96 g, 16.2 mmol) was dissolved in methylene chloride (100 mL) then cooled to −78° C. and 1.0 M Diisobutylaluminum hydride in DCM (81 mL, 81 mmol) was added. The resulting mixture was stirred at −78° C. for 1 hour. The crude reaction mixture was quenched with aqueous $NH_4Cl$ (30 mL), diluted with saturated sodium potassium tartrate (200 mL), then stirred at room temperature for 12 h or until clear distinct layers were present. The organic layer was separated and dried over $Na_2SO_4$, concentrated to dryness to give the desired compound which was used directly in the next step without further purification. LC-MS calculated for $C_{17}H_{26}BrON_3O_3$ $(M+H)^+$: m/z=434.1. found 434.1.

Step 5: (R)-tert-butyl 3-((5-bromo-6-chloro-2-(formamidomethyl)pyridin-3-yloxy)methyl) piperidine-1-carboxylate

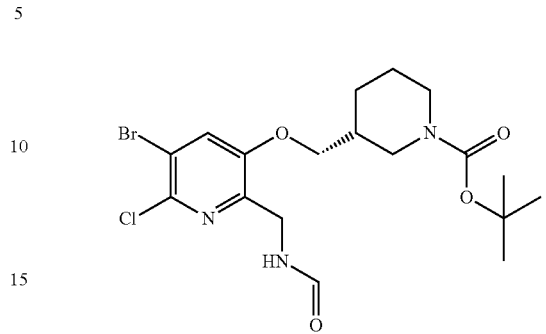

The crude residue of tert-butyl(3R)-3-({[2-(aminomethyl)-5-bromo-6-chloropyridin-3-yl]oxy}methyl) piperidine-1-carboxylate from Step 4 was dissolved in methylene chloride (73 mL) then 7.32 M acetic formic anhydride in formic acid [2.65 mL, 19.4 mmol; prepared by stirring formic acid (3.4 mL, 89 mmol) and acetic anhydride (7.6 mL, 81 mmol) at 50° C. for 2 hours.] was added. The resulting mixture was stirred at room temperature for 2 hours. The volatiles were removed under reduced pressure and the residue was used in the next step without further purification. LC-MS calculated for $C_{13}H_{15}BrClN_3O_2(M+H)^+$: m/z=362.0. found 361.9.

Step 6: (R)-6-bromo-5-chloro-8-(piperidin-3-ylmethoxy)imidazo[1,5-a]pyridine

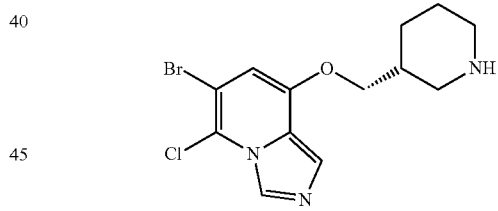

Tert-butyl (3R)-3-[({5-bromo-6-chloro-2-[(formylamino)methyl]pyridin-3-yl}oxy) methyl]piperidine-1-carboxylate (product from Step 5) was dissolved in 1,2-dichloroethane (80 mL) then phosphoryl chloride (1.8 mL, 19 mmol) was added and the resulting mixture was heated to 70° C. for 1.5 h. The reaction mixture was cooled to room temperature and was carefully quenched with saturated $NaHCO_3$. The organic layer was separated and washed with water, followed by brine. The organic layer was dried over $Na_2SO_4$ and concentrated under reduced pressure. The crude residue was then treated with 4.0 M hydrogen chloride in dioxane (60 mL, 200 mmol) and MeOH (20 mL). The resulting mixture was stirred at room temperature for 1 h then concentrated under reduced pressure affording the title compound as the HCl salt which was used in the next step without further purification. LC-MS calculated for $C_{13}H_{16}BrClN_3O(M+H)^+$: m/z=344.0. found 344.0.

(some minor impurities (8.38 g, 96% yield). LC-MS calculated for $C_{12}H_{14}BrClN_2O_3(M-^tBu+2H)^+$: m/z=474.9. found 474.9.)

Step 7: (R)-6-bromo-5-chloro-8-((1-methylpiperidin-3-yl)methoxy)imidazo[1,5-a]pyridine

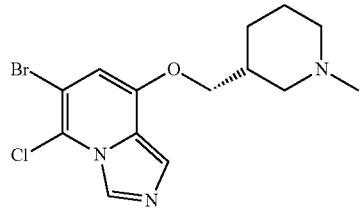

A mixture of 6-bromo-5-chloro-8-[(3R)-piperidin-3-ylmethoxy]imidazo[1,5-a]pyridine dihydrochloride (crude product from Step 6: 2 g, 5 mmol) and 12.3 M formaldehyde in water (3.89 mL, 47.9 mmol) in methylene chloride (40 mL) and methanol (8 mL) was stirred at room temperature for 10 min then sodium triacetoxyborohydride (3 g, 10 mmol) was carefully added portion-wise. The reaction mixture was allowed to stir at room temperature for 1 hour. The crude reaction mixture was quenched carefully with saturated NaHCO$_3$ aqueous solution (50 mL). The organic layer was separated and the aqueous layer was extracted with DCM (50 mL). The combined organic layers were washed with brine (100 mL) and dried over Na$_2$SO$_4$ and concentrated under reduced pressure. The residue was purified by flash chromatography on a silica gel column eluting with 0 to 20% MeOH/DCM to give the title compound (230 mg, 30% yield). LC-MS calculated for C$_{14}$H$_{15}$BrClN$_3$O (M+H)$^+$: m/z=358.0. found 357.9.

Step 8: (R)-4-(5-chloro-8-((1-methylpiperidin-3-yl)methoxy)imidazo[1,5-a]pyridin-6-yl) benzonitrile

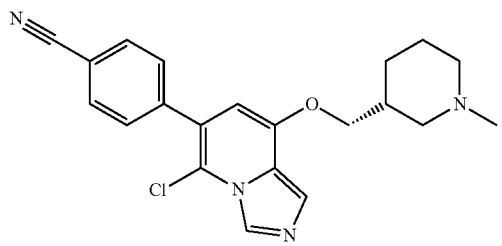

In a vial was combined a mixture of 6-bromo-5-chloro-8-{[(3R)-1-methylpiperidin-3-yl]methoxy}imidazo[1,5-a]pyridine (226 mg, 0.63 mmol), (4-cyanophenyl)boronic acid (Sigma Aldrich cat#521418: 139 mg, 0.945 mmol), palladium acetate (14.1 mg, 0.0630 mmol), tri-o-tolylphosphine (38.3 mg, 0.126 mmol) and sodium carbonate (200. mg, 1.89 mmol) in 1,4-dioxane (2.46 mL) and water (0.54 mL). The vial was capped, sealed and de-gassed by bubbling nitrogen through the solvent for 5 minutes. The reaction mixture was then heated to 80° C. for 1 hour. After cooling it was filtered and concentrated under reduced pressure. The residue was purified by flash chromatography on a silica gel column eluting with 0 to 20% MeOH/DCM to give the title compound (196 mg, 82% yield). LC-MS calculated for C$_{21}$H$_{22}$ClN$_4$O (M+H)$^+$: m/z=381.1. found 381.1.

Step 9: (R)-4-(8-((1-methylpiperidin-3-yl)methoxy)-5-(quinoxalin-6-yl)imidazo[1,5-a]pyridin-6-yl)benzonitrile In a glass reaction vial were combined: 4-(5-chloro-8-{[(3R)-1-methylpiperidin-3-yl]methoxy}imidazo[1,5-a]pyridin-6-yl)benzonitrile (12 mg, 0.032 mmol), 6-(4,4,5,5-tetramethyl-1,3,2-dioxaborolan-2-yl)quinoxaline (Combi-Blocks cat#BB-5429: 16.1 mg, 0.0630 mmol), dichloro (bis{di-tert-butyl[4-(dimethylamino)phenyl]phosphoranyl}) palladium (Sigma-Aldrich, cat#678740: 2.23 mg, 0.00315 mmol), cesium carbonate (10.3 mg, 0.0315 mmol), cesium fluoride (9.57 mg, 0.0630 mmol), water (0.2 mL), and tert-butyl alcohol (0.9 mL). The vial was capped and sealed and the solvent was degassed by bubbling nitrogen through the reaction mixture. The reaction mixture was heated to 90° C. for 2 hours. After cooling to room temperature, the crude reaction mixture was diluted with MeOH, passed through a syringe filter then purified by prep-HPLC (pH=2, acetonitrile/water+TFA) to give the desired product as the TFA salt. LC-MS calculated for C$_{29}$H$_{27}$N$_6$O (M+H)$^+$: m/z=475.2. found 475.2.

Example 57

(R)-4-(5-(3-methyl-2-oxo-2,3-dihydrooxazolo[4,5-b]pyridin-6-yl)-8-((1-methylpiperidin-3-yl)methoxy)imidazo[1,5-a]pyridin-6-yl)benzonitrile

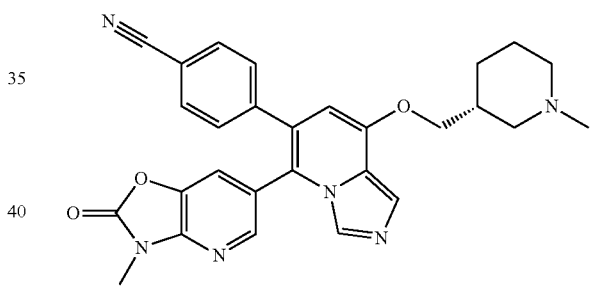

Step 1: 6-bromo-3-methyl[1,3]oxazolo[4,5-b]pyridin-2(3H)-one

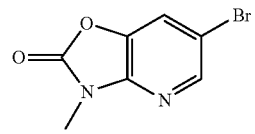

To a solution of 6-bromo[1,3]oxazolo[4,5-b]pyridin-2(3H)-one (Ark Pharm, cat#AK-24539: 0.394 g, 1.83 mmol) in N,N-dimethylformamide (5 mL) at −40° C. was added sodium hydride (60 wt % in mineral oil, 290 mg, 7.3 mmol). The resulting mixture was stirred at −40° C. for 1 hour then methyl iodide (1.14 mL, 18.3 mmol) was added dropwise. The reaction mixture was stirred at −40° C. for another 2 hours, then warmed to 0° C. and quenched by saturated NH$_4$Cl aqueous solution. The mixture was extracted with EtOAc, then DCM/iPrOH (2:1). The combined extracts were dried over Na$_2$SO$_4$, filtered and concentrated. The residue was used in the next step without further purification. LC-MS calculated for $C_7H_6BrN_2O_2$ (M+H)$^+$: m/z=229.0. found 229.0.

Step 2: 3-methyl-6-(4,4,5,5-tetramethyl-1,3,2-dioxaborolan-2-yl)[1,3]oxazolo[4,5-b]pyridin-2(3H)-one

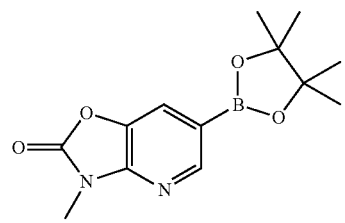 [SMILES: Cn1c(=O)oc2cc(B3OC(C)(C)C(C)(C)O3)cnc21]

A mixture of 6-bromo-3-methyl[1,3]oxazolo[4,5-b]pyridin-2(3H)-one (0.15 g, 0.66 mmol), 4,4,5,5,4',4',5',5'-octamethyl-[2,2']bi[[1,3,2]dioxaborolanyl] (250 mg, 0.98 mmol), [1,1'-bis(diphenylphosphino)ferrocene]dichloropalladium (II) complex with dichloromethane (1:1) (30 mg, 0.03 mmol) and potassium acetate (190 mg, 2.0 mmol) in 1,4-dioxane (6 mL) was purged with nitrogen then heated at 90° C. overnight. After cooling to room temperature, the reaction mixture was concentrated. The crude material was purified by flash chromatography on a silica gel column eluting with 0 to 5% MeOH in DCM to give the desired product. LC-MS calculated for $C_{13}H_{18}BN_2O_4$ (M+H)$^+$: m/z=277.1. found 277.1.

Step 3: (R)-4-(5-(3-methyl-2-oxo-2,3-dihydrooxazolo[4,5-b]pyridin-6-yl)-8-((1-methylpiperidin-3-yl)methoxy)imidazo[1,5-a]pyridin-6-yl)benzonitrile This compound was prepared using a similar procedure as described for Example 56, Step 9 with 3-methyl-6-(4,4,5,5-tetramethyl-1,3,2-dioxaborolan-2-yl)oxazolo[4,5-b]pyridin-2(3H)-one replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{28}H_{27}N_6O_3$ (M+H)$^+$: m/z=495.2. found 495.1.

Example 58

(R)-4-(5-(3-methyl-3H-imidazo[4,5-b]pyridin-6-yl)-8-((1-methylpiperidin-3-yl)methoxy)imidazo[1,5-a]pyridin-6-yl)benzonitrile

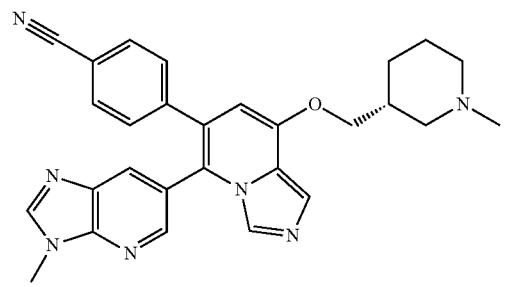 [SMILES: CN1CCC[C@@H](COc2cc(-c3ccc(C#N)cc3)c(-c3cnc4c(c3)ncn4C)n3cncc23)C1]

The title compound was prepared using procedures analogous to those described in Example 56, Step 9 with 3-methyl-6-(4,4,5,5-tetramethyl-1,3,2-dioxaborolan-2-yl)-3H-imidazo[4,5-b]pyridine (Adesis catalog#6-103) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{28}H_{28}N_7O$ (M+H)$^+$: m/z=478.2. found 478.2. $^1$H NMR (400 MHz, CD$_3$OD) δ: 8.44-8.34 (m, 3H), 8.13 (s, 1H), 7.94 (s, 1H), 7.60 (d, J=8.3 Hz, 2H), 7.43 (d, J=8.3 Hz, 2H), 6.58 (s, 1H), 4.39-4.28 (m, 1H), 4.26-4.16 (m, 1H), 4.13-4.02 (m, 4H), 3.79 (d, J=10.4 Hz, 1H), 3.58 (d, J=9.4 Hz, 1H), 3.08-2.91 (m, 4H), 2.57-2.37 (m, 1H), 2.16-1.78 (m, 3H), 1.66-1.43 (m, 1H).

Example 59

(R)-4-(8-((1-methylpiperidin-3-yl)methoxy)-5-(1,5-naphthyridin-3-yl)imidazo[1,5-a]pyridin-6-yl)benzonitrile

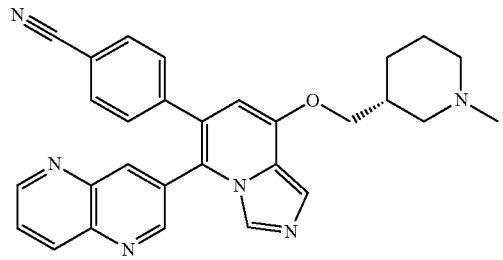 [SMILES: CN1CCC[C@@H](COc2cc(-c3ccc(C#N)cc3)c(-c3cnc4cccnc4c3)n3cncc23)C1]

The title compound was prepared using procedures analogous to those described in Example 56, Step 9 with 3-(4,4,5,5-tetramethyl-1,3,2-dioxaborolan-2-yl)-1,5-naphthyridine (Adesis catalog#3-141) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{27}N_6O$ (M+H)$^+$: m/z=475.2. found 475.2.

Example 60

(R)-4-(5-(furo[3,2-b]pyridin-6-yl)-8-((1-methylpiperidin-3-yl)methoxy)imidazo[1,5-a]pyridin-6-yl)benzonitrile

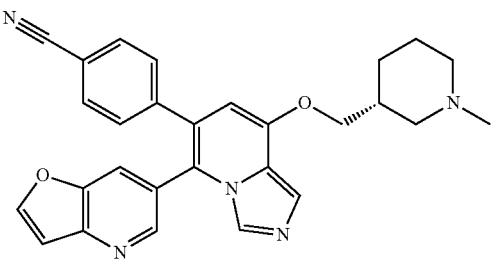 [SMILES: CN1CCC[C@@H](COc2cc(-c3ccc(C#N)cc3)c(-c3cnc4ccoc4c3)n3cncc23)C1]

The title compound was prepared using procedures analogous to those described in Example 56, Step 9 with 6-(4,4,5,5-tetramethyl-1,3,2-dioxaborolan-2-yl)furo[3,2-b]pyridine (Adesis catalog#5-119) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{28}H_{26}N_5O_2$ (M+H)⁺: m/z=464.2. found 464.2. ¹H NMR (400 MHz, CD₃OD) δ: 8.53 (s, 1H), 8.37 (d, J=1.5 Hz, 1H), 8.23 (d, J=2.3 Hz, 1H), 8.20 (s, 1H), 7.98 (s, 1H), 7.62 (d, J=8.3 Hz, 2H), 7.44 (d, J=8.3 Hz, 2H), 7.08 (s, 1H), 6.61 (s, 1H), 4.40-4.12 (m, 2H), 3.79 (d, J=11.6 Hz, 1H), 3.58 (d, J=11.4 Hz, 1H), 3.08-2.94 (m, 5H), 2.55-2.39 (m, 1H), 2.20-1.76 (m, 3H), 1.62-1.51 (m, 1H).

Example 61

(R)-4-(5-(3,4-dihydro-2H-pyrano[2,3-b]pyridin-6-yl)-8-((1-methylpiperidin-3-yl)methoxy)imidazo[1,5-a]pyridin-6-yl)benzonitrile

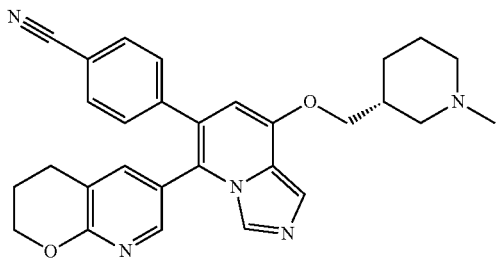 [SMILES: CN1CCC[C@@H](COc2cc(-c3ccc(C#N)cc3)c(-c3cnc4c(c3)CCCO4)n3cncc23)C1]

The title compound was prepared using procedures analogous to those described in Example 56, Step 9 with 6-(4,4,5,5-tetramethyl-1,3,2-dioxaborolan-2-yl)-3,4-dihydro-2H-pyrano[2,3-b]pyridine (Adesis catalog#10-106) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{30}N_5O_2$ (M+H)⁺: m/z=480.2. found 480.2. ¹H NMR (400 MHz, CD₃OD) δ: 9.12 (s, 1H), 8.29 (s, 1H), 7.88 (s, 1H), 7.83-7.61 (m, 3H), 7.47 (d, J=8.3 Hz, 2H), 6.74 (s, 1H), 4.48-4.29 (m, 3H), 4.30-4.13 (m, 1H), 3.78 (d, J=11.7 Hz, 1H), 3.57 (d, J=11.2 Hz, 1H), 3.09-2.73 (m, 7H), 2.61-2.37 (m, 1H), 2.17-1.75 (m, 5H), 1.62-1.41 (m, 1H).

Example 62

(R)-4-(5-(2,3-dihydro-[1,4]dioxino[2,3-b]pyridin-7-yl)-8-((1-methylpiperidin-3-yl)methoxy)imidazo[1,5-a]pyridin-6-yl)benzonitrile

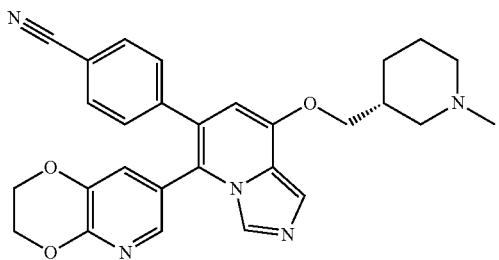 [SMILES: CN1CCC[C@@H](COc2cc(-c3ccc(C#N)cc3)c(-c3cnc4c(c3)OCCO4)n3cncc23)C1]

The title compound was prepared using procedures analogous to those described in Example 56, Step 9 with 7-(4,4,5,5-tetramethyl-1,3,2-dioxaborolan-2-yl)-2,3-dihydro-[1,4]dioxino[2,3-b]pyridine (Adesis catalog#11-118) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{28}H_{28}N_5O_3$(M+H)⁺: m/z=482.2. found 482.2.

Example 63

(R)-4-(5-(3-methyl-2-oxo-2,3-dihydrobenzo[d]oxazol-6-yl)-8-((1-methylpiperidin-3-yl)methoxy)imidazo[1,5-a]pyridin-6-yl)benzonitrile

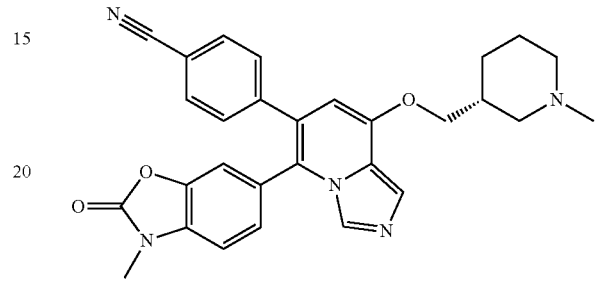

The title compound was prepared using procedures analogous to those described in Example 56, Step 9 with 3-methyl-6-(4,4,5,5-tetramethyl[1,3,2]dioxaborolan-2-yl)-3H-benzooxazol-2-one (Example 21, Step 8) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{28}N_5O_3$(M+H)⁺: m/z=494.2. found 494.2. ¹H NMR (400 MHz, CD₃OD) δ: 8.57 (s, 1H), 8.02 (s, 1H), 7.63 (d, J=8.4 Hz, 2H), 7.52-7.32 (m, 3H), 7.29-7.12 (m, 2H), 6.61 (s, 1H), 4.43-4.27 (m, 1H), 4.26-4.13 (m, 1H), 3.78 (d, J=10.5 Hz, 1H), 3.58 (d, J=11.2 Hz, 1H), 3.42 (s, 3H), 3.14-2.74 (m, 5H), 2.61-2.33 (m, 1H), 2.21-1.73 (m, 3H), 1.64-1.39 (m, 1H).

Example 64

(R)-4-(5-(1-methyl-2-oxoindolin-5-yl)-8-((1-methylpiperidin-3-yl)methoxy)imidazo[1,5-a]pyridin-6-yl)benzonitrile

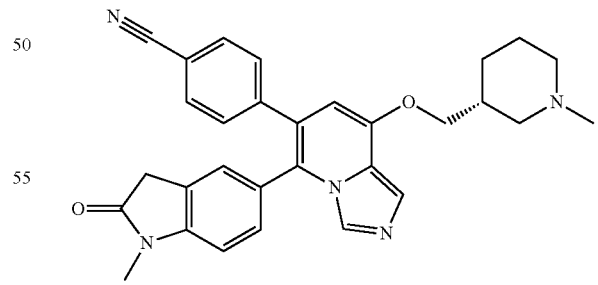

The title compound was prepared using procedures analogous to those described in Example 56, Step 9 with 1-methyl-5-(4,4,5,5-tetramethyl-1,3,2-dioxaborolan-2-yl)indolin-2-one (Combi-Blocks catalog#FF-5929) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{30}H_{30}N_5O_2(M+H)^+$: m/z=492.2. found 492.2. $^1$H NMR (400 MHz, CD$_3$OD) δ: 8.74 (s, 1H), 8.13 (s, 1H), 7.63 (d, J=8.4 Hz, 2H), 7.45 (d, J=8.3 Hz, 2H), 7.37 (s, 1H), 7.27 (d, J=8.0 Hz, 1H), 7.03 (d, J=8.1 Hz, 1H), 6.67 (s, 1H), 4.40-4.28 (m, 1H), 4.27-4.14 (m, 1H), 3.79 (d, J=12.0 Hz, 1H), 3.57 (d, J=5.1 Hz, 2H), 3.22 (s, 3H), 3.10-2.88 (m, 6H), 2.57-2.40 (m, 1H), 2.18-1.81 (m, 3H), 1.62-1.46 (m, 1H).

Example 65

(R)-4-(5-(4-methyl-3-oxo-3,4-dihydro-2H-benzo[b] [1,4]oxazin-7-yl)-8-((1-methylpiperidin-3-yl) methoxy)imidazo[1,5-a]pyridin-6-yl)benzonitrile

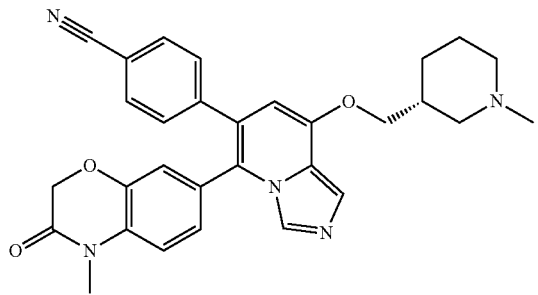 [SMILES: CN1CCC[C@@H](COc2cc(-c3ccc(C#N)cc3)c(-c3ccc4c(c3)OCC(=O)N4C)n3cncc23)C1]

The title compound was prepared using procedures analogous to those described in Example 56, Step 9 with 4-methyl-7-(4,4,5,5-tetramethyl-1,3,2-dioxaborolan-2-yl)-2H-benzo[b][1,4] oxazin-3(4H)-one (Example 25, Step 1) replacing 6-(4,4,5,5-tetramethyl-1,3,2-dioxaborolan-2-yl) quinoxaline. The reaction mixture was purified by prep-HPLC (pH=2, acetonitrile/water+TFA) to give the desired product as the TFA salt. LC-MS calculated for $C_{30}H_{30}N_5O_3$ (M+H)$^+$: m/z=508.2. found 508.2. $^1$H NMR (400 MHz, CD$_3$OD) δ: 8.62 (s, 1H), 8.03 (s, 1H), 7.66 (d, J=8.4 Hz, 2H), 7.46 (d, J=8.4 Hz, 2H), 7.21 (d, J=8.3 Hz, 1H), 7.10-6.93 (m, 2H), 6.61 (s, 1H), 4.66 (s, 2H), 4.37-4.27 (m, 1H), 4.25-4.12 (m, 1H), 3.78 (d, J=11.6 Hz, 1H), 3.58 (d, J=12.4 Hz, 1H), 3.36 (s, 3H), 3.09-2.83 (m, 5H), 2.54-2.37 (m, 1H), 2.17-1.80 (m, 3H), 1.60-1.46 (m, 1H).

Example 66

(R)-4-(8-((1-ethylpiperidin-3-yl)methoxy)-5-(3-methyl-3H-imidazo[4,5-b]pyridin-6-yl)imidazo[1,5-a]pyridin-6-yl)benzonitrile

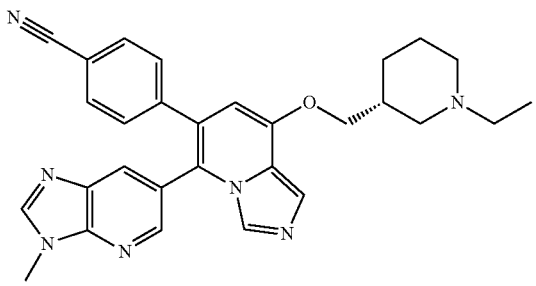 [SMILES: CCN1CCC[C@@H](COc2cc(-c3ccc(C#N)cc3)c(-c3cnc4c(c3)ncn4C)n3cncc23)C1]

Step 1: (R)-6-bromo-5-chloro-8-((1-ethylpiperidin-3-yl)methoxy)imidazo[1,5-a]pyridine

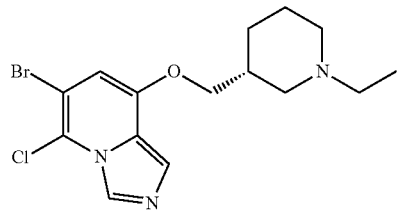 [SMILES: CCN1CCC[C@@H](COc2cc(Br)c(Cl)n3cncc23)C1]

This compound was prepared using a similar procedure as described from Example 56, Step 7 with acetaldehyde replacing formaldehyde. The reaction mixture was purified by flash chromatography on a silica gel column eluting with 0 to 20% MeOH/DCM to give the title compound. LC-MS calculated for $C_{15}H_{20}BrClN_3O$ (M+H)$^+$: m/z=372.1. found 372.0.

Step 2: (R)-4-(5-chloro-8-((1-ethylpiperidin-3-yl) methoxy)imidazo[1,5-a]pyridin-6-yl) benzonitrile

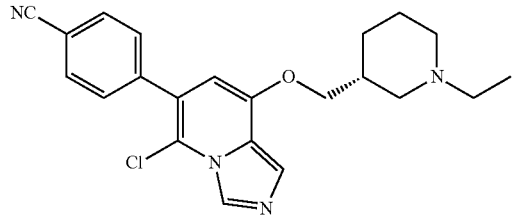 [SMILES: CCN1CCC[C@@H](COc2cc(-c3ccc(C#N)cc3)c(Cl)n3cncc23)C1]

This compound was prepared using a similar procedure as described from Example 56, Step 8 with (R)-6-bromo-5-chloro-8-((1-ethylpiperidin-3-yl)methoxy)imidazo[1,5-a] pyridine replacing 6-bromo-5-chloro-8-{[(3R)-1-methylpiperidin-3-yl]methoxy}imidazo[1,5-a]pyridine. The reaction mixture was purified by flash chromatography on a silica gel column eluting with 0 to 20% MeOH/DCM to give the title compound. LC-MS calculated for $C_{22}H_{24}ClN_4O$ (M+H)$^+$: m/z=395.2. found 395.1.

Step 3: (R)-4-(8-((1-ethylpiperidin-3-yl)methoxy)-5-(3-methyl-3H-imidazo[4,5-b]pyridin-6-yl)imidazo[1,5-a]pyridin-6-yl)benzonitrile A mixture of 4-(5-chloro-8-{[(3R)-1-ethylpiperidin-3-yl] methoxy}imidazo[1,5-a]pyridin-6-yl)benzonitrile (12 mg, 0.032 mmol), dichloro(bis{di-tert-butyl[4-(dimethylamino) phenyl]phosphoranyl})palladium (2.23 mg, 0.00315 mmol), cesium carbonate (10.3 mg, 0.0315 mmol), cesium fluoride (9.57 mg, 0.0630 mmol), 3-methyl-6-(4,4,5,5-tetramethyl-1,3,2-dioxaborolan-2-yl)-3H-imidazo[4,5-b]pyridine (Adesis catalog#6-103: 16.3 mg, 0.0630 mmol) in tert-butyl alcohol (0.9 mL) and water (0.2 mL) was purged with nitrogen then stirred at 90° C. for 2 h. The reaction mixture was cooled to room temperature then diluted with MeOH, filtered and purified by prep-HPLC (pH=2, acetonitrile/water+TFA) to give the desired product as the TFA salt. LC-MS calculated for $C_{29}H_{30}N_7O$ (M+H)$^+$: m/z=492.3. found 492.2.

Example 67

(R)-4-(5-(2,3-dihydro-[1,4]dioxino[2,3-b]pyridin-7-yl)-8-((1-ethylpiperidin-3-yl)methoxy)imidazo[1,5-a]pyridin-6-yl)benzonitrile

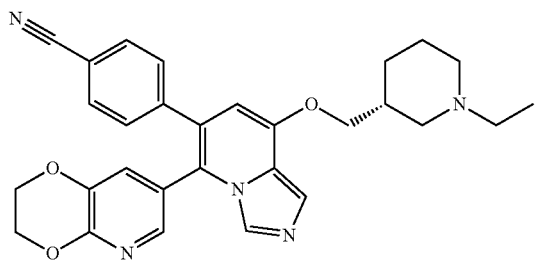 [SMILES: CCN1CCC[C@@H](COc2cc(-c3ccc(C#N)cc3)c(-c3cnc4c(c3)OCCO4)n3cncc23)C1]

The title compound was prepared using procedures analogous to those described in Example 66, Step 3 with 7-(4,4,5,5-tetramethyl-1,3,2-dioxaborolan-2-yl)-2,3-dihydro-[1,4]dioxino[2,3-b]pyridine (Adesis catalog#11-118) replacing 3-methyl-6-(4,4,5,5-tetramethyl-1,3,2-dioxaborolan-2-yl)-3H-imidazo[4,5-b]pyridine. The reaction mixture was purified by prep-HPLC (pH=2, acetonitrile/water+TFA) to give the desired product as the TFA salt. LC-MS calculated for $C_{29}H_{30}N_5O_3(M+H)^+$: m/z=496.2. found 496.2.

Example 68

(R)-4-(5-(3,4-dihydro-2H-pyrano[2,3-b]pyridin-6-yl)-8-((1-ethylpiperidin-3-yl)methoxy)imidazo[1,5-a]pyridin-6-yl)benzonitrile

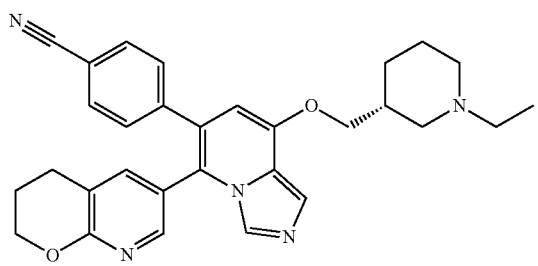 [SMILES: CCN1CCC[C@@H](COc2cc(-c3ccc(C#N)cc3)c(-c3cnc4c(c3)CCCO4)n3cncc23)C1]

The title compound was prepared using procedures analogous to those described in Example 66, Step 3 with 6-(4,4,5,5-tetramethyl-1,3,2-dioxaborolan-2-yl)-3,4-dihydro-2H-pyrano[2,3-b]pyridine (Adesis catalog#10-106) replacing 3-methyl-6-(4,4,5,5-tetramethyl-1,3,2-dioxaborolan-2-yl)-3H-imidazo[4,5-b]pyridine. The reaction mixture was purified by prep-HPLC (pH=2, acetonitrile/water+TFA) to give the desired product as the TFA salt. LC-MS calculated for $C_{30}H_{32}N_5O_2(M+H)^+$: m/z=494.3. found 494.2.

Example 69

(R)-4-(5-(5-amino-6-methoxypyridin-3-yl)-8-((1-methylpiperidin-3-yl)methoxy)imidazo[1,5-a]pyridin-6-yl)benzonitrile

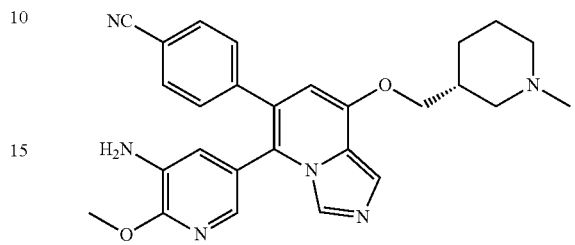

A mixture of 4-(5-chloro-8-{[(3R)-1-methylpiperidin-3-yl]methoxy}imidazo[1,5-a]pyridin-6-yl)benzonitrile (Example 56, Step 8: 10.4 mg, 0.0272 mmol), 2-methoxy-5-(4,4,5,5-tetramethyl-1,3,2-dioxaborolan-2-yl)pyridin-3-amine (Alfa Aesar, cat#H54570: 13.6 mg, 0.0545 mmol), sodium carbonate (0.00612 g, 0.0578 mmol), and dichloro[1,1'-bis(dicyclohexylphosphino)ferrocene] palladium(II) (0.0021 g, 0.0027 mmol) in water (0.3 mL) and tert-butyl alcohol (0.3 mL) in a reaction vial was purged with nitrogen then sealed. The reaction mixture was stirred at 90° C. for 4 h. After cooling to room temperature, the reaction mixture was diluted with methanol, filtered then purified by prep-HPLC (pH=2, acetonitrile/water+TFA) to give the desired product as the TFA salt. LC-MS calculated for $C_{27}H_{29}N_6O_2$ $(M+H)^+$: m/z=469.2. found 469.2.

Example 70

(R)-4-(5-(5-fluoro-6-methoxypyridin-3-yl)-8-((1-methylpiperidin-3-yl)methoxy)imidazo[1,5-a]pyridin-6-yl)benzonitrile

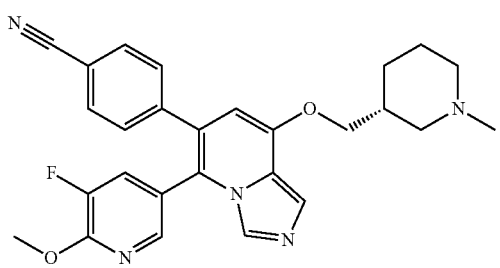 [SMILES: COc1ncc(-c2c(-c3ccc(C#N)cc3)cc(OC[C@@H]3CCCN(C)C3)c3cncn23)cc1F]

This compound was prepared using similar procedure as described for Example 69 with (5-fluoro-6-methoxypyridin-3-yl)boronic acid (Combi-Blocks, cat#BB-8460) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{27}H_{27}FN_5O_2$ $(M+H)^+$: m/z=472.2. found 472.2.

Example 71

(R)-4-(8-((1-methylpiperidin-3-yl)methoxy)-5-(6-(2-oxopyrrolidin-1-yl)pyridin-3-yl)imidazo[1,5-a]pyridin-6-yl)benzonitrile

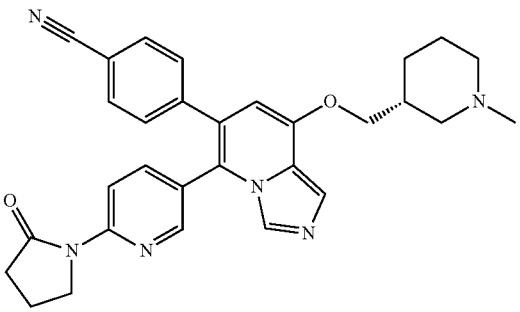 [SMILES: CN1CCC[C@@H](COc2cc(-c3ccc(C#N)cc3)c(-c3ccc(N4CCCC4=O)nc3)n3cncc23)C1]

The title compound was prepared using procedures analogous to those described in Example 69 with 1-[5-(4,4,5,5-tetramethyl-[1,3,2]dioxaborolan-2-yl)-pyridin-2-yl]-pyrrolidin-2-one (JPM2 Pharmaceuticals, cat#JPM2-00-744) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{30}H_{31}N_6O_2$ (M+H)$^+$: m/z=507.2. found 507.2. $^1$H NMR (500 MHz, CD$_3$OD) δ 9.04 (d, J=1.0 Hz, 1H), 8.48 (d, J=8.5 Hz, 1H), 8.27-8.25 (m, 2H), 7.90 (dd, J=8.5, 2.5 Hz, 1H), 7.67 (d, J=8.5 Hz, 2H), 7.45 (d, J=8.5 Hz, 2H), 6.74 (s, 1H), 4.39-4.31 (m, 1H), 4.25-4.20 (m, 1H), 4.07 (m, 2H), 3.78 (d, J=10.2 Hz, 1H), 3.57 (d, J=10.2 Hz, 1H), 3.03-2.95 (m, 2H), 2.94 (s, 3H), 2.69-2.640 (m, 2H), 2.53-2.43 (m, 1H), 2.18-2.00 (m, 4H), 1.99-1.84 (m, 1H), 1.58-1.47 (m, 1H).

Example 72

4-(5-(6-methoxypyridin-3-yl)-8-{[(3R)-1-methylpiperidin-3-yl]methoxy}imidazo[1,5-a]pyridin-6-yl)benzonitrile

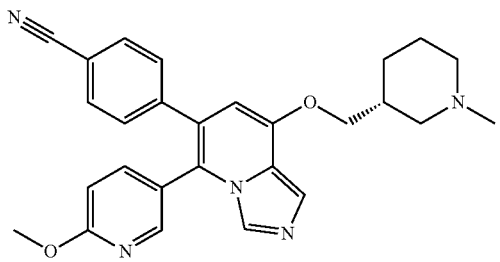 [SMILES: COc1ccc(-c2c(-c3ccc(C#N)cc3)cc(OC[C@@H]3CCCN(C)C3)c3cncn23)cn1]

The title compound was prepared using procedures analogous to those described in Example 69 with (6-methoxypyridin-3-yl)boronic acid (Aldrich, cat#637610) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{27}H_{28}N_5O_2$ (M+H)$^+$: m/z=454.2. found 454.2.

Example 73

(R)-4-(5-(3,5-difluoro-4-(hydroxymethyl)phenyl)-8-((1-methylpiperidin-3-yl)methoxy)imidazo[1,5-a]pyridin-6-yl)benzonitrile

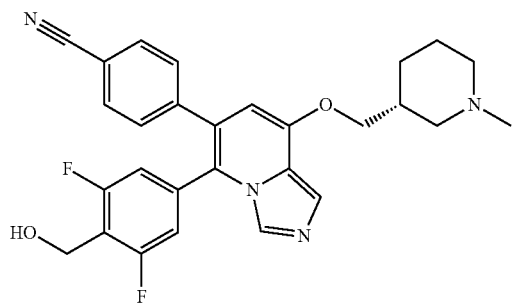 [SMILES: CN1CCC[C@@H](COc2cc(-c3ccc(C#N)cc3)c(-c3cc(F)c(CO)c(F)c3)n3cncc23)C1]

The title compound was prepared using procedures analogous to those described in Example 69 with [3,5-difluoro-4-(hydroxymethyl)phenyl]boronic acid (Combi-Blocks, cat#BB-8390) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{28}H_{27}F_2N_4O_2$ (M+H)$^+$: m/z=489.2. found 489.2.

Example 74

Methyl[5-(6-(4-cyanophenyl)-8-{[(3R)-1-methylpiperidin-3-yl]methoxy}imidazo[1,5-a]pyridin-5-yl)pyridin-2-yl]methylcarbamate

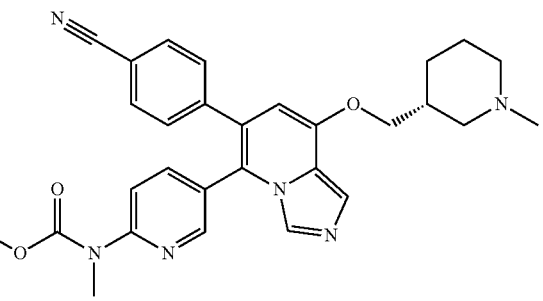

The title compound was prepared using procedures analogous to those described in Example 69 with methyl methyl [5-(4,4,5,5-tetramethyl-1,3,2-dioxaborolan-2-yl)pyridin-2-yl]carbamate (Example 49, Step 2) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{29}H_{31}N_6O_3$ (M+H)$^+$: m/z=511.2. found 511.2. $^1$H NMR (400 MHz, CD$_3$OD) δ 8.31 (s, 1H), 8.26 (s, 1H), 7.97 (d, J=8.8 Hz, 1H), 7.91-7.83 (m, 2H), 7.68 (d, J=8.4 Hz, 2H), 7.46 (d, J=8.4 Hz, 2H), 6.52 (s, 1H), 4.35-4.30 (m, 1H), 4.24-4.17 (m, 1H), 3.85 (s, 3H), 3.79 (d, J=11.6 Hz, 1H), 3.59 (d, J=11.2 Hz, 1H), 3.45 (s, 3H), 3.07-2.95 (m, 2H), 2.98 (s, 3H), 2.52-2.42 (m, 1H), 2.18-1.85 (m, 3H), 1.62-1.50 (m, 1H).

Example 75

4-(5-[3-fluoro-4-(hydroxymethyl)-5-methylphenyl]-8-{[(3R)-1-methylpiperidin-3-yl]methoxy}imidazo[1,5-a]pyridin-6-yl)benzonitrile

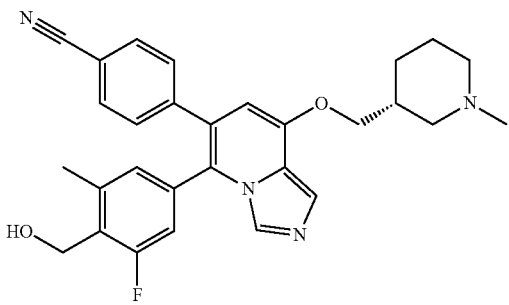

The title compound was prepared using procedures analogous to those described in Example 69 with [2-fluoro-6-methyl-4-(4,4,5,5-tetramethyl-1,3,2-dioxaborolan-2-yl)phenyl]methanol (Example 44, Step 1) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{29}H_{30}FN_4O_2$ (M+H)+: m/z=485.2. found 485.1.

Example 76

4-(5-(5-hydroxy-6-methylpyridin-3-yl)-8-{[(3R)-1-methylpiperidin-3-yl]methoxy}imidazo[1,5-a]pyridin-6-yl)benzonitrile

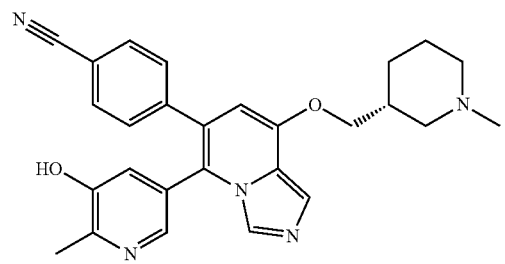 [SMILES: Cc1ncc(-c2c(-c3ccc(C#N)cc3)cc(OC[C@@H]3CCCN(C)C3)c3cncn23)cc1O]

Step 1: 2-methyl-5-(4,4,5,5-tetramethyl-1,3,2-dioxaborolan-2-yl)pyridin-3-ol

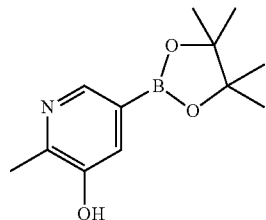

The title compound was prepared using procedures analogous to those described in Example 22, Step 1 with 5-bromo-2-methylpyridin-3-ol (Combi-Blocks, cat#QA-0238) replacing 5-bromo-1-methyl-1,3-dihydro-2H-indol-2-one. The crude boronic ester was used in the next step without further purification. LC-MS calculated for $C_{12}H_{19}BNO_3$ (M+H)+: m/z=236.1. found 236.1.

Step 2: 4-(5-(5-hydroxy-6-methylpyridin-3-yl)-8-{[(3R)-1-methylpiperidin-3-yl]methoxy}imidazo[1,5-a]pyridin-6-yl)benzonitrile The title compound was prepared using procedures analogous to those described in Example 69, with 2-methyl-5-(4,4,5,5-tetramethyl-1,3,2-dioxaborolan-2-yl)pyridin-3-ol replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{27}H_{28}N_5O_2$ (M+H)+: m/z=454.2. found 454.1.

Example 77

4-(5-[4-(1-hydroxy-1-methylethyl)phenyl]-8-{[(3R)-1-methylpiperidin-3-yl]methoxy}imidazo[1,5-a]pyridin-6-yl)benzonitrile

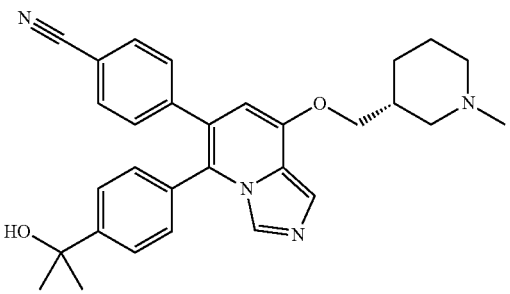 [SMILES: CN1CCC[C@@H](COc2cc(-c3ccc(C#N)cc3)c(-c3ccc(C(C)(C)O)cc3)n3cncc23)C1]

The title compound was prepared using procedures analogous to those described in Example 69 with [4-(1-hydroxy-1-methylethyl)phenyl]boronic acid (Combi-Blocks, cat#FA-1716) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{30}H_{33}N_4O_2$ (M+H)+: m/z=481.3. found 481.2.

Example 78

4-(5-(5-fluoro-6-morpholin-4-ylpyridin-3-yl)-8-{[(3R)-1-methylpiperidin-3-yl]methoxy}imidazo[1,5-a]pyridin-6-yl)benzonitrile

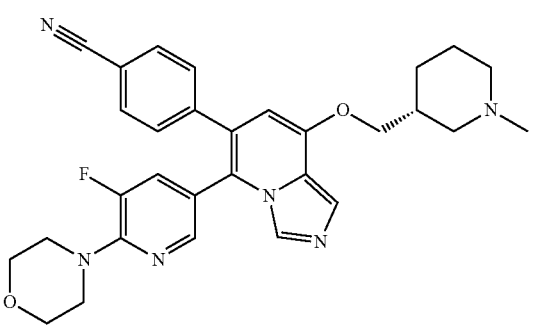 [SMILES: CN1CCC[C@@H](COc2cc(-c3ccc(C#N)cc3)c(-c3cnc(N4CCOCC4)c(F)c3)n3cncc23)C1]

Step 1: 4-(5-bromo-3-fluoropyridin-2-yl)morpholine

To a solution of 5-bromo-2,3-difluoropyridine (Alfa Aesar, cat#H64566: 0.200 g, 1.03 mmol) and triethylamine (0.144 mL, 1.03 mmol) in tetrahydrofuran (1.0 mL) was added morpholine (89.9 µL, 1.03 mmol). The resulting mixture was stirred at room temperature for 12 h then concentrated. The residue was used in the next step without further purification. LC-MS calculated for $C_9H_{11}BrFN_2O$ (M+H)$^+$: m/z=261.0. found 260.9.

Step 2: 4-[3-fluoro-5-(4,4,5,5-tetramethyl-1,3,2-dioxaborolan-2-yl)pyridin-2-yl]morpholine

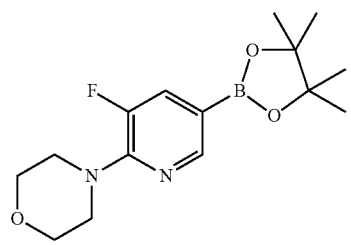 [SMILES: CC1(C)OB(c2cnc(N3CCOCC3)c(F)c2)OC1(C)C]

The title compound was prepared using procedures analogous to those described in Example 22, Step 1 with 4-(5-bromo-3-fluoropyridin-2-yl)morpholine replacing 5-bromo-1-methyl-1,3-dihydro-2H-indol-2-one. The reaction mixture was concentrated and the residue was purified by flash chromatography on a silica gel column eluting with 0 to 40% EtOAc/hexanes to give the desired product. LC-MS calculated for $C_{15}H_{23}BFN_2O_3$ (M+H)$^+$: m/z=309.2. found 309.1.

Step 3: 4-(5-(5-fluoro-6-morpholin-4-ylpyridin-3-yl)-8-{[(3R)-1-methylpiperidin-3-yl]methoxy}imidazo[1,5-a]pyridin-6-yl)benzonitrile The title compound was prepared using procedures analogous to those described in Example 69 with 4-[3-fluoro-5-(4,4,5,5-tetramethyl-1,3,2-dioxaborolan-2-yl)pyridin-2-yl]morpholine replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{30}H_{32}FN_6O_2$ (M+H)$^+$: m/z=527.3. found 527.3.

Example 79

4-(5-[4-(hydroxymethyl)-3-methylphenyl]-8-{[(3R)-1-methylpiperidin-3-yl]methoxy}imidazo[1,5-a]pyridin-6-yl)benzonitrile

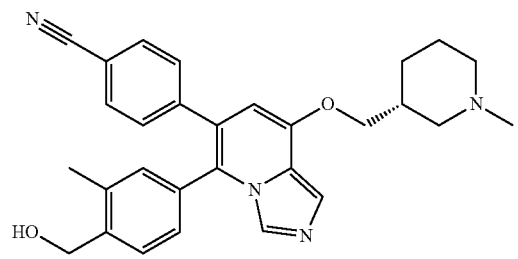 [SMILES: Cc1cc(-c2c(-c3ccc(C#N)cc3)cc(OC[C@@H]3CCCN(C)C3)c3cncn23)ccc1CO]

The title compound was prepared using procedures analogous to those described in Example 69 with [4-(hydroxymethyl)-3-methylphenyl]boronic acid (Combi-Blocks, cat#BB-9056) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{29}H_{31}N_4O_2$ (M+H)$^+$: m/z=467.2. found 467.2.

Example 80

4-(5-[6-(dimethylamino)pyridin-3-yl]-8-{[(3R)-1-methylpiperidin-3-yl]methoxy}imidazo[1,5-a]pyridin-6-yl)benzonitrile

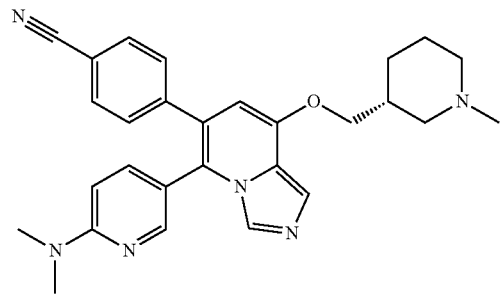 [SMILES: CN1CCC[C@@H](COc2cc(-c3ccc(C#N)cc3)c(-c3ccc(N(C)C)nc3)n3cncc23)C1]

The title compound was prepared using procedures analogous to those described in Example 69 with [6-(dimethylamino)pyridin-3-yl]boronic acid (Combi-Blocks, cat#FA-2296) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{28}H_{31}N_6O$ (M+H)$^+$: m/z=467.3. found 467.2.

Example 81

4-(5-(5,6-dimethylpyridin-3-yl)-8-{[(3R)-1-methyl-piperidin-3-yl]methoxy}imidazo[1,5-a]pyridin-6-yl)benzonitrile

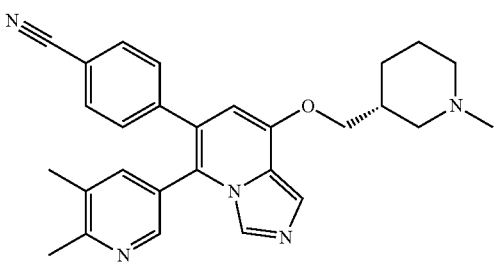 [SMILES: Cc1cc(-c2c(-c3ccc(C#N)cc3)cc(OC[C@@H]3CCCN(C)C3)c3cncn23)cnc1C]

The title compound was prepared using procedures analogous to those described in Example 69 with 2,3-dimethyl-5-(4,4,5,5-tetramethyl-1,3,2-dioxaborolan-2-yl)pyridine (Combi-Blocks, cat#FM-6236) replacing 2-methoxy-5-(4,4,5,5-tetramethyl-1,3,2-dioxaborolan-2-yl) pyridin-3-amine. The reaction mixture was purified by prep-HPLC (pH=2, acetonitrile/water+TFA) to give the desired product as the TFA salt. LC-MS calculated for $C_{28}H_{30}N_5O$ $(M+H)^+$: m/z=452.2. found 452.2.

Example 82

N-[4-(6-(4-cyanophenyl)-8-{[(3R)-1-methylpiperidin-3-yl]methoxy}imidazo[1,5-a]pyridin-5-yl)-2-fluorobenzyl]-N,N',N'-trimethylurea

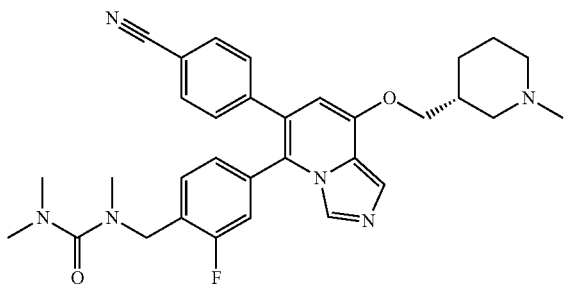

Step 1: N-[2-fluoro-4-(4,4,5,5-tetramethyl-1,3,2-dioxaborolan-2-yl)benzyl]-N,N',N'-trimethylurea

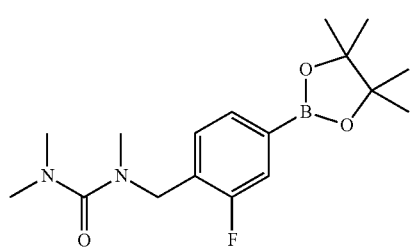

To a solution of 2.0 M methylamine in THF (6 mL, 12 mmol) was added dropwise a solution of 2-[3-(bromomethyl)-4-fluorophenyl]-4,4,5,5-tetramethyl-1,3,2-dioxaborolane (Alfa Aesar, cat#H62840: 400 mg, 1 mmol) in tetrahydrofuran (20 mL) with stirring over 1 h at room temperature. After completion of addition, the reaction mixture was stirred for another 2 h then concentrated. To a solution of the crude material (100 mg, 0.4 mmol) in methylene chloride (1.5 mL) was added N,N-diisopropylethylamine (130 µL, 0.75 mmol), followed by N,N-dimethylcarbamoyl chloride (42 µL, 0.45 mmol). The mixture was stirred at room temperature for 1 h then concentrated. The residue was used in the next step without further purification. LC-MS calculated for $C_{17}H_{27}BFN_2O_3$ $(M+H)^+$: m/z=337.2. found 337.2.

Step 2: N-[4-(6-(4-cyanophenyl)-8-{[(3R)-1-methyl-piperidin-3-yl]methoxy}imidazo[1,5-a]pyridin-5-yl)-2-fluorobenzyl]-N,N',N'-trimethylurea The title compound was prepared using procedures analogous to those described in Example 69 with N-[2-fluoro-4-(4,4,5,5-tetramethyl-1,3,2-dioxaborolan-2-yl)benzyl]-N,N',N'-trimethylurea replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{32}H_{36}FN_6O_2$ $(M+H)^+$: m/z=555.3. found 555.3.

Example 83

4-[8-[4-(dimethylamino)piperidin-1-yl]-5-(1-methyl-1H-benzimidazol-5-yl)imidazo[1,5-a]pyrazin-6-yl]benzonitrile

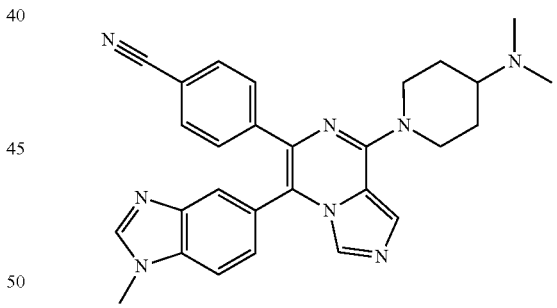

The title compound was prepared using procedures analogous to those described in Example 50, Step 2 with (1-methyl-1H-benzimidazol-5-yl)boronic acid [Combi-Blocks, cat# FA-4841] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8$ $(M+H)^+$: m/z=477.2. found 477.2. $^1$H NMR (400 MHz, CD$_3$OD) δ 9.25 (s, 1H), 8.26-8.16 (m, 2H), 8.02 (d, J=8.6 Hz, 1H), 7.93 (s, 1H), 7.67 (dd, J=8.6, 1.2 Hz, 1H), 7.55-7.51 (m, 4H), 5.01-4.88 (m, 2H), 4.16 (s, 3H), 3.69-3.54 (m, 1H), 3.34-3.25 (m, 2H), 2.95 (s, 6H), 2.32-2.23 (m, 2H), 2.03-1.85 (m, 2H).

Example 84

4-(8-(4-(dimethylamino)piperidin-1-yl)-5-(1-methyl-1H-pyrrolo[2,3-b]pyridin-5-yl)imidazo[1,5-a]pyrazin-6-yl)benzonitrile

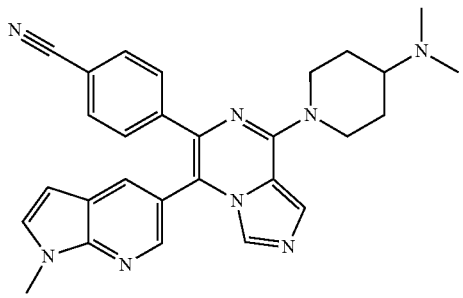 [SMILES: CN(C)C1CCN(c2nc(-c3ccc(C#N)cc3)c(-c3cnc4c(ccn4C)c3)n3cncc23)CC1]

The title compound was prepared using procedures analogous to those described in Example 50, Step 2 with 1-methyl-5-(4,4,5,5-tetramethyl-1,3,2-dioxaborolan-2-yl)-1H-pyrrolo[2,3-b]pyridine [Astatech, cat#37406] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8$ (M+H)$^+$: m/z=477.2. found 477.2.

Example 85

4-[8-{[(3R)-1-methylpiperidin-3-yl]methoxy}-5-(1-methyl-1H-pyrrolo[2,3-b]pyridin-5-yl)imidazo[1,5-a]pyrazin-6-yl]benzonitrile

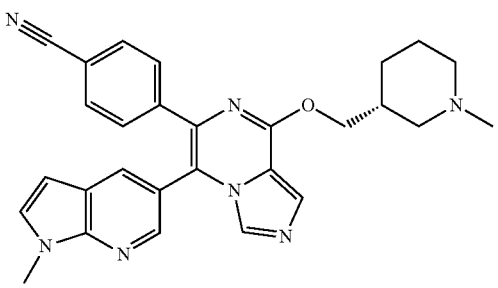 [SMILES: CN1CCC[C@@H](COc2nc(-c3ccc(C#N)cc3)c(-c3cnc4c(ccn4C)c3)n3cncc23)C1]

The title compound was prepared using procedures analogous to those described in Example 21, Step 9 with 1-methyl-5-(4,4,5,5-tetramethyl-1,3,2-dioxaborolan-2-yl)-1H-pyrrolo[2,3-b]pyridine [Astatech, cat#37406] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{28}H_{28}N_7O$ (M+H)$^+$: m/z=478.2. found 478.2. $^1$H NMR (500 MHz, CD$_3$OD) δ 8.18 (d, J=2.0 Hz, 1H), 8.14 (d, J=1.9 Hz, 1H), 8.00 (s, 1H), 7.83 (s, 1H), 7.54-7.51 (m, 4H), 7.49 (d, J=3.5 Hz, 1H), 6.58 (d, J=3.5 Hz, 1H), 4.58-4.50 (m, 1H), 4.49-4.40 (m, 1H), 2.31-2.25 (m, 1H), 3.89 (s, 3H), 3.12-3.03 (m, 1H), 2.93-2.80 (m, 1H), 2.32 (s, 3H), 2.10-1.86 (m, 3H), 1.85-1.76 (m, 1H), 1.73-1.61 (m, 1H), 1.25-1.13 (m, 1H).

Example 86

4-(5-(5,6-dimethylpyridin-3-yl)-8-{[(3R)-1-methylpiperidin-3-yl]methoxy}imidazo[1,5-a]pyrazin-6-yl)benzonitrile

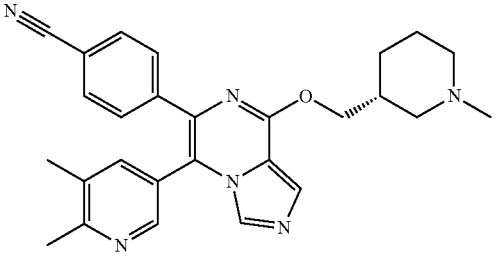 [SMILES: Cc1cc(-c2c(-c3ccc(C#N)cc3)nc(OC[C@@H]3CCCN(C)C3)c3cncn23)cnc1C]

The title compound was prepared using procedures analogous to those described in Example 21, Step 9 with 2,3-dimethyl-5-(4,4,5,5-tetramethyl-1,3,2-dioxaborolan-2-yl)pyridine [Combi-Blocks, cat#FM-6236] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for $C_{27}H_{29}N_6O$ (M+H)$^+$: m/z=453.2. found 453.2. $^1$H NMR (400 MHz, CD$_3$OD) δ 8.52 (d, J=1.6 Hz, 1H), 8.34-8.27 (m, 2H), 8.03 (s, 1H), 7.67 (d, J=8.5 Hz, 2H), 7.58 (d, J=8.5 Hz, 2H), 4.67 (dd, J=11.1, 4.9 Hz, 1H), 4.56 (dd, J=11.1, 6.9 Hz, 1H), 3.81-3.70 (m, 1H), 3.63-3.51 (m, 1H), 3.05-2.96 (m, 2H), 2.96 (s, 3H), 2.73 (s, 3H), 2.54-2.50 (m, 1H), 2.49 (s, 3H), 2.16-1.99 (m, 2H), 1.97-1.78 (m, 1H), 1.59-1.44 (m, 1H).

Example 87

(R)-methyl (4-(6-(4-cyanophenyl)-8-((1-methylpiperidin-3-yl)methoxy)imidazo[1,5-a]pyrazin-5-yl)-2-fluorophenyl)(methyl)carbamate

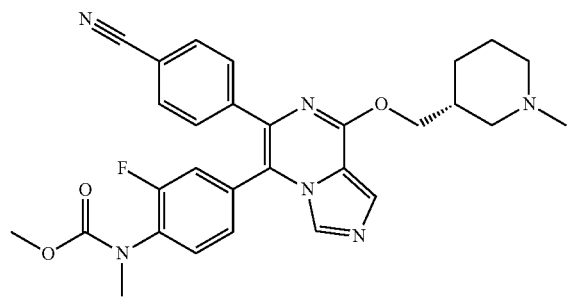

Step 1: methyl (4-bromo-2-fluorophenyl)methylcarbamate

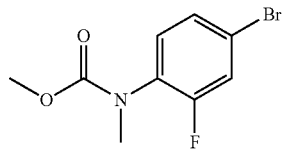

To a solution of 4-bromo-2-fluoro-N-methylaniline hydrochloride (Combi-Blocks, cat#HC-3277, 60 mg, 0.2 mmol) and N,N-diisopropylethylamine (100 μL, 0.7 mmol) in methylene chloride (0.2 mL) was added methyl chloroformate (23 μL, 0.30 mmol). The resulting mixture was stirred at room temperature overnight. The mixture was diluted with DCM, washed with aqueous NaHCO$_3$, water and brine. The organic layer was dried over Na$_2$SO$_4$, filtered and concentrated. The residue was purified by flash chromatography on a silica gel column eluting with 0 to 40% EtOAc in hexanes to give the desired product.

Step 2: methyl[2-fluoro-4-(4,4,5,5-tetramethyl-1,3,2-dioxaborolan-2-yl)phenyl]methylcarbamate

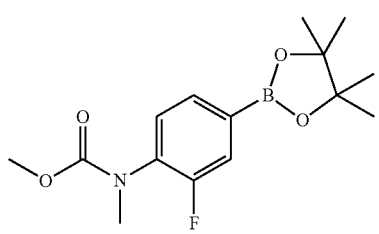

A mixture of methyl (4-bromo-2-fluorophenyl)methylcarbamate (39 mg, 0.15 mmol), 4,4,5,5,4',4',5',5'-octamethyl-[2,2']bi[[1,3,2]dioxaborolanyl] (42 mg, 0.16 mmol), [1,1'-bis(diphenylphosphino)ferrocene]dichloropalladium(II) complexed with dichloromethane (1:1) (6 mg, 0.007 mmol) and potassium acetate (36 mg, 0.37 mmol) in 1,4-dioxane (0.2 mL) was purged with nitrogen then stirred at 100° C. overnight. The reaction mixture was cooled to room temperature then concentrated. The residue was used in the next step without further purification.

Step 3: methyl[4-(6-(4-cyanophenyl)-8-{[(3R)-1-methylpiperidin-3-yl]methoxy}imidazo[1,5-a]pyrazin-5-yl)-2-fluorophenyl]methylcarbamate The title compound was prepared using procedures analogous to those described in Example 21, Step 9 with methyl [2-fluoro-4-(4,4,5,5-tetramethyl-1,3,2-dioxaborolan-2-yl)phenyl]methylcarbamate replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for C$_{29}$H$_{30}$FN$_6$O$_3$(M+H)$^+$: m/z=529.2. found 529.2.

Example 88

4-(5-(5-fluoro-6-methylpyridin-3-yl)-8-{[(3R)-1-methylpiperidin-3-yl]methoxy}imidazo[1,5-a]pyrazin-6-yl)benzonitrile

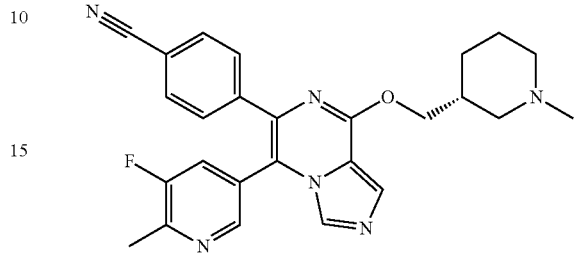

The title compound was prepared using procedures analogous to those described in Example 21, Step 9 with (5-fluoro-6-methylpyridin-3-yl)boronic acid [PharmaBlock Product List, cat#PBS07313] replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for C$_{26}$H$_{26}$FN$_6$O (M+H)$^+$: m/z=457.2. found 457.3.

Example 89

4-[8-[4-(dimethylamino)piperidin-1-yl]-5-(5,6-dimethylpyridin-3-yl)imidazo[1,5-a]pyrazin-6-yl]benzonitrile

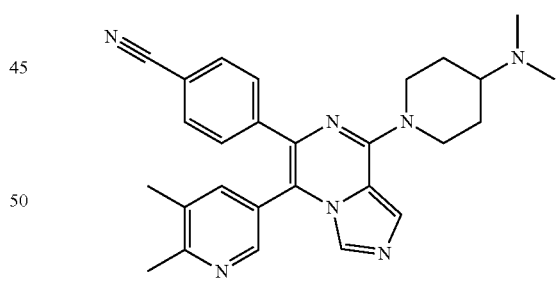

The title compound was prepared using procedures analogous to those described in Example 50, Step 2 with 2,3-dimethyl-5-(4,4,5,5-tetramethyl-1,3,2-dioxaborolan-2-yl)pyridine [Combi-Blocks, cat#FM-6236] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for C$_{27}$H$_{30}$N$_7$ (M+H)$^+$: m/z=452.2. found 452.2.

Example 90

4-[8-[4-(dimethylamino)piperidin-1-yl]-5-(5-fluoro-6-methoxypyridin-3-yl)imidazo[1,5-a]pyrazin-6-yl]benzonitrile

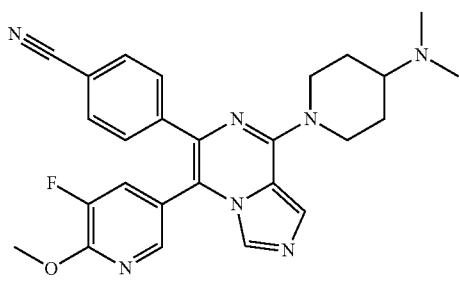 [SMILES: COc1ncc(-c2c(-c3ccc(C#N)cc3)nc(N3CCC(N(C)C)CC3)c3cncn23)cc1F]

The title compound was prepared using procedures analogous to those described in Example 50, Step 2 with (5-fluoro-6-methoxypyridin-3-yl)boronic acid [Combi-Blocks, cat#BB-5725] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{26}H_{27}FN_{7}O$ (M+H)$^{+}$: m/z=472.2. found 472.1.

Example 91

4-{8-[4-(dimethylamino)piperidin-1-yl]-5-[3-(hydroxymethyl)-4-methylphenyl]imidazo[1,5-a]pyrazin-6-yl}benzonitrile

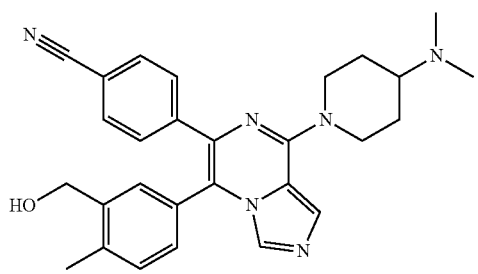 [SMILES: Cc1ccc(-c2c(-c3ccc(C#N)cc3)nc(N3CCC(N(C)C)CC3)c3cncn23)cc1CO]

The title compound was prepared using procedures analogous to those described in Example 50, Step 2 with [2-methyl-5-(4,4,5,5-tetramethyl-1,3,2-dioxaborolan-2-yl)phenyl]methano1 [Combi-Blocks, cat#FM-2080] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{31}N_{6}O$ (M+H)$^{+}$: m/z=467.2. found 467.1.

Example 92

4-{8-[4-(dimethylamino)piperidin-1-yl]-5-[2-(hydroxymethyl)-4-methylphenyl]imidazo[1,5-a]pyrazin-6-yl}benzonitrile

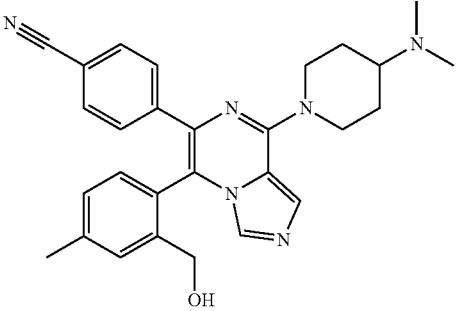 [SMILES: Cc1ccc(-c2c(-c3ccc(C#N)cc3)nc(N3CCC(N(C)C)CC3)c3cncn23)c(CO)c1]

The title compound was prepared using procedures analogous to those described in Example 50, Step 2 with [2-(hydroxymethyl)-4-methylphenyl]boronic acid [Aurum Pharmatech, cat#Q-7538] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{31}N_{6}O$ (M+H)$^{+}$: m/z=467.2. found 467.3.

Example 93

4-[8-[4-(dimethylamino)piperidin-1-yl]-5-(6-methoxy-5-methylpyridin-3-yl)imidazo[1,5-a]pyrazin-6-yl]benzonitrile

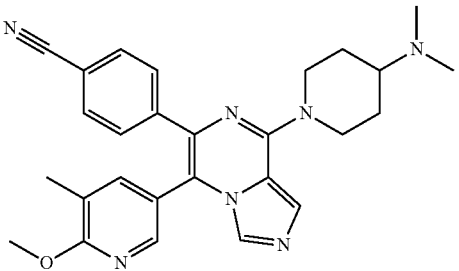 [SMILES: COc1ncc(-c2c(-c3ccc(C#N)cc3)nc(N3CCC(N(C)C)CC3)c3cncn23)cc1C]

The title compound was prepared using procedures analogous to those described in Example 50, Step 2 with (6-methoxy-5-methylpyridin-3-yl)boronic acid [Ark Pharma, cat#AK-61439] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{30}N_{7}O$ (M+H)$^{+}$: m/z=468.2. found 468.2.

Example 94 methyl (4-{6-(4-cyanophenyl)-8-[4-(dimethylamino)piperidin-1-yl]imidazo[1,5-a]pyrazin-5-yl}-2-fluorophenyl)methylcarbamate

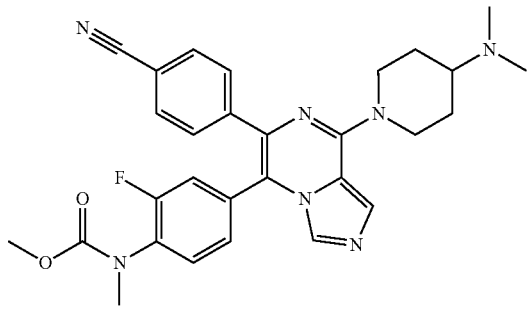

The title compound was prepared using procedures analogous to those described in Example 50, Step 2 with methyl [2-fluoro-4-(4,4,5,5-tetramethyl-1,3,2-dioxaborolan-2-yl)phenyl]methylcarbamate (Example 87, Step 2) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{31}FN_7O_2$ (M+H)$^+$: m/z=528.2. found 528.2. $^1$H NMR (400 MHz, CD$_3$OD) δ 8.29 (s, 1H), 8.13 (s, 1H), 7.67-7.56 (m, 4H), 7.49 (dt, J=16.0, 8.1 Hz, 1H), 7.34 (dd, J=10.6, 1.8 Hz, 1H), 7.27 (dd, J=8.1, 1.5 Hz, 1H), 4.98-4.85 (m, 2H), 3.74 (s, 3H), 3.68-3.52 (m, 1H), 3.31 (s, 3H), 3.32-3.25 (m, 2H), 2.94 (s, 6H), 2.32-2.19 (m, 2H), 1.99-1.79 (m, 2H).

Example 95 methyl (4-(6-(4-cyanophenyl)-8-(4-(dimethylamino)piperidin-1-yl)imidazo[1,5-a]pyrazin-5-yl)phenyl)(methyl)carbamate

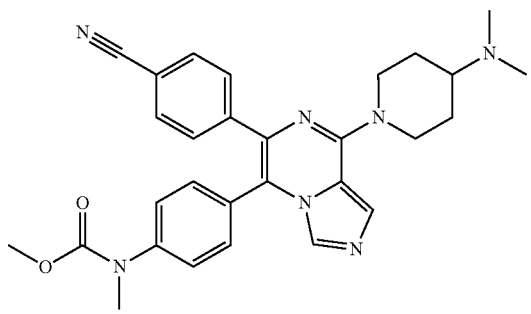

The title compound was prepared using procedures analogous to those described in Example 50, Step 2 with methyl methyl[4-(4,4,5,5-tetramethyl-1,3,2-dioxaborolan-2-yl)phenyl]carbamate (Example 46, Step 1) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{32}N_7O_2$ (M+H)$^+$: m/z=510.2. found 510.3. $^1$H NMR (400 MHz, CD$_3$OD) δ 8.43 (s, 1H), 8.26 (s, 1H), 7.64-7.54 (m, 4H), 7.53-7.39 (m, 4H), 4.93-4.86 (m, 2H), 3.78 (s, 3H), 3.67-3.59 (m, 1H), 3.37 (s, 3H), 3.34-3.29 (m, 2H), 2.94 (s, 6H), 2.29 (m, 2H), 1.98-1.87 (m, 2H).

Example 96 methyl(5-{6-(4-cyanophenyl)-8-[4-(dimethylamino)piperidin-1-yl]imidazo[1,5-a]pyrazin-5-yl}pyridin-2-yl)methylcarbamate

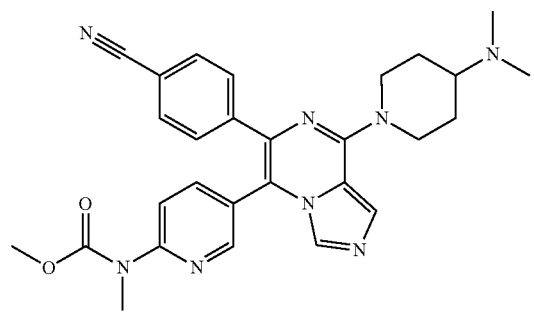

The title compound was prepared using procedures analogous to those described in Example 50, Step 2 with methyl methyl[5-(4,4,5,5-tetramethyl-1,3,2-dioxaborolan-2-yl)pyridin-2-yl]carbamate (Example 49, Step 2) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{31}N_8O_2$ (M+H)$^+$: m/z=511.2. found 511.3. $^1$H NMR (500 MHz, CD$_3$OD) δ 8.40 (s, 1H), 8.26 (d, J=2.0 Hz, 1H), 8.20 (s, 1H), 8.00 (d, J=8.7 Hz, 1H), 7.90 (dd, J=8.7, 2.4 Hz, 1H), 7.61 (d, J=8.5 Hz, 2H), 7.55 (d, J=8.5 Hz, 2H), 4.93-4.88 (m, 2H), 3.84 (s, 3H), 3.66-3.56 (m, 1H), 3.46 (s, 3H), 3.30-3.25 (m, 2H), 2.92 (s, 6H), 2.31-2.22 (m, 2H), 1.96-1.84 (m, 2H).

Example 97

4-[8-[4-(dimethylamino)piperidin-1-yl]-5-(5-fluoro-6-methylpyridin-3-yl)imidazo[1,5-a]pyrazin-6-yl]benzonitrile

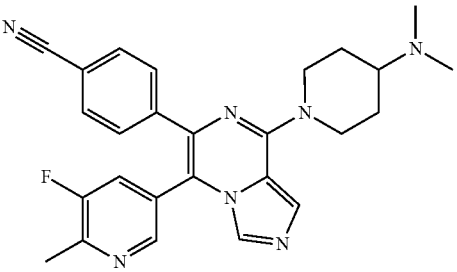 [SMILES: Cc1ncc(-c2c(-c3ccc(C#N)cc3)nc(N3CCC(N(C)C)CC3)c3cncn23)cc1F]

The title compound was prepared using procedures analogous to those described in Example 50, Step 2 with (5-fluoro-6-methylpyridin-3-yl)boronic acid [PharmaBlock Product List, cat#PBS07313] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{26}H_{27}FN_7$ (M+H)$^+$: m/z=456.2. found 456.2. $^1$H NMR (400 MHz, CD$_3$OD) δ 8.56 (s, 1H), 8.28 (s, 1H), 8.17 (s, 1H), 7.81 (d, J=9.7 Hz, 1H), 7.63 (d, J=8.4 Hz, 2H), 7.54 (d, J=8.4 Hz, 2H), 4.95-4.89 (m, 2H), 3.68-3.55 (m, 1H), 3.30-3.25 (m, 2H), 2.92 (s, 6H), 2.57 (d, J=2.8 Hz, 3H), 2.34-2.21 (m, 2H), 1.98-1.82 (m, 2H).

Example 98

4-{5-[6-(difluoromethoxy)pyridin-3-yl]-8-[4-(dimethylamino)piperidin-1-yl]imidazo[1,5-a]pyrazin-6-yl}benzonitrile

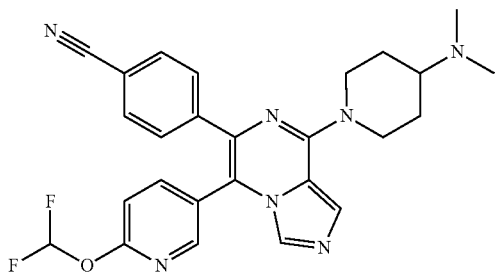 [SMILES: CN(C)C1CCN(c2nc(-c3ccc(C#N)cc3)c(-c3ccc(OC(F)F)nc3)n3cncc23)CC1]

The title compound was prepared using procedures analogous to those described in Example 50, Step 2 with 2-(difluoromethoxy)-5-(4,4,5,5-tetramethyl-1,3,2-dioxaborolan-2-yl)pyridine (Ark Pharma, cat#AK131545) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{26}H_{26}F_2N_7O$ (M+H)$^+$: m/z=490.2. found 490.2.

Example 99

4-[8-[4-(dimethylamino)piperidin-1-yl]-5-(6-ethoxypyridin-3-yl)imidazo[1,5-a]pyrazin-6-yl]benzonitrile

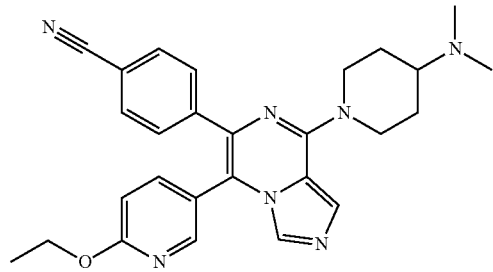 [SMILES: CCOc1ccc(-c2c(-c3ccc(C#N)cc3)nc(N3CCC(N(C)C)CC3)c3cncn23)cn1]

The title compound was prepared using procedures analogous to those described in Example 50, Step 2 with (6-ethoxypyridin-3-yl)boronic acid (Sigma-Aldrich, cat#718815) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{30}N_7O$ (M+H)$^+$: m/z=468.2. found 468.2.

Example 100

4-[8-[4-(dimethylamino)piperidin-1-yl]-5-(1-methyl-1H-indazol-5-yl)imidazo[1,5-a]pyrazin-6-yl]benzonitrile

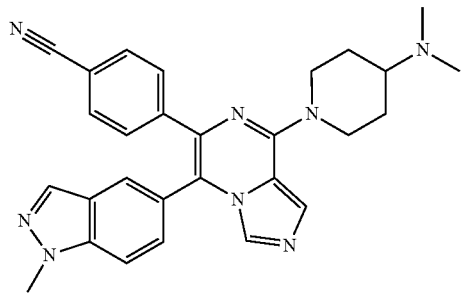 [SMILES: CN(C)C1CCN(c2nc(-c3ccc(C#N)cc3)c(-c3ccc4c(cnn4C)c3)n3cncc23)CC1]

The title compound was prepared using procedures analogous to those described in Example 50, Step 2 with (1-methyl-1H-indazol-5-yl)boronic acid [Combi-Blocks, cat#BB-9020] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{29}N_8$ (M+H)$^+$: m/z=477.2. found 477.2.

Example 101

4-(5-(2-hydroxy-2,3-dihydro-1H-inden-5-yl)-8-{[(3R)-1-methylpiperidin-3-yl]methoxy}imidazo[1,5-a]pyrazin-6-yl)benzonitrile

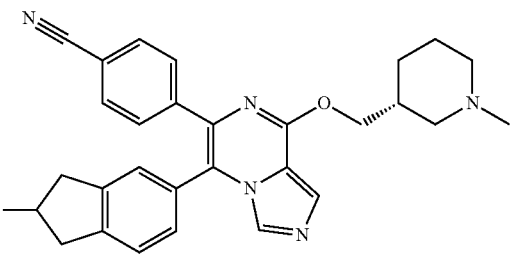

Step 1: 5-(4,4,5,5-tetramethyl-1,3,2-dioxaborolan-2-yl)indan-2-ol

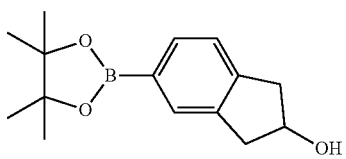 [SMILES: CC1(C)OB(c2ccc3c(c2)CC(O)C3)OC1(C)C]

A suspension of 5-bromoindan-2-ol (Combi-Blocks, cat#QA3834: 114 mg, 0.535 mmol), potassium acetate (160 mg, 1.6 mmol) and 4,4,5,5,4',4',5',5'-octamethyl-[2,2']bi[[1,3,2]dioxaborolanyl] (200 mg, 0.80 mmol) in 1,4-dioxane (2.4 mL) was first degassed with stream of nitrogen for ~5 min, then [1,1′-bis(diphenylphosphino)ferrocene]dichloropalladium(II), complex with dichloromethane (1:1) (20 mg, 0.03 mmol) was added and the mixture was heated to 100° C. overnight. The reaction mixture was cooled to room temperature, concentrated then diluted with 1:1 ethyl acetate/hexanes, filtered through celite, and concentrated. The residue obtained was purified by flash chromatography on a silica gel column eluting with 0 to 40% EtOAc/Hexanes to provide the desired intermediate in nearly quantitative yield.

Step 2: 4-(5-(2-hydroxy-2,3-dihydro-1H-inden-5-yl)-8-{[(3R)-1-methylpiperidin-3-yl]methoxy}imidazo[1,5-a]pyrazin-6-yl)benzonitrile The title compound was prepared using procedures analogous to those described in Example 21, Step 9 with 5-(4,4,5,5-tetramethyl-1,3,2-dioxaborolan-2-yl)indan-2-ol replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product (a mixture of two diastereomers) as the TFA salt. LC-MS calculated for $C_{29}H_{30}N_5O_2$ (M+H)$^+$: m/z=480.2. found 480.2.

Example 102

2-fluoro-4-(5-(1-methyl-2-oxo-1,2,3,4-tetrahydroquinolin-6-yl)-8-{[(3R)-1-methylpiperidin-3-yl]methoxy}imidazo[1,5-a]pyrazin-6-yl)benzonitrile

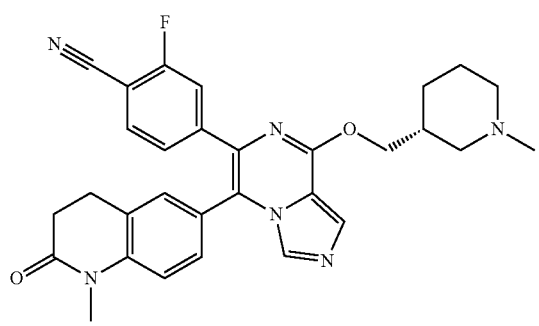 [SMILES: CN1CCC[C@@H](COc2nc(-c3ccc(C#N)c(F)c3)c(-c3ccc4c(c3)CCC(=O)N4C)n3cncc23)C1]

The title compound was prepared using procedures analogous to those described in Example 21, Step 9 with 1-methyl-6-(4,4,5,5-tetramethyl-1,3,2-dioxaborolan-2-yl)-3,4-dihydroquinolin-2(1H)-one (Example 24, Step 2) replacing 3-methyl-6-(4,4,5,5-tetramethyl-1,3,2-dioxaborolan-2-yl)-1,3-benzoxazol-2(3H)-one, and with (4-cyano-3-fluorophenyl)boronic acid [Combi-Blocks, PN-3408] replacing (4-cyanophenyl)boronic acid. The reaction mixture was purified by prep-HPLC (pH=2, acetonitrile/water+TFA) to give the desired product as the TFA salt. LC-MS calculated for $C_{30}H_{30}FN_6O_2$(M+H)$^+$: m/z=525.2. found 525.3.

Example 103

4-(8-(4-(dimethylamino)piperidin-1-yl)-5-(quinoxalin-6-yl)imidazo[1,5-a]pyrazin-6-yl)benzonitrile

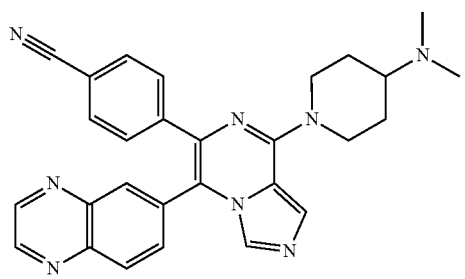 [SMILES: CN(C)C1CCN(c2nc(-c3ccc(C#N)cc3)c(-c3ccc4nccnc4c3)n3cncc23)CC1]

The title compound was prepared using procedures analogous to those described in Example 50, Step 2 with 6-(4,4,5,5-tetramethyl-1,3,2-dioxaborolan-2-yl)quinoxaline [Combi-Blocks cat#BB-5429] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{27}N_8$ (M+H)$^+$: m/z=475.2. found 475.1.

Example 104

4-(8-(4-(dimethylamino)piperidin-1-yl)-5-(furo[3,2-b]pyridin-6-yl)imidazo[1,5-a]pyrazin-6-yl)benzonitrile

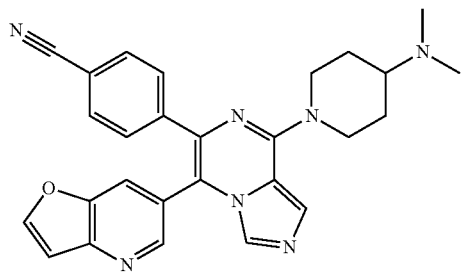 [SMILES: CN(C)C1CCN(c2nc(-c3ccc(C#N)cc3)c(-c3cnc4ccoc4c3)n3cncc23)CC1]

The title compound was prepared using procedures analogous to those described in Example 50, Step 2 with 6-(4,4,5,5-tetramethyl-1,3,2-dioxaborolan-2-yl)furo[3,2-b]pyridine [Adesis catalog#5-119] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{26}N_7O$ (M+H)$^+$: m/z=464.2. found 464.2.

Example 105

4-[8-[4-(dimethylamino)piperidin-1-yl]-5-(4-methyl-3-oxo-3,4-dihydro-2H-pyrido[3,2-b][1,4]oxazin-7-yl)imidazo[1,5-a]pyrazin-6-yl]benzonitrile

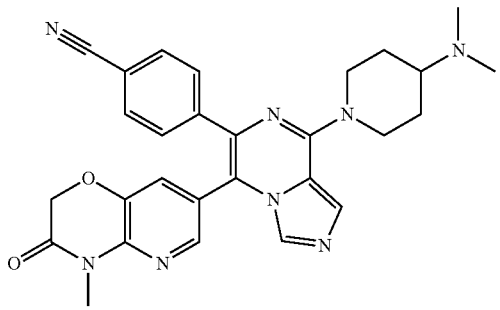 [SMILES: CN1C(=O)COc2cc(-c3c(-c4ccc(C#N)cc4)nc(N4CCC(N(C)C)CC4)c4cncn34)cnc21]

Step 1: 7-bromo-4-methyl-2H-pyrido[3,2-b][1,4]oxazin-3(4H)-one

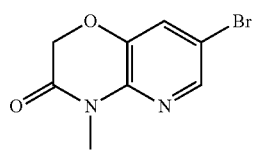

To a mixture of 7-bromo-2H-pyrido[3,2-b][1,4]oxazin-3(4H)-one (Ark Pharma, cat# AK-30821: 204 mg, 0.893 mmol) and cesium carbonate (440 mg, 1.3 mmol) in tetrahydrofuran (3 mL) was added methyl iodide (2.0 mL, 30 mmol). The mixture was stirred at 50° C. overnight. After cooling to room temperature, the reaction mixture was filtered and concentrated. The residue was used in the next step without further purification. LC-MS calculated for $C_8H_8BrN_2O_2$ (M+H)+: m/z=243.0. found 242.9.

Step 2: 4-methyl-7-(4,4,5,5-tetramethyl-1,3,2-dioxaborolan-2-yl)-2H-pyrido[3,2-b][1,4]oxazin-3(4H)-one

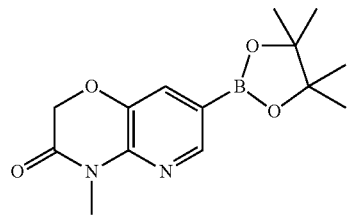 [SMILES: CN1C(=O)COc2cc(B3OC(C)(C)C(C)(C)O3)cnc21]

A mixture of 7-bromo-4-methyl-2H-pyrido[3,2-b][1,4]oxazin-3(4H)-one (200 mg, 0.8 mmol), 4,4,5,5,4',4',5',5'-octamethyl-[2,2']bi[[1,3,2]dioxaborolanyl] (230 mg, 0.90 mmol), [1,1'-bis(diphenylphosphino)ferrocene]dichloropalladium(II) complexed with dichloromethane (1:1) (70 mg, 0.08 mmol) and potassium acetate (300 mg, 3 mmol) in 1,4-dioxane (3 mL) was purged with nitrogen then stirred at 90° C. for 6 h. After cooling to room temperature, the reaction mixture was concentrated and the residue was dissolved in EtOAc then filtered. The filtrate was concentrated and the residue was purified by flash chromatography on a silica gel column eluting with 0-90% EtOAc in hexanes to afford the desired product. LC-MS calculated for $C_{14}H_{20}BN_2O_4$ (M+H)+: m/z=291.2. found 291.1.

Step 3: 4-[8-[4-(dimethylamino)piperidin-1-yl]-5-(4-methyl-3-oxo-3,4-dihydro-2H-pyrido[3,2-b][1,4]oxazin-7-yl)imidazo[1,5-a]pyrazin-6-yl]benzonitrile The title compound was prepared using procedures analogous to those described in Example 50, Step 2 with 4-methyl-7-(4,4,5,5-tetramethyl-1,3,2-dioxaborolan-2-yl)-2H-pyrido[3,2-b][1,4]oxazin-3(4H)-one replacing 1-methyl-5-(4,4,5,5-tetramethyl-1,3,2-dioxaborolan-2-yl)-1H-pyrazolo[3,4-b]pyridine. The reaction mixture was first purified by prep-HPLC (pH=2, acetonitrile/water+TFA) and the compound was further purified with prep-HPLC (pH=10, acetonitrile/water+NH$_4$OH) to give the desired product. LC-MS calculated for $C_{28}H_{29}N_8O_2$(M+H)+: m/z=509.2. found 509.2.

Example 106

4-[8-[4-(dimethylamino)piperidin-1-yl]-5-(1-methyl-2-oxo-1,4-dihydro-2H-3,1-benzoxazin-6-yl)imidazo[1,5-a]pyrazin-6-yl]benzonitrile

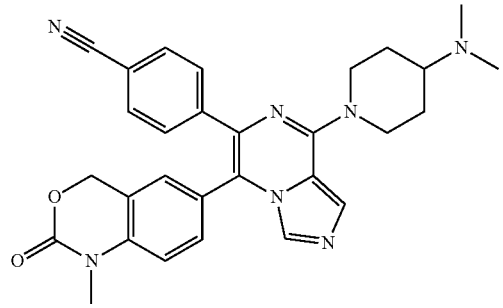 [SMILES: CN1C(=O)OCc2cc(-c3c(-c4ccc(C#N)cc4)nc(N4CCC(N(C)C)CC4)c4cncn34)ccc21]

Step 1: 6-bromo-1-methyl-1,4-dihydro-2H-3,1-benzoxazin-2-one

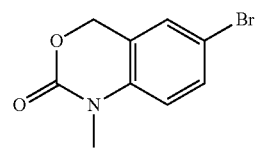

To a solution of 6-bromo-1,4-dihydro-2H-3,1-benzoxazin-2-one (Ark Pharma, cat# AK-37763, 350.0 mg, 1.535 mmol) in N,N-dimethylformamide (7 mL) at 0° C. was added NaH (60 wt % in mineral oil, 92 mg, 2.3 mmol). The mixture was stirred at 0° C. for 30 min, then methyl iodide (190 μL, 3.1 mmol) was added. After stirring at 0° C. for 1 h, the reaction mixture was quenched with water and extract with EtOAc. The combined extracts were washed with brine then dried over Na$_2$SO$_4$ and concentrated. The residue was used in the next step without further purification. LC-MS calculated for $C_9H_9BrNO_2$ (M+H)$^+$: m/z=242.0. found 242.0.

Step 2: 1-methyl-6-(4,4,5,5-tetramethyl-1,3,2-dioxaborolan-2-yl)-1,4-dihydro-2H-3,1-benzoxazin-2-one

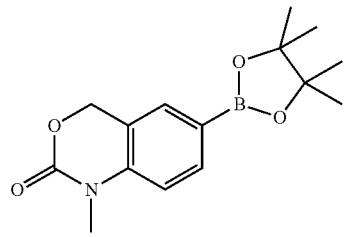 [SMILES: CN1C(=O)OCc2cc(B3OC(C)(C)C(C)(C)O3)ccc21]

A mixture of 6-bromo-1-methyl-1,4-dihydro-2H-3,1-benzoxazin-2-one (360.0 mg, 1.487 mmol), 4,4,5,5,4',4',5',5'-Octamethyl-[2,2']bi[[1,3,2]dioxaborolanyl] (760 mg, 3.0 mmol), [1,1'-bis(diphenylphosphino)ferrocene]dichloropalladium(II) complexed with dichloromethane (1:1) (60 mg, 0.07 mmol) and potassium acetate (440 mg, 4.5 mmol) in 1,4-dioxane (10 mL) was purged with nitrogen then heated at 90° C. overnight. After cooling to room temperature, the reaction mixture was concentrated and the residue was purified by flash chromatography on a silica gel column eluting with 0 to 40% EtOAc in hexanes to afford desired product. LC-MS calculated for $C_{15}H_{21}BNO_4$ (M+H)$^+$: m/z=290.2. found 290.1.

Step 3: 4-[8-[4-(dimethylamino)piperidin-1-yl]-5-(1-methyl-2-oxo-1,4-dihydro-2H-3,1-benzoxazin-6-yl)imidazo[1,5-a]pyrazin-6-yl]benzonitrile The title compound was prepared using procedures analogous to those described in Example 50, Step 2 with 1-methyl-6-(4,4,5,5-tetramethyl-1,3,2-dioxaborolan-2-yl)-1,4-dihydro-2H-3,1-benzoxazin-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) and the compound was further purified by prep-HPLC (pH=10, acetonitrile/water+NH$_4$OH) to give the desired product. LC-MS calculated for $C_{29}H_{30}N_7O_2$ (M+H)$^+$: m/z=508.2. found 508.3.

Example 107

4-[8-[4-(dimethylamino)piperidin-1-yl]-5-(3-methyl-3H-imidazo[4,5-b]pyridin-6-yl)imidazo[1,5-a]pyrazin-6-yl]benzonitrile

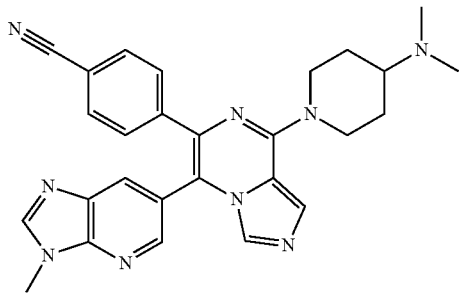 [SMILES: CN(C)C1CCN(c2nc(-c3ccc(C#N)cc3)c(-c3cnc4c(c3)ncn4C)n3cncc23)CC1]

The title compound was prepared using procedures analogous to those described in Example 50, Step 2 with 3-methyl-6-(4,4,5,5-tetramethyl-1,3,2-dioxaborolan-2-yl)-3H-imidazo[4,5-b]pyridine [Combi-Blocks, cat#FM-3151] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=10, acetonitrile/water+NH$_4$OH) to give the desired product. LC-MS calculated for $C_{27}H_{28}N_9$ (M+H)$^+$: m/z=478.2. found 478.2.

Example 108

4-[8-[4-(dimethylamino)piperidin-1-yl]-5-(3-ethyl-2-oxo-2,3-dihydro-1,3-benzoxazol-6-yl)imidazo[1,5-a]pyrazin-6-yl]benzonitrile

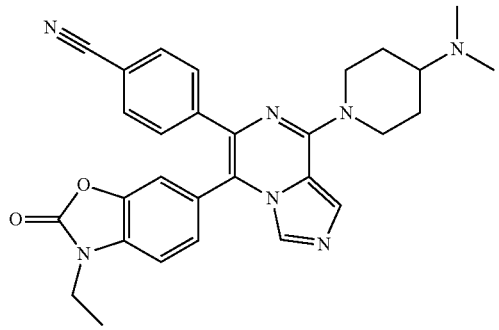 [SMILES: CCn1c(=O)oc2cc(-c3c(-c4ccc(C#N)cc4)nc(N4CCC(N(C)C)CC4)c4cncn34)ccc21]

Step 1: 6-bromo-3-ethyl-1,3-benzoxazol-2(3H)-one

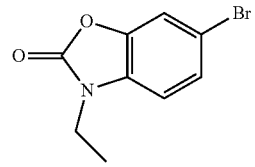

Iodoethane (100 µL, 1 mmol) was added to a mixture of 6-bromo-1,3-benzoxazol-2(3H)-one (Acros, cat#CC75710DA, 150 mg, 0.70 mmol) and potassium carbonate (0.3 g, 2 mmol) in Acetone (3 mL). The reaction mixture was stirred at 80° C. for 2 h then cooled to room temperature and filtered. The filtrate was concentrated and the residue was purified by flash chromatography on a silica gel column eluting with 0 to 30% EtOAc in Hexanes to give the desired product. LC-MS calculated for $C_9H_9BrNO_2$ (M+H)$^+$: m/z=242.0. found 242.0.

Step 2: 3-ethyl-6-(4,4,5,5-tetramethyl-1,3,2-dioxaborolan-2-yl)-1,3-benzoxazol-2(3H)-one

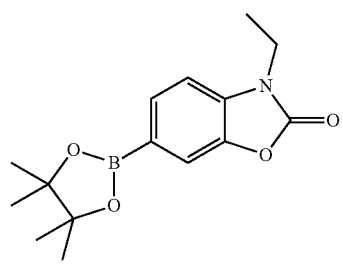 [SMILES: CCn1c(=O)oc2cc(B3OC(C)(C)C(C)(C)O3)ccc21]

A mixture of [1,1'-Bis(diphenylphosphino)ferrocene]dichloropalladium(II), complex with dichloromethane (1:1)

(30 mg, 0.04 mmol) was added to a mixture of 6-bromo-3-ethyl-1,3-benzoxazol-2(3H)-one (0.2 g, 0.7 mmol) 4,4,5,5,4',4',5',5'-octamethyl-[2,2']bi[[1,3,2]dioxaborolanyl] (0.27 g, 1.0 mmol), potassium acetate (0.2 g, 2 mmol) in 1,4-dioxane (5 mL) was purged with nitrogen then stirred at 90° C. overnight. The reaction mixture was cooled to room temperature then concentrated. The residue was purified by flash chromatography on a silica gel column eluting with 0 to 25% EtOAc in hexanes to give the desired product. LC-MS calculated for $C_{15}H_{21}BNO_4(M+H)^+$: m/z=290.2. found 290.2.

Step 3: 4-[8-[4-(dimethylamino)piperidin-1-yl]-5-(3-ethyl-2-oxo-2,3-dihydro-1,3-benzoxazol-6-yl)imidazo[1,5-a]pyrazin-6-yl]benzonitrile The title compound was prepared using procedures analogous to those described in Example 50, Step 2 with 3-ethyl-6-(4,4,5,5-tetramethyl-1,3,2-dioxaborolan-2-yl)-1,3-benzoxazol-2(3H)-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}N_7O_2$ $(M+H)^+$: m/z=508.2. found 508.2.

Example 109

4-[8-[4-(dimethylamino)piperidin-1-yl]-5-(4-fluoro-1,3-dimethyl-2-oxo-2,3-dihydro-1H-benzimidazol-5-yl)imidazo[1,5-a]pyrazin-6-yl]benzonitrile

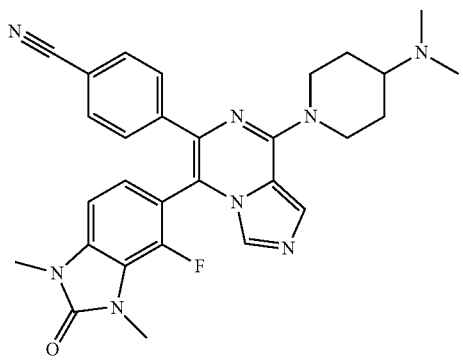 [SMILES: CN(C)C1CCN(c2nc(-c3ccc(C#N)cc3)c(-c3ccc4c(c3F)n(C)c(=O)n4C)n3cncc23)CC1]

Step 1: 5-bromo-4fluoro-1,3-dimethyl-1,3-dihydro-2H-benzimidazol-2-one

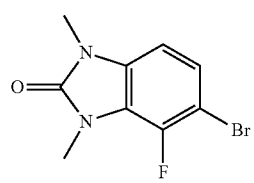

To a solution of 4-bromo-3-fluorobenzene-1,2-diamine (Astatech, cat#BL009140, 0.3 g, 1 mmol) in tetrahydrofuran (20 mL) at 0° C. was added triethylamine (1.0 mL, 7.3 mmol), followed by triphosgene (0.52 g, 1.8 mmol). The resulting mixture was stirred at 0° C. for 1 h then 1.0 M sodium hydroxide aqueous solution (2.9 mL, 2.9 mmol) was added. The mixture was stirred at room temperature for another 1 h then diluted with EtOAc and washed with water and brine. The organic layer was dried over $Na_2SO_4$, filtered and concentrated. The residue was dissolved in acetone (5 mL) then potassium carbonate (0.6 g, 4 mmol) and methyl iodide (0.4 mL, 6 mmol) were added. The mixture was stirred at 80° C. for 3 h then cooled to room temperature, filtered and concentrated. The residue was purified by flash chromatography on a silica gel column eluting with 0 to 10% MeOH in DCM to give the desired product. LC-MS calculated for $C_9H_9BrFN_2O$ $(M+H)^+$: m/z=259.0. found 259.1.

Step 2: 4-fluoro-1,3-dimethyl-5-(4,4,5,5-tetramethyl-1,3,2-dioxaborolan-2-yl)-1,3-dihydro-2H-benzimidazol-2-one

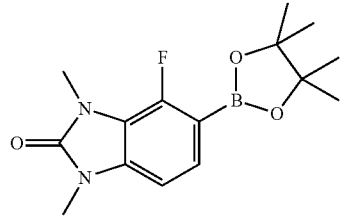 [SMILES: Cn1c(=O)n(C)c2c(F)c(B3OC(C)(C)C(C)(C)O3)ccc21]

A mixture of [1,1'-bis(diphenylphosphino)ferrocene]dichloropalladium(II) complexed with dichloromethane (1:1) (30 mg, 0.04 mmol), 5-bromo-4-fluoro-1,3-dimethyl-1,3-dihydro-2H-benzimidazol-2-one (0.2 g, 0.7 mmol) 4,4,5,5,4',4',5',5'-octamethyl-[2,2']bi[[1,3,2]dioxaborolanyl] (0.27 g, 1.0 mmol) and potassium acetate (0.2 g, 2 mmol) in 1,4-dioxane (5 mL) was purged with nitrogen then stirred at 90° C. overnight. The reaction mixture was cooled to room temperature then concentrated. The residue was purified by flash chromatography on a silica gel column eluting with 0 to 10% MeOH in DCM to give the desired product. LC-MS calculated for $C_{15}H_{21}BFN_2O_3(M+H)^+$: m/z=307.2. found 307.1.

Step 3: 4-[8-[4-(dimethylamino)piperidin-1-yl]-5-(4-fluoro-1,3-dimethyl-2-oxo-2,3-dihydro-1H-benzimidazol-5-yl)imidazo[1,5-a]pyrazin-6-yl]benzonitrile The title compound was prepared using procedures analogous to those described in Example 50, Step 2 with 4-fluoro-1,3-dimethyl-5-(4,4,5,5-tetramethyl-1,3,2-dioxaborolan-2-yl)-1,3-dihydro-2H-benzimidazol-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}FN_8O$ $(M+H)^+$: m/z=525.2. found 525.2.

Example 110

4-[8-{[(3R)-1-ethylpiperidin-3-yl]methoxy}-5-(1-methyl-2-oxo-2,3-dihydro-1H-indol-5-yl)imidazo[1,5-a]pyrazin-6-yl]benzonitrile

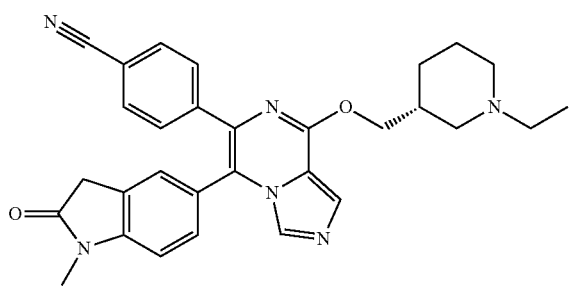 [SMILES: CCN1CCC[C@@H](COc2nc(-c3ccc(C#N)cc3)c(-c3ccc4c(c3)CC(=O)N4C)n3cncc23)C1]

Step 1: 5-bromo-6-chloro-8-{[(3R)-1-ethylpiperidin-3-yl]methoxy}imidazo[1,5-a]pyrazine

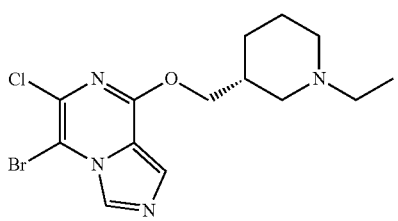

4.0 M Hydrogen chloride in 1,4-dioxane (1 mL, 4 mmol) was added to a solution of tert-butyl (3R)-3-{[(5-bromo-6-chloroimidazo[1,5-a]pyrazin-8-yl)oxy]methyl}piperidine-1-carboxylate (Example 21, Step 6, 240 mg, 0.54 mmol) in methylene chloride (0.70 mL) and the resulting mixture was stirred at room temperature for 30 min then concentrated. The residue was dissolved in methylene chloride (1 mL) then N,N-diisopropylethylamine (200 µL, 1 mmol) was added, followed acetaldehyde (90 µL, 2 mmol). The mixture was stirred at room temperature for 1 h then sodium triacetoxyborohydride (170 mg, 0.81 mmol) was added. The reaction mixture was stirred at room temperature for another 1 h then diluted with DCM and washed with 1N NaOH, water and brine. The organic layer was dried over Na$_2$SO$_4$, filtered and concentrated. The residue was used in the next step without further purification. LC-MS calculated for C$_{14}$H$_{19}$BrClN$_4$O (M+H)$^+$: m/z=373.0. found 373.0.

Step 2: 4-[8-{[(3R)-1-ethylpiperidin-3-yl]methoxy}-5-(1-methyl-2-oxo-2,3-dihydro-1H-indol-5-yl)imidazo[1,5-a]pyrazin-6-yl]benzonitrile A mixture of 5-bromo-6-chloro-8-{[(3R)-1-ethylpiperidin-3-yl]methoxy}imidazo[1,5-a]pyrazine (10 mg, 0.03 mmol), 1-methyl-5-(4,4,5,5-tetramethyl-1,3,2-dioxaborolan-2-yl)-1,3-dihydro-2H-indol-2-one (Example 22, Step 1, 9.1 mg, 0.033 mmol), tetrakis(triphenylphosphine)palladium(0) (2 mg, 0.001 mmol) and potassium carbonate (12 mg, 0.083 mmol) in 1,4-dioxane (310 µL) and water (60 µL) was purged with nitrogen and then stirred at 100° C. for 2 hours. The reaction mixture was cooled to room temperature then (4-cyanophenyl)boronic acid (6.1 mg, 0.042 mmol), dichloro[1,1'-bis(dicyclohexylphosphino)ferrocene]palladium(II) (2 mg, 0.003 mmol), cesium carbonate (18 mg, 0.056 mmol) and tert-butyl alcohol (0.2 mL) were added. The mixture was purged with nitrogen and stirred at 90° C. for 1 hour. After cooling to room temperature, the reaction mixture was diluted with methanol, purified by prep-HPLC (pH=10, acetonitrile/water+NH$_4$OH), then purified again by prep-HPLC (pH=2, acetonitrile/water+TFA) to give the desired product as the TFA salt. LC-MS calculated for C$_{30}$H$_{31}$N$_6$O$_2$ (M+H)$^+$: m/z=507.2. found 507.2.

Example 111

4-[8-{[(3R)-1-ethylpiperidin-3-yl]methoxy}-5-(5-fluoro-3-methyl-2-oxo-2,3-dihydro-1,3-benzoxazol-6-yl)imidazo[1,5-a]pyrazin-6-yl]benzonitrile

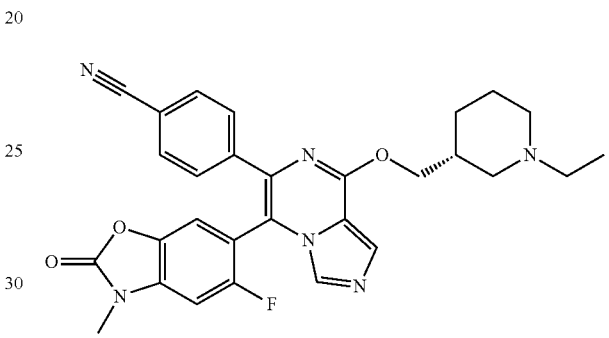

The title compound was prepared using procedures analogous to those described in Example 110, Step 2 with 5-fluoro-3-methyl-6-(4,4,5,5-tetramethyl-1,3,2-dioxaborolan-2-yl)-1,3-benzoxazol-2(3H)-one (Example 30, Step 3) replacing 1-methyl-5-(4,4,5,5-tetramethyl-1,3,2-dioxaborolan-2-yl)-1,3-dihydro-2H-indol-2-one. The reaction mixture was purified by prep-HPLC (pH=2, acetonitrile/water+TFA) to give the desired product as the TFA salt. LC-MS calculated for C$_{29}$H$_{28}$FN$_6$O$_3$ (M+H)$^+$: m/z=527.2. found 527.2.

Example 112

(S)-4-(8-(3-(dimethylamino)pyrrolidin-1-yl)-5-(3-methyl-2-oxo-2,3-dihydrobenzo[d]oxazol-6-yl)imidazo[1,5-a]pyrazin-6-yl)benzonitrile

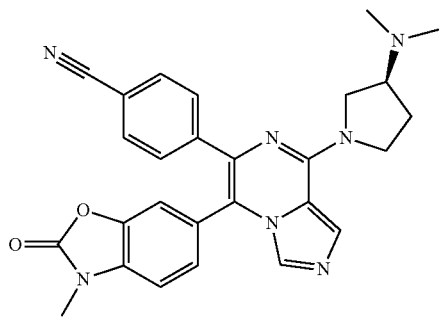 [SMILES: CN(C)[C@H]1CCN(c2nc(-c3ccc(C#N)cc3)c(-c3ccc4c(c3)oc(=O)n4C)n3cncc23)C1]

Step 1: (3S)-1-(5-bromo-6-chloroimidazo[1,5-a]pyrazin-8-yl)-N,N-dimethylpyrrolidin-3-amine

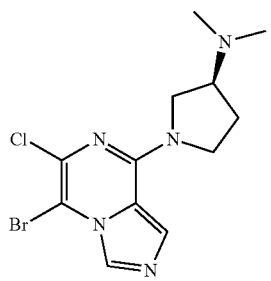 [SMILES: CN(C)[C@H]1CCN(c2nc(Cl)c(Br)n3cncc23)C1]

To a solution of 5-bromo-6-chloroimidazo[1,5-a]pyrazin-8-ol (Example 21, Step 4: 100 mg, 0.4 mmol) in methylene chloride (2 mL) was added triethylamine (100 µL, 1 mmol) and 4-dimethylaminopyridine (5 mg, 0.04 mmol), followed by methanesulfonyl chloride (40 µL, 0.5 mmol) at 0° C. The resulting mixture was stirred at room temperature for 1 h then quenched with water. The organic layer was separated, dried over Na$_2$SO$_4$, filtered and concentrated. The residue was dissolved in acetonitrile (2 mL) then N,N-diisopropylethylamine (200 µL, 1 mmol) and (3S)—N,N-dimethylpyrrolidin-3-amine (Sigma-Aldrich, cat#656704, 77 µL, 0.60 mmol) were added. The resulting mixture was stirred at 80° C. for 2 h then cooled to room temperature and diluted with DCM. The mixture was washed with 1N NaOH, water and brine. The organic layer was dried over Na$_2$SO$_4$, filtered and concentrated. The residue was purified by flash chromatography on a silica gel column eluting with 5 to 10% MeOH in DCM (5% triethylamine in DCM) to give the desired product. LC-MS calculated for C$_{12}$H$_{16}$BrClN$_5$ (M+H)+: m/z=344.0. found 344.0.

Step 2: (S)-4-(8-(3-(dimethylamino)pyrrolidin-1-yl)-5-(3-methyl-2-oxo-2,3-dihydrobenzo[d]oxazol-6-yl)imidazo[1,5-a]pyrazin-6-yl)benzonitrile A mixture of (3S)-1-(5-bromo-6-chloroimidazo[1,5-a]pyrazin-8-yl)-N,N-dimethylpyrrolidin-3-amine (10 mg, 0.03 mmol), 3-methyl-6-(4,4,5,5-tetramethyl-1,3,2-dioxaborolan-2-yl)-1,3-benzoxazol-2(3H)-one (Example 21, Step 8, 8 mg, 0.03 mmol), tetrakis(triphenylphosphine)palladium (0) (3 mg, 0.003 mmol) and potassium carbonate (10 mg, 0.09 mmol) in 1,4-dioxane (320 µL) and water (50 µL) was purged with nitrogen and then stirred at 100° C. for 2 hours. The reaction mixture was cooled to room temperature, then (4-cyanophenyl)boronic acid (6.4 mg, 0.044 mmol), dichloro[1,1'-bis(dicyclohexylphosphino)ferrocene]palladium(II) (2 mg, 0.003 mmol), cesium carbonate (20 mg, 0.06 mmol) and tert-butyl alcohol (0.2 mL) were added. The mixture was purged with nitrogen and stirred at 90° C. for 1 hour. After cooling to room temperature, the mixture was diluted with methanol, purified by prep-HPLC (pH=2, acetonitrile/water+TFA), then purified again by prep-HPLC (pH=10, acetonitrile/water+NH$_4$OH) to afford desired compound. LC-MS calculated for C$_{27}$H$_{26}$N$_7$O$_2$ (M+H)$^+$: m/z=480.2. found 480.1.

Example 113

4-[8-[(3S)-3-(dimethylamino)pyrrolidin-1-yl]-5-(5-fluoro-3-methyl-2-oxo-2,3-dihydro-1,3-benzoxazol-6-yl)imidazo[1,5-a]pyrazin-6-yl]benzonitrile

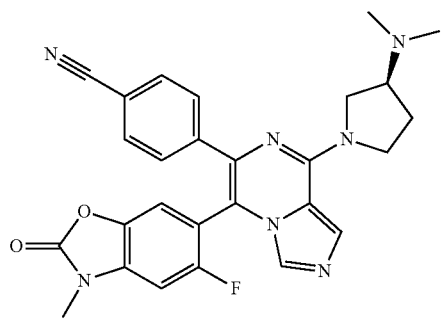 [SMILES: CN(C)[C@H]1CCN(c2nc(-c3ccc(C#N)cc3)c(-c3cc4oc(=O)n(C)c4cc3F)n3cncc23)C1]

The title compound was prepared using procedures analogous to those described in Example 112, Step 2 with 5-fluoro-3-methyl-6-(4,4,5,5-tetramethyl-1,3,2-dioxaborolan-2-yl)-1,3-benzoxazol-2(3H)-one (Example 30, Step 3) replacing 3-methyl-6-(4,4,5,5-tetramethyl-1,3,2-dioxaborolan-2-yl)-1,3-benzoxazol-2(3H)-one. The reaction mixture was purified by prep-HPLC (pH=2, acetonitrile/water+TFA) to give the desired product as the TFA salt. LC-MS calculated for C$_{27}$H$_{25}$FN$_7$O$_2$ (M+H)$^+$: m/z=498.2. found 498.2.

Example 114

(R)-4-(8-((1-ethylpiperidin-3-yl)methoxy)-5-(1-methyl-2-oxoindolin-5-yl)imidazo[1,5-a]pyridin-6-yl)benzonitrile

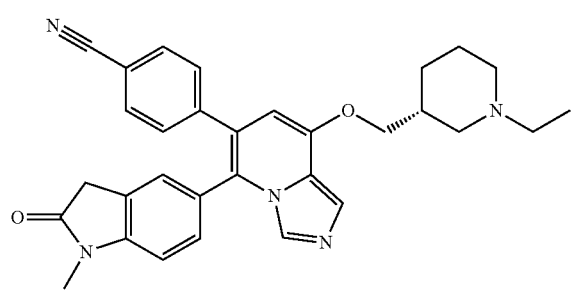 [SMILES: CCN1CCC[C@@H](COc2cc(-c3ccc(C#N)cc3)c(-c3ccc4c(c3)CC(=O)N4C)n3cncc23)C1]

This compound was prepared using a similar procedure as described for Example 66, Step 3 with 1-methyl-5-(4,4,5,5-tetramethyl-1,3,2-dioxaborolan-2-yl)-1,3-dihydro-2H-indol-2-one (Example 22, Step 1) replacing 3-methyl-6-(4,4,5,5-tetramethyl-1,3,2-dioxaborolan-2-yl)-3H-imidazo[4,5-b]pyridine. The reaction mixture was purified by prep-HPLC (pH=2, acetonitrile/water+TFA) to give the desired product as the TFA salt. LC-MS calculated for C$_{31}$H$_{32}$N$_5$O$_2$ (M+H)$^+$: m/z=506.3. found 506.2.

Example 115

(R)-4-(5-(2,3-dihydro-[1,4]dioxino[2,3-b]pyridin-7-yl)-8-((1-(2-methoxyethyl)piperidin-3-yl)methoxy)imidazo[1,5-a]pyridin-6-yl)benzonitrile

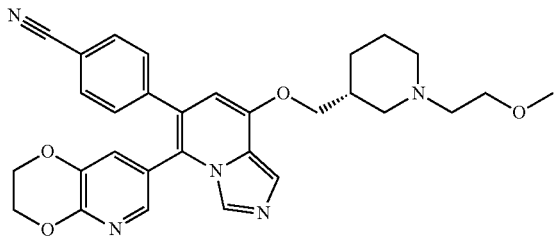 [SMILES: COCCN1CCC[C@@H](COc2cc(-c3ccc(C#N)cc3)c(-c3cnc4c(c3)OCCO4)n3cncc23)C1]

Step 1: (R)-6-bromo-5-chloro-8-((1-(2-methoxyethyl)piperidin-3-yl)methoxy) imidazo[1,5-a]pyridine

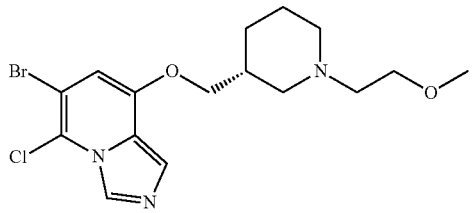 [SMILES: COCCN1CCC[C@@H](COc2cc(Br)c(Cl)n3cncc23)C1]

To the solution of 6-bromo-5-chloro-8-[(3R)-piperidin-3-ylmethoxy]imidazo[1,5-a]pyridine (Example 56, Step 6: 500.00 mg, 1.1013 mmol) in DMF (10 mL) was added triethylamine (3.837 mL, 27.53 mmol), followed by 1-bromo-2-methoxy ethane (0.52 mL, 5.5 mmol). The resulting mixture was stirred at room temperature overnight then concentrated. The residue was purified by flash chromatography on a silica gel column eluting with 0 to 20% MeOH/DCM to give the title compound (100 mg, 20% yield). LC-MS calculated for $C_{16}H_{22}BrClN_3O_2$ (M+H)$^+$: m/z=402.1. found 402.0.

Step 2: (R)-4-(5-chloro-8-((1-(2-methoxyethyl)piperidin-3-yl)methoxy)imidazo[1,5-a]pyridin-6-yl)benzonitrile

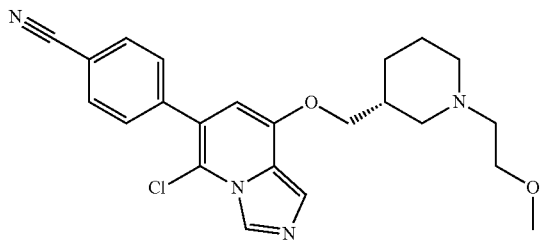 [SMILES: COCCN1CCC[C@@H](COc2cc(-c3ccc(C#N)cc3)c(Cl)n3cncc23)C1]

This compound was prepared using a similar procedure as described from Example 56, Step 8 with 6-bromo-5-chloro-8-{[(3R)-1-(2-methoxyethyl)piperidin-3-yl]methoxy}imidazo [1,5-a]pyridine replacing 6-bromo-5-chloro-8-{[(3R)-1-methylpiperidin-3-yl]methoxy}imidazo[1,5-a]pyridine. The reaction mixture was purified by flash chromatography on a silica gel column eluting with 0 to 20% MeOH/DCM to give the title compound. LC-MS calculated for $C_{23}H_{26}ClN_4O_2$ (M+H)$^+$: m/z=425.2. found 425.1.

Step 3: (R)-4-(5-(2,3-dihydro-[1,4]dioxino[2,3-b]pyridin-7-yl)-8-((1-(2-methoxyethyl)piperidin-3-yl)methoxy)imidazo[1,5-a]pyridin-6-yl)benzonitrile In a glass reaction vial were combined: 4-(5-chloro-8-{[(3R)-1-(2-methoxyethyl)piperidin-3-yl]methoxy}imidazo[1,5-a]pyridin-6-yl)benzonitrile (13.6 mg, 0.032 mmol), 7-(4,4,5,5-tetramethyl-1,3,2-dioxaborolan-2-yl)-2,3-dihydro[1,4]dioxino[2,3-b]pyridine (Adesis, cat#11-118: 16.6 mg, 0.0630 mmol), dichloro(bis{di-tert-butyl[4-(dimethylamino)phenyl]phosphoranyl}) palladium (Sigma-Aldrich, cat#678740: 2.23 mg, 0.00315 mmol), cesium carbonate (10.3 mg, 0.0315 mmol), cesium fluoride (9.57 mg, 0.0630 mmol), water (0.2 mL), and tert-butyl alcohol (0.9 mL). The vial was capped and sealed and the solvent was degassed by bubbling nitrogen through. The reaction mixture was heated to 90° C. for 2 hours. After cooling to room temperature, the crude reaction mixture was diluted with MeOH, passed through a syringe filter then purified by prep-HPLC (pH=2, acetonitrile/water+TFA) to give the desired product as the TFA salt. LC-MS calculated for $C_{30}H_{32}N_5O_4$ (M+H)$^+$: m/z=526.2. found 526.2.

Example 116

(R)-4-(5-(4-methyl-3,4-dihydro-2H-pyrido[3,2-b][1,4]oxazin-7-yl)-8-((1-methylpiperidin-3-yl)methoxy)imidazo[1,5-a]pyridin-6-yl)benzonitrile

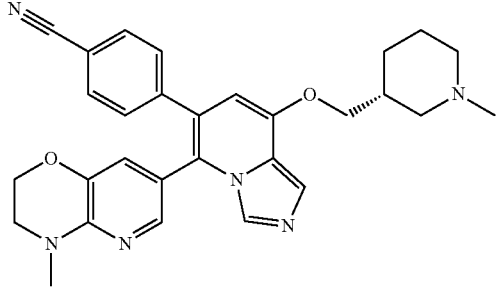 [SMILES: CN1CCC[C@@H](COc2cc(-c3ccc(C#N)cc3)c(-c3cnc4c(c3)OCCN4C)n3cncc23)C1]

The title compound was prepared using procedures analogous to those described in Example 56, Step 9 with 4-methyl-7-(4,4,5,5-tetramethyl-1,3,2-dioxaborolan-2-yl)-3,4-dihydro-2H-pyrido[3,2-b][1,4]oxazine (Example 29, Step 1) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{31}N_6O_2$ (M+H)$^+$: m/z=495.3. found 495.2. $^1$H NMR (500 MHz, CD$_3$OD) δ: 8.15 (s, 1H), 7.72 (s, 1H), 7.67 (d, J=8.3 Hz, 2H), 7.49-7.40 (m, 3H), 7.04 (d, J=1.9 Hz, 1H), 6.42 (s, 1H), 4.36-4.19 (m, 3H), 4.20-4.06 (m, 1H), 3.76 (d, J=12.0 Hz, 1H), 3.65-3.42 (m, 3H), 3.10 (s, 3H), 3.06-2.89 (m, 5H), 2.53-2.33 (m, 1H), 2.18-1.77 (m, 3H), 1.62-1.43 (m, 1H).

Example 117

4-(5-(3-ethyl-3H-[1,2,3]triazolo[4,5-b]pyridin-6-yl)-8-{[(3R)-1-methylpiperidin-3-yl]methoxy}imidazo[1,5-a]pyridin-6-yl)benzonitrile

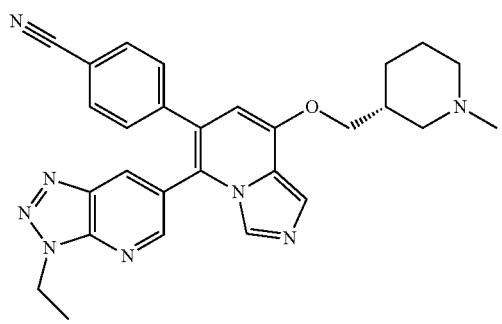 [SMILES: CCn1nnc2cc(-c3c(-c4ccc(C#N)cc4)cc(OC[C@@H]4CCCN(C)C4)c4cncn34)cnc21]

Step 1: 3-ethyl-6-(4,4,5,5-tetramethyl-1,3,2-dioxaborolan-2-yl)-3H-[1,2,3]triazolo[4,5-b]pyridine

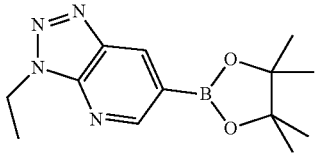 [SMILES: CCn1nnc2cc(B3OC(C)(C)C(C)(C)O3)cnc21]

In a vial were combined: 6-bromo-3-ethyl-3H-[1,2,3]triazolo[4,5-b]pyridine (Combi-Blocks, cat#HI-1471: 93.8 mg, 0.413 mmol) 4,4,5,5,4',4',5',5'-octamethyl-[2,2']bi[[1,3,2]dioxaborolanyl] (0.220 g, 0.868 mmol) potassium acetate (122 mg, 1.24 mmol), 1,4-dioxane (2.1 mL, 26 mmol), and [1,1'-bis(diphenylphosphino)ferrocene]dichloropalladium (II) (15.1 mg, 0.0206 mmol). The vial was de-gassed by bubbling nitrogen through the solvent for 5 minutes. It was then sealed and heated to 90° C. overnight. The crude reaction mixture was cooled to room temperature and passed through a syringe filter. The filtrate was concentrated and used directly in the next step.

Step 2: 4-(5-(3-ethyl-3H-[1,2,3]triazolo[4,5-b]pyridin-6-yl)-8-{[(3R)-1-methylpiperidin-3-yl]methoxy}imidazo[1,5-a]pyridin-6-yl)benzonitrile The title compound was prepared using procedures analogous to those described in Example 56, Step 9 with 3-ethyl-6-(4,4,5,5-tetramethyl-1,3,2-dioxaborolan-2-yl)-3H-[1,2,3]triazolo[4,5-b]pyridine replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{28}H_{29}N_8O$ (M+H)$^+$: m/z=493.3. found 493.1.

Example 118

4-(5-(2,3-dihydro[1,4]dioxino[2,3-b]pyridin-7-yl)-8-{[(3R)-1-(2-hydroxypropyl)piperidin-3-yl]methoxy}imidazo[1,5-a]pyridin-6-yl)benzonitrile

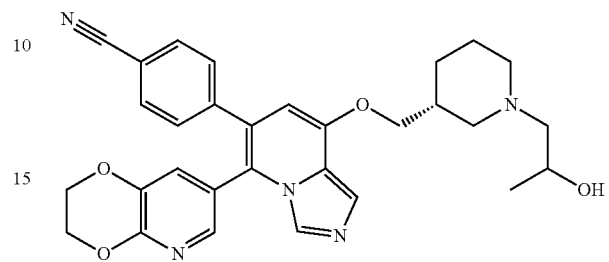

Step 1: 1-((3R)-3-{[(6-bromo-5-chloroimidazo[1,5-a]pyridin-8-yl)oxy]methyl}piperidin-1-yl)propan-2-ol

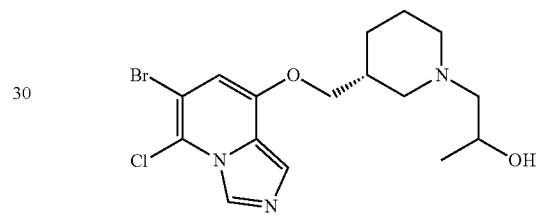

Propylene oxide (60 µL, 0.8 mmol) was diluted with water (0.3 mL, 20 mmol). To this was added 6-bromo-5-chloro-8-[(3R)-piperidin-3-ylmethoxy]imidazo[1,5-a]pyridine (Example 56, Step 6: 350 mg, 1.0 mmol) in one portion and was allowed to stir at room temperature overnight. The crude reaction mixture was diluted with DCM and passed through a phase separator and concentrated under reduced pressure. The reaction mixture was purified by flash chromatography on a silica gel column eluting with 0 to 20% MeOH/DCM to give the title compound (95 mg, 30% yield). LC-MS calculated for $C_{16}H_{22}BrClN_3O_2$ (M+H)$^+$: m/z=402.1.
found 402.0.

Step 2: 4-(5-chloro-8-{[(3R)-1-(2-hydroxypropyl)piperidin-3-yl]methoxy}imidazo[1,5-a]pyridin-6-yl)benzonitrile

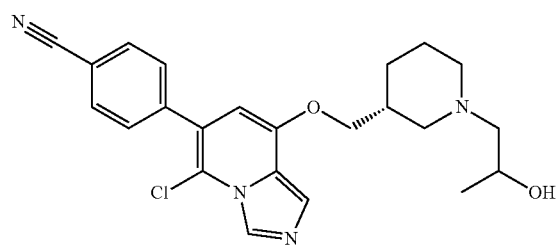 [SMILES: CC(O)CN1CCC[C@@H](COc2cc(-c3ccc(C#N)cc3)c(Cl)n3cncc23)C1]

This compound was prepared using a similar procedure as described from Example 56, Step 8 with 1-((3R)-3-{[(6-bromo-5-chloroimidazo[1,5-a]pyridin-8-yl)oxy]methyl}piperidin-1-yl)propan-2-ol replacing 6-bromo-5-chloro-8-{[(3R)-1-methylpiperidin-3-yl]methoxy}imidazo[1,5-a]pyridine. The reaction mixture was purified by flash chromatography on a silica gel column eluting with 0 to 20% MeOH/DCM to give the title compound. LC-MS calculated for $C_{23}H_{26}ClN_4O_2$ (M+H)$^+$: m/z=425.2. found 425.2.

Step 3: 4-(5-(2,3-dihydro[1,4]dioxino[2,3-b]pyridin-7-yl)-8-{[(3R)-1-(2-hydroxypropyl) piperidin-3-yl]methoxy}imidazo[1,5-a]pyridin-6-yl)benzonitrile In a glass reaction vial were combined: 4-(5-chloro-8-{[(3R)-1-(2-hydroxypropyl) piperidin-3-yl]methoxy}imidazo[1,5-a]pyridin-6-yl)benzonitrile (12.9 mg, 0.032 mmol), 7-(4,4,5,5-tetramethyl-1,3,2-dioxaborolan-2-yl)-2,3-dihydro[1,4]dioxino[2,3-b]pyridine (Adesis, cat#11-118: 16.6 mg, 0.0630 mmol), dichloro(bis{di-tert-butyl[4-(dimethylamino)phenyl]phosphoranyl}) palladium (Sigma-Aldrich, cat#678740: 2.23 mg, 0.00315 mmol), cesium carbonate (10.3 mg, 0.0315 mmol), cesium fluoride (9.57 mg, 0.0630 mmol), water (0.2 mL), and tert-butyl alcohol (0.9 mL). The vial was capped and sealed and the solvent was degassed by bubbling nitrogen through. The reaction mixture was heated to 90° C. for 2 hours. After cooling to room temperature, the crude reaction mixture was diluted with MeOH, passed through a syringe filter then purified by prep-HPLC (pH=2, acetonitrile/water+TFA) to give the desired product (a mixture of two diastereomers) as the TFA salt. LC-MS calculated for $C_{30}H_{32}N_5O_4$ (M+H)$^+$: m/z=526.3. found 526.2.

Example 119

4-(5-(furo[3,2-b]pyridin-6-yl)-8-(((3R)-1-(2-hydroxypropyl)piperidin-3-yl)methoxy)imidazo[1,5-a]pyridin-6-yl)benzonitrile

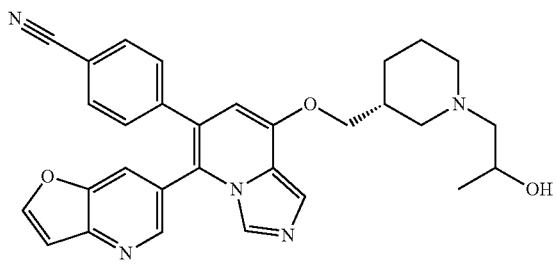 [SMILES: CC(O)CN1CCC[C@@H](COc2cc(-c3ccc(C#N)cc3)c(-c3cnc4ccoc4c3)n3cncc23)C1]

The title compound was prepared using procedures analogous to those described in Example 118, Step 3 with 6-(4,4,5,5-tetramethyl-1,3,2-dioxaborolan-2-yl)furo[3,2-b]pyridine (Adesis cat#5-119) replacing 7-(4,4,5,5-tetramethyl-1,3,2-dioxaborolan-2-yl)-2,3-dihydro[1,4]dioxino[2,3-b]pyridine. The reaction mixture was purified by prep-HPLC (pH=2, acetonitrile/water+TFA) to give the desired product (a mixture of two diastereomers) as the TFA salt. LC-MS calculated for $C_{30}H_{30}N_5O_3$ (M+H)$^+$: m/z=508.2. found 508.2.

Example 120

4-(8-(((3R)-1-(2-hydroxypropyl)piperidin-3-yl)methoxy)-5-(quinoxalin-6-yl)imidazo[1,5-a]pyridin-6-yl)benzonitrile

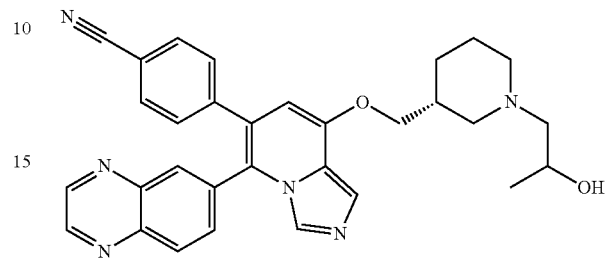

The title compound was prepared using procedures analogous to those described in Example 118, Step 3 with 6-(4,4,5,5-tetramethyl-1,3,2-dioxaborolan-2-yl)quinoxaline (Combi-Blocks cat#BB-5429) replacing 7-(4,4,5,5-tetramethyl-1,3,2-dioxaborolan-2-yl)-2,3-dihydro[1,4]dioxino[2,3-b]pyridine. The reaction mixture was purified by prep-HPLC (pH=2, acetonitrile/water+TFA) to give the desired product (a mixture of two diastereomers) as the TFA salt. LC-MS calculated for $C_{31}H_{31}N_6O_2$ (M+H)$^+$: m/z=519.3. found 519.2.

Example 121

4-(5-furo[3,2-b]pyridin-6-yl-8-{[(3R)-1-(2-methoxyethyl)piperidin-3-yl]methoxy}imidazo[1,5-a]pyridin-6-yl)benzonitrile

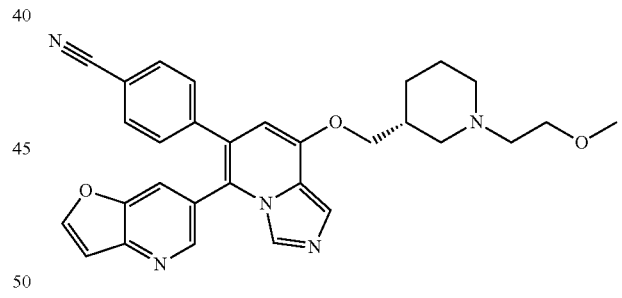

The title compound was prepared using procedures analogous to those described in Example 115, Step 3 with 6-(4,4,5,5-tetramethyl-1,3,2-dioxaborolan-2-yl)furo[3,2-b]pyridine (Adesis cat#5-119) replacing 7-(4,4,5,5-tetramethyl-1,3,2-dioxaborolan-2-yl)-2,3-dihydro [1,4]dioxino[2,3-b]pyridine. The reaction mixture was purified by prep-HPLC (pH=2, acetonitrile/water+TFA) to give the desired product as the TFA salt. LC-MS calculated for $C_{30}H_{30}N_5O_3$ (M+H)$^+$: m/z=508.2. found 508.2. $^1$H NMR (500 MHz, CD$_3$OD) δ: δ: 8.34 (d, J=1.7 Hz, 1H), 8.22 (d, J=2.3 Hz, 1H), 8.17 (s, 1H), 7.99 (s, 1H), 7.67 (s, 1H), 7.60 (d, J=8.3 Hz, 2H), 7.42 (d, J=8.3 Hz, 2H), 7.07 (d, J=1.5 Hz, 1H), 6.44 (s, 1H), 4.39-4.25 (m, 1H), 4.23-4.10 (m, 1H), 3.89-3.81 (m, 1H), 3.77 (t, J=4.8 Hz, 2H), 3.73-3.60 (m, 1H), 3.52-3.37 (m, 5H), 3.09-2.88 (m, 2H), 2.63-2.39 (m, 1H), 2.22-1.78 (m, 3H), 1.68-1.47 (m, 1H).

Example 122

(R)-4-(5-(3,4-dihydro-2H-pyrano[2,3-b]pyridin-6-yl)-8-((1-(2-methoxyethyl)piperidin-3-yl)methoxy)imidazo[1,5-a]pyridin-6-yl)benzonitrile

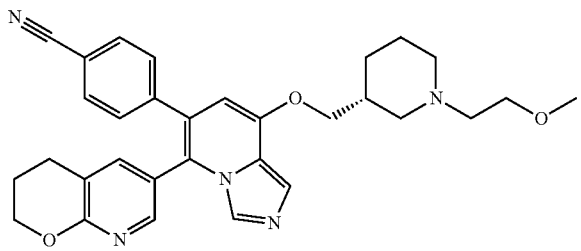 [SMILES: COCCN1CCC[C@@H](COc2cc(-c3ccc(C#N)cc3)c(-c3cnc4c(c3)CCCO4)n3cncc23)C1]

The title compound was prepared using procedures analogous to those described in Example 115, Step 3 with 6-(4,4,5,5-tetramethyl-1,3,2-dioxaborolan-2-yl)-3,4-dihydro-2H-pyrano[2,3-b]pyridine (Adesis, cat#10-106) replacing 7-(4,4,5,5-tetramethyl-1,3,2-dioxaborolan-2-yl)-2,3-dihydro[1,4]dioxino[2,3-b]pyridine. The reaction mixture was purified by prep-HPLC (pH=2, acetonitrile/water+TFA) to give the desired product as the TFA salt. LC-MS calculated for $C_{31}H_{34}N_5O_3(M+H)^+$: m/z=524.3. found 524.3. $^1$H NMR (500 MHz, $CD_3OD$) δ: 8.05 (s, 1H), 7.78 (d, J=2.2 Hz, 1H), 7.73-7.60 (m, 4H), 7.43 (d, J=8.3 Hz, 2H), 6.41 (s, 1H), 4.46-4.32 (m, 2H), 4.34-4.24 (m, 1H), 4.22-4.09 (m, 1H), 3.84 (d, J=12.0 Hz, 1H), 3.77 (t, J=5.0 Hz, 2H), 3.67 (d, J=12.9 Hz, 1H), 3.48-3.36 (m, 5H), 3.08-2.93 (m, 2H), 2.95-2.70 (m, 2H), 2.59-2.39 (m, 1H), 2.20-1.84 (m, 5H), 1.64-1.45 (m, 1H).

Example 123

4-(5-[4-(1-hydroxyethyl)phenyl]-8-{[(3R)-1-methylpiperidin-3-yl]methoxy}imidazo[1,5-a]pyridin-6-yl)benzonitrile

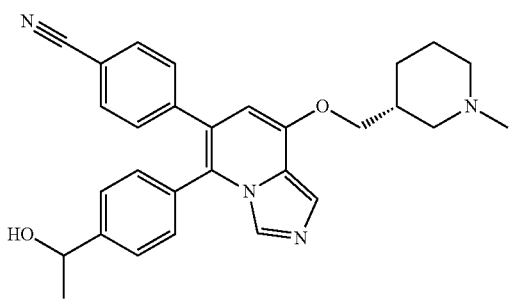 [SMILES: CC(O)c1ccc(-c2c(-c3ccc(C#N)cc3)cc(OC[C@@H]3CCCN(C)C3)c3cncn23)cc1]

Step 1: Benzenemethanol, 4-bromo-α-methyl-

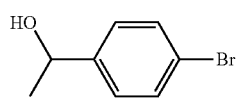

To a solution of 4-bromoacetophenone (Aldrich, cat#B56404: 1.0 g, 5.0 mmol) in ethanol (10 mL) was added sodium tetrahydroborate (0.28 g, 7.5 mmol) at 0° C. The mixture was stirred for 10 min, then the ice/water bath was removed and it was stirred at rt. for 2 h. 1N HCl was added dropwise, and the aqueous layer was extracted with ethyl acetate. The combined organic extracts were washed with brine and dried over $Na_2SO_4$. After filtration the filtrate was concentrated to provide the desired product, which was used in the next step without further purification. LC-MS calculated for $C_8H_8Br$ (M+H—$H_2O$)$^+$: m/z=183.0. found 183.2.

Step 2: 1-[4-(4,4,5,5-tetramethyl-1,3,2-dioxaborolan-2-yl)phenyl]ethanol

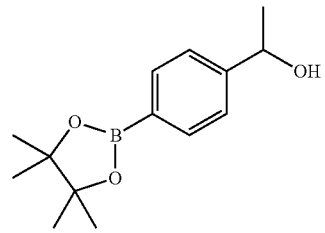 [SMILES: CC(O)c1ccc(B2OC(C)(C)C(C)(C)O2)cc1]

A mixture of benzenemethanol, 4-bromo-α-methyl- (300 mg, 1 mmol), 4,4,5,5,4',4',5',5'-octamethyl-[2,2']bi[[1,3,2]dioxaborolanyl] (450 mg, 1.8 mmol), [1,1'-bis(diphenylphosphino)ferrocene]dichloropalladium(II) complexed with dichloromethane (1:1) (60 mg, 0.07 mmol), potassium acetate (370 mg, 3.7 mmol) and 1,1'-bis(diphenylphosphino)ferrocene (40 mg, 0.07 mmol) in 1,4-dioxane (2 mL) was purged with nitrogen then stirred at 100° C. for 3 h. After cooling it was concentrated and the residue was used in the next step without further purification. LC-MS calculated for $C_{14}H_{20}BO_2$ (M+H-H2O)$^+$: m/z=231.2. found 231.2.

Step 3: 4-(5-[4-(1-hydroxyethyl)phenyl]-8-{[(3R)-1-methylpiperidin-3-yl]methoxy}imidazo[1,5-a]pyridin-6-yl)benzonitrile The title compound was prepared using procedures analogous to those described in Example 69 with 1-[4-(4,4,5,5-tetramethyl-1,3,2-dioxaborolan-2-yl)phenyl]ethano 1 replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product (a mixture of two diastereomers) as the TFA salt. LC-MS calculated for $C_{29}H_{31}N_4O_2$ (M+H)$^+$: m/z=467.2. found 467.2.

Example 124

4-(5-[3,5-difluoro-4-(1-hydroxyethyl)phenyl]-8-{[(3R)-1-methylpiperidin-3-yl]methoxy}imidazo[1,5-a]pyridin-6-yl)benzonitrile

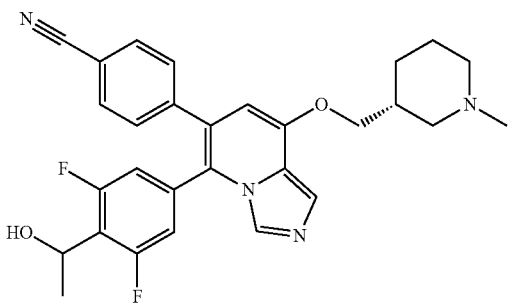

Step 1: 1-(4-bromo-2,6-difluorophenyl)ethanol

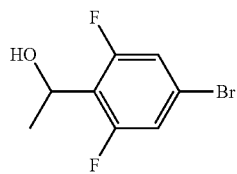

To a solution of 4-bromo-2,6-difluorobenzaldehyde (Aldrich, cat#706957: 200 mg, 1 mmol) in tetrahydrofuran (5 mL) was added 3.0 M methylmagnesium bromide in ether (0.39 mL, 1.2 mmol) at −78° C. The resultant reaction mixture was warmed up to room temperature over 30 min then quenched by saturated aqueous NH$_4$Cl after stirring for 1 h at rt. The aqueous layer was extracted with DCM, and the combined organic extracts were dried over sodium sulfate, filtered, and concentrated to provide the desired product which was used in the next step without further purification. LC-MS calculated for $C_8H_6BrF_2$ (M+H-H$_2$O)$^+$: m/z=219.0. found 219.0.

Step 2: 1-[2,6-difluoro-4-(4,4,5,5-tetramethyl-1,3,2-dioxaborolan-2-yl)phenyl]ethanol

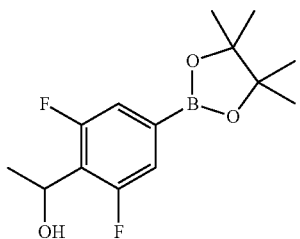 [SMILES: CC(O)c1c(F)cc(B2OC(C)(C)C(C)(C)O2)cc1F]

The title compound was prepared using procedures analogous to those described in Example 123, Step 2 with 1-(4-bromo-2,6-difluorophenyl)ethanol replacing 1-(5-bromo-2-methylphenyl)ethanol. The crude product was used in the next step without further purification. LC-MS calculated for $C_{14}H_{18}BF_2O_2$ (M+H-H$_2$O)$^+$: m/z=267.1. found 267.2.

Step 3: 4-(5-[3,5-difluoro-4-(1-hydroxyethyl)phenyl]-8-{[(3R)-1-methylpiperidin-3-yl]methoxy}imidazo[1,5-a]pyridin-6-yl)benzonitrile The title compound was prepared using procedures analogous to those described in Example 69 with 1-[2,6-difluoro-4-(4,4,5,5-tetramethyl-1,3,2-dioxaborolan-2-yl)phenyl]ethanol replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product (a mixture of two diastereomers) as the TFA salt. LC-MS calculated for $C_{29}H_{29}F_2N_4O_2$ (M+H)$^+$: m/z=503.2. found 503.2. $^1$H NMR (400 MHz, CD$_3$OD) δ 8.50 (s, 1H), 7.97 (s, 1H), 7.70 (d, J=8.2 Hz, 2H), 7.48 (d, J=8.2 Hz, 2H), 7.07 (d, J=9.4 Hz, 2H), 6.56 (s, 1H), 5.26 (q, J=6.6 Hz, 1H), 4.38-4.13 (m, 2H), 3.79 (d, J=12.0 Hz, 1H), 3.59 (d, J=12.0 Hz, 1H), 3.06-2.96 (m, 2H), 2.97 (s, 3H), 2.54-2.40 (m, 1H), 2.16-1.77 (m, 3H), 1.61 (d, J=6.8 Hz, 3H), 1.60-1.50 (m, 1H).

Example 125

4-[8-{[(3R)-1-methylpiperidin-3-yl]methoxy}-5-(6-methylpyridin-3-yl)imidazo[1,5-a]pyridin-6-yl]benzonitrile

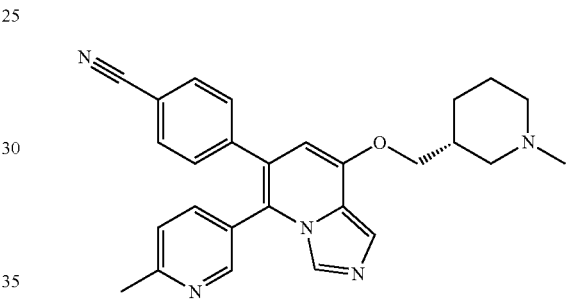

The title compound was prepared using procedures analogous to those described in Example 69 with 2-methyl-5-(4,4,5,5-tetramethyl-1,3,2-dioxaborolan-2-yl)pyridine (Aldrich, cat#CDS003793) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{27}H_{28}N_5O$ (M+H)$^+$: m/z=438.2. found 438.2.

Example 126

4-(5-[3-fluoro-4-(1-hydroxyethyl)-5-methylphenyl]-8-{[(3R)-1-methylpiperidin-3-yl]methoxy}imidazo[1,5-a]pyridin-6-yl)benzonitrile

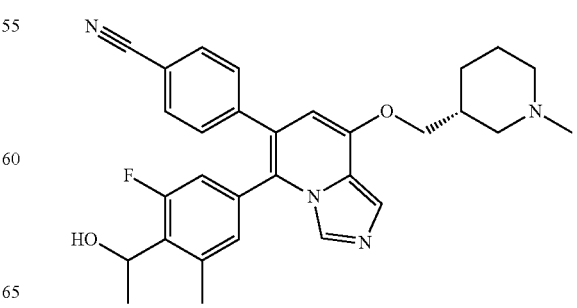

147

Step 1: 1-(4-bromo-2fluoro-6-methylphenyl)ethanol

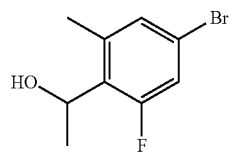

To a solution of methyl 4-bromo-2-fluoro-6-methylbenzoate (Combi-Blocks, cat#QD-8352: 0.2 g, 0.8 mmol) in toluene (4 mL) was added 1.0 M diisobutylaluminum hydride in DCM (0.850 mL, 0.850 mmol) at −78° C. for 2 h. The reaction mixture was quenched with MeOH (0.5 mL), then 1 N HCl was added. The aqueous layer was extracted with DCM (×2). The combined extracts were washed with saturated aqueous NaHCO$_3$, dried over sodium sulfate, filtered, and concentrated. The residue was dissolved in methylene chloride (4 mL) then Dess-Martin periodinane (520 mg, 1.2 mmol) was added. After stirring for 1 h at room temperature, the mixture was diluted with DCM, washed with saturated aqueous NaHCO$_3$, and extracted with DCM. The combined organic extracts were dried over Na$_2$SO$_4$. The desired intermediate compound was then passed through a plug of silica (10:90 EtOAc in hexanes) and used as an intermediate without purification. To a solution of crude residue containing the intermediate in tetrahydrofuran (4 mL) was added 3.0 M methylmagnesium bromide in ether (0.5 mL, 2 mmol) at −78° C. The resultant reaction mixture was warmed up to room temperature over 30 min then quenched by saturated aqueous NH$_4$Cl after another 1 h. The mixture was extracted with DCM. The combined extracts were dried over Na$_2$SO$_4$, filtered and concentrated. The residue was used in the next step without further purification.

Step 2: 1-[2-fluoro-6-methyl-4-(4,4,5,5-tetramethyl-1,3,2-dioxaborolan-2-yl)phenyl]ethanol

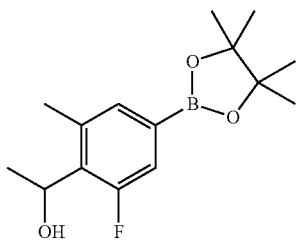 [SMILES: Cc1cc(B2OC(C)(C)C(C)(C)O2)cc(F)c1C(C)O]

A mixture of 1-(4-bromo-2-fluoro-6-methylphenyl)ethanol (129 mg, 0.553 mmol), 4,4,5,5,4',4',5',5'-octamethyl-[2,2']bi[[1,3,2]dioxaborolanyl] (150 mg, 0.61 mmol), [1,1'-bis(diphenylphosphino)ferrocene]dichloropalladium(II) complexed with dichloromethane (1:1) (20 mg, 0.03 mmol) and potassium acetate (140 mg, 1.4 mmol) in 1,4-dioxane (0.7 mL) was purged with nitrogen then stirred at 100° C. for 3 h. After cooling the mixture was filtered and concentrated to dryness and used directly in the next step. LC-MS calculated for C$_{15}$H$_{21}$BFO$_2$ (M+H−H$_2$O)$^+$: m/z=263.2. found 263.2.

148

Step 3: 4-(5-[3-fluoro-4-(1-hydroxyethyl)-5-methylphenyl]-8-{[(3R)-1-methylpiperidin-3-yl]methoxy}imidazo[1,5-a]pyridin-6-yl)benzonitrile The title compound was prepared using procedures analogous to those described in Example 69 with 1-[2-fluoro-6-methyl-4-(4,4,5,5-tetramethyl-1,3,2-dioxaborolan-2-yl)phenyl]ethanol replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product (a mixture of two diastereomers) as the TFA salt. LC-MS calculated for C$_{30}$H$_{32}$FN$_4$O$_2$ (M+H)$^+$: m/z=499.2. found 499.3.

Example 127

4-(5-(5-fluoro-6-methylpyridin-3-yl)-8-{[(3R)-1-methylpiperidin-3-yl]methoxy}imidazo[1,5-a]pyridin-6-yl)benzonitrile

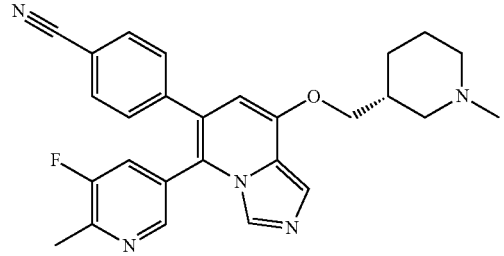 [SMILES: Cc1ncc(-c2c(-c3ccc(C#N)cc3)cc(OC[C@@H]3CCCN(C)C3)c3cncn23)cc1F]

The title compound was prepared using procedures analogous to those described in Example 69 with 3-fluoro-2-methyl-5-(4,4,5,5-tetramethyl-1,3,2-dioxaborolan-2-yl)pyridine (Anichem, cat#GS2820) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for C$_{27}$H$_{27}$FN$_5$O (M+H)$^+$: m/z=456.2. found 456.2.

Example 128

4-{8-{[(3R)-1-ethylpiperidin-3-yl]methoxy}-5-[3-fluoro-4-(hydroxymethyl)-5-methylphenyl]imidazo[1,5-a]pyridin-6-yl}benzonitrile

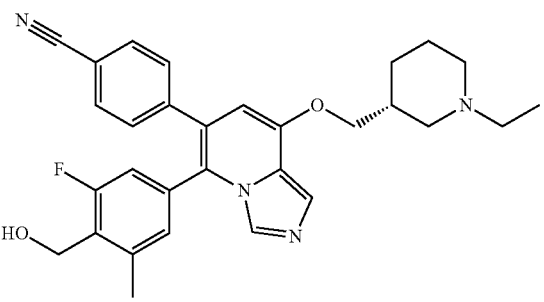 [SMILES: CCN1CCC[C@@H](COc2cc(-c3ccc(C#N)cc3)c(-c3cc(C)c(CO)c(F)c3)n3cncc23)C1]

A mixture of 4-(5-chloro-8-{[(3R)-1-ethylpiperidin-3-yl]methoxy}imidazo[1,5-a]pyridin-6-yl)benzonitrile (Example 66, Step 2: 10.0 mg, 0.0253 mmol), [2-fluoro-6-methyl-4-

(4,4,5,5-tetramethyl-1,3,2-dioxaborolan-2-yl)phenyl] methanol (Example 44, step 1: 13.5 mg, 0.0506 mmol), sodium carbonate (0.00569 g, 0.0537 mmol), and dichloro[1,1'-bis(dicyclohexylphosphino)ferrocene] palladium(II) (0.0019 g, 0.0025 mmol) in water (0.3 mL, 20 mmol) and tert-butyl alcohol (0.3 mL, 3 mmol) in a reaction vial was purged with nitrogen and sealed. The reaction mixture was stirred at 90° C. for 4 h. After cooling to room temperature, the reaction mixture was diluted with methanol, filtered then purified by prep-HPLC (pH=2, acetonitrile/water+TFA) to give the desired product as the TFA salt. LC-MS calculated for $C_{30}H_{32}FN_4O_2$ $(M+H)^+$: m/z=499.2. found 499.1. $^1$H NMR (400 MHz, CD$_3$OD) δ 8.17 (s, 1H), 7.80 (s, 1H), 7.63 (d, J=8.4 Hz, 2H), 7.43 (d, J=8.4 Hz, 2H), 7.07 (s, 1H), 6.97 (d, J=10.4 Hz, 1H), 6.47 (s, 1H), 4.69 (s, 2H), 4.34-4.15 (m, 2H), 3.80-3.56 (m, 2H), 3.28-2.22 (m, 2H), 3.00-2.87 (m, 2H), 2.50-2.40 (m, 1H), 2.41 (s, 3H), 2.16-2.00 (m, 2H), 1.95-1.82 (m, 1H), 1.61-1.52 (m, 1H), 1.39 (t, J=7.4 Hz, 3H).

Example 129

4-(5-[3-fluoro-4-(hydroxymethyl)-5-methylphenyl]-8-{[(3R)-1-(2-methoxyethyl)piperidin-3-yl]methoxy}imidazo[1,5-a]pyridin-6-yl)benzonitrile

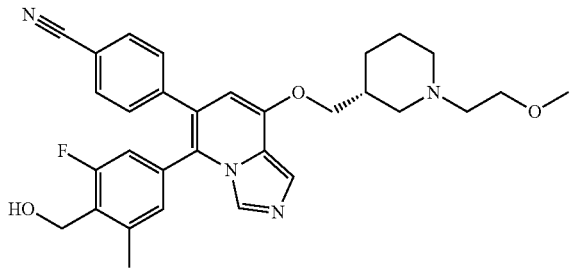 [SMILES: COCCN1CCC[C@@H](COc2cc(-c3ccc(C#N)cc3)c(-c3cc(C)c(CO)c(F)c3)n3cncc23)C1]

A mixture of 4-(5-chloro-8-{[(3R)-1-(2-methoxyethyl)piperidin-3-yl]methoxy}imidazo[1,5-a]pyridin-6-yl)benzonitrile (Example 115, Step 2: 10.0 mg, 0.0235 mmol), [2-fluoro-6-methyl-4-(4,4,5,5-tetramethyl-1,3,2-dioxaborolan-2-yl)phenyl]methanol (Example 44, Step 1: 12.5 mg, 0.0471 mmol), sodium carbonate (0.00529 g, 0.0499 mmol), and dichloro[1,1'-bis(dicyclohexylphosphino)ferrocene] palladium(II) (0.0018 g, 0.0024 mmol) in water (0.2 mL, 10 mmol) and tert-butyl alcohol (0.2 mL, 3 mmol) in a reaction vial was purged with nitrogen and sealed. It was stirred at 90° C. for 4 h. After cooling to room temperature, the reaction mixture was diluted with methanol, filtered then purified by prep-HPLC (pH=2, acetonitrile/water+TFA) to give the desired product as the TFA salt. LC-MS calculated for $C_{31}H_{34}FN_4O_3$ $(M+H)^+$: m/z=529.3. found 529.1. $^1$H NMR (400 MHz, CD$_3$OD) δ 8.26 (s, 1H), 7.83 (s, 1H), 7.63 (d, J=8.4 Hz, 2H), 7.44 (d, J=8.4 Hz, 2H), 7.07 (s, 1H), 6.98 (d, J=10.0 Hz, 1H), 6.49 (s, 1H), 4.69 (d, J=1.2 Hz, 2H), 4.32-4.26 (m, 1H), 4.20-4.13 (m, 1H), 3.86-3.64 (m, 4H), 3.48-3.35 (m, 2H), 3.43 (s, 3H), 3.05-2.95 (m, 2H), 2.55-2.43 (m, 1H), 2.41 (s, 3H), 2.12-1.85 (m, 3H), 1.60-1.51 (m, 1H).

Example 130

4-(5-(5,6-dimethylpyridin-3-yl)-8-{[(3R)-1-(2-methoxyethyl)piperidin-3-yl]methoxy}imidazo[1,5-a]pyridin-6-yl)benzonitrile

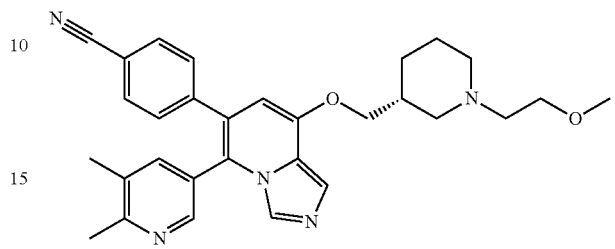

The title compound was prepared using procedures analogous to those described in Example 129 with 2,3-dimethyl-5-(4,4,5,5-tetramethyl-1,3,2-dioxaborolan-2-yl)pyridine (Combi-Blocks, cat#FM-6236) replacing [2-fluoro-6-methyl-4-(4,4,5,5-tetramethyl-1,3,2-dioxaborolan-2-yl)phenyl]methanol. The reaction mixture was purified by prep-HPLC (pH=2, acetonitrile/water+TFA) to give the desired product as the TFA salt. LC-MS calculated for $C_{30}H_{34}N_5O_2$ $(M+H)^+$: m/z=496.3. found 496.2. $^1$H NMR (400 MHz, CD$_3$OD) δ 8.47 (s, 1H), 8.30 (s, 1H), 8.03 (s, 1H), 7.94 (s, 1H), 7.67 (d, J=8.4 Hz, 2H), 7.45 (d, J=8.4 Hz, 2H), 6.57 (s, 1H), 4.35-4.28 (m, 1H), 4.25-4.17 (m, 1H), 3.87-3.63 (m, 4H), 3.46-3.38 (m, 2H), 3.44 (s, 3H), 3.09-2.94 (m, 2H), 2.61 (s, 3H), 2.56-2.45 (m, 1H), 2.40 (s, 3H), 2.15-1.86 (m, 3H), 1.65-1.50 (m, 1H).

Example 131

4-(5-(5,6-dimethylpyridin-3-yl)-8-{[(3R)-1-ethylpiperidin-3-yl]methoxy}imidazo[1,5-a]pyridin-6-yl)benzonitrile

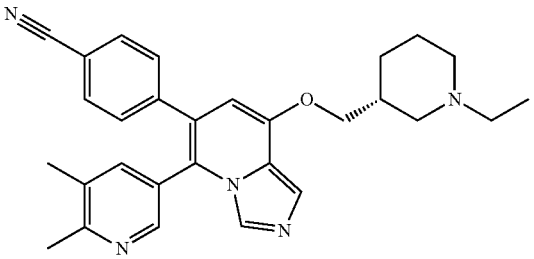 [SMILES: CCN1CCC[C@@H](COc2cc(-c3ccc(C#N)cc3)c(-c3cnc(C)c(C)c3)n3cncc23)C1]

The title compound was prepared using procedures analogous to those described in Example 128 with 2,3-dimethyl-5-(4,4,5,5-tetramethyl-1,3,2-dioxaborolan-2-yl)pyridine (Combi-Blocks, cat#FM-6236) replacing [2-fluoro-6-methyl-4-(4,4,5,5-tetramethyl-1,3,2-dioxaborolan-2-yl)phenyl]methanol. The reaction mixture was purified by prep-HPLC (pH=2, acetonitrile/water+TFA) to give the desired product as the TFA salt. LC-MS calculated for $C_{29}H_{32}N_5O$ $(M+H)^+$: m/z=466.3. found 466.2. $^1$H NMR (400 MHz, CD$_3$OD) δ 8.17 (s, 2H), 7.88 (s, 1H), 7.79 (s, 1H), 7.67 (d, J=8.4 Hz, 2H), 7.44 (d, J=8.4 Hz, 2H), 6.48 (s, 1H), 4.35-4.27 (m, 1H), 4.23-4.18 (m, 1H), 3.84-3.77 (m, 1H), 3.67-3.63 (m, 1H), 3.37-3.25 (m, 2H), 3.04-2.93 (m, 2H), 2.57 (s, 3H), 2.50-2.43 (m, 1H), 2.38 (s, 3H), 2.18-1.82 (m, 3H), 1.67-1.53 (m, 1H), 1.42 (t, J=7.4 Hz, 3H).

Example 132

4-(5-[6-(1-cyano-1-methylethyl)pyridin-3-yl]-8-{[(3R)-1-methylpiperidin-3-yl]methoxy}imidazo[1,5-a]pyridin-6-yl)benzonitrile

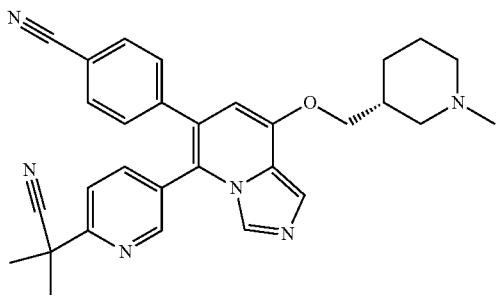 [SMILES: CN1CCC[C@@H](COc2cc(-c3ccc(C#N)cc3)c(-c3ccc(C(C)(C)C#N)nc3)n3cncc23)C1]

The title compound was prepared using procedures analogous to those described in Example 69 with 2-methyl-2-[5-(4,4,5,5-tetramethyl-1,3,2-dioxaborolan-2-yl)pyridin-2-yl]propanenitrile (Combi-Blocks, cat#PN-5112) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{30}H_{31}N_6O$ (M+H)$^+$: m/z=491.2. found 491.2.

Example 133

4-(5-(6-ethylpyridin-3-yl)-8-{[(3R)-1-methylpiperidin-3-yl]methoxy}imidazo[1,5-a]pyridin-6-yl)benzonitrile

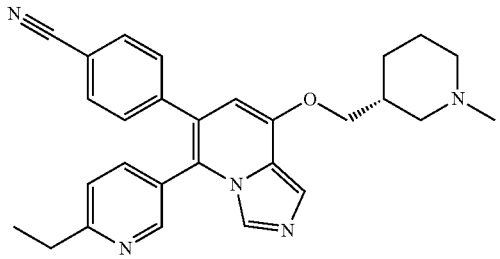 [SMILES: CCc1ccc(-c2c(-c3ccc(C#N)cc3)cc(OC[C@@H]3CCCN(C)C3)c3cncn23)cn1]

The title compound was prepared using procedures analogous to those described in Example 69 with (6-ethylpyridin-3-yl)boronic acid (CombiPhos, cat#BA864) replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. LC-MS calculated for $C_{28}H_{30}N_5O$ (M+H)$^+$: m/z=452.2. found 452.2. $^1$H NMR (400 MHz, CD$_3$OD) δ 8.33 (s, 1H), 8.22 (s, 1H), 7.91 (dd, J=8.0, 1.6 Hz, 1H), 7.82 (s, 1H), 7.64 (d, J=8.4 Hz, 2H), 7.47 (d, J=8.0 Hz, 1H), 7.41 (d, J=8.4 Hz, 2H), 6.49 (s, 1H), 4.34-4.25 (m, 1H), 4.21-4.04 (m, 1H), 3.77 (d, J=11.6 Hz, 1H), 3.56 (d, J=12.8 Hz, 1H), 3.05-2.90 (m, 2H), 2.95 (s, 3H), 2.86 (q, J=7.6 Hz, 2H), 2.50-2.36 (m, 1H), 2.15-1.98 (m, 2H), 1.94-1.81 (m, 1H), 1.59-1.46 (m, 1H), 1.30 (t, J=7.6 Hz, 3H).

Example 134

4-(5-(1-cyclobutyl-1H-pyrazol-4-yl)-8-{[(3R)-1-methylpiperidin-3-yl]methoxy}imidazo[1,5-a]pyridin-6-yl)benzonitrile

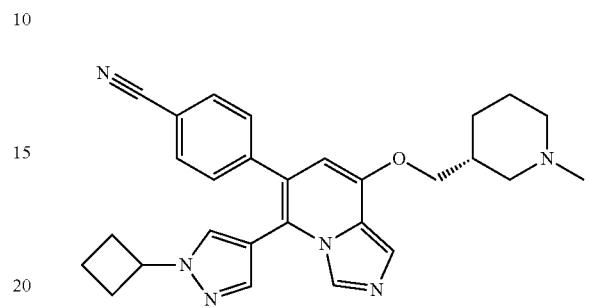

The title compound was prepared using procedures analogous to those described in Example 69 with 1-cyclobutyl-4-(4,4,5,5-tetramethyl-1,3,2-dioxaborolan-2-yl)-1H-pyrazole (Combi-Blocks, cat#FF-5131) replacing 2-methoxy-5-(4,4,5,5-tetramethyl-1,3,2-dioxaborolan-2-yl) pyridin-3-amine. The reaction mixture was purified by prep-HPLC (pH=2, acetonitrile/water+TFA) to give the desired product as the TFA salt. LC-MS calculated for $C_{28}H_{31}N_6O$ (M+H)$^+$: m/z=467.2. found 467.2. $^1$H NMR (400 MHz, CD$_3$OD) δ 8.73 (s, 1H), 7.97 (s, 1H), 7.86 (s, 1H), 7.72 (d, J=8.4 Hz, 2H), 7.51 (s, 1H) 7.49 (d, J=8.4 Hz, 2H), 6.56 (s, 1H), 4.36-4.08 (m, 2H), 3.78 (d, J=11.6 Hz, 1H), 3.59 (d, J=12.0 Hz, 1H), 3.06-2.91 (m, 2H), 2.97 (s, 3H), 2.59-2.37 (m, 5H), 2.16-1.78 (m, 6H), 1.61-1.47 (m, 1H).

Example 135

5-(6-(4-cyanophenyl)-8-{[(3R)-1-methylpiperidin-3-yl]methoxy}imidazo[1,5-a]pyridin-5-yl)-N-methylpyridine-2-carboxamide

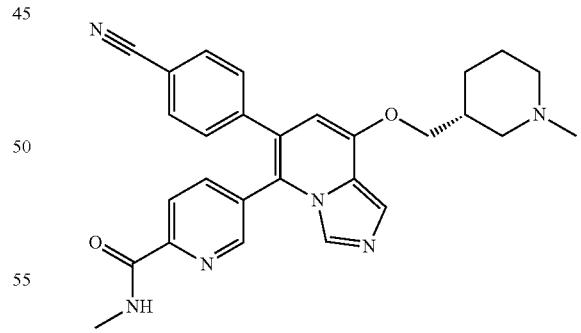

The title compound was prepared using procedures analogous to those described in Example 69 with N-methyl-5-(4,4,5,5-tetramethyl-1,3,2-dioxaborolan-2-yl)pyridine-2-carboxamide (Combi-Blocks, cat#BB-8552) replacing 2-methoxy-5-(4,4,5,5-tetramethyl-1,3,2-dioxaborolan-2-yl) pyridin-3-amine. The reaction mixture was purified by prep-HPLC (pH=10, acetonitrile/water+NH$_4$OH) to give the desired product. LC-MS calculated for $C_{28}H_{29}N_6O_2$ (M+H)$^+$: m/z=481.2. found 481.1.

Example 136

4-[8-[4-(dimethylamino)piperidin-1-yl]-5-(2-hydroxy-2,3-dihydro-1H-inden-5-yl)imidazo[1,5-a]pyrazin-6-yl]benzonitrile

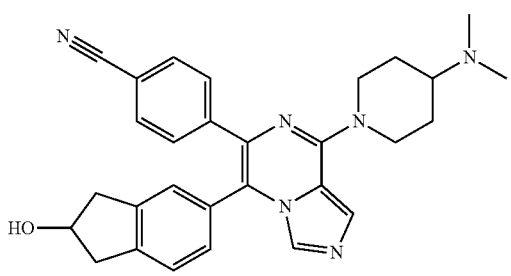 [SMILES: CN(C)C1CCN(c2nc(-c3ccc(C#N)cc3)c(-c3ccc4c(c3)CC(O)C4)n3cncc23)CC1]

The title compound was prepared using procedures analogous to those described in Example 50, Step 2 with 5-(4,4,5,5-tetramethyl-1,3,2-dioxaborolan-2-yl)indan-2-ol (Example 101, Step 1) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product (racemic) as the TFA salt. LC-MS calculated for $C_{29}H_{31}N_6O$ $(M+H)^+$: m/z=479.2. found 479.2.

Example 137

4-[8-[4-(dimethylamino)piperidin-1-yl]-5-(1-methyl-2-oxo-1,2,3,4-tetrahydroquinolin-6-yl)imidazo[1,5-a]pyrazin-6-yl]benzonitrile

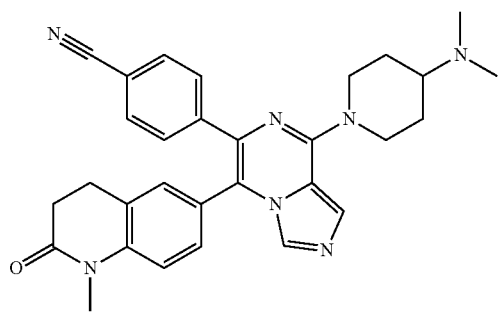 [SMILES: CN1C(=O)CCc2cc(-c3c(-c4ccc(C#N)cc4)nc(N4CCC(N(C)C)CC4)c4cncn34)ccc21]

The title compound was prepared using procedures analogous to those described in Example 50, Step 2 with 1-methyl-6-(4,4,5,5-tetramethyl-1,3,2-dioxaborolan-2-yl)-3,4-dihydroquinolin-2(1H)-one (Example 24, Step 2) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{30}H_{32}N_7O$ $(M+H)^+$: m/z=506.2. found 506.3.

Example 138

4-(8-(4-(dimethylamino)piperidin-1-yl)-5-(7-fluoro-1,3-dimethyl-2-oxo-2,3-dihydro-1H-benzo[d]imidazol-5-yl)imidazo[1,5-a]pyrazin-6-yl)benzonitrile

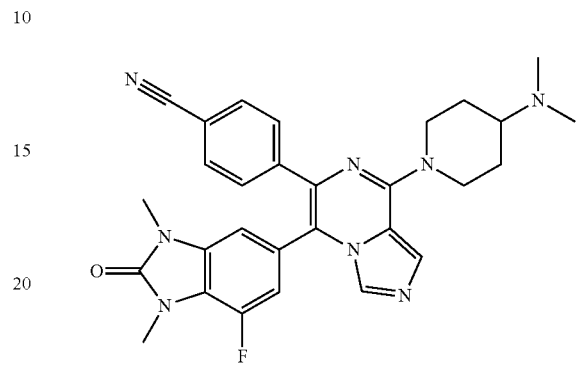

Step 1: 6-bromo-4fluoro-1,3-dimethyl-1,3-dihydro-2H-benzimidazol-2-one

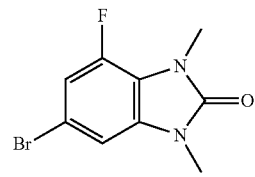

To a solution of 5-bromo-3-fluorobenzene-1,2-diamine (Combi-Blocks, cat#HC-2839: 0.3 g, 1 mmol) in tetrahydrofuran (20 mL) at 0° C. was added triethylamine (1.0 mL, 7.3 mmol) followed by the addition of triphosgene (0.52 g, 1.8 mmol). The resulting reaction mixture was stirred for 1 h, then 1.0 M sodium hydroxide in water (2.9 mL, 2.9 mmol) was added. The mixture was stirred at room temperature for another 1 h then diluted with EtOAc, washed with water and brine. The organic layer was dried over $Na_2SO_4$, filtered and concentrated. The residue was dissolved in acetone (5 mL) then potassium carbonate (0.6 g, 4 mmol) and methyl iodide (0.4 mL, 6 mmol) were added. The reaction mixture was heated at 80° C. for 3 h then cooled to room temperature, diluted with EtOAc, washed with water and brine. The organic layer was dried over $Na_2SO_4$, filtered and concentrated. The residue was purified by flash chromatography on a silica gel column eluting with 0 to 10% MeOH in DCM to give the desired product. LC-MS calculated for $C_9H_9BrFN_2O$ $(M+H)^+$: m/z=259.0. found 259.1.

155

Step 2: 4-fluoro-1,3-dimethyl-6-(4,4,5,5-tetramethyl-1,3,2-dioxaborolan-2-yl)-1,3-dihydro-2H-benzimidazol-2-one

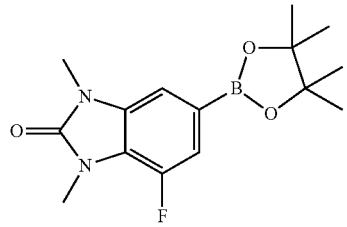 [SMILES: Cn1c(=O)n(C)c2c(F)cc(B3OC(C)(C)C(C)(C)O3)cc21]

A mixture of [1,1'-bis(diphenylphosphino)ferrocene]dichloropalladium(II) complexed with dichloromethane (1:1) (30 mg, 0.04 mmol), 6-bromo-4-fluoro-1,3-dimethyl-1,3-dihydro-2H-benzimidazol-2-one (0.2 g, 0.7 mmol), 4,4,5,5,4',4',5',5'-octamethyl-[2,2']bi[[1,3,2]dioxaborolanyl] (0.27 g, 1.0 mmol) and potassium acetate (0.2 g, 2 mmol) in 1,4-dioxane (5 mL) was purged with nitrogen then stirred at 90° C. overnight. The reaction mixture was cooled to room temperature then concentrated. The residue was purified by flash chromatography on a silica gel column eluting with 0 to 10% MeOH in DCM to give the desired product. LC-MS calculated for $C_{15}H_{21}BFN_2O_3(M+H)^+$: m/z=307.1. found 307.1.

Step 3: 4-(8-(4-(dimethylamino)piperidin-1-yl)-5-(7-fluoro-1,3-dimethyl-2-oxo-2,3-dihydro-1H-benzo[d]imidazol-5-yl)imidazo[1,5-a]pyrazin-6-yl)benzonitrile The title compound was prepared using procedures analogous to those described in Example 50, Step 2 with 4-fluoro-1,3-dimethyl-6-(4,4,5,5-tetramethyl-1,3,2-dioxaborolan-2-yl)-1,3-dihydro-2H-benzimidazol-2-one replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{30}FN_8O$ $(M+H)^+$: m/z=525.2. found 525.2.

Example 139

4-{5-(1-cyclobutyl-1H-pyrazol-4-yl)-8-[4-(dimethylamino)piperidin-1-yl]imidazo[1,5-a]pyrazin-6-yl}benzonitrile

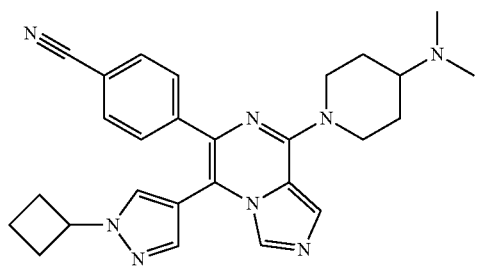 [SMILES: CN(C)C1CCN(c2nc(-c3ccc(C#N)cc3)c(-c3cnn(C4CCC4)c3)n3cncc23)CC1]

The title compound was prepared using procedures analogous to those described in Example 50, Step 2 with 1-cyclobutyl-4-(4,4,5,5-tetramethyl-1,3,2-dioxaborolan-2-yl)-1H-pyrazole [Ark Pharma, cat#AK-38138] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{31}N_8$ $(M+H)^+$: m/z=467.2. found 467.2.

Example 140

4-{5-[5-(difluoromethyl)-6-methylpyridin-3-yl]-8-[4-(dimethylamino)piperidin-1-yl]imidazo[1,5-a]pyrazin-6-yl}benzonitrile

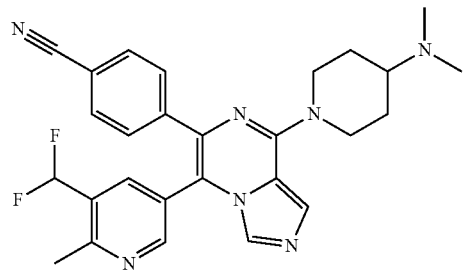 [SMILES: Cc1ncc(-c2c(-c3ccc(C#N)cc3)nc(N3CCC(N(C)C)CC3)c3cncn23)cc1C(F)F]

Step 1: (5-bromo-2-methylpyridin-3-yl)methanol

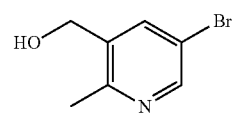

To a solution of ethyl 5-bromo-2-methylnicotinate (Ark Pharm, cat#Ak-41146: 1.0 g, 4.1 mmol) in tetrahydrofuran (10 mL) at room temperature was added dropwise 1.0 M lithium tetrahydroaluminate in THF (4.1 mL, 4.1 mmol). The reaction mixture was stirred at room temperature for 1 h then quenched with water and filtered. The filtrate was concentrated under reduced pressure. The residue was used in the next step without further purification. LC-MS calculated for $C_7H_9BrNO$ $(M+H)^+$: m/z=202.0. found 202.0.

Step 2: 5-bromo-2-methylnicotinaldehyde

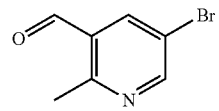

A slurry of Dess-Martin periodinane (2.1 g, 4.8 mmol) in methylene chloride (3.6 mL) was treated with tert-butyl alcohol (430 μL), and the mixture was stirred at room temperature for 15 min then a solution of (5-bromo-2-methylpyridin-3-yl)methanol (0.72 g, 3.6 mmol) in methylene chloride (3.6 mL) was added over 5 min. The mixture was stirred at room temperature for 30 min then diluted with ethyl acetate and 1N NaOH solution, and stirred for 10 min. The layers were separated and the organic layer was washed with water, brine, dried over $Na_2SO_4$, filtered and concentrated. The residue was purified by flash chromatography on a silica gel column to give the desired product. LC-MS calculated for $C_7H_7BrNO$ (M+H)⁺: m/z=200.0. found 200.0.

Step 3: 5-bromo-3-(difluoromethyl)-2-methylpyridine

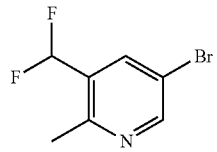

To a solution of 5-bromo-2-methylnicotinaldehyde (110 mg, 0.55 mmol) in methylene chloride (5 mL) at room temperature was added diethylaminosulfur trifluoride (Aldrich, cat#235253: 600 μL, 4 mmol). The resulting reaction mixture was stirred at room temperature overnight then concentrated. The residue was purified by flash chromatography on a silica gel column to afford the desired product. LC-MS calculated for $C_7H_7BrF_2N$ (M+H)⁺: m/z=222.0. found 222.0.

Step 4: 3-(difluoromethyl)-2-methyl-5-(4,4,5,5-tetramethyl-1,3,2-dioxaborolan-2-yl)pyridine

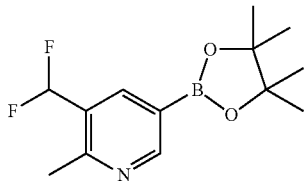 [SMILES: Cc1ncc(B2OC(C)(C)C(C)(C)O2)cc1C(F)F]

A mixture of 5-bromo-3-(difluoromethyl)-2-methylpyridine (420 mg, 1.9 mmol), 4,4,5,5,4',4',5',5'-octamethyl-[2,2']bi[[1,3,2]dioxaborolanyl] (580 mg, 2.3 mmol), [1,1'-bis(diphenylphosphino)ferrocene]dichloropalladium(II) complexed with dichloromethane (1:1) (80 mg, 0.09 mmol), potassium acetate (460 mg, 4.7 mmol) and 1,1'-bis(diphenylphosphino)ferrocene (50 mg, 0.09 mmol) in 1,4-dioxane (4 mL) was purged with nitrogen and stirred at 100° C. for 3 hours. The reaction mixture was cooled to room temperature and concentrated. The residue was purified by flash chromatography on a silica gel column to give the desired product.

Step 5: 4-{5-[5-(difluoromethyl)-6-methylpyridin-3-yl]-8-[4-(dimethylamino)piperidin-1-yl]imidazo[1,5-a]pyrazin-6-yl}benzonitrile The title compound was prepared using procedures analogous to those described in Example 50, Step 2 with 3-(difluoromethyl)-2-methyl-5-(4,4,5,5-tetramethyl-1,3,2-dioxaborolan-2-yl)pyridine replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{28}F_2N_7$ (M+H)⁺: m/z=488.2. found 488.1.

Example 141

5-{6-(4-cyanophenyl)-8-[4-(dimethylamino)piperidin-1-yl]imidazo[1,5-a]pyrazin-5-yl}-N-methylpyridine-2-carboxamide

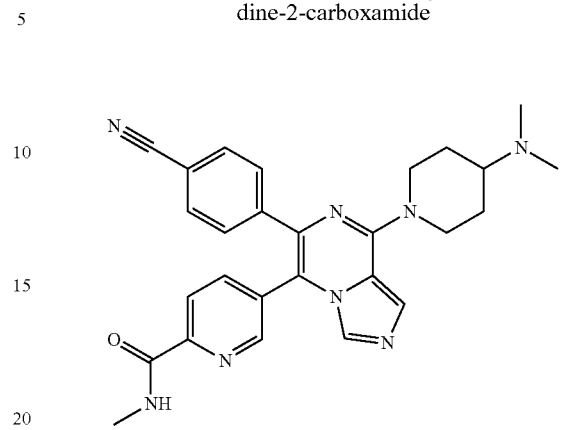

The title compound was prepared using procedures analogous to those described in Example 50, Step 2 with N-methyl-5-(4,4,5,5-tetramethyl-1,3,2-dioxaborolan-2-yl)pyridine-2-carboxamide (Matrix Scientific, cat#069139) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{29}N_8O$ (M+H)⁺: m/z=481.2. found 481.3.

Example 142

4-{8-[4-(dimethylamino)piperidin-1-yl]-5-[5-(hydroxymethyl)-6-methylpyridin-3-yl]imidazo[1,5-a]pyrazin-6-yl}benzonitrile

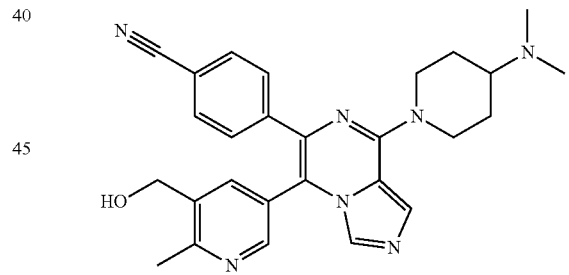

Step 1: (2-methyl-5-(4,4,5,5-tetramethyl-1,3,2-dioxaborolan-2-yl)pyridin-3-yl)methanol

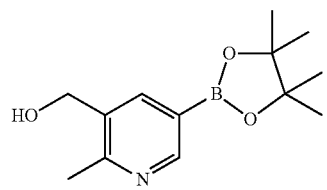 [SMILES: Cc1ncc(B2OC(C)(C)C(C)(C)O2)cc1CO]

A mixture of (5-bromo-2-methylpyridin-3-yl)methanol (Example 140, Step 1: 220 mg, 1.1 mmol), potassium acetate (530 mg, 5.4 mmol), 4,4,5,5,4',4',5',5'-octamethyl-[2,2']bi[[1,3,2]dioxaborolanyl] (410 mg, 1.6 mmol) and [1,1'-bis(diphenylphosphino)ferrocene]dichloropalladium (II) complexed with dichloromethane (1:1) (89 mg, 0.11 mmol) in 1,4-dioxane (3.2 mL) was purged with nitrogen then stirred at 90° C. overnight. The reaction mixture was cooled to room temperature, diluted with 1,4-dioxane, filtered through celite and concentrated. The residue was used in the next step without further purification.

Step 2: 4-{8-[4-(dimethylamino)piperidin-1-yl]-5-[5-(hydroxymethyl)-6-methylpyridin-3-yl]imidazo[1,5-a]pyrazin-6-yl}benzonitrile The title compound was prepared using procedures analogous to those described in Example 50, Step 2 with (2-methyl-5-(4,4,5,5-tetramethyl-1,3,2-dioxaborolan-2-yl)pyridin-3-yl)methanol replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{30}N_7O$ (M+H)$^+$: m/z=468.2. found 468.2.

Example 143

4-{5-[2-(difluoromethyl)-1-methyl-1H-benzimidazol-5-yl]-8-[4-(dimethylamino)piperidin-1-yl]imidazo[1,5-a]pyrazin-6-yl}benzonitrile

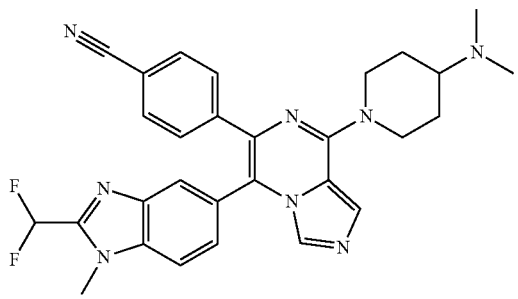 [SMILES: CN(C)C1CCN(c2nc(-c3ccc(C#N)cc3)c(-c3ccc4c(c3)nc(C(F)F)n4C)n3cncc23)CC1]

Step 1: 5-bromo-2-(difluoromethyl)-1-methyl-1H-benzimidazole

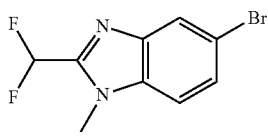

A mixture of 4-bromo-N1-methylbenzene-1,2-diamine (Combi-Blocks, cat# AN-3666: 0.5 g, 2.5 mmol), difluoroacetic acid (0.79 mL) and a few drops of concentrated hydrochloric acid was stirred at 120° C. overnight. After cooling to room temperature, the reaction mixture was concentrated, diluted with EtOAc, washed over sat'd NaHCO$_3$. The organic layer was dried over Na$_2$SO$_4$, filtered and concentrated. The residue was used in the next step without further purification. LC-MS calculated for $C_9H_8BrF_2N_2$ (M+H)$^+$: m/z=261.0. found 261.0.

Step 2: 2-(difluoromethyl)-1-methyl-5-(4,4,5,5-tetramethyl-1,3,2-dioxaborolan-2-yl)-1H-benzimidazole

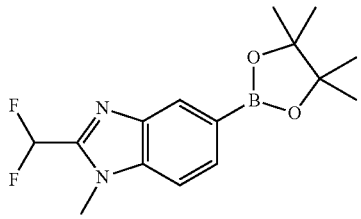 [SMILES: Cn1c(C(F)F)nc2cc(B3OC(C)(C)C(C)(C)O3)ccc21]

A mixture of 5-bromo-2-(difluoromethyl)-1-methyl-1H-benzimidazole (0.59 g, 2.2 mmol), 4,4,5,5,4',4',5',5'-octamethyl-[2,2']bi[[1,3,2]dioxaborolanyl] (860 mg, 3.4 mmol), [1,1'-bis(diphenylphosphino)ferrocene]dichloropalladium (II) complexed with dichloromethane (1:1) (90 mg, 0.1 mmol) and potassium acetate (660 mg, 6.8 mmol) in 1,4-dioxane (20 mL) was purged with nitrogen then heated at 90° C. for overnight. After cooling to room temperature, the reaction mixture was concentrated. The residue was purified by flash chromatography on a silica gel column eluting with 0 to 15% AcOEt in hexanes to give the desired product. LC-MS calculated for $C_{15}H_{20}BF_2N_2O_2$ (M+H)$^+$: m/z=309.2. found 309.2.

Step 3: 4-{5-[2-(difluoromethyl)-1-methyl-1H-benzimidazol-5-yl]-8-[4-(dimethylamino) piperidin-1-yl] imidazo[1,5-a]pyrazin-6-yl}benzonitrile The title compound was prepared using procedures analogous to those described in Example 50, Step 2 with 2-(difluoromethyl)-1-methyl-5-(4,4,5,5-tetramethyl-1,3,2-dioxaborolan-2-yl)-1H-benzimidazole replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{29}F_2N_8$ (M+H)$^+$: m/z=527.2. found 527.2.

Example 144

4-{8-[4-(dimethylamino)piperidin-1-yl]-5-quinolin-3-ylimidazo[1,5-a]pyrazin-6-yl}benzonitrile

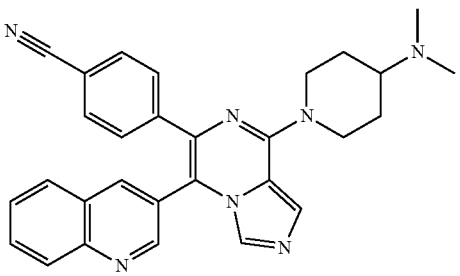 [SMILES: CN(C)C1CCN(c2nc(-c3ccc(C#N)cc3)c(-c3ccc4ncccc4c3)n3cncc23)CC1]

The title compound was prepared using procedures analogous to those described in Example 50, Step 2 with quinolin-3-ylboronic acid [Sigma-Aldrich, cat#709522] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{28}N_7$ (M+H)$^+$: m/z=474.2. found 474.2.

Example 145

4-{8-[4-(dimethylamino)piperidin-1-yl]-5-quinolin-6-ylimidazo[1,5-a]pyrazin-6-yl}benzonitrile

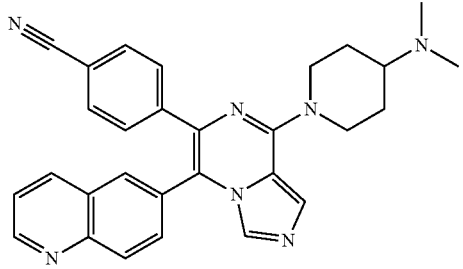

The title compound was prepared using procedures analogous to those described in Example 50, Step 2 with 6-(4,4,5,5-tetramethyl-1,3,2-dioxaborolan-2-yl)quinoline [Sigma-Aldrich, cat#641618] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{29}H_{28}N_7$ (M+H)$^+$: m/z=474.2. found 474.2.

Example 146

4-[8-{[(3R)-1-ethylpiperidin-3-yl]methoxy}-5-(6-methylpyridin-3-yl)imidazo[1,5-a]pyrazin-6-yl]benzonitrile

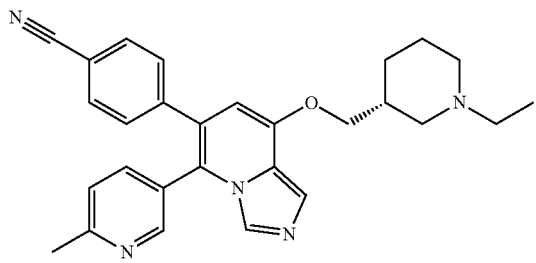 [SMILES: CCN1CCC[C@@H](COc2cc(-c3ccc(C#N)cc3)c(-c3ccc(C)nc3)n3cncc23)C1]

The title compound was prepared using procedures analogous to those described in Example 128 with 2-methyl-5-(4,4,5,5-tetramethyl-1,3,2-dioxaborolan-2-yl)pyridine (Aldrich, cat#CDS003793) replacing [2-fluoro-6-methyl-4-(4,4,5,5-tetramethyl-1,3,2-dioxaborolan-2-yl)phenyl]methanol. The reaction mixture was purified by prep-HPLC (pH=2, acetonitrile/water+TFA) to give the desired product as the TFA salt. LC-MS calculated for $C_{28}H_{30}N_5O$ (M+H)$^+$: m/z=452.2. found 452.2.

Example 147

4-(5-[5-(methoxymethyl)-6-methylpyridin-3-yl]-8-{[(3R)-1-methylpiperidin-3-yl]methoxy}imidazo[1,5-a]pyridin-6-yl)benzonitrile

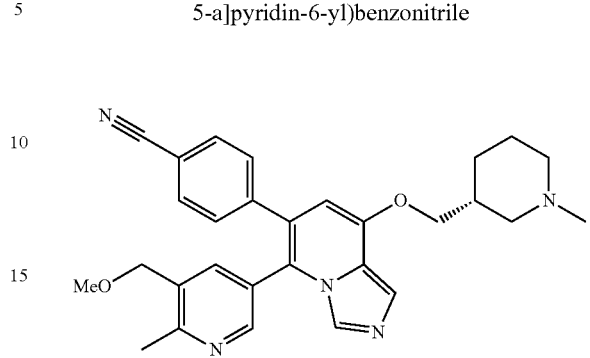

Step 1:
5-bromo-3-(methoxymethyl)-2-methylpyridine

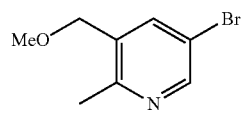

To a solution of (5-bromo-2-methylpyridin-3-yl)methanol (Anichem, cat#xz1288: 0.040 g, 0.20 mmol) in dimethyl sulfoxide (0.50 mL) was added potassium hydroxide (56 mg, 0.99 mmol) and methyl iodide (0.025 mL, 0.40 mmol). The reaction mixture was stirred at room temperature for 2 h then diluted with EtOAc, washed with water and brine. The organic layer was dried over $Na_2SO_4$, filtered and concentrated. The residue was used in the next step without further purification. LC-MS calculated for $C_8H_{11}BrNO$ (M+1)$^+$: m/z=216.0. found 216.0.

Step 2: 3-(methoxymethyl)-2-methyl-5-(4,4,5,5-tetramethyl-1,3,2-dioxaborolan-2-yl)pyridine

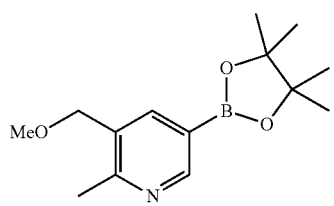 [SMILES: COCc1cc(B2OC(C)(C)C(C)(C)O2)cnc1C]

A mixture of 5-bromo-3-(methoxymethyl)-2-methylpyridine (0.042 g, 0.19 mmol), 4,4,5,5,4',4',5',5'-octamethyl-[2,2']bi[[1,3,2]dioxaborolanyl] (74.0 mg, 0.291 mmol), potassium acetate (0.0572 g, 0.582 mmol), and [1,1'-bis(diphenylphosphino)ferrocene]dichloropalladium (II) (7 mg, 0.01 mmol) in 1,4-dioxane (0.88 mL) was purged with nitrogen then stirred at 90° C. overnight. The reaction mixture was cooled to room temperature then diluted with 1,4-dioxane, filtered and concentrated. The residue was used in the next step without further purification. LC-MS calculated for $C_{14}H_{23}BNO_3$ (M+1)$^+$: m/z=264.2. found 264.1.

Step 3: 4-(5-[5-(methoxymethyl)-6-methylpyridin-3-yl]-8-{[(3R)-1-methylpiperidin-3-yl]methoxy}imidazo[1,5-a]pyridin-6-yl)benzonitrile The title compound was prepared using procedures analogous to those described in Example 69 with 3-(methoxymethyl)-2-methyl-5-(4,4,5,5-tetramethyl-1,3,2-dioxaborolan-2-yl)pyridine replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. $C_{29}H_{32}N_5O_2$ (M+H)$^+$: m/z=482.2. found 482.2.

Example 148

5-{6-(4-cyanophenyl)-8-[4-(dimethylamino)piperidin-1-yl]imidazo[1,5-a]pyrazin-5-yl}-2-methoxynicotinonitrile

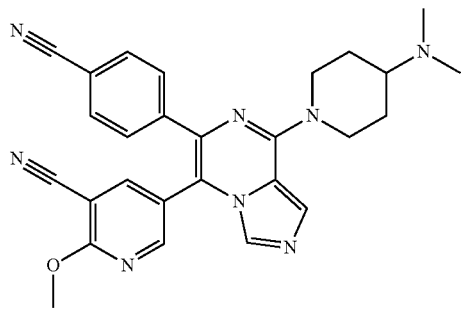 [SMILES: COc1ncc(-c2c(-c3ccc(C#N)cc3)nc(N3CCC(N(C)C)CC3)c3cncn23)cc1C#N]

The title compound was prepared using procedures analogous to those described in Example 50, Step 2 with 2-methoxy-5-(4,4,5,5-tetramethyl-1,3,2-dioxaborolan-2-yl)nicotinonitrile [Astatatech, cat#72152] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{27}N_8O$ (M+H)$^+$: m/z=479.2. found 479.2.

Example 149

4-{8-[4-(dimethylamino)piperidin-1-yl]-5-[4-(hydroxymethyl)-3-methylphenyl]imidazo[1,5-a]pyrazin-6-yl}benzonitrile

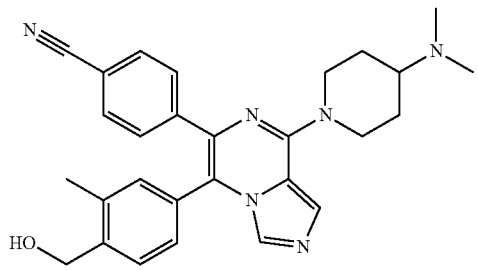 [SMILES: Cc1cc(-c2c(-c3ccc(C#N)cc3)nc(N3CCC(N(C)C)CC3)c3cncn23)ccc1CO]

The title compound was prepared using procedures analogous to those described in Example 50, Step 2 with [4-(hydroxymethyl)-3-methylphenyl]boronic acid [Ark Pharma, cat#AK-61520] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{28}H_{31}N_6O$ (M+H)$^+$: m/z=467.2. found 467.3.

Example 150

4-[8-[4-(dimethylamino)piperidin-1-yl]-5-(2-methoxypyrimidin-5-yl)imidazo[1,5-a]pyrazin-6-yl]benzonitrile

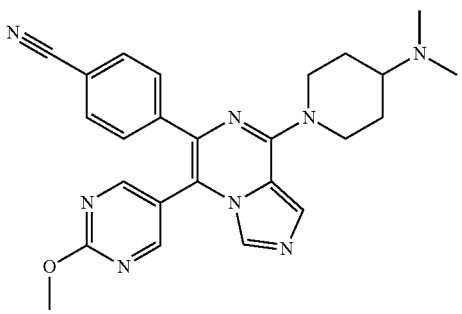 [SMILES: COc1ncc(-c2c(-c3ccc(C#N)cc3)nc(N3CCC(N(C)C)CC3)c3cncn23)cn1]

The title compound was prepared using procedures analogous to those described in Example 50, Step 2 with (2-methoxypyrimidin-5-yl)boronic acid [Ark Pharma, cat#AK-26204] replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{25}H_{27}N_8O$ (M+H)$^+$: m/z=455.2. found 455.2.

Example 151

4-(5-[6-(1-hydroxy-1-methylethyl)pyridin-3-yl]-8-{[(3R)-1-methylpiperidin-3-yl]methoxy}imidazo[1,5-a]pyridin-6-yl)benzonitrile

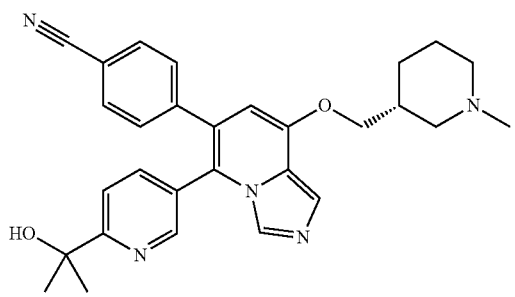 [SMILES: CN1CCC[C@@H](COc2cc(-c3ccc(C#N)cc3)c(-c3ccc(C(C)(C)O)nc3)n3cncc23)C1]

Step 1: 2-(5-(4,4,5,5-tetramethyl-1,3,2-dioxaborolan-2-yl)pyridin-2-yl)propan-2-ol

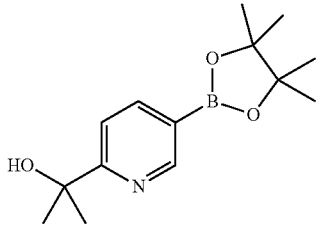 [SMILES: CC(C)(O)c1ccc(B2OC(C)(C)C(C)(C)O2)cn1]

A mixture of 2-(5-bromopyridin-2-yl)propan-2-ol (Astatech, cat#82909: 0.142 g, 0.658 mmol), 4,4,5,5,4',4',5',5'-octamethyl-[2,2']bi[[1,3,2]dioxaborolanyl] (0.250 g, 0.985 mmol), potassium acetate (0.193 g, 1.97 mmol) and [1,1'-bis(diphenylphosphino)ferrocene]dichloropalladium (II) (24 mg, 0.033 mmol) in 1,4-dioxane (3.0 mL) was purged with nitrogen then stirred at 90° C. for 12 h. The mixture was cooled to room temperature, filtered, and concentrated. The residue was used directly in the next step without further purification.

Step 2: 4-(5-[6-(1-hydroxy-1-methylethyl)pyridin-3-yl]-8-{[(3R)-1-methylpiperidin-3-yl]methoxy}imidazo[1,5-a]pyridin-6-yl)benzonitrile The title compound was prepared using procedures analogous to those described in Example 69 with 2-(5-(4,4,5,5-tetramethyl-1,3,2-dioxaborolan-2-yl)pyridin-2-yl)propan-2-ol replacing 2-methoxy-5-(4,4,5,5-tetramethyl-1,3,2-dioxaborolan-2-yl)pyridin-3-amine. The reaction mixture was purified by prep-HPLC (pH=2, acetonitrile/water+TFA) to give the desired product as the TFA salt. $C_{29}H_{32}N_5O_2$ (M+H)$^+$: m/z=482.2. found 482.2.

Example 152

(R)-4-(5-(4-methyl-3-oxo-3,4-dihydro-2H-pyrido[3,2-b][1,4]oxazin-7-yl)-8-((1-methylpiperidin-3-yl)methoxy)imidazo[1,5-a]pyridin-6-yl)benzonitrile

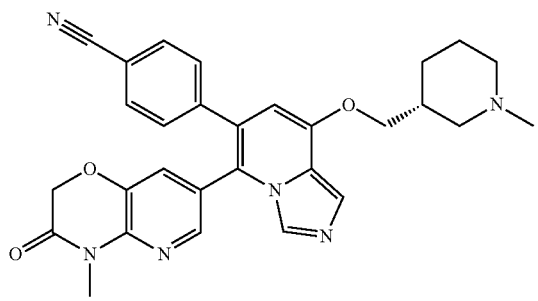

The title compound was prepared using procedures analogous to those described in Example 56, Step 9 with 4-methyl-7-(4,4,5,5-tetramethyl-1,3,2-dioxaborolan-2-yl)-2H-pyrido[3,2-b][1,4]oxazin-3(4H)-one (Example 105, Step 2) replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{29}N_6O_3$ (M+H)$^+$: m/z=509.2. found 509.2.

Example 153

4-(5-(1,2-dimethyl-1H-benzimidazol-5-yl)-8-{[(3R)-1-methylpiperidin-3-yl]methoxy}imidazo[1,5-a]pyridin-6-yl)benzonitrile

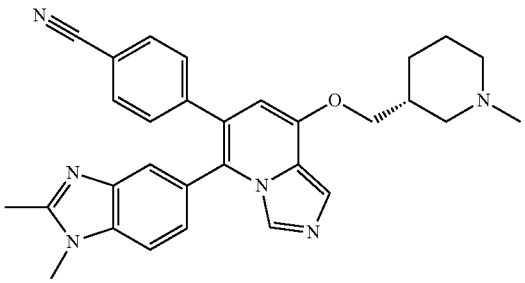

Step 1: 1,2-dimethyl-5-(4,4,5,5-tetramethyl-1,3,2-dioxaborolan-2-yl)-1H-benzimidazole

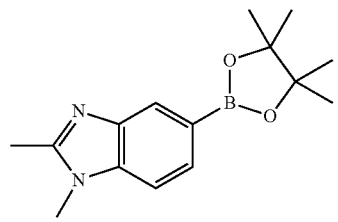

A mixture of [1,1'-bis(diphenylphosphino)ferrocene]dichloropalladium(II) complexed with dichloromethane (1:1) (40 mg, 0.04 mmol), 5-bromo-1,2-dimethyl-1H-benzimidazole (Combi-Blocks, cat#WZ-9484: 200 mg, 0.9 mmol), 4,4,5,5,4',4',5',5'-octamethyl-[2,2']bi[[1,3,2]dioxaborolanyl] (340 mg, 1.3 mmol) and potassium acetate (300 mg, 3 mmol) in 1,4-dioxane (7 mL) was purged with nitrogen then stirred at 90° C. overnight. The reaction mixture was cooled to room temperature then filtered and concentrated. The residue was purified by flash chromatography on a silica gel column eluting with 0 to 30% MeOH in DCM to give the desired product. LC-MS calculated for $C_{15}H_{22}BN_2O_2$ (M+H)$^+$: m/z=273.2. found 273.2.

Step 2: 4-(5-(1,2-dimethyl-1H-benzimidazol-5-yl)-8-{[(3R)-1-methylpiperidin-3-yl]methoxy}imidazo[1,5-a]pyridin-6-yl)benzonitrile The title compound was prepared using procedures analogous to those described in Example 56, Step 9 with 1,2-dimethyl-5-(4,4,5,5-tetramethyl-1,3,2-dioxaborolan-2-yl)-1H-benzimidazole replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{30}H_{31}N_6O$ (M+H)$^+$: m/z=491.3. found 491.2. $^1$H NMR (500 MHz, CD$_3$OD) δ 8.15 (s, 1H), 7.93-7.83 (m, 2H), 7.75 (s, 1H), 7.62-7.52 (m, 3H), 7.42 (d, J=8.4 Hz, 2H), 6.53 (s, 1H), 4.38-4.27 (m, 1H), 4.25-4.11 (m, 1H), 3.98 (s, 3H), 3.78 (d, J=11.1 Hz, 1H), 3.58 (d, J=12.8 Hz, 1H), 3.09-2.90 (m, 5H), 2.83 (s, 3H), 2.54-2.40 (m, 1H), 2.23-1.76 (m, 3H), 1.65-1.41 (m, 1H).

Example 154

4-(5-(2-methyl-1-oxo-2,3-dihydro-1H-isoindol-5-yl)-8-{[(3R)-1-methylpiperidin-3-yl]methoxy}imidazo[1,5-a]pyridin-6-yl)benzonitrile

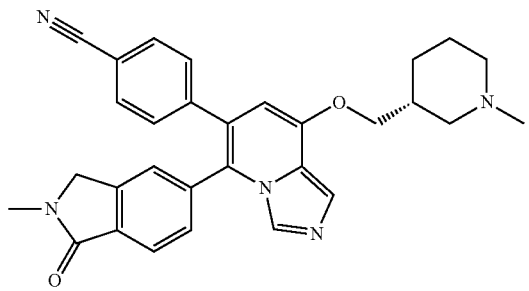

Step 1: 2-methyl-5-(4,4,5,5-tetramethyl-1,3,2-dioxaborolan-2-yl)isoindolin-1-one

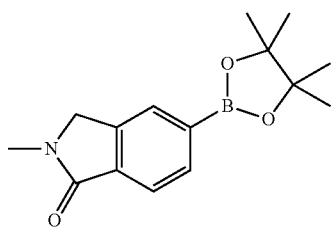

In a vial was combined 5-bromo-2-methylisoindolin-1-one (226 mg, 1.00 mmol) [Ark Pharm cat# AK-37748], 4,4,5,5,4',4',5',5'-octamethyl-[2,2']bi[[1,3,2]dioxaborolanyl] (0.533 g, 2.10 mmol), potassium acetate (294 mg, 3.00 mmol), 1,4-dioxane (5.0 mL), and [1,1'-bis(diphenylphosphino)ferrocene]dichloropalladium (II) (36.6 mg, 0.050 mmol). The vial was de-gassed by bubbling nitrogen through the solvent for 5 minutes then heated to 90° C. overnight. The mixture was allowed to cool to room temperature and was then filtered using a syringe filter. The filtrate was then concentrated under reduced pressure and used without further purification. LC-MS calculated for $C_{15}H_{21}BNO_3(M+H)^+$: m/z=274.2. found 274.1.

Step 2: 4-(5-(2-methyl-1-oxo-2,3-dihydro-1H-isoindol-5-yl)-8-{[(3R)-1-methylpiperidin-3-yl]methoxy}imidazo[1,5-a]pyridin-6-yl)benzonitrile The title compound was prepared using procedures analogous to those described in Example 21, Step 9 with 2-methyl-5-(4,4,5,5-tetramethyl-1,3,2-dioxaborolan-2-yl) isoindolin-1-one replacing 3-methyl-6-(4,4,5,5-tetramethyl-1,3,2-dioxaborolan-2-yl)-1,3-benzoxazol-2 (3H)-one. The reaction mixture was purified by prep-HPLC (pH=2, acetonitrile/water+TFA) to give the desired product as the TFA salt. LC-MS calculated for $C_{30}H_{30}N_5O_2$ $(M+H)^+$: m/z=492.2. found 492.2.

Example 155

(R)-4-(5-(3-isopropyl-3H-[1,2,3]triazolo[4,5-b]pyridin-6-yl)-8-((1-methylpiperidin-3-yl)methoxy)imidazo[1,5-a]pyridin-6-yl)benzonitrile

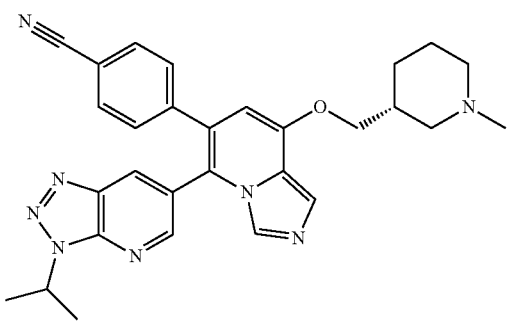 [SMILES: CC(C)n1nnc2cc(-c3c(-c4ccc(C#N)cc4)cc(OC[C@@H]4CCCN(C)C4)c4cncn34)cnc21]

Step 1: 5-bromo-N-isopropyl-3-nitropyridin-2-amine

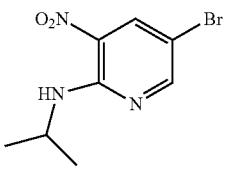

In a vial was combined 5-bromo-2-chloro-3-nitropyridine (Aldrich, cat#734756: 1.00 g, 4.21 mmol), 2-propanamine (358 μL, 4.21 mmol), THF (10 mL), and triethylamine (3 mL, 20 mmol). The mixture was allowed to stir at room temperature overnight. The crude reaction mixture was then partitioned between saturated $NaHCO_3$ and DCM. The organic phase was then washed with brine and dried over $Na_2SO_4$ and concentrated under reduced pressure. The crude residue was used without further purification. LC-MS calculated for $C_8H_{11}BrN_3O_2(M+H)^+$: m/z=260.0. found 260.0.

Step 2: 5-bromo-N2-isopropylpyridine-2,3-diamine

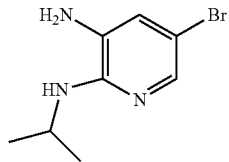

In a flask was combined 5-bromo-N-isopropyl-3-nitropyridin-2-amine (0.107 g, 0.41 mmol), a 1:1 mixture of ethanol and water (0.71 mL), and ammonium chloride (92 mg, 1.7 mmol). To this was slowly added iron (96 mg, 1.7 mmol) and the reaction mixture was refluxed for 1 hour. The crude reaction mixture was cooled to room temperature and diluted with EtOH. The slurry was then filtered through celite and concentrated under reduced pressure. The crude residue was used without further purification. LC-MS calculated for $C_8H_{13}BrN_3(M+H)^+$: m/z=230.0. found 230.0.

Step 3: 6-bromo-3-isopropyl-3H-[1,2,3]triazolo[4,5-b]pyridine

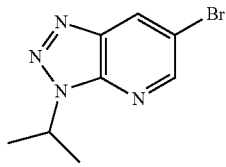

5-bromo-N2-isopropylpyridine-2,3-diamine (92.0 mg, 0.400 mmol) was diluted with 2.0 M HCl in water (5 mL, 10 mmol) and was cooled to 0° C. To this sodium nitrite (33. mg, 0.48 mmol) was added as a solution in water (0.7 mL). The reaction mixture was stirred at 0° C. for 1 hour. The crude reaction mixture was neutralized with 2M NaOH and extracted with EtOAc. The organic layer was washed with brine, dried over $Na_2SO_4$ and concentrated under reduced pressure. The crude residue was used without further purification. LC-MS calculated for $C_8H_{10}BrN_4(M+H)^+$: m/z=241.1. found 240.9.

Step 4: 3-isopropyl-6-(4,4,5,5-tetramethyl-1,3,2-dioxaborolan-2-yl)-3H-[1,2,3]triazolo[4,5-b]pyridine

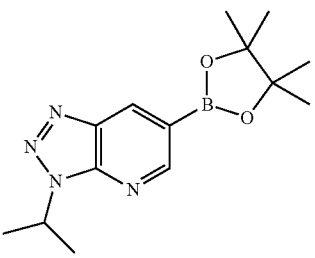 [SMILES: CC(C)n1nnc2cc(B3OC(C)(C)C(C)(C)O3)cnc21]

In a vial was combined 6-bromo-3-isopropyl-3H-[1,2,3]triazolo[4,5-b]pyridine (100 mg, 0.4 mmol), 4,4,5,5,4',4',5',5'-octamethyl-[2,2']bi[[1,3,2]dioxaborolanyl] (0.213 g, 0.840 mmol), potassium acetate (118 mg, 1.20 mmol), 1,4-dioxane (2.0 mL), and [1,1'-bis(diphenylphosphino)ferrocene]dichloropalladium (II) (14.6 mg, 0.0200 mmol). The vial was de-gassed by bubbling nitrogen through the solvent for 5 minutes then heated to 90° C. overnight. The reaction mixture was allowed to cool to room temperature and was then filtered using a syringe filter. The filtrate was then concentrated under reduced pressure and used without further purification. LC-MS calculated for $C_{14}H_{22}BN_4O_2(M+H)^+$: m/z=289.2. found 289.2.

Step 5: (R)-4-(5-(3-isopropyl-3H-[1,2,3]triazolo[4,5-b]pyridin-6-yl)-8-((1-methylpiperidin-3-yl)methoxy)imidazo[1,5-a]pyridin-6-yl)benzonitrile The title compound was prepared using procedures analogous to those described in Example 56, Step 9 with 3-isopropyl-6-(4,4,5,5-tetramethyl-1,3,2-dioxaborolan-2-yl)-3H-[1,2,3]triazolo[4,5-b]pyridine replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{29}H_{31}N_8O$ (M+H)$^+$: m/z=507.3. found 507.2. $^1$H NMR (500 MHz, $CD_3OD$) δ 8.63 (d, J=1.8 Hz, 1H), 8.59 (d, J=1.8 Hz, 1H), 8.34 (s, 1H), 7.89 (s, 1H), 7.62 (d, J=8.4 Hz, 2H), 7.46 (d, J=8.4 Hz, 2H), 6.55 (s, 1H), 5.48-5.20 (m, 1H), 4.39-4.28 (m, 1H), 4.27-4.12 (m, 1H), 3.79 (d, J=12.7 Hz, 1H), 3.58 (d, J=12.0 Hz, 1H), 3.08-2.90 (m, 5H), 2.57-2.34 (m, 1H), 2.22-1.79 (m, 3H), 1.81-1.67 (m, 6H), 1.63-1.42 (m, 1H).

Example 156

(R)-4-(5-(3-cyclopropyl-3H-[1,2,3]triazolo[4,5-b]pyridin-6-yl)-8-((1-methylpiperidin-3-yl)methoxy)imidazo[1,5-a]pyridin-6-yl)benzonitrile

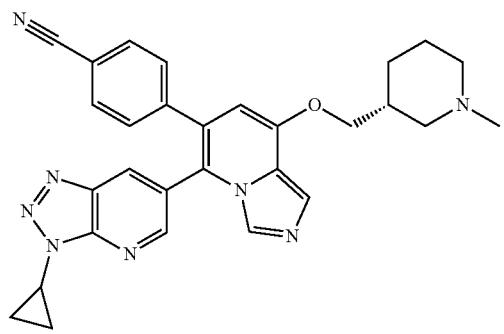 [SMILES: CN1CCC[C@@H](COc2cc(-c3ccc(C#N)cc3)c(-c3cnc4c(c3)nnn4C3CC3)n3cncc23)C1]

This compound was prepared using similar procedures as described for Example 155, with cyclopropylamine replacing 2-propanamine in Step 1. The reaction mixture was purified by prep-HPLC (pH=2, acetonitrile/water+TFA) to give the desired product as the TFA salt. LC-MS calculated for $C_{29}H_{29}N_8O$ (M+H)$^+$: m/z=505.3. found 505.1.

Example 157

(R)-4-(5-(2-isopropyl-3-methyl-3H-imidazo[4,5-b]pyridin-6-yl)-8-((1-methylpiperidin-3-yl)methoxy)imidazo[1,5-a]pyridin-6-yl)benzonitrile

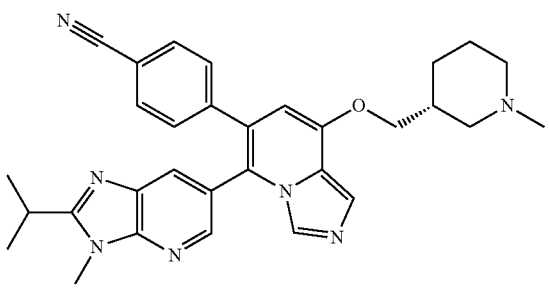 [SMILES: CC(C)c1nc2cc(-c3c(-c4ccc(C#N)cc4)cc(OC[C@@H]4CCCN(C)C4)c4cncn34)cnc2n1C]

Step 1: 6-bromo-2-isopropyl-3-methyl-3H-imidazo[4,5-b]pyridine

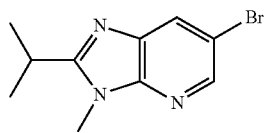

In a flask were combined 2-methylpropanamide (Aldrich, cat#144436: 285 mg, 3.28 mmol), THF (2 mL) and triethyloxonium tetrafluoroborate (Aldrich, cat#90520: 0.617 g, 3.25 mmol). The reaction mixture was allowed to stir at room temperature for 2 hours. The solvent was removed under reduced pressure and the residue was dissolved in ethanol (1.9 mL). To this residue was added a suspension of 5-bromo-N2-methylpyridine-2,3-diamine (200 mg, 0.99 mmol) [Combi-Blocks cat# AN-3965] in ethanol (6.7 mL). The mixture was then stirred at 80° C. for 1 hour. After the crude reaction mixture had cooled to room temperature the solvent was removed under reduced pressure. The residue was purified by flash chromatography on a silica gel column eluting with 0 to 20% MeOH/DCM to give the desired product (48 mg, 19% yield). LC-MS calculated for $C_{10}H_{13}BrN_3$ $(M+H)^+$: m/z=254.0. found 254.0.

Step 2: 2-isopropyl-3-methyl-6-(4,4,5,5-tetramethyl-1,3,2-dioxaborolan-2-yl)-3H-imidazo[4,5-b]pyridine

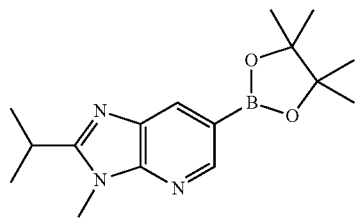 [SMILES: CC(C)c1nc2cc(B3OC(C)(C)C(C)(C)O3)cnc2n1C]

In a vial was combined 6-bromo-2-isopropyl-3-methyl-3H-imidazo[4,5-b]pyridine (48 mg, 0.19 mmol), 4,4,5,5,4',4',5',5'-octamethyl-[2,2']bi[[1,3,2]dioxaborolanyl] (0.101 g, 0.398 mmol), potassium acetate (56 mg, 0.569 mmol), 1,4-dioxane (0.95 mL), and [1,1'-bis(diphenylphosphino)ferrocene]dichloropalladium (II) (6.9 mg, 0.0095 mmol). The vial was de-gassed by bubbling nitrogen through the solvent for 5 minutes then heated to 90° C. overnight. The mixture was allowed to cool to room temperature and then filtered using a syringe filter. The filtrate was then concentrated under reduced pressure and the residue was used in the next step without further purification. LC-MS calculated for $C_{16}H_{25}BN_3O_2(M+H)^+$: m/z=302.2. found 302.3.

Step 3: (R)-4-(5-(2-isopropyl-3-methyl-3H-imidazo [4,5-b]pyridin-6-yl)-8-((1-methylpiperidin-3-yl) methoxy)imidazo[1,5-a]pyridin-6-yl)benzonitrile The title compound was prepared using procedures analogous to those described in Example 56, Step 9 with 2-isopropyl-3-methyl-6-(4,4,5,5-tetramethyl-1,3,2-dioxaborolan-2-yl)-3H-imidazo[4,5-b]pyridine replacing 6-(4,4,5,5-tetramethyl-1,3,2-dioxaborolan-2-yl)quinoxaline. The reaction mixture was purified by prep-HPLC (pH=2, acetonitrile/water+TFA) to give the desired product as the TFA salt. LC-MS calculated for $C_{31}H_{34}N_7O$ $(M+H)^+$: m/z=520.3. found 520.2. $^1H$ NMR (500 MHz, $CD_3OD$) δ 8.61 (s, 1H), 8.29 (d, J=1.8 Hz, 1H), 8.16-8.01 (m, 2H), 7.61 (d, J=8.4 Hz, 2H), 7.45 (d, J=8.4 Hz, 2H), 6.65 (s, 1H), 4.40-4.29 (m, 1H), 4.28-4.17 (m, 1H), 3.91 (s, 3H), 3.79 (d, J=10.2 Hz, 1H), 3.58 (d, J=10.8 Hz, 1H), 3.52-3.41 (m, 1H), 3.09-2.89 (m, 5H), 2.48 (s, 1H), 2.20-1.78 (m, 3H), 1.65-1.36 (m, 7H).

Example 158

(R)-4-(5-(2-cyclopropyl-3-methyl-3H-imidazo[4,5-b]pyridin-6-yl)-8-((1-methylpiperidin-3-yl)methoxy) imidazo[1,5-a]pyridin-6-yl)benzonitrile

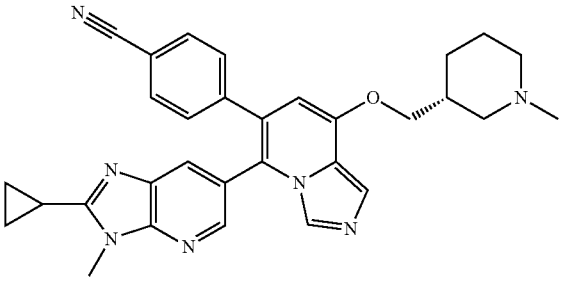 [SMILES: CN1CCC[C@@H](COc2cc(-c3ccc(C#N)cc3)c(-c3cnc4c(c3)nc(C3CC3)n4C)n3cncc23)C1]

This compound was prepared using similar procedures as described for Example 157 with cyclopropanecarboxamide (Alfa Aesar, cat#B21871) replacing 2-methylpropanamide in Step 1. The reaction mixture was purified by prep-HPLC (pH=2, acetonitrile/water+TFA) to give the desired product as the TFA salt. LC-MS calculated for $C_{31}H_{32}N_7O$ $(M+H)^+$: m/z=518.3. found 518.2. $^1H$ NMR (500 MHz, $CD_3OD$) δ 8.60 (s, 1H), 8.25 (s, 1H), 8.05 (s, 1H), 8.00 (s, 1H), 7.60 (d, J=8.2 Hz, 2H), 7.44 (d, J=8.2 Hz, 2H), 6.65 (s, 1H), 4.41-4.28 (m, 1H), 4.26-4.16 (m, 1H), 3.98 (s, 3H), 3.79 (d, J=11.7 Hz, 1H), 3.58 (d, J=12.3 Hz, 1H), 3.07-2.89 (m, 5H), 2.56-2.40 (m, 1H), 2.40-2.28 (m, 1H), 2.20-1.77 (m, 3H), 1.64-1.44 (m, 1H), 1.38-1.13 (m, 4H).

Example A

LSD1 Histone Demethylase Biochemical Assay

LANCE LSD1/KDM1A demethylase assay-10 µL of 1 nM LSD-1 enzyme (ENZO BML-SE544-0050) in the assay buffer (50 mM Tris, pH 7.5, 0.01% Tween-20, 25 mM NaCl, 5 mM DTT) were preincubated for 1 hour at 25° C. with 0.8 µL compound/DMSO dotted in black 384 well polystyrene plates. Reactions were started by addition of 10 µL of assay buffer containing 0.4 µM Biotin-labeled Histone H3 peptide substrate: ART-K(Me1)-QTARKSTGGKAPRKQLA-GGK (Biotin) SEQ ID NO:1 (AnaSpec 64355) and incubated for 1 hour at 25° C. Reactions were stopped by addition of 10 µL 1× LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). $IC_{50}$ data for the example compounds is provided in Table 1 (+ refers to $IC_{50}$≤50 nM; ++ refers to $IC_{50}$>50 nM and ≤100 nM; +++ refers to $IC_{50}$>100 nM and ≤500 nM; ++++ refers to $IC_{50}$>500 nM and ≤1000 nM).

TABLE 1

| Example No. | $IC_{50}$ (nM) |
| --- | --- |
| 1 | + |
| 2 | ++++ |
| 3 | + |

TABLE 1-continued

| Example No. | IC$_{50}$ (nM) |
|---|---|
| 4 | + |
| 5 | + |
| 6 | ++ |
| 7 | ++ |
| 8 | + |
| 9 | + |
| 10 | +++ |
| 11 | + |
| 12 | + |
| 13 | ++ |
| 14 | + |
| 15 | + |
| 16 | + |
| 17 | ++ |
| 18 | + |
| 19 | + |
| 20 | + |
| 21 | ++ |
| 22 | +++ |
| 23 | + |
| 24 | +++ |
| 25 | ++ |
| 26 | +++ |
| 27 | ++ |
| 28 | + |
| 29 | + |
| 30 | + |
| 31 | ++ |
| 32 | ++ |
| 33 | ++ |
| 34 | + |
| 35 | + |
| 36 | + |
| 37 | + |
| 38 | + |
| 39 | +++ |
| 40 | + |
| 41 | ++ |
| 42 | + |
| 43 | + |
| 44 | + |
| 45 | + |
| 46 | ++ |
| 47 | + |
| 48 | + |
| 49 | +++ |
| 50 | + |
| 51 | + |
| 52 | ++ |
| 53 | + |
| 54 | + |
| 55 | ++ |
| 56 | + |
| 57 | + |
| 58 | + |
| 59 | +++ |
| 60 | ++ |
| 61 | ++ |
| 62 | + |
| 63 | + |
| 64 | + |
| 65 | + |
| 66 | ++ |
| 67 | + |
| 68 | ++ |
| 69 | ++ |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | ++ |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | ++ |
| 105 | + |
| 106 | + |
| 107 | + |
| 108 | + |
| 109 | + |
| 110 | ++ |
| 111 | + |
| 112 | ++ |
| 113 | + |
| 114 | + |
| 115 | + |
| 116 | + |
| 117 | ++ |
| 118 | ++ |
| 119 | ++ |
| 120 | + |
| 121 | + |
| 122 | + |
| 123 | + |
| 124 | ++ |
| 125 | + |
| 126 | + |
| 127 | + |
| 128 | + |
| 129 | + |
| 130 | + |
| 131 | + |
| 132 | ++ |
| 133 | ++ |
| 134 | + |
| 135 | ++ |
| 136 | + |
| 137 | + |
| 138 | + |
| 139 | + |
| 140 | ++ |
| 141 | +++ |
| 142 | + |
| 143 | + |
| 144 | + |
| 145 | + |
| 146 | ++ |
| 147 | ++ |
| 148 | + |
| 149 | +++ |
| 150 | +++ |
| 151 | +++ |
| 152 | ++ |
| 153 | + |
| 154 | +++ |
| 155 | +++ |
| 156 | +++ |
| 157 | +++ |
| 158 | +++ |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

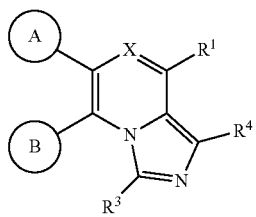

or a pharmaceutically acceptable salt thereof, wherein:
X is N or $CR^X$;
Ring A is $C_{6-10}$ aryl or 5-10 membered heteroaryl comprising carbon and 1, 2, 3, or 4 heteroatoms selected from N, O, and S, wherein said $C_{6-10}$ aryl and 5-10 membered heteroaryl are each optionally substituted by 1, 2, 3, or 4 substituents independently selected from $R^A$;
Ring B is $C_{6-10}$ aryl; 5-10 membered heteroaryl comprising carbon and 1, 2, 3 or 4 heteroatoms selected from N, O, and S; $C_{3-10}$ cycloalkyl; or 4-10 membered heterocycloalkyl comprising carbon and 1, 2, 3 or 4 heteroatoms selected from N, O, and S; wherein said $C_{6-10}$ aryl, 5-10 membered heteroaryl, $C_{3-10}$ cycloalkyl, and 4-10 membered heterocycloalkyl are each optionally substituted by 1, 2, 3, or 4 substituents independently selected from $R^B$;
$R^1$ is halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^3$ is H, halo, $C_{1-6}$ alkyl, $C_{2-6}$ alkenyl, $C_{2-6}$ alkynyl, $C_{1-6}$ haloalkyl, $Cy^2$, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted by 1, 2, or 3 substituents selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;
$R^4$ is $Cy^3$, H, halo, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^2R^{d2}$, $S(O)_2R^{b2}$, and $S(O)_2NR^2R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^2R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^2R^{d2}$, $S(O)R^{b2}$, $S(O)NR^2R^{d2}$, $S(O)_2R^{b2}$, and $S(O)_2NR^{c2}R^{d2}$;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^B$ is independently selected from $Cy^4$, halo, $C_{1-6}$ alkyl, $C_{2-6}$ alkenyl, $C_{2-6}$ alkynyl, $C_{1-6}$ haloalkyl, =O, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2Rb$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, and $C_{2-6}$ alkynyl are each optionally substituted by 1, 2, or 3 substituents independently selected from $Cy^4$, halo, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

$R^X$ is H, halo, $C_{1-6}$ alkyl, $C_{2-6}$ alkenyl, $C_{2-6}$ alkynyl, $C_{1-6}$ haloalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $NR^{c8}C(=NR^{e8})NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, or $S(O)_2NR^{c8}R^{d8}$;

each $Cy^1$, $Cy^3$, $Cy^4$, and $Cy^5$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $Cy^2$ is independently selected from phenyl, $C_{3-7}$ cycloalkyl, 5-6 membered heteroaryl, and 4-7 membered heterocycloalkyl, each of which is optionally substituted with 1, 2, or 3 substituents independently selected from $R^{Cy}$;

each $R^{Cy}$ is selected from halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, oxo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-4}$ alkyl, $C_{1-4}$ haloalkyl, $C_{1-4}$ cyanoalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^6R^{d6}$, $S(O)_2R^{b6}$, and $S(O)_2NR^{c6}R^{d6}$;

each $R^{a1}$ is independently selected from H, $C_{1-6}$ alkyl, $C_{2-6}$ alkenyl, $C_{2-6}$ alkynyl, and $Cy^5$, wherein said $C_{1-6}$ alkyl, $C_{2-6}$ alkenyl, and $C_{2-6}$ alkynyl are each optionally substituted with 1, 2, or 3 substituents independently selected from $Cy^5$, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$;

each $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})R^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}SR^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^8R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}SR^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a6}$, $R^{b6}$, $R^{c6}$, and $R^{d6}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a7}$, $R^{b7}$, $R^{c7}$, and $R^{d7}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^{c7}$ and $R^{d7}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

each $R^{a8}$, $R^{b8}$, $R^{c8}$, and $R^{d8}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e1}$, $R^{e2}$, $R^{e3}$, $R^{e4}$, $R^{e5}$, $R^{e6}$, $R^{e7}$, and $R^{e8}$ is independently selected from H, $C_{1-4}$ alkyl, and CN.

2. The compound of claim 1, or a pharmaceutically acceptable salt thereof, wherein:

Ring A is $C_{6-10}$ aryl optionally substituted by 1, 2, 3, or 4 substituents independently selected from $R^A$;

$R^1$ is $OR^{a1}$ or $Cy^1$;

$R^3$ is H;

$R^4$ is H;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)R^{b4}$, $S(O)NR^{c4}R^{d4}$, $S(O)_2R^{b4}$, and $S(O)_2NR^4R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $C(O)R^{b4}$, $C(O)NR^4R^{d4}$, $C(O)OR^{a4}$, $NR^{c4}R^{d4}$ $NR^{c4}C(O)R^{b4}S(O)R^{b4}$, $S(O)NR^{c4}R^{d4}$, $S(O)_2R^{b4}$, and $S(O)_2NR^{c4}R^{d4}$;

Rx is H;

each $R^{a1}$ is independently selected from $C_{1-6}$ alkyl optionally substituted with 1, 2, or 3 substituents independently selected from $Cy^5$;

and each $R^{e5}$, $R^{e6}$, and $R^{e8}$ is independently selected from H, $C_{1-4}$ alkyl, and CN.

3. The compound of claim 1, or a pharmaceutically acceptable salt thereof, wherein:

Ring A is $C_{6-10}$ aryl optionally substituted by 1, 2, 3, or 4 substituents independently selected from $R^A$;

$R^1$ is $OR^{a1}$;

$R^3$ is H;

$R^4$ is H;

each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)R^{b4}$, $S(O)NR^4R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $C(O)R^{b4}$, $C(O)NR^4R^{d4}$, $C(O)OR^{a4}$, $NR^{c4}R^{d4}$ $NR^{c4}C(O)R^{b4}S(O)R^{b4}$, $S(O)NR^{c4}R^{d4}$, $S(O)_2R^{b4}$, and $S(O)_2NR^{c4}R^{d4}$;

$R^X$ is H;

each $Cy^4$ and $Cy^5$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $R^{a1}$ is independently selected from $C_{1-6}$ alkyl optionally substituted with 1, 2, or 3 substituents independently selected from $Cy^5$; and each Res, $R^6$, and $R^{e8}$ is independently selected from H, $C_{1-4}$ alkyl, and CN.

4. The compound of claim 1, or a pharmaceutically acceptable salt thereof, wherein:

X is $CR^X$;

Ring A is phenyl optionally substituted by 1 or 2 substituents independently selected from $R^A$;

Ring B is phenyl; 5-10 membered heteroaryl comprising carbon and 1, 2, 3 or 4 heteroatoms selected from N, O, and S; $C_{3-7}$ cycloalkyl; or 4-10 membered heterocycloalkyl comprising carbon and 1, 2, 3 or 4 heteroatoms selected from N, O, and S; wherein said phenyl, 5-10 membered heteroaryl, $C_{3-7}$ cycloalkyl, and 4-10 membered heterocycloalkyl are each optionally substituted by 1, 2, 3, or 4 substituents independently selected from $R^B$;

$R^1$ is $OR^{a1}$;

$R^3$ is H;

$R^4$ is H;

each $R^A$ is independently selected from halo, CN, and $NO_2$;

each $R^B$ is independently selected from $Cy^4$, halo, $C_{1-6}$ alkyl, =O, and $C(O)OR^{a5}$, wherein said $C_{1-6}$ alkyl is optionally substituted by $Cy^4$;

$R^X$ is H;

each $Cy^4$ is independently selected from $C_{3-7}$ cycloalkyl and 4-7 membered heterocycloalkyl, each of which is optionally substituted with 1 or 2 substituents independently selected from $R^{Cy}$;

each $Cy^5$ is independently selected from 4-7 membered heterocycloalkyl optionally substituted with 1 or 2 substituents independently selected from $R^{Cy}$;

each $R^{Cy}$ is selected from halo, $C_{1-4}$ alkyl, $C_{1-4}$ haloalkyl, $C_{1-4}$ cyanoalkyl, $C_{2-6}$ alkenyl, $C_{2-6}$ alkynyl, oxo, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $S(O)_2R^{b6}$, and $S(O)_2NR^{c6}R^{d6}$, wherein said $C_{1-4}$ alkyl, $C_{2-6}$ alkenyl, and $C_{2-6}$ alkynyl are each optionally substituted by 1 or 2 substituents independently selected from halo, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $S(O)_2R^{b6}$, and $S(O)_2NR^{c6}R^{d6}$;

each $R^{a1}$ is independently selected from $C_{1-3}$ alkyl optionally substituted with 1 or 2 substituents independently selected from $Cy^5$; and each $R^{a5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a8}$, $SR^{a5}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$ $NR^{c8}C(O)R^{b8}$, $NR^{c8}C(O)NR^{c8}R^{d8}$, $NR^{c8}C(O)OR^{a5}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$;

or any $R^5$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a8}$, $SR^{a8}$, $C(O)R^{b8}$, $C(O)NR^{c8}R^{d8}$, $C(O)OR^{a5}$, $OC(O)R^{b8}$, $OC(O)NR^{c8}R^{d8}$, $NR^{c8}R^{d8}$ $NR^{c8}C(O)R^{b8}$, $NR^{c8}C(O)NR^{c8}R^{d8}$, $NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$, $NR^{c8}S(O)_2NR^{c8}R^{d8}$, and $S(O)_2NR^{c8}R^{d8}$.

5. The compound of claim 1, or a pharmaceutically acceptable salt thereof, wherein X is N.

6. The compound of claim 1, or a pharmaceutically acceptable salt thereof, wherein X is $CR^X$.

7. The compound of claim 1, or a pharmaceutically acceptable salt thereof, wherein $R^X$ is H.

8. The compound of claim 1, or a pharmaceutically acceptable salt thereof, wherein Ring A is $C_{6-10}$ aryl optionally substituted by 1, 2, 3, or 4 substituents independently selected from $R^A$.

9. The compound of claim 1, or a pharmaceutically acceptable salt thereof, wherein Ring A is phenyl optionally substituted by 1 or 2 substituents independently selected from $R^A$.

10. The compound of claim 1, or a pharmaceutically acceptable salt thereof, wherein Ring A is phenyl optionally substituted by 1 or 2 substituents independently selected from halo, CN, and $NO_2$.

11. The compound of claim 1, or a pharmaceutically acceptable salt thereof, wherein Ring B is phenyl; 5-10 membered heteroaryl comprising carbon and 1, 2, 3 or 4 heteroatoms selected from N, O, and S; $C_{3-7}$ cycloalkyl; or 4-10 membered heterocycloalkyl comprising carbon and 1, 2, 3 or 4 heteroatoms selected from N, O, and S; wherein said phenyl, 5-10 membered heteroaryl, $C_{3-7}$ cycloalkyl, and 4-10 membered heterocycloalkyl are each optionally substituted by 1, 2, or 3 substituents independently selected from $R^B$.

12. The compound of claim 1, or a pharmaceutically acceptable salt thereof, wherein Ring B is phenyl, pyrazolyl, cyclohexenyl, dihydropyridinyl, 1H-indazolyl, 2,3-dihydro-1H-indolyl, 3,4-dihydro-2H-1,4-benzoxazinyl, 2,3-dihydro-1,4-benzodioxinyl, 2,3-dihydro-1,3-benzoxazolyl, 1,2,3,4-tetrahydroquinolinyl, 2,3-dihydro-benzimidazolyl, 1H-pyrazolo[3,4-b]pyridinyl, 1H-benzimidazolyl, 3,4-dihydro-2H-pyrido[3,2-b][1,4]oxazinyl, quinolinyl, 1,3-benzothiazolyl, pyridinyl, 1,5-naphthyridinyl, quinoxalinyl, 2,3-dihydrooxazolo[4,5-b]pyridinyl, 3H-imidazo[4,5-b]pyridinyl, furo[3,2-b]pyridinyl, 3,4-dihydro-2H-pyrano[2,3-b]pyridinyl, 2,3-dihydro-[1,4]dioxino[2,3-b]pyridinyl, 1H-pyrrolo[2,3-b]pyridinyl, 2,3-dihydro-1H-indenyl, 1,4-dihydro-2H-3,1-benzoxazinyl, 3H-[1,2,3]triazolo[4,5-b]pyridinyl, 2,3-dihydro-1H-isoindolyl, imidazo[4,5-b]pyridinyl, or pyrimidinyl, each optionally substituted by 1, 2, or 3 substituents independently selected from $C_{3-7}$ cycloalkyl, 5-6 membered heterocycloalkyl, halo, $C_{1-6}$ alkyl, $C_{1-6}$ haloalkyl, =O, CN, $OR^{a5}$, $NR^{c5}C(O)OR^{a5}$, $NR^{c5}R^{d5}$, $C(O)NR^{c5}R^{d5}$, and $C(O)OR^{a5}$, wherein said $C_{1-6}$ alkyl is optionally substituted by 5-6 membered heterocycloalkyl, CN, $OR^{a5}$, $NR^{c5}C(O)OR^{a5}$, or $NR^{c5}C(O)NR^{c5}R^{d5}$.

13. The compound of claim 1, or a pharmaceutically acceptable salt thereof, wherein Ring B is phenyl, pyrazolyl, cyclohexenyl, dihydropyridinyl, 1H-indazolyl, 2,3-dihydro-1H-indolyl, 3,4-dihydro-2H-1,4-benzoxazinyl, or 2,3-dihydro-1,4-benzodioxinyl, each optionally substituted by 1, 2, or 3 substituents independently selected from $C_{3-7}$ cycloalkyl, 5-6 membered heterocycloalkyl, halo, $C_{1-6}$ alkyl, =O, and $C(O)OR^{a5}$, wherein said $C_{1-6}$ alkyl is optionally substituted by 5-6 membered heterocycloalkyl.

14. The compound of claim 1, or a pharmaceutically acceptable salt thereof, wherein each $R^A$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)R^{b4}$, $S(O)NR^4R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, or 3, substituents independently selected from halo, $C_{1-6}$ haloalkyl, CN, $NO_2$, $OR^{a4}$, $C(O)R^{b4}$, $C(O)NR^4R^{d4}$, $C(O)OR^{a4}$, $NR^{c4}R^{d4}$ $NR^{c4}C(O)R^{b4}$ $S(O)R^{b4}$, $S(O)NR^{c4}R^{d4}$, $S(O)_2R^{b4}$, and $S(O)_2NR^{c4}R^{d4}$.

15. The compound of claim 1, or a pharmaceutically acceptable salt thereof, wherein each $R^A$ is independently selected from halo, CN, and $NO_2$.

16. The compound of claim 1, or a pharmaceutically acceptable salt thereof, wherein $R^A$ is CN.

17. The compound of claim 1, or a pharmaceutically acceptable salt thereof, wherein each $R^B$ is independently selected from $Cy^4$, halo, CN, $C_{1-6}$ alkyl, $C_{1-6}$ haloalkyl, =O, $OR^{a5}$, $NR^{c5}C(O)OR^{a5}$, $NR^{c5}R^{d5}$, $C(O)NR^{c5}R^{d5}$, and $C(O)OR^{a5}$, wherein said $C_{1-6}$ alkyl is optionally substituted by $Cy^4$, CN, $OR^{a5}$, $NR^{c5}C(O)OR^{a5}$, or $NR^{c5}C(O)NR^{c5}R^{d5}$.

18. The compound of claim 1, or a pharmaceutically acceptable salt thereof, wherein each $R^B$ is independently selected from $Cy^4$, halo, $C_{1-6}$ alkyl, =O, and $C(O)OR^{a5}$, wherein said $C_{1-6}$ alkyl is optionally substituted by $Cy^4$.

19. The compound of claim 1, or a pharmaceutically acceptable salt thereof, wherein each $R^B$ is independently selected from $C_{3-7}$ cycloalkyl, 5-6 membered heterocycloalkyl, halo, $C_{1-4}$ alkyl wherein said $C_{1-4}$ alkyl is optionally substituted by CN, OH, $N(C_{1-4}$ alkyl)$C(O)O(C_{1-4}$ alkyl), —O—$(C_{1-4}$ alkyl) or $N(C_{1-4}$ alkyl)$C(O)N(C_{1-4}$ alkyl)$_2$; $C_{1-6}$ haloalkyl, =O, $C(O)O(C_{1-4}$ alkyl), OH, $C_{1-4}$ alkoxy, $N(C_{1-4}$ alkyl)$C(O)O(C_{1-4}$ alkyl), CN, $NH_2$, $NH(C_{1-4}$ alkyl), $C(O)NH(C_{1-4}$ alkyl), and (5-6 membered heterocycloalkyl)-$C_{1-4}$ alkyl- wherein said (5-6 membered heterocycloalkyl)-$C_{1-4}$ alkyl- is optionally substituted by $C_{1-4}$ alkyl.

20. The compound of claim 1, or a pharmaceutically acceptable salt thereof, wherein each $R^B$ is independently selected from $C_{3-7}$ cycloalkyl, 5-6 membered heterocycloalkyl, halo, $C_{1-4}$ alkyl, =O, $C(O)O(C_{1-4}$ alkyl), and (5-6 membered heterocycloalkyl)-$C_{1-4}$ alkyl- wherein said (5-6 membered heterocycloalkyl)-$C_{1-4}$ alkyl- is optionally substituted by $C_{1-4}$ alkyl.

21. The compound of claim 1, or a pharmaceutically acceptable salt thereof, wherein each $R^B$ is independently selected from cyclobutyl, morpholino, chloro, fluoro, methyl, ethyl, 2-propyl, cyclopropyl, difluoromethyl, =O, t-butoxycarbonyl, morpholinomethyl, morpholinoethyl, hydroxymethyl, methoxy, —$N(CH_3)C(O)O(CH_3)$, —$CH_2$—$N(CH_3)C(O)O(CH_3)$, 2-oxopyrrolidinyl, CN, $NH_2$, OH, 1-hydroxy-1-methylethyl, dimethylamino, —$CH_2$—$N(CH_3)C(O)N(CH_3)_2$, difluoromethoxy, ethoxy, methoxymethyl, 1-hydroxyethyl, 1-cyano-1-methylethyl, $C(O)NH(CH_3)$ and 4-methyl-piperazinylmethyl.

22. The compound of claim 1, or a pharmaceutically acceptable salt thereof, wherein each $R^B$ is independently selected from cyclobutyl, morpholino, chloro, fluoro, methyl, ethyl, =O, t-butoxycarbonyl, morpholinomethyl, morpholinoethyl, and 4-methyl-piperazinylmethyl.

23. The compound of claim 1, or a pharmaceutically acceptable salt thereof, wherein $R^1$ is $OR^{a1}$ or $Cy^1$.

24. The compound of claim 1, or a pharmaceutically acceptable salt thereof, wherein $R^1$ is $OR^{a1}$ or 4-10 membered heterocycloalkyl.

25. The compound of claim 1, or a pharmaceutically acceptable salt thereof, wherein $R^1$ is $OR^{a1}$.

26. The compound of claim 1, or a pharmaceutically acceptable salt thereof, wherein $R^1$ is (i) $C_{1-6}$ alkyl substituted with $NR^{c1}R^{d1}$ or (ii) $NR^{c1}R^{d1}$, wherein $R^{c1}$ is H and $R^{d1}$ is substituted with $NR^{c8}R^{d8}$; or $R^{c1}$ and $R^{d1}$ together with the N atom to which they are attached form a 4-, 5-, 6-, or 7-membered heterocycloalkyl group substituted with $NR^{c8}R^{d8}$.

27. The compound of claim 1, or a pharmaceutically acceptable salt thereof, wherein $R^1$ is independently selected from pyrrolidinylmethoxy optinally substituted by methyl; piperidinylmethoxy optionally substituted by methyl, ethyl, 2-hydroxyethyl, 2-cyanoethyl, 2-hydroxypropyl, 2-methoxyethyl, or 2-hydroxy-2-methylpropyl; 4-(dimethylamino)piperidinyl; and 3-(dimethylamino)pyrrolidinyl.

28. The compound of claim 1, or a pharmaceutically acceptable salt thereof, wherein $R^1$ is 3-piperidinylmethoxy, 3-pyrrolidinylmethoxy, 1-piperidinyl, or 1-pyrrolidinyl, each of which is optionally substituted with a member selected from methyl, ethyl, 2-hydroxyethyl, 2-cyanoethyl, 2-hydroxypropyl, 2-methoxyethyl, 2-hydroxy-2-methylpropyl and 4-(dimethylamino).

29. The compound of claim 1, or a pharmaceutically acceptable salt thereof, wherein $R^1$ is 3-piperidinylmethoxy, 3-pyrrolidinylmethoxy, 1-piperidinyl, 1-pyrrolidinyl, 1-methylpiperidin-3-yl-methoxy, 1-(2-hydroxyethyl)piperidin-3-yl, 1-(2-cyanoethyl)piperidin-3-yl, 1-(2-hydroxypropyl)piperidin-3-yl, 1-(2-methoxyethyl)piperidin-3-yl, 1-(2-hydroxy-2-methylpropyl)piperidin-3-yl, 4-(dimethylamino)piperidin-1-yl, 1-ethylpiperidin-3-yl-methoxy, or 3-(dimethylamino)pyrrolidin-1-yl.

30. The compound of claim 1, or a pharmaceutically acceptable salt thereof, wherein $R^1$ is pyrrolidinylmethoxy optionally substituted by methyl.

31. The compound of claim 1, or a pharmaceutically acceptable salt thereof, wherein $R^3$ is H.

32. The compound of claim 1, or a pharmaceutically acceptable salt thereof, wherein $R^4$ is H.

33. The compound of claim 1, or a pharmaceutically acceptable salt thereof, wherein each $R^{a1}$ is independently selected from $C_{1-6}$ alkyl optionally substituted with 1, 2, or 3 substituents independently selected from $Cy^5$.

34. The compound of claim 1, or a pharmaceutically acceptable salt thereof, wherein each $R^{a1}$ is independently selected from $C_{1-3}$ alkyl optionally substituted with 1 or 2 substituents independently selected from $Cy^5$.

35. The compound of claim 1, or a pharmaceutically acceptable salt thereof, wherein each $R^{a1}$ is independently selected from (pyrrolidinyl)methyl which is optionally substituted on the pyrrolidinyl moiety by a methyl group-; and (piperidinyl)methyl- which is optionally substituted on the piperidinyl moiety by methyl, ethyl, 2-hydroxyethyl, 2-cyanoethyl, 2-hydroxypropyl, 2-methoxyethyl, or 2-hydroxy-2-methylpropyl.

36. The compound of claim 1, or a pharmaceutically acceptable salt thereof, wherein each $R^{a1}$ is independently selected from (pyrrolidinyl)methyl- which is optionally substituted on the pyrrolidinyl moiety by a methyl group.

37. The compound of claim 1, or a pharmaceutically acceptable salt thereof, wherein each $Cy^1$, $Cy^3$, $Cy^4$, and $Cy^5$ is independently selected from phenyl, $C_{3-7}$ cycloalkyl, 5-6 membered heteroaryl, and 4-7 membered heterocycloalkyl, each of which is optionally substituted with 1, 2, 3, or 4 substituents independently selected from $R^{Cy}$.

38. The compound of claim 1, or a pharmaceutically acceptable salt thereof, wherein each $Cy^4$ is independently selected from $C_{3-7}$ cycloalkyl and 4-7 membered heterocycloalkyl, each of which is optionally substituted with 1 or 2 substituents independently selected from $R^{Cy}$.

39. The compound of claim 1, or a pharmaceutically acceptable salt thereof, wherein each $Cy^4$ is independently selected from cyclobutyl, morpholino, 2-oxopyrrolidinyl and piperazinyl, each of which is optionally substituted with $C_{1-4}$ alkyl.

40. The compound of claim 1, or a pharmaceutically acceptable salt thereof, wherein each $Cy^4$ is independently selected from cyclobutyl, morpholino, and piperazinyl, each of which is optionally substituted with $C_{1-4}$ alkyl.

41. The compound of claim 1, or a pharmaceutically acceptable salt thereof, wherein each $Cy^5$ is independently selected from 4-10 membered heterocycloalkyl optionally substituted with 1 or 2 substituents independently selected from $R^{Cy}$.

42. The compound of claim 1, or a pharmaceutically acceptable salt thereof, wherein each $Cy^5$ is independently selected from pyrrolidinyl and piperidinyl, each of which is optionally substituted with 1 or 2 substituents independently selected from $R^{Cy}$.

43. The compound of claim 1, or a pharmaceutically acceptable salt thereof, wherein each $R^{Cy}$ is independently selected from $C_{1-4}$ alkyl, oxo, and $NR^{c6}R^{d6}$, wherein said $C_{1-4}$ alkyl is optionally substituted with 1 or 2 substituents independently selected from CN and $OR^{a6}$.

44. The compound of claim 1, or a pharmaceutically acceptable salt thereof, wherein group:

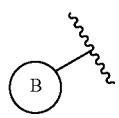

is selected from any one of Formulae (B-1) to (B-30):

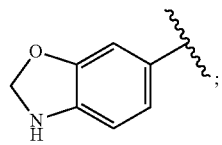
(B-1)

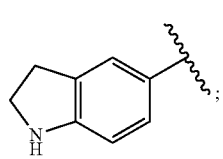
(B-2)

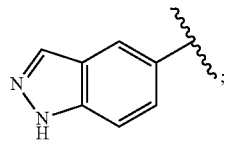
(B-3)

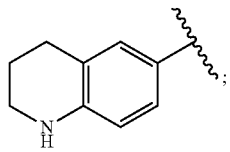
(B-4)

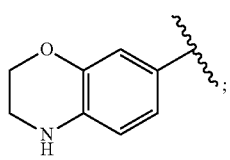
(B-5)

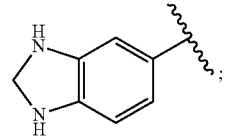
(B-6)

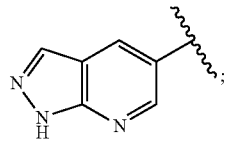
(B-7)

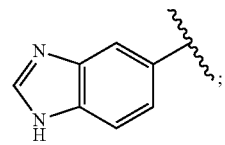
(B-8)

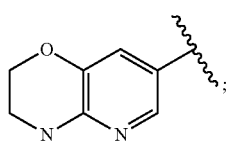
(B-9)

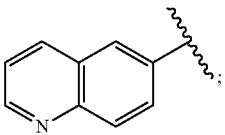
(B-10)

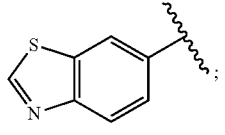
(B-11)

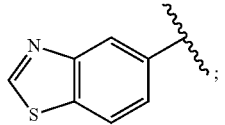
(B-12)

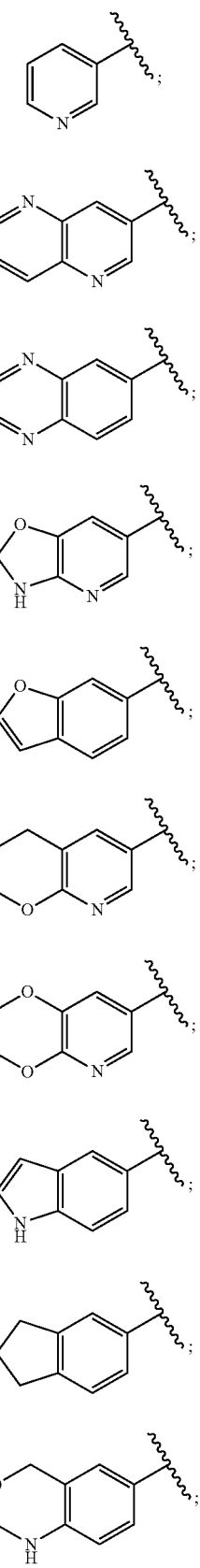
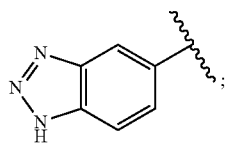
(B-13)
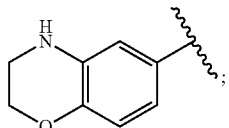
(B-14)
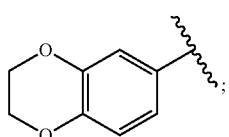
(B-15)
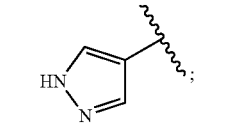
(B-16)
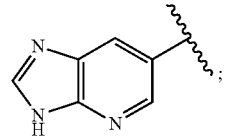
(B-17)
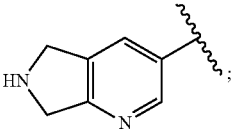
(B-18)
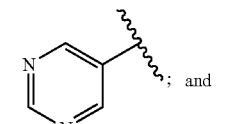
(B-19)
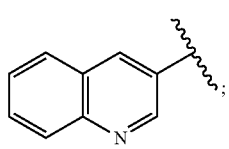
(B-20)
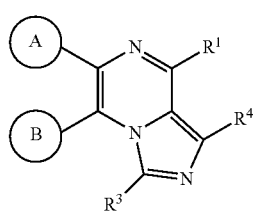
(B-21)
wherein any one of the groups of Formulae (B-1) to (B-30) is optionally substituted with 1, 2, 3, or 4 substituents independently selected from $R^B$.
45. The compound of claim 1 having Formula IIa:
IIa
or a pharmaceutically acceptable salt thereof.

46. The compound of claim 1, having Formula IIb:

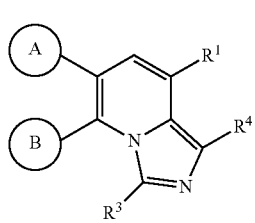

IIb or a pharmaceutically acceptable salt thereof.

47. The compound of claim 1, having Formula IIIa:

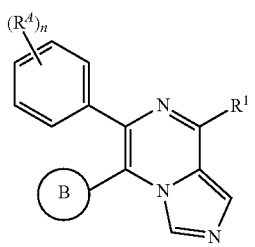

IIIa or a pharmaceutically acceptable salt thereof, wherein n is 0, 1, 2, 3, or 4.

48. The compound of claim 1 having Formula IIIb:

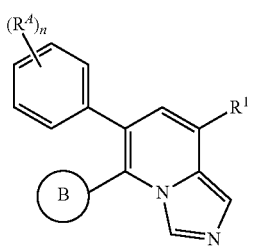

IIIb or a pharmaceutically acceptable salt thereof, wherein n is 0, 1, 2, 3, or 4.

49. The compound of claim 1, having Formula IVa:

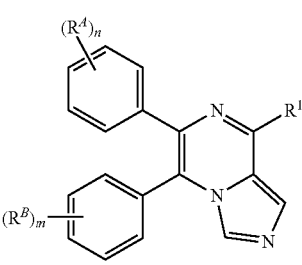

IVa or a pharmaceutically acceptable salt thereof, wherein:
n is 0, 1, 2, 3, or 4; and
m is 0, 1, 2, 3, or 4.

50. The compound of claim 1 having Formula IVb:

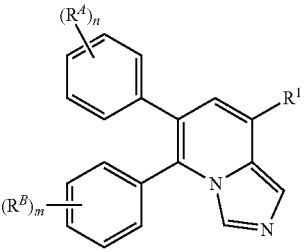

IVb or a pharmaceutically acceptable salt thereof, wherein:
n is 0, 1, 2, 3, or 4; and
m is 0, 1, 2, 3, or 4.

51. The compound of claim 1, having Formula Va:

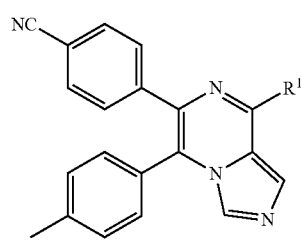

Va or a pharmaceutically acceptable salt thereof.

52. The compound of claim 1 having Formula Vb:

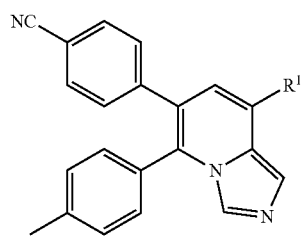

Vb or a pharmaceutically acceptable salt thereof.

53. The compound of claim 1, having Formula VIa or Formula VIb:

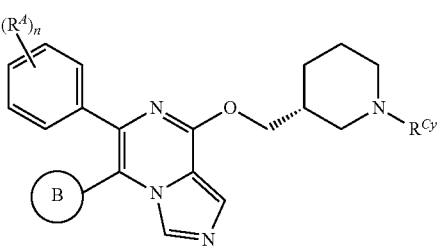

VIa

-continued

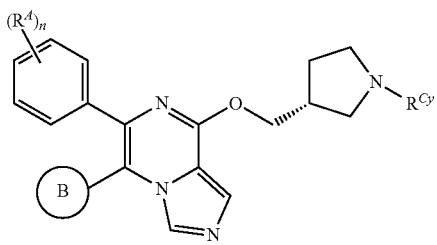

VIb or a pharmaceutically acceptable salt thereof, wherein n is 0, 1, 2, 3, or 4.

54. The compound of claim 1, having Formula VIIa or Formula VIIb:

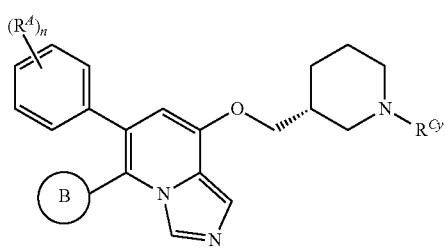

VIIa

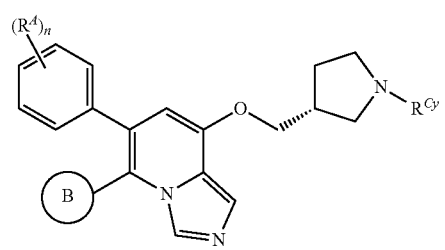

VIIb or a pharmaceutically acceptable salt thereof, wherein n is 0, 1, 2, 3, or 4.

55. The compound of claim 1, having Formula VIIIa or Formula VIIIb:

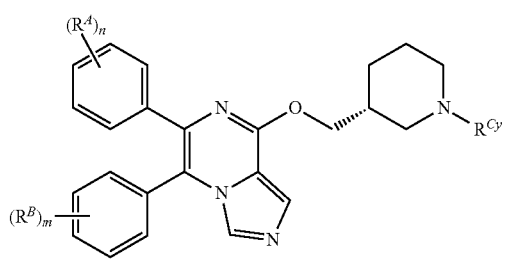

VIIIa

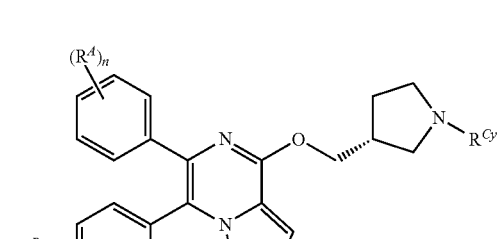

VIIIb or a pharmaceutically acceptable salt thereof, wherein:
n is 0, 1, 2, 3, or 4; and
m is 0, 1, 2, 3, or 4.

56. The compound of claim 1, having Formula IXa or Formula IXb:

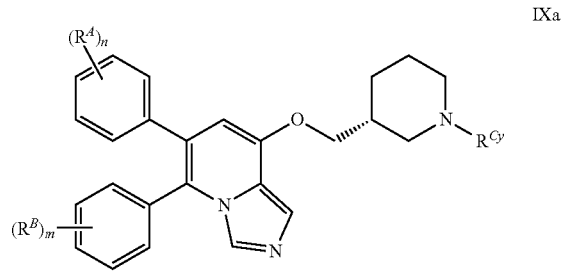

IXa

IXb

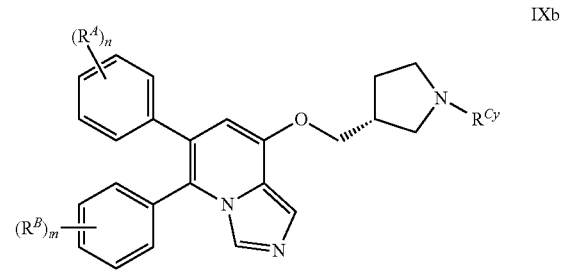

or a pharmaceutically acceptable salt thereof, wherein:
n is 0, 1, 2, 3, or 4; and
m is 0, 1, 2, 3, or 4.

57. The compound of claim 1, having Formula Xa or Formula Xb

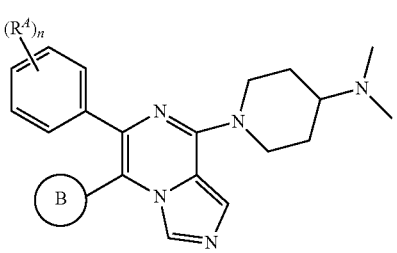

Xa

Xb

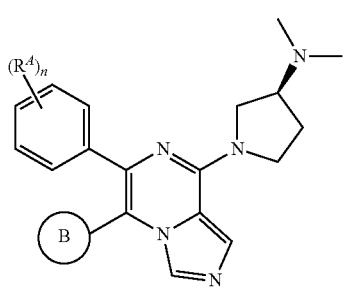

or a pharmaceutically acceptable salt thereof, wherein n is 0, 1, 2, 3, or 4.

58. The compound of claim 1, having Formula XIa or Formula XIb

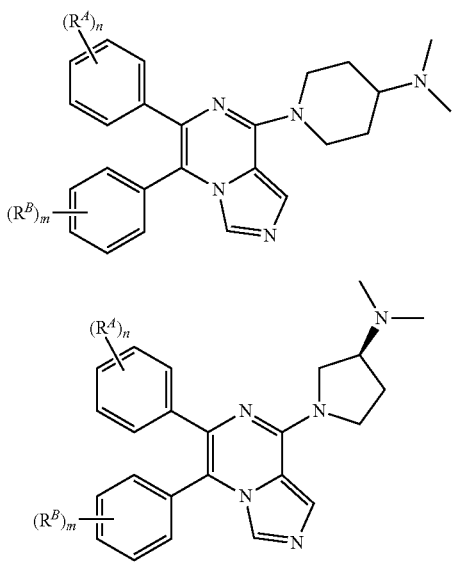

XIa

XIb or a pharmaceutically acceptable salt thereof, wherein:
n is 0, 1, 2, 3, or 4; and
m is 0, 1, 2, 3, or 4.

59. The compound of claim 1 selected from:
4-{5-(4-methylphenyl)-8-[(3R)-pyrrolidin-3-ylmethoxy]imidazo [1, 5-a]pyridin-6-yl}benzonitrile;
6-(4-fluorophenyl)-5-(4-methylphenyl)-8-[(3R)-pyrrolidin-3-ylmethoxy]imidazo[1,5-a]pyridine;
5-(4-methylphenyl)-6-(4-nitrophenyl)-8-[(3R)-pyrrolidin-3-ylmethoxy]imidazo[1,5-a]pyridine;
2-fluoro-4-{5-(4-methylphenyl)-8-[(3R)-pyrrolidin-3-ylmethoxy]imidazo[1,5-a]pyridin-6-yl}benzonitrile;
3-fluoro-4-{5-(4-methylphenyl)-8-[(3R)-pyrrolidin-3-ylmethoxy]imidazo[1,5-a]pyridin-6-yl}benzonitrile;
4-{5-(4-chlorophenyl)-8-[(3R)-pyrrolidin-3-ylmethoxy]imidazo[1, 5-a]pyridin-6-yl}benzonitrile;
4-{5-(1-cyclobutyl-1H-pyrazol-4-yl)-8-[(3R)-pyrrolidin-3-ylmethoxy]imidazo [1,5-a]pyridin-6-yl}benzonitrile;
4-{5-(2-fluoro-4-methylphenyl)-8-[(3R)-pyrrolidin-3-ylmethoxy]imidazo[1,5-a]pyridin-6-yl}benzonitrile;
4-{5-(4-ethylcyclohex-1-en-1-yl)-8-[(3R)-pyrrolidin-3-ylmethoxy]imidazo[1,5-a]pyridin-6-yl}benzonitrile;
tert-butyl 4-{6-(4-cyanophenyl)-8-[(3R)-pyrrolidin-3-ylmethoxy]imidazo[1,5-a]pyridin-5-yl}-3, 6-dihydropyridine-1(2H)-carboxylate;
4-{5-(1-methyl-1H-indazol-5-yl)-8-[(3R)-pyrrolidin-3-ylmethoxy]imidazo[1,5-a]pyridin-6-yl}benzonitrile;
4-{5-(1-methyl-2-oxo-2,3-dihydro-1H-indol-5-yl)-8-[(3R)-pyrrolidin-3-ylmethoxy]imidazo-[1,5-a]pyridin-6-yl}benzonitrile;
4-{5-(4-morpholin-4-ylphenyl)-8-[(3R)-pyrrolidin-3-ylmethoxy]imidazo[1,5-a]pyridin-6-yl}benzonitrile;
4-{5-(4-methyl-3,4-dihydro-2H-1, 4-benzoxazin-7-yl)-8-[(3R)-pyrrolidin-3-ylmethoxy]imidazo [1, 5-a]pyridin-6-yl}benzonitrile;
4-{5-(4-methyl-3,4-dihydro-2H-1, 4-benzoxazin-6-yl)-8-[(3R)-pyrrolidin-3-ylmethoxy]imidazo [1, 5-a]pyridin-6-yl}benzonitrile;
4-{5-(2,3-dihydro-1,4-benzodioxin-6-yl)-8-[(3R)-pyrrolidin-3-ylmethoxy]imidazo[1,5-a]pyridin-6-yl}benzonitrile;
4-{5-[4-(morpholin-4-ylmethyl)phenyl]-8-[(3R)-pyrrolidin-3-ylmethoxy]imidazo[1,5-a]pyridin-6-yl}benzonitrile;
4-{5-[4-(2-morpholin-4-ylethyl)phenyl]-8-[(3R)-pyrrolidin-3-ylmethoxy]imidazo[1,5-a]pyridin-6-yl}benzonitrile;
4-{5-{4-[(4-methylpiperazin-1-yl)methyl]phenyl})-8-[(3R)-pyrrolidin-3-ylmethoxy]imidazo-[1,5-a]pyridin-6-yl})benzonitrile; and
4-(5-(4-methylphenyl)-8-{[(3R)-1-methylpyrrolidin-3-yl]methoxy}imidazo[1,5-a]pyridin-6-yl)benzonitrile,
or a pharmaceutically acceptable salt of any of the aforementioned.

60. The compound of claim 1 selected from:
4-(5-(3-methyl-2-oxo-2,3-dihydro-1,3-benzoxazol-6-yl)-8-{[(3R)-1-methylpiperidin-3-yl]methoxy}imidazo[1,5-a]pyrazin-6-yl)benzonitrile;
4-(5-(1-methyl-2-oxo-2,3-dihydro-1H-indol-5-yl)-8-{[(3R)-1-methylpiperidin-3-yl]methoxy}imidazo[1,5-a]pyrazin-6-yl)benzonitrile;
4-(5-(1-methyl-1H-indazol-5-yl)-8-{[(3R)-1-methylpiperidin-3-yl]methoxy}imidazo[1,5-a]pyrazin-6-yl)benzonitrile;
4-(5-(1-methyl-2-oxo-1,2,3,4-tetrahydroquinolin-6-yl)-8-{[(3R)-1-methylpiperidin-3-yl]methoxy}imidazo[1,5-a]pyrazin-6-yl)benzonitrile;
4-(5-(4-methyl-3-oxo-3,4-dihydro-2H-1,4-benzoxazin-7-yl)-8-{[(3R)-1-methylpiperidin-3-yl]methoxy}imidazo[1,5-a]pyrazin-6-yl)benzonitrile;
4-(5-(1,3-dimethyl-2-oxo-2,3-dihydro-1H-benzimidazol-5-yl)-8-{[(3R)-1-methylpiperidin-3-yl]methoxy}imidazo[1,5-a]pyrazin-6-yl)benzonitrile;
4-[8-{[(3R)-1-methylpiperidin-3-yl]methoxy}-5-(1-methyl-1H-pyrazolo[3,4-b]pyridin-5-yl)imidazo [1, 5-a]pyrazin-6-yl]benzonitrile;
4-(5-(1-methyl-1H-benzimidazol-5-yl)-8-{[(3R)-1-methylpiperidin-3-yl]methoxy}imidazo[1, 5-a]pyrazin-6-yl)benzonitrile;
4-(5-(4-methyl-3,4-dihydro-2H-pyrido[3,2-b][1,4]oxazin-7-yl)-8-{[(3R)-1-methylpiperidin-3-yl]methoxy}imidazo[1,5-a]pyrazin-6-yl)benzonitrile;
4-(5-(5-fluoro-3-methyl-2-oxo-2, 3-dihydro-1,3-benzoxazol-6-yl)-8-{[(3R)-1-methylpiperidin-3-yl]methoxy}imidazo[1,5-a]pyrazin-6-yl)benzonitrile;
4-(8-{[(3R)-1-methylpiperidin-3-yl]methoxy}-5-quinolin-6-ylimidazo[1, 5-a]pyrazin-6-yl)benzonitrile;
4-(5-(1,3-dimethyl-1H-indazol-5-yl)-8-{[(3R)-1-methylpiperidin-3-yl]methoxy}imidazo[1, 5-a]pyrazin-6-yl)benzonitrile;
4-(5-(1,3-benzothiazol-6-yl)-8-{[(3R)-1-methylpiperidin-3-yl]methoxy}imidazo[1,5-a]pyrazin-6-yl)benzonitrile;
(R)-4-(5-(benzo[d]thiazol-5-yl)-8-((1-methylpiperidin-3-yl)methoxy)imidazo[1,5-a]pyrazin-6-yl)benzonitrile;
4-(5-(2-methyl-1,3-benzothiazol-5-yl)-8-{[(3R)-1-methylpiperidin-3-yl]methoxy}imidazo[1, 5-a]pyrazin-6-yl)benzonitrile;
2-fluoro-4-[8-{[(3R)-1-methylpiperidin-3-yl]methoxy}-5-(1-methyl-1H-pyrazolo[3,4-b]pyridin-5-yl)imidazo [1, 5-a]pyrazin-6-yl]benzonitrile;
4-[8-{[(3R)-1-(2-hydroxyethyl)piperidin-3-yl]methoxy}-5-(1-methyl-1H-pyrazolo[3,4-b]pyridin-5-yl)imidazo [1, 5-a]pyrazin-6-yl]benzonitrile;
4-[8-{[(3R)-1-(2-cyanoethyl)piperidin-3-yl]methoxy}-5-(1-methyl-1H-pyrazolo[3,4-b]pyridin-5-yl)imidazo [1, 5-a]pyrazin-6-yl]benzonitrile;

4-[8-{[(3R)-1-(2-hydroxypropyl)piperidin-3-yl]
methoxy}-5-(1-methyl-1H-pyrazolo[3,4-b]pyridin-5-
yl)imidazo [1, 5-a]pyrazin-6-yl]benzonitrile;

4-[8-{[(3R)-1-(2-methoxyethyl)piperidin-3-yl]
methoxy}-5-(1-methyl-1H-pyrazolo[3,4-b]pyridin-5-
yl)imidazo [1, 5-a]pyrazin-6-yl]benzonitrile;

4-[8-{[(3R)-1-(2-hydroxy-2-methylpropyl)piperidin-3-
yl]methoxy}-5-(1-methyl-1H-pyrazolo[3,4-b]pyridin-
5-yl)imidazo[1,5-a]pyrazin-6-yl]benzonitrile;

4-(5-[3-(hydroxymethyl)-4-methylphenyl]-8-{[(3R)-1-
methylpiperidin-3-yl]methoxy}imidazo[1, 5-a]
pyrazin-6-yl)benzonitrile;

4-(5-(5-fluoro-6-methoxypyridin-3-yl)-8-{[(3R)-1-methylpiperidin-3-yl]methoxy}imidazo[1, 5-a]pyrazin-6-yl)benzonitrile;

4-(5-[3-fluoro-4-(hydroxymethyl)-5-methylphenyl]-8-
{[(3R)-1-methylpiperidin-3-yl]methoxy}imidazo[1,
5-a]pyrazin-6-yl)benzonitrile;

4-(5-[4-(hydroxymethyl)-3-methylphenyl]-8-{[(3R)-1-
methylpiperidin-3-yl]methoxy}imidazo[1, 5-a]
pyrazin-6-yl)benzonitrile;

Methyl [4-(6-(4-cyanophenyl)-8-{[(3R)-1-methylpiperidin-3-yl]methoxy)}imidazo [1,5-a]pyrazin-5-yl)phenyl]methylcarbamate;

4-(5-[3,5-difluoro-4-(hydroxymethyl)phenyl]-8-{[(3R)-1-methylpiperidin-3-yl]methoxy}imidazo[1, 5-a]pyrazin-6-yl)benzonitrile;

methyl [4-(6-(4-cyanophenyl)-8-{[(3R)-1-methylpiperidin-3-yl]methoxy)}imidazo [1,5-a]pyrazin-5-yl)-2-fluorobenzyl]methylcarbamate;

methyl [5-(6-(4-cyanophenyl)-8-{[(3R)-1-methylpiperidin-3-yl]methoxy}imidazo [1,5-a]pyrazin-5-yl)pyridin-2-yl]methylcarbamate;

4-[8-[4-(dimethylamino)piperidin-1-yl]-5-(1-methyl-1H-pyrazolo[3,4-b]pyridin-5-yl)imidazo [1, 5-a]pyrazin-6-yl]benzonitrile;

4-[8-[4-(dimethylamino)piperidin-1-yl]-5-(3-methyl-2-oxo-2,3-dihydro-1,3-benzoxazol-6-yl)imidazo[1,5-a]pyrazin-6-yl]benzonitrile;

4-[8-[4-(dimethylamino)piperidin-1-yl]-5-(1-methyl-2-oxo-2,3-dihydro-1H-indol-5-yl)imidazo [1, 5-a]pyrazin-6-yl]benzonitrile;

4-[8-[4-(dimethylamino)piperidin-1-yl]-5-(6-methoxypyridin-3-yl)imidazo[1,5-a]pyrazin-6-yl]benzonitrile;

4-{8-[4-(dimethylamino)piperidin-1-yl]-5-[6-(2-oxopyrrolidin-1-yl)pyridin-3-yl]imidazo [1,5-a]pyrazin-6-yl}benzonitrile;

4-[8-[4-(dimethylamino)piperidin-1-yl]-5-(1,5-naphthyridin-3-yl)imidazo[1,5-a]pyrazin-6-yl]benzonitrile;

(R)-4-(8-((1-methylpiperidin-3-yl)methoxy)-5-(quinoxalin-6-yl)imidazo[1,5-a]pyridin-6-yl)benzonitrile;

(R)-4-(5-(3-methyl-2-oxo-2,3-dihydrooxazolo[4,5-b]pyridin-6-yl)-8-((1-methylpiperidin-3-yl)methoxy)imidazo[1,5-a]pyridin-6-yl)benzonitrile;

(R)-4-(5-(3-methyl-3H-imidazo[4,5-b]pyridin-6-yl)-8-((1-methylpiperidin-3-yl)methoxy)imidazo[1,5-a]pyridin-6-yl)benzonitrile;

(R)-4-(8-((1-methylpiperidin-3-yl)methoxy)-5-(1,5-naphthyridin-3-yl)imidazo[1,5-a]pyridin-6-yl)benzonitrile;

(R)-4-(5-(furo[3,2-b]pyridin-6-yl)-8-((1-methylpiperidin-3-yl)methoxy)imidazo[1,5-a]pyridin-6-yl)benzonitrile;

(R)-4-(5-(3,4-dihydro-2H-pyrano[2,3-b]pyridin-6-yl)-8-((1-methylpiperidin-3-yl)methoxy)imidazo[1,5-a]pyridin-6-yl)benzonitrile;

(R)-4-(5-(2,3-dihydro-[1,4]dioxino[2,3-b]pyridin-7-yl)-8-((1-methylpiperidin-3-yl)methoxy)imidazo[1,5-a]pyridin-6-yl)benzonitrile;

(R)-4-(5-(3-methyl-2-oxo-2, 3-dihydrobenzo[d]oxazol-6-yl)-8-((1-methylpiperidin-3-yl)methoxy)imidazo[1,5-a]pyridin-6-yl)benzonitrile;

(R)-4-(5-(1-methyl-2-oxoindolin-5-yl)-8-((1-methylpiperidin-3-yl)methoxy)imidazo[1,5-a]pyridin-6-yl)benzonitrile;

(R)-4-(5-(4-methyl-3-oxo-3,4-dihydro-2H-benzo[b][1,4]oxazin-7-yl)-8-((1-methylpiperidin-3-yl)methoxy)imidazo[1,5-a]pyridin-6-yl)benzonitrile;

(R)-4-(8-((1-ethylpiperidin-3-yl)methoxy)-5-(3-methyl-3H-imidazo[4,5-b]pyridin-6-yl)imidazo [1, 5-a]pyridin-6-yl)benzonitrile;

(R)-4-(5-(2,3-dihydro-[1,4]dioxino[2,3-b]pyridin-7-yl)-8-((1-ethylpiperidin-3-yl)methoxy)imidazo[1,5-a]pyridin-6-yl)benzonitrile;

(R)-4-(5-(3,4-dihydro-2H-pyrano[2,3-b]pyridin-6-yl)-8-((1-ethylpiperidin-3-yl)methoxy)imidazo[1,5-a]pyridin-6-yl)benzonitrile;

(R)-4-(5-(5-amino-6-methoxypyridin-3-yl)-8-((1-methylpiperidin-3-yl)methoxy)imidazo[1,5-a]pyridin-6-yl)benzonitrile;

(R)-4-(5-(5-fluoro-6-methoxypyridin-3-yl)-8-((1-methylpiperidin-3-yl)methoxy)imidazo[1,5-a]pyridin-6-yl)benzonitrile;

(R)-4-(8-((1-methylpiperidin-3-yl)methoxy)-5-(6-(2-oxopyrrolidin-1-yl)pyridin-3-yl)imidazo [1, 5-a]pyridin-6-yl)benzonitrile;

4-(5-(6-methoxypyridin-3-yl)-8-{[(3R)-1-methylpiperidin-3-yl]methoxy}imidazo[1,5-a]pyridin-6-yl)benzonitrile;

(R)-4-(5-(3,5-difluoro-4-(hydroxymethyl)phenyl)-8-((1-methylpiperidin-3-yl)methoxy)imidazo[1,5-a]pyridin-6-yl)benzonitrile;

Methyl [5-(6-(4-cyanophenyl)-8-{[(3R)-1-methylpiperidin-3-yl]methoxy}imidazo [1,5-a]pyridin-5-yl)pyridin-2-yl]methylcarbamate;

4-(5-[3-fluoro-4-(hydroxymethyl)-5-methylphenyl]-8-{[(3R)-1-methylpiperidin-3-yl]methoxy}imidazo[1, 5-a]pyridin-6-yl)benzonitrile;

4-(5-(5-hydroxy-6-methylpyridin-3-yl)-8-{[(3R)-1-methylpiperidin-3-yl]methoxy}imidazo[1, 5-a]pyridin-6-yl)benzonitrile;

4-(5-[4-(1-hydroxy-1-methylethyl)phenyl]-8-{[(3R)-1-methylpiperidin-3-yl]methoxy}imidazo[1, 5-a]pyridin-6-yl)benzonitrile;

4-(5-(5-fluoro-6-morpholin-4-ylpyridin-3-yl)-8-{[(3R)-1-methylpiperidin-3-yl]methoxy}imidazo[1, 5-a]pyridin-6-yl)benzonitrile;

4-(5-[4-(hydroxymethyl)-3-methylphenyl]-8-{[(3R)-1-methylpiperidin-3-yl]methoxy}imidazo[1, 5-a]pyridin-6-yl)benzonitrile;

4-(5-[6-(dimethylamino)pyridin-3-yl]-8-{[(3R)-1-methylpiperidin-3-yl]methoxy}imidazo[1, 5-a]pyridin-6-yl)benzonitrile;

4-(5-(5,6-dimethylpyridin-3-yl)-8-{[(3R)-1-methylpiperidin-3-yl]methoxy}imidazo[1,5-a]pyridin-6-yl)benzonitrile;

N-[4-(6-(4-cyanophenyl)-8-{[(3R)-1-methylpiperidin-3-yl]methoxy}imidazo[1,5-a]pyridin-5-yl)-2-fluorobenzyl]-N,N',N'-trimethylurea;

4-[8-[4-(dimethylamino)piperidin-1-yl]-5-(1-methyl-1H-benzimidazol-5-yl)imidazo[1,5-a]pyrazin-6-yl]benzonitrile;

4-(8-(4-(dimethylamino)piperidin-1-yl)-5-(1-methyl-1H-pyrrolo[2,3-b]pyridin-5-yl)imidazo [1, 5-a]pyrazin-6-yl)benzonitrile;

4-[8-{[(3R)-1-methylpiperidin-3-yl]methoxy}-5-(1-methyl-1H-pyrrolo[2,3-b]pyridin-5-yl)imidazo [1, 5-a]pyrazin-6-yl]benzonitrile;

4-(5-(5,6-dimethylpyridin-3-yl)-8-{[(3R)-1-methylpiperidin-3-yl]methoxy}imidazo[1,5-a]pyrazin-6-yl)benzonitrile;

(R)-methyl (4-(6-(4-cyanophenyl)-8-((1-methylpiperidin-3-yl)methoxy)imidazo[1,5-a]pyrazin-5-yl)-2-fluorophenyl)(methyl)carbamate;

4-(5-(5-fluoro-6-methylpyridin-3-yl)-8-{[(3R)-1-methylpiperidin-3-yl]methoxy}imidazo[1, 5-a]pyrazin-6-yl)benzonitrile;

4-[8-4-(dimethylamino)piperidin-1-yl]-5-(5,6-dimethylpyridin-3-yl)imidazo[1,5-a]pyrazin-6-yl]benzonitrile;

4-[8-[4-(dimethylamino)piperidin-1-yl]-5-(5-fluoro-6-methoxypyridin-3-yl)imidazo [1,5-a]pyrazin-6-yl]benzonitrile;

4-{8-[4-(dimethylamino)piperidin-1-yl]-5-[3-(hydroxymethyl)-4-methylphenyl]imidazo [1, 5-a]pyrazin-6-yl}benzonitrile;

4-{8-[4-(dimethylamino)piperidin-1-yl]-5-[2-(hydroxymethyl)-4-methylphenyl]imidazo [1, 5-a]pyrazin-6-yl}benzonitrile;

4-[8-[4-(dimethylamino)piperidin-1-yl]-5-(6-methoxy-5-methylpyridin-3-yl)imidazo [1,5-a]pyrazin-6-yl]benzonitrile;

methyl (4-{6-(4-cyanophenyl)-8-[4-(dimethylamino)piperidin-1-yl]imidazo[1,5-a]pyrazin-5-yl}-2-fluorophenyl)methylcarbamate;

methyl (4-(6-(4-cyanophenyl)-8-(4-(dimethylamino)piperidin-1-yl)imidazo [1,5-a]pyrazin-5-yl)phenyl)(methyl)carbamate;

methyl (5-(6-(4-cyanophenyl)-8-(4-(dimethylamino)piperidin-1-yl)imidazo[1,5-a]pyrazin-5-yl)pyridin-2-yl)(methyl)carbamate;

4-[8-[4-(dimethylamino)piperidin-1-yl]-5-(5-fluoro-6-methylpyridin-3-yl)imidazo [1,5-a]pyrazin-6-yl]benzonitrile;

4-{5-[6-(difluoromethoxy)pyridin-3-yl]-8-[4-(dimethylamino)piperidin-1-yl]imidazo [1,5-a]pyrazin-6-yl]}benzonitrile;

4-[8-[4-(dimethylamino)piperidin-1-yl]-5-(6-ethoxypyridin-3-yl)imidazo[1,5-a]pyrazin-6-yl]benzonitrile;

4-[8-[4-(dimethylamino)piperidin-1-yl]-5-(l-methyl-1H-indazol-5-yl)imidazo[1,5-a]pyrazin-6-yl]benzonitrile;

4-(5-(2-hydroxy-2,3-dihydro-1H-inden-5-yl)-8-{[(3R)-1-methylpiperidin-3-yl]methoxy}imidazo[1, 5-a]pyrazin-6-yl)benzonitrile;

2-fluoro-4-(5-(1-methyl-2-oxo-1,2,3,4-tetrahydroquinolin-6-yl)-8-{[(3R)-1-methylpiperidin-3-yl]methoxy}imidazo[1,5-a]pyrazin-6-yl)benzonitrile;

4-(8-(4-(dimethylamino)piperidin-1-yl)-5-(quinoxalin-6-yl)imidazo[1,5-a]pyrazin-6-yl)benzonitrile;

4-(8-(4-(dimethylamino)piperidin-1-yl)-5-(furo[3,2-b]pyridin-6-yl)imidazo[1,5-a]pyrazin-6-yl)benzonitrile;

4-[8-[4-(dimethylamino)piperidin-1-yl]-5-(4-methyl-3-oxo-3,4-dihydro-2H-pyrido[3,2-b][1,4]oxazin-7-yl)imidazo[1, 5-a]pyrazin-6-yl]benzonitrile;

4-[8-[4-(dimethylamino)piperidin-1-yl]-5-(1-methyl-2-oxo-1,4-dihydro-2H-3,1-benzoxazin-6-yl)imidazo [1, 5-a]pyrazin-6-yl]benzonitrile;

4-[8-[4-(dimethylamino)piperidin-1-yl]-5-(3-methyl-3H-imidazo[4, 5-b]pyridin-6-yl)imidazo [1, 5-a]pyrazin-6-yl]benzonitrile;

4-[8-[4-(dimethylamino)piperidin-1-yl]-5-(3-ethyl-2-oxo-2,3-dihydro-1,3-benzoxazol-6-yl)imidazo [1, 5-a]pyrazin-6-yl]benzonitrile;

4-[8-[4-(dimethylamino)piperidin-1-yl]-5-(4-fluoro-1,3-dimethyl-2-oxo-2,3-dihydro-1H-benzimidazol-5-yl)imidazo[1,5-a]pyrazin-6-yl]benzonitrile;

4-[8-{[(3R)-1-ethylpiperidin-3-yl]methoxy}-5-(1-methyl-2-oxo-2,3-dihydro-1H-indol-5-yl)imidazo [1, 5-a]pyrazin-6-yl]benzonitrile;

4-[8-{[(3R)-1-ethylpiperidin-3-yl]methoxy}-5-(5-fluoro-3-methyl-2-oxo-2,3-dihydro-1,3-benzoxazol-6-yl)imidazo[1, 5-a]pyrazin-6-yl]benzonitrile;

(S)-4-(8-(3-(dimethylamino)pyrrolidin-1-yl)-5-(3-methyl-2-oxo-2,3-dihydrobenzo[d]oxazol-6-yl)imidazo[1, 5-a]pyrazin-6-yl)benzonitrile;

4-[8-[(3 S)-3-(dimethylamino)pyrrolidin-1-yl]-5-(5-fluoro-3-methyl-2-oxo-2,3-dihydro-1,3-benzoxazol-6-yl)imidazo[1, 5-a]pyrazin-6-yl]benzonitrile;

(R)-4-(8-((1-ethylpiperidin-3-yl)methoxy)-5-(1-methyl-2-oxoindolin-5-yl)imidazo[1,5-a]pyridin-6-yl)benzonitrile;

(R)-4-(5-(2,3-dihydro-[1,4]dioxino[2,3-b]pyridin-7-yl)-8-((1-(2-methoxyethyl)piperidin-3-yl)methoxy)imidazo[1,5-a]pyridin-6-yl)benzonitrile;

(R)-4-(5-(4-methyl-3,4-dihydro-2H-pyrido[3,2-b][1,4]oxazin-7-yl)-8-((1-methylpiperidin-3-yl)methoxy)imidazo[1,5-a]pyridin-6-yl)benzonitrile;

4-(5-(3-ethyl-3H-[1,2,3]triazolo[4, 5-b]pyridin-6-yl)-8-{[(3R)-1-methylpiperidin-3-yl]methoxy}imidazo[1, 5-a]pyridin-6-yl)benzonitrile;

4-(5-(2,3-dihydro[1,4]dioxino[2,3-b]pyridin-7-yl)-8-{[(3R)-1-(2-hydroxypropyl)piperidin-3-yl]methoxy}imidazo[1,5-a]pyridin-6-yl)benzonitrile;

4-(5-(furo[3,2-b]pyridin-6-yl)-8-(((3R)-1-(2-hydroxypropyl)piperidin-3-yl)methoxy)imidazo[1,5-a]pyridin-6-yl)benzonitrile;

4-(8-(((3R)-1-(2-hydroxypropyl)piperidin-3-yl)methoxy)-5-(quinoxalin-6-yl)imidazo[1,5-a]pyridin-6-yl)benzonitrile;

4-(5-furo[3,2-b]pyridin-6-yl-8-{[(3R)-1-(2-methoxyethyl)piperidin-3-yl]methoxy}imidazo[1, 5-a]pyridin-6-yl)benzonitrile;

(R)-4-(5-(3,4-dihydro-2H-pyrano[2,3-b]pyridin-6-yl)-8-((1-(2-methoxyethyl)piperidin-3-yl)methoxy)imidazo [1,5-a]pyridin-6-yl)benzonitrile;

4-(5-[4-(1-hydroxyethyl)phenyl]-8-{[(3R)-1-methylpiperidin-3-yl]methoxy}imidazo[1,5-a]pyridin-6-yl)benzonitrile;

4-(5-[3,5-difluoro-4-(1-hydroxyethyl)phenyl]-8-{[(3R)-1-methylpiperidin-3-yl]methoxy}imidazo[1, 5-a]pyridin-6-yl)benzonitrile;

4-[8-{[(3R)-1-methylpiperidin-3-yl]methoxy}-5-(6-methylpyridin-3-yl)imidazo[1,5-a]pyridin-6-yl]benzonitrile;

4-(5-[3-fluoro-4-(1-hydroxyethyl)-5-methylphenyl]-8-{[(3R)-1-methylpiperidin-3-yl]methoxy}imidazo[1, 5-a]pyridin-6-yl)benzonitrile;

4-(5-(5-fluoro-6-methylpyridin-3-yl)-8-{[(3R)-1-methylpiperidin-3-yl]methoxy}imidazo[1, 5-a]pyridin-6-yl)benzonitrile;

4-{8-{[(3R)-1-ethylpiperidin-3-yl]methoxy}-5-[3-fluoro-4-(hydroxymethyl)-5-methylphenyl]imidazo [1,5-a]pyridin-6-yl}benzonitrile;

4-(5-[3-fluoro-4-(hydroxymethyl)-5-methylphenyl]-8-{[(3R)-1-(2-methoxyethyl)piperidin-3-yl]methoxy}imidazo[1,5-a]pyridin-6-yl)benzonitrile;

4-(5-(5,6-dimethylpyridin-3-yl)-8-{[(3R)-1-(2-methoxyethyl)piperidin-3-yl]methoxy}imidazo[1, 5-a]pyridin-6-yl)benzonitrile;

4-(5-(5,6-dimethylpyridin-3-yl)-8-{[(3R)-1-ethylpiperidin-3-yl]methoxy}imidazo[1,5-a]pyridin-6-yl)benzonitrile;

4-(5-[6-(1-cyano-1-methylethyl)pyridin-3-yl]-8-{[(3R)-1-methylpiperidin-3-yl]methoxy}imidazo[1, 5-a]pyridin-6-yl)benzonitrile;

4-(5-(6-ethylpyridin-3-yl)-8-{[(3R)-1-methylpiperidin-3-yl]methoxy}imidazo[1,5-a]pyridin-6-yl)benzonitrile;

4-(5-(1-cyclobutyl-1H-pyrazol-4-yl)-8-{[(3R)-1-methylpiperidin-3-yl]methoxy}imidazo[1,5-a]pyridin-6-yl)benzonitrile; and 5-(6-(4-cyanophenyl)-8-{[(3R)-1-methylpiperidin-3-yl]methoxy}imidazo[1,5-a]pyridin-5-yl)-N-methylpyridine-2-carboxamide;

or a pharmaceutically acceptable salt of any of the aforementioned.

61. The compound of claim 1 selected from:

4-[8-[4-(dimethylamino)piperidin-1-yl]-5-(2-hydroxy-2,3-dihydro-1H-inden-5-yl)imidazo [1, 5-a]pyrazin-6-yl]benzonitrile;

4-[8-[4-(dimethylamino)piperidin-1-yl]-5-(1-methyl-2-oxo-1,2,3,4-tetrahydroquinolin-6-yl)imidazo [1, 5-a]pyrazin-6-yl]benzonitrile;

4-(8-(4-(dimethylamino)piperidin-1-yl)-5-(7-fluoro-1,3-dimethyl-2-oxo-2,3-dihydro-1H-benzo[d]imidazol-5-yl)imidazo[1,5-a]pyrazin-6-yl)benzonitrile;

4-{5-(1-cyclobutyl-1H-pyrazol-4-yl)-8-[4-(dimethylamino)piperidin-1-yl]imidazo[1,5-a]pyrazin-6-yl}benzonitrile;

4-{5-[5-(difluoromethyl)-6-methylpyridin-3-yl]-8-[4-(dimethylamino)piperidin-1-yl]imidazo [1, 5-a]pyrazin-6-yl}benzonitrile;

5-{6-(4-cyanophenyl)-8-[4-(dimethylamino)piperidin-1-yl]imidazo[1,5-a]pyrazin-5-yl}-N-methylpyridine-2-carboxamide;

4-{8-[4-(dimethylamino)piperidin-1-yl]-5-[5-(hydroxymethyl)-6-methylpyridin-3-yl]imidazo [1, 5-a]pyrazin-6-yl}benzonitrile;

4-{5-[2-(difluoromethyl)-1-methyl-1H-benzimidazol-5-yl]-8-[4-(dimethylamino)piperidin-1-yl]imidazo [1,5-a]pyrazin-6-yl}benzonitrile;

4-{8-[4-(dimethylamino)piperidin-1-yl]-5-quinolin-3-ylimidazo[1,5-a]pyrazin-6-yl}benzonitrile;

4-{8-[4-(dimethylamino)piperidin-1-yl]-5-quinolin-6-ylimidazo[1,5-a]pyrazin-6-yl}benzonitrile;

4-[8-{[(3R)-1-ethylpiperidin-3-yl]methoxy}-5-(6-methylpyridin-3-yl)imidazo[1,5-a]pyridin-6-yl]benzonitrile;

4-(5-[5-(methoxymethyl)-6-methylpyridin-3-yl]-8-{[(3R)-1-methylpiperidin-3-yl]methoxy}imidazo[1,5-a]pyridin-6-yl)benzonitrile;

5-{6-(4-cyanophenyl)-8-[4-(dimethylamino)piperidin-1-yl]imidazo[1,5-a]pyrazin-5-yl}-2-methoxynicotinonitrile;

4-{8-[4-(dimethylamino)piperidin-1-yl]-5-[4-(hydroxymethyl)-3-methylphenyl]imidazo[1, 5-a]pyrazin-6-yl}benzonitrile;

4-[8-[4-(dimethylamino)piperidin-1-yl]-5-(2-methoxypyrimidin-5-yl)imidazo[1,5-a]pyrazin-6-yl]benzonitrile;

4-(5-[6-(1-hydroxy-1-methylethyl)pyridin-3-yl]-8-{[(3R)-1-methylpiperidin-3-yl]methoxy}imidazo[1,5-a]pyridin-6-yl)benzonitrile;

(R)-4-(5-(4-methyl-3-oxo-3,4-dihydro-2H-pyrido[3,2-b][1,4]oxazin-7-yl)-8-((1-methylpiperidin-3-yl)methoxy)imidazo[1,5-a]pyridin-6-yl)benzonitrile;

4-(5-(1,2-dimethyl-1H-benzimidazol-5-yl)-8-{[(3R)-1-methylpiperidin-3-yl]methoxy}imidazo[1, 5-a]pyridin-6-yl)benzonitrile;

4-(5-(2-methyl-1-oxo-2,3-dihydro-1H-isoindol-5-yl)-8-{[(3R)-1-methylpiperidin-3-yl]methoxy}imidazo[1,5-a]pyridin-6-yl)benzonitrile;

(R)-4-(5-(3-isopropyl-3H-[1,2,3]triazolo[4, 5-b]pyridin-6-yl)-8-((1-methylpiperidin-3-yl)methoxy)imidazo[1,5-a]pyridin-6-yl)benzonitrile;

(R)-4-(5-(3-cyclopropyl-3H-[1,2,3]triazolo[4,5-b]pyridin-6-yl)-8-((1-methylpiperidin-3-yl)methoxy)imidazo[1,5-a]pyridin-6-yl)benzonitrile;

(R)-4-(5-(2-isopropyl-3-methyl-3H-imidazo[4,5-b]pyridin-6-yl)-8-((1-methylpiperidin-3-yl)methoxy)imidazo[1,5-a]pyridin-6-yl)benzonitrile; and (R)-4-(5-(2-cyclopropyl-3-methyl-3H-imidazo[4,5-b]pyridin-6-yl)-8-((1-methylpiperidin-3-yl)methoxy)imidazo[1,5-a]pyridin-6-yl)benzonitrile;

or a pharmaceutically acceptable salt of any of the aforementioned.

62. A pharmaceutical composition comprising a compound of claim 1, or a pharmaceutically acceptable salt thereof, and at least one pharmaceutically acceptable carrier.

63. A method of inhibiting lysine specific demethylase-1 comprising contacting a compound of claim 1, or a pharmaceutically acceptable salt thereof, with said lysine specific demethylase-1.

* * * * *

UNITED STATES PATENT AND TRADEMARK OFFICE
CERTIFICATE OF CORRECTION

PATENT NO. : 9,695,168 B2
APPLICATION NO. : 14/795536
DATED : July 4, 2017
INVENTOR(S) : Liangxing Wu et al.

It is certified that error appears in the above-identified patent and that said Letters Patent is hereby corrected as shown below:

On the Title Page

Other Publications, Lines 11-12, delete "Pharamcological" and insert -- Pharmacological --.

In the Claims

Column 176, Lines 55-56, Claim 1, delete "$S(O)NR^2R^{d2}$," and insert -- $S(O)NR^{c2}R^{d2}$, --;

Column 176, Line 56, Claim 1, delete "$S(O)_2NR^2R^{d2}$;" and insert -- $S(O)_2NR^{c2}R^{d2}$; --;

Column 176, Line 65, Claim 1, delete "$NR^{c2}S(O)_2NR^2R^{d2}$," and insert -- $NR^{c2}S(O)_2NR^{c2}R^{d2}$, --;

Column 176, Line 66, Claim 1, delete "$S(O)NR^2R^{d2}$," and insert -- $S(O)NR^{c2}R^{d2}$, --;

Column 177, Lines 26-27, Claim 1, delete "$NR^{c5}S(O)_2Rb$," and insert -- $NR^{c5}S(O)_2R^{b5}$, --;

Column 178, Line 16, Claim 1, delete "$S(O)NR^6R^{d6}$," and insert -- $S(O)NR^{c6}R^{d6}$, --;

Column 179, Line 60, Claim 1, delete "$C(O)NR^8R^{d8}$," and insert -- $C(O)NR^{c8}R^{d8}$, --.

Column 182, Lines 36-37, Claim 2, delete "$C(O)NR^4R^{d4}$," and insert -- $C(O)NR^{c4}R^{d4}$, --;

Column 182, Line 37, Claim 2, delete "$NR^{c4}R^{d4}$" and insert -- $NR^{c4}R^{d4}$, --;

Column 182, Line 37, Claim 2, delete "$NR^{c4}C(O)R^{b4}S(O)R^{b4}$," and insert -- $NR^{c4}C(O)R^{b4}$, $S(O)R^{b4}$, --.

Column 182, Line 55, Claim 3, delete "$S(O)NR^4R^{d4}$," and insert -- $S(O)NR^{c4}R^{d4}$, --;

Column 182, Lines 59-60, Claim 3, delete "$C(O)NR^4R^{d4}$," and insert -- $C(O)NR^{c4}R^{d4}$, --;

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,695,168 B2

Column 182, Line 60, Claim 3, delete "$NR^{c4}C(O)R^{b4}S(O)R^{b4}$," and insert -- $NR^{c4}C(O)R^{b4}$, $S(O)R^{b4}$, --;

Column 183, Line 4, Claim 3, delete "$R^{e5}$, $R^6$," and insert -- $R^{e5}$, $R^{e6}$, --.

Column 183, Line 39, Claim 4, delete "$NR^{c6}R^{d6}$" and insert -- $NR^{c6}R^{d6}$, --;

Column 183, Line 62, Claim 4, delete "$SR^{a5}$," and insert -- $SR^{a8}$, --;

Column 183, Line 64, Claim 4, delete "$NR^{c8}R^{d8}$" and insert -- $NR^{c8}R^{d8}$, --;

Column 183, Lines 64-65, Claim 4, delete "$NR^{c8}C(O)OR^{a5}$," and insert -- $NR^{c8}C(O)OR^{a8}$, --;

Column 184, Line 1, Claim 4, delete "$R^5$" and insert -- $R^{e5}$ --;

Column 184, Line 18, Claim 4, delete "$C(O)OR^{a5}$," and insert -- $C(O)OR^{a8}$, --.

Column 185, Lines 23-24, Claim 14, delete "$C(O)NR^4R^{d4}$," and insert -- $C(O)NR^{c4}R^{d4}$, --;

Column 185, Line 24, Claim 14, delete "$NR^{c4}R^{d4}$" and insert -- $NR^{c4}R^{d4}$, --;

Column 185, Line 24, Claim 14, delete "$NR^{c4}C(O)R^{b4}S(O)R^{b4}$," and insert -- $NR^{c4}C(O)R^{b4}$, $S(O)R^{b4}$, --.

Column 186, Line 24, Claim 27, delete "optinally" and insert -- optionally --.

Column 194, Line 36, Claim 57, delete "Xb" and insert -- Xb: --.

Column 194, Line 67, Claim 58, delete "Xlb" and insert -- Xlb: --.

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: synthetic peptide

<400> SEQUENCE: 1

Gln Thr Ala Arg Lys Ser Thr Gly Gly Lys Ala Pro Arg Lys Gln Leu
 1               5                   10                  15

Ala Gly Gly Lys
            20
```